(12) United States Patent
Takakura et al.

(10) Patent No.: US 8,771,997 B2
(45) Date of Patent: Jul. 8, 2014

(54) METHOD FOR PRODUCING MONATIN USING AN L-AMINO ACID AMINOTRANSFERASE

(75) Inventors: Yasuaki Takakura, Kawasaki (JP); Hiroomi Ogino, Kawasaki (JP); Masakazu Sugiyama, Kawasaki (JP); Kenichi Mori, Kawasaki (JP); Eri Tabuchi, Kawasaki (JP); Koki Ishikawa, Kawasaki (JP); Uno Tagami, Kawasaki (JP); Hidemi Fujii, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 127 days.

(21) Appl. No.: 13/271,280

(22) Filed: Oct. 12, 2011

(65) Prior Publication Data

US 2012/0270279 A1 Oct. 25, 2012

Related U.S. Application Data

(60) Provisional application No. 61/477,402, filed on Apr. 20, 2011.

(51) Int. Cl.
| | |
|---|---|
| C12P 17/10 | (2006.01) |
| C12N 9/10 | (2006.01) |
| C12P 13/22 | (2006.01) |
| C12N 9/00 | (2006.01) |

(52) U.S. Cl.
USPC ............ 435/121; 435/193; 435/108; 435/183

(58) Field of Classification Search
USPC ............................ 435/121, 193, 320.1, 252.3
See application file for complete search history.

(56) References Cited

U.S. PATENT DOCUMENTS

| | | | |
|---|---|---|---|
| 4,518,692 | A | 5/1985 | Rozzell |
| 6,582,935 | B2 | 6/2003 | Yan et al. |
| 7,314,974 | B2 | 1/2008 | Cao et al. |
| 7,396,941 | B2 | 7/2008 | Mori et al. |
| 7,534,590 | B2 | 5/2009 | Mori et al. |
| 7,582,455 | B2 | 9/2009 | Brazeau et al. |
| 7,951,835 | B2 | 5/2011 | Amino et al. |
| 2005/0009153 | A1 | 1/2005 | Sugiyama et al. |
| 2005/0221455 | A1 | 10/2005 | McFarlan et al. |
| 2005/0244939 | A1* | 11/2005 | Sugiyama et al. ............ 435/121 |
| 2005/0282260 | A1* | 12/2005 | Hicks et al. .................... 435/121 |
| 2006/0003426 | A1 | 1/2006 | Sugiyama et al. |
| 2006/0252135 | A1* | 11/2006 | Brazeau et al. ............... 435/108 |
| 2007/0066832 | A1 | 3/2007 | Mori et al. |
| 2008/0020434 | A1 | 1/2008 | Brazeau et al. |
| 2010/0221795 | A1 | 9/2010 | Takakura et al. |
| 2010/0255548 | A1 | 10/2010 | Sugiyama et al. |

FOREIGN PATENT DOCUMENTS

| | | |
|---|---|---|
| EP | 1 445 323 A1 | 8/2004 |
| EP | 1 605 041 A2 | 12/2005 |
| JP | 64-025757 | 1/1989 |
| RU | 2351587 C2 | 4/2009 |
| WO | WO 03/056026 A1 | 7/2003 |
| WO | WO 03/059865 | 7/2003 |
| WO | WO 2005/001105 A1 | 1/2005 |
| WO | WO 2005/042756 | 5/2005 |
| WO | WO 2007/133184 | 11/2007 |

OTHER PUBLICATIONS

Branden et al., Introduction to Protein Structure, Garland Publishing Inc., New York, p. 247, 1991.*
Witkowski et al., Biochemistry 38:11643-11650, 1999.*
Seffernick et al., J. Bacteriol. 183(8):2405-2410, 2001.*
Gioia et al., GenBank Accession No. YP_001487343; Apr. 1, 2010.*
U.S. Appl. No. 13/492,140, filed Jun. 8, 2012, Mori.
Russian Office Actoin issued Nov. 1, 2012 in Patent Application No. 2012110249 with English Translation.
EMBL:"Protein Sequence ID: AAK87940.1: *Agrobacterium fabrum* str. C58 Aspartate Aminotransferase A", http://www.ebi.ac.uk/ena/data/view/AAK87940, Mar. 9, 2006, 2 pages.
Jason Gioia et al., "Paradoxical DNA Repair and Peroxide Resistance Gene Conservation in *Bacillus pumilus* SAFR-032", PLoS ONE I www.plosone.org, Issue 9, e928, Sep. 2007, pp. 1-10.
U.S. Appl. No. 13/189,799, filed Jul. 25, 2011, Takakura, et al.
U.S. Appl. No. 13/455,381, filed Apr. 25, 2012, Sugiyama, et al.
U.S. Appl. No. 13/678,909, filed Nov. 16, 2012, Mori, et al.
Office Action issued Apr. 16, 2013 in Russian Patent Application No. 2012110249/10 with English language translation.
Andrew A. Pakula, et al., "Genetic Analysis of Protein Stability and Function", Annu. Rev. Genet. , 1989, pp. 289-310.
Murry, et al., Human Biochemistry, Moscow, "Mir", vol. 2,1993, p. 95 with cover page.
Chinese Office Action issued Mar. 21, 2013, in China Patent Application No. 201180004246.0 (with English translation).
GenBank: ABV62783.1, published on Sep. 26, 2007, (possible aminotransferase [*Bacillus pumilus* SAFR-032] 2 pages.
Extended Search Report issued Oct. 21, 2013 in European Application No. 11820789.3.
R. J. Dodson, et al., "Genome sequence of *Bacillus pumilus* ATCC 7061", Database UniProt, Database Accession No. B4ALA8, 2008, 1 page.
Office Action issued in Chinese Patent Application No. 2011 80004246.0 dated Feb. 8, 2014, 9 pp.

* cited by examiner

*Primary Examiner* — Delia Ramirez
(74) *Attorney, Agent, or Firm* — Oblon, Spivak, McClelland, Maier & Neustadt, L.L.P.

(57) ABSTRACT

The present invention provides a methodology for improving a yield of 2R,4R-Monatin. Specifically, the present invention provides a method for producing 2S,4R-Monatin or a salt thereof, comprising contacting 4R-IHOG with an L-amino acid aminotransferase in the presence of an L-amino acid to form the 2S,4R-Monatin; a method for producing 2R,4R-Monatin or a salt thereof, comprising isomerizing the 2S,4R-Monatin to form the 2R,4R-Monatin; and the like. These production methods may further comprise condensing indole-3-pyruvate and pyruvate to form the 4R-IHOG, and deaminating a tryptophan to form the indole-3-pyruvate.

16 Claims, 6 Drawing Sheets

SEQUENCE LISTING

<160> NUMBER OF SEQ ID NOS: 112

<210> SEQ ID NO 1
<211> LENGTH: 1308
<212> TYPE: DNA
<213> ORGANISM: Bacillus altitudinis
<220> FEATURE:
<221> NAME/KEY: CDS
<222> LOCATION: (1)..(1308)

<400> SEQUENCE: 1

| | | | | | | | | | | | | | | | | |
|---|---|---|---|---|---|---|---|---|---|---|---|---|---|---|---|---|
| atg | agc | ggt | ttt | aca | gcg | tta | agt | gaa | gca | gaa | tta | aat | gac | cta | tat | 48 |
| Met | Ser | Gly | Phe | Thr | Ala | Leu | Ser | Glu | Ala | Glu | Leu | Asn | Asp | Leu | Tyr | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| gca | gca | cga | caa | aaa | gag | tat | gaa | acg | tac | aaa | agt | aaa | aac | tta | cac | 96 |
| Ala | Ala | Arg | Gln | Lys | Glu | Tyr | Glu | Thr | Tyr | Lys | Ser | Lys | Asn | Leu | His | |
| | | | 20 | | | | | 25 | | | | | 30 | | | |

| | | | | | | | | | | | | | | | | |
|---|---|---|---|---|---|---|---|---|---|---|---|---|---|---|---|---|
| tta | gac | atg | tct | aga | ggg | aaa | cct | tca | cca | aaa | cag | ctc | gat | tta | tct | 144 |
| Leu | Asp | Met | Ser | Arg | Gly | Lys | Pro | Ser | Pro | Lys | Gln | Leu | Asp | Leu | Ser | |
| | | 35 | | | | | 40 | | | | | 45 | | | | |

| | | | | | | | | | | | | | | | | |
|---|---|---|---|---|---|---|---|---|---|---|---|---|---|---|---|---|
| atg | ggc | atg | ctc | gat | gtc | gtg | aca | tca | aag | gat | gca | atg | aca | gct | gag | 192 |
| Met | Gly | Met | Leu | Asp | Val | Val | Thr | Ser | Lys | Asp | Ala | Met | Thr | Ala | Glu | |
| 50 | | | | | 55 | | | | | 60 | | | | | | |

| | | | | | | | | | | | | | | | | |
|---|---|---|---|---|---|---|---|---|---|---|---|---|---|---|---|---|
| gat | ggt | aca | gat | gtg | cga | aac | tat | ggc | ggc | ttg | aca | ggc | ctt | cct | gaa | 240 |
| Asp | Gly | Thr | Asp | Val | Arg | Asn | Tyr | Gly | Gly | Leu | Thr | Gly | Leu | Pro | Glu | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| aca | aag | aaa | ttt | ttt | gca | agt | gtg | ctc | aat | ctg | aag | cca | gaa | caa | atc | 288 |
| Thr | Lys | Lys | Phe | Phe | Ala | Ser | Val | Leu | Asn | Leu | Lys | Pro | Glu | Gln | Ile | |
| | | | | 85 | | | | | 90 | | | | | 95 | | |

| | | | | | | | | | | | | | | | | |
|---|---|---|---|---|---|---|---|---|---|---|---|---|---|---|---|---|
| atc | att | ggc | ggt | aat | tct | agc | cta | aat | atg | atg | cat | gac | aca | att | gcc | 336 |
| Ile | Ile | Gly | Gly | Asn | Ser | Ser | Leu | Asn | Met | Met | His | Asp | Thr | Ile | Ala | |
| | | | | 100 | | | | | 105 | | | | | 110 | | |

| | | | | | | | | | | | | | | | | |
|---|---|---|---|---|---|---|---|---|---|---|---|---|---|---|---|---|
| cgt | gct | atg | act | cac | ggc | gta | tat | ggc | agc | aaa | aca | cct | tgg | gga | gag | 384 |
| Arg | Ala | Met | Thr | His | Gly | Val | Tyr | Gly | Ser | Lys | Thr | Pro | Trp | Gly | Glu | |
| | | | 115 | | | | | 120 | | | | | 125 | | | |

| | | | | | | | | | | | | | | | | |
|---|---|---|---|---|---|---|---|---|---|---|---|---|---|---|---|---|
| ctt | cca | aag | gta | aaa | ttc | ctt | gca | cca | agc | cca | ggg | tat | gat | cgt | cat | 432 |
| Leu | Pro | Lys | Val | Lys | Phe | Leu | Ala | Pro | Ser | Pro | Gly | Tyr | Asp | Arg | His | |
| | | 130 | | | | | 135 | | | | | 140 | | | | |

| | | | | | | | | | | | | | | | | |
|---|---|---|---|---|---|---|---|---|---|---|---|---|---|---|---|---|
| ttt | gcc | att | tgt | gag | cat | ttt | aac | ata | gag | atg | att | acg | gta | gat | atg | 480 |
| Phe | Ala | Ile | Cys | Glu | His | Phe | Asn | Ile | Glu | Met | Ile | Thr | Val | Asp | Met | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| aag | tcg | gat | gga | cct | gac | atg | gat | cag | gtg | gaa | aaa | ttg | gtt | gca | gaa | 528 |
| Lys | Ser | Asp | Gly | Pro | Asp | Met | Asp | Gln | Val | Glu | Lys | Leu | Val | Ala | Glu | |
| | | | | 165 | | | | | 170 | | | | | 175 | | |

| | | | | | | | | | | | | | | | | |
|---|---|---|---|---|---|---|---|---|---|---|---|---|---|---|---|---|
| gat | gaa | gcc | atc | aaa | ggg | att | tgg | tgt | gta | cca | aaa | tat | agc | aac | cct | 576 |
| Asp | Glu | Ala | Ile | Lys | Gly | Ile | Trp | Cys | Val | Pro | Lys | Tyr | Ser | Asn | Pro | |
| | | | 180 | | | | | 185 | | | | | 190 | | | |

| | | | | | | | | | | | | | | | | |
|---|---|---|---|---|---|---|---|---|---|---|---|---|---|---|---|---|
| gac | ggc | att | acg | tat | tca | gat | gag | gtt | gtc | gac | cgt | ctt | gct | tcc | atg | 624 |
| Asp | Gly | Ile | Thr | Tyr | Ser | Asp | Glu | Val | Val | Asp | Arg | Leu | Ala | Ser | Met | |
| | | 195 | | | | | 200 | | | | | 205 | | | | |

| | | | | | | | | | | | | | | | | |
|---|---|---|---|---|---|---|---|---|---|---|---|---|---|---|---|---|
| cag | aca | aaa | gca | gac | gac | ttc | cgt | att | ttt | tgg | gat | gat | gcc | tat | gca | 672 |
| Gln | Thr | Lys | Ala | Asp | Asp | Phe | Arg | Ile | Phe | Trp | Asp | Asp | Ala | Tyr | Ala | |
| | 210 | | | | | 215 | | | | | 220 | | | | | |

| | | | | | | | | | | | | | | | | |
|---|---|---|---|---|---|---|---|---|---|---|---|---|---|---|---|---|
| gtc | cac | cat | cta | aca | gat | acg | cct | gat | acg | tta | aaa | gat | att | ttt | caa | 720 |
| Val | His | His | Leu | Thr | Asp | Thr | Pro | Asp | Thr | Leu | Lys | Asp | Ile | Phe | Gln | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| gca | gta | gac | aaa | gca | ggg | cat | gca | aac | cgt | gtg | ttt | atg | ttc | gcc | tct | 768 |
| Ala | Val | Asp | Lys | Ala | Gly | His | Ala | Asn | Arg | Val | Phe | Met | Phe | Ala | Ser | |
| | | | | 245 | | | | | 250 | | | | | 255 | | |

| | | | | | | | | | | | | | | | | |
|---|---|---|---|---|---|---|---|---|---|---|---|---|---|---|---|---|
| act | tct | aaa | att | acg | ttc | cca | ggc | tca | ggt | gtt | gca | ctg | atg | gca | tct | 816 |
| Thr | Ser | Lys | Ile | Thr | Phe | Pro | Gly | Ser | Gly | Val | Ala | Leu | Met | Ala | Ser | |

```
                    260                 265                 270
agt cag gac aac gtc agc ttt att caa aaa cag cta tca gtt caa acc    864
Ser Gln Asp Asn Val Ser Phe Ile Gln Lys Gln Leu Ser Val Gln Thr
        275                 280                 285 att ggg cca gat aaa atc aat caa tta aga cac ctt cgt ttc ttc aag    912
Ile Gly Pro Asp Lys Ile Asn Gln Leu Arg His Leu Arg Phe Phe Lys
290                 295                 300 aat cca gaa gga ttg aag gaa cat atg aaa aag cat gca gcg att att    960
Asn Pro Glu Gly Leu Lys Glu His Met Lys Lys His Ala Ala Ile Ile
305                 310                 315                 320 aag ccg aaa ttt gac ctc gtt ctt tcg atc ctt gat gaa aag ctt ggt   1008
Lys Pro Lys Phe Asp Leu Val Leu Ser Ile Leu Asp Glu Lys Leu Gly
                325                 330                 335 gga aca ggc atc gct gag tgg cac aaa cca aat ggc gga tat ttt att   1056
Gly Thr Gly Ile Ala Glu Trp His Lys Pro Asn Gly Gly Tyr Phe Ile
            340                 345                 350 agc tta aat aca ctc gat cat tgt gca aaa gct gtt gtg caa aaa gcg   1104
Ser Leu Asn Thr Leu Asp His Cys Ala Lys Ala Val Val Gln Lys Ala
        355                 360                 365 aaa gaa gcc ggt gtg aca cta aca ggt gca ggg gcg aca tat cct tat   1152
Lys Glu Ala Gly Val Thr Leu Thr Gly Ala Gly Ala Thr Tyr Pro Tyr
370                 375                 380 gga aac gac ccg ctt gat cgt aac atc cgt att gcg cca acg ttc cca   1200
Gly Asn Asp Pro Leu Asp Arg Asn Ile Arg Ile Ala Pro Thr Phe Pro
385                 390                 395                 400 acg ctt gaa gaa cta gag cag gcg att gat atc ttt acg tta tgc gtt   1248
Thr Leu Glu Glu Leu Glu Gln Ala Ile Asp Ile Phe Thr Leu Cys Val
                405                 410                 415 cag ctt gtc agc att gaa aag ctg ctg tct gag aaa agt caa tca gca   1296
Gln Leu Val Ser Ile Glu Lys Leu Leu Ser Glu Lys Ser Gln Ser Ala
            420                 425                 430 cca acg gta taa                                                    1308
Pro Thr Val
        435

<210> SEQ ID NO 2
<211> LENGTH: 435
<212> TYPE: PRT
<213> ORGANISM: Bacillus altitudinis

<400> SEQUENCE: 2

Met Ser Gly Phe Thr Ala Leu Ser Glu Ala Glu Leu Asn Asp Leu Tyr
1               5                   10                  15

Ala Ala Arg Gln Lys Glu Tyr Glu Thr Tyr Lys Ser Lys Asn Leu His
            20                  25                  30

Leu Asp Met Ser Arg Gly Lys Pro Ser Pro Lys Gln Leu Asp Leu Ser
        35                  40                  45

Met Gly Met Leu Asp Val Val Thr Ser Lys Asp Ala Met Thr Ala Glu
    50                  55                  60

Asp Gly Thr Asp Val Arg Asn Tyr Gly Gly Leu Thr Gly Leu Pro Glu
65                  70                  75                  80

Thr Lys Lys Phe Phe Ala Ser Val Leu Asn Leu Lys Pro Glu Gln Ile
                85                  90                  95

Ile Ile Gly Gly Asn Ser Ser Leu Asn Met Met His Asp Thr Ile Ala
            100                 105                 110

Arg Ala Met Thr His Gly Val Tyr Gly Ser Lys Thr Pro Trp Gly Glu
        115                 120                 125

Leu Pro Lys Val Lys Phe Leu Ala Pro Ser Pro Gly Tyr Asp Arg His
```

```
                130              135              140
    Phe Ala Ile Cys Glu His Phe Asn Ile Glu Met Ile Thr Val Asp Met
    145                 150                 155                 160

Lys Ser Asp Gly Pro Asp Met Asp Gln Val Glu Lys Leu Val Ala Glu
                    165                 170                 175

Asp Glu Ala Ile Lys Gly Ile Trp Cys Val Pro Lys Tyr Ser Asn Pro
                180                 185                 190

Asp Gly Ile Thr Tyr Ser Asp Glu Val Val Asp Arg Leu Ala Ser Met
                    195                 200                 205

Gln Thr Lys Ala Asp Asp Phe Arg Ile Phe Trp Asp Asp Ala Tyr Ala
                210                 215                 220

Val His His Leu Thr Asp Thr Pro Asp Thr Leu Lys Asp Ile Phe Gln
    225                 230                 235                 240

Ala Val Asp Lys Ala Gly His Ala Asn Arg Val Phe Met Phe Ala Ser
                    245                 250                 255

Thr Ser Lys Ile Thr Phe Pro Gly Ser Gly Val Ala Leu Met Ala Ser
                260                 265                 270

Ser Gln Asp Asn Val Ser Phe Ile Gln Lys Gln Leu Ser Val Gln Thr
                    275                 280                 285

Ile Gly Pro Asp Lys Ile Asn Gln Leu Arg His Leu Arg Phe Phe Lys
                290                 295                 300

Asn Pro Glu Gly Leu Lys Glu His Met Lys Lys His Ala Ala Ile Ile
    305                 310                 315                 320

Lys Pro Lys Phe Asp Leu Val Leu Ser Ile Leu Asp Glu Lys Leu Gly
                    325                 330                 335

Gly Thr Gly Ile Ala Glu Trp His Lys Pro Asn Gly Gly Tyr Phe Ile
                340                 345                 350

Ser Leu Asn Thr Leu Asp His Cys Ala Lys Ala Val Val Gln Lys Ala
                    355                 360                 365

Lys Glu Ala Gly Val Thr Leu Thr Gly Ala Gly Ala Thr Tyr Pro Tyr
                370                 375                 380

Gly Asn Asp Pro Leu Asp Arg Asn Ile Arg Ile Ala Pro Thr Phe Pro
    385                 390                 395                 400

Thr Leu Glu Glu Leu Glu Gln Ala Ile Asp Ile Phe Thr Leu Cys Val
                    405                 410                 415

Gln Leu Val Ser Ile Glu Lys Leu Leu Ser Glu Lys Ser Gln Ser Ala
                420                 425                 430

Pro Thr Val
            435

<210> SEQ ID NO 3
<211> LENGTH: 1678
<212> TYPE: DNA
<213> ORGANISM: Bacillus altitudinis

<400> SEQUENCE: 3
gaaacaatta ctcaaagaag cccgcgatat attcccgctg actgaagctg cacatgattt     60
cttttctttt cctattgacc gtaccctgta aaaattggat gaatcgtcaa aaatagttgt    120 gtgattttt tgatatttat gatgacgctc tttttcaggt agtggtaaaa tggtgaagaa    180
aaaacaaatg acgaattaca ctatgaagaa tacgggaggc acaatcaaag atgagcggtt    240
ttacagcgtt aagtgaagca gaattaaatg acctatatgc agcacgacaa aaagagtatg    300
aaacgtacaa aagtaaaaac ttacacttag acatgtctag agggaaacct tcaccaaaac    360
```

```
agctcgattt atctatgggc atgctcgatg tcgtgacatc aaaggatgca atgacagctg    420
aggatggtac agatgtgcga aactatggcg gcttgacagg ccttcctgaa acaaagaaat    480
tttttgcaag tgtgctcaat ctgaagccag aacaaatcat cattggcggt aattctagcc    540
taaatatgat gcatgacaca attgcccgtg ctatgactca cggcgtatat ggcagcaaaa    600
caccttgggg agagcttcca aaggtaaaat tccttgcacc aagcccaggg tatgatcgtc    660
attttgccat ttgtgagcat tttaacatag agatgattac ggtagatatg aagtcggatg    720
gacctgacat ggatcaggtg gaaaaattgg ttgcagaaga tgaagccatc aaagggattt    780
ggtgtgtacc aaaatatagc aaccctgacg gcattacgta ttcagatgag gttgtcgacc    840
gtcttgcttc catgcagaca aaagcagacg acttccgtat tttttgggat gatgcctatg    900
cagtccacca tctaacagat acgcctgata cgttaaaaga tattttcaa gcagtagaca    960 aagcagggca tgcaaaccgt gtgtttatgt tcgcctctac ttctaaaatt acgttcccag   1020
gctcaggtgt tgcactgatg gcatctagtc aggacaacgt cagctttatt caaaaacagc   1080
tatcagttca aaccattggg ccagataaaa tcaatcaatt aagacacctt cgtttcttca   1140
agaatccaga aggattgaag gaacatatga aaaagcatgc agcgattatt aagccgaaat   1200
ttgacctcgt tctttcgatc cttgatgaaa agcttggtgg aacaggcatc gctgagtggc   1260
acaaaccaaa tggcggatat tttattagct aaatacact cgatcattgt gcaaaagctg   1320
ttgtgcaaaa agcgaaagaa gccggtgtga cactaacagg tgcaggggcg acatatcctt   1380
atggaaacga cccgcttgat cgtaacatcc gtattgcgcc aacgttccca acgcttgaag   1440
aactagagca ggcgattgat atctttacgt tatgcgttca gcttgtcagc attgaaaagc   1500
tgctgtctga gaaaagtcaa tcagcaccaa cggtataacg aaaaaactcc ttgactgatg   1560
tccggtcaag gagttttgt ttttagttag ctgtttgata ataagtggca ggctgttttg   1620
ctgcacacca tacatcataa atcgcaagct gcacaatatg tggttcatcg tgatgaat    1678
```

<210> SEQ ID NO 4
<211> LENGTH: 15
<212> TYPE: PRT
<213> ORGANISM: Bacillus altitudinis

<400> SEQUENCE: 4

Ser Gly Phe Thr Ala Leu Ser Glu Ala Glu Leu Asn Asp Leu Tyr
1               5                   10                  15

<210> SEQ ID NO 5
<211> LENGTH: 12
<212> TYPE: PRT
<213> ORGANISM: Bacillus altitudinis

<400> SEQUENCE: 5

Gln Leu Asp Leu Ser Met Gly Met Leu Asp Val Val
1               5                   10

<210> SEQ ID NO 6
<211> LENGTH: 30
<212> TYPE: DNA
<213> ORGANISM: Artificial Sequence
<220> FEATURE:
<223> OTHER INFORMATION: Forward primer for amplifying DNA fragment
      containing aminotransferase gene derived from Bacillus altitudinis
      (Bp-u200-f)

<400> SEQUENCE: 6
ctcaggaagc aggcgcaaa

<210> SEQ ID NO 7
<211> LENGTH: 30
<212> TYPE: DNA
<213> ORGANISM: Artificial Sequence
<220> FEATURE:
<223> OTHER INFORMATION: Reverse primer for amplifying DNA fragment
      containing aminotransferase gene derived from Bacillus altitudinis
      (Bp-d200-r)

<400> SEQUENCE: 7
ggatgctgtc tttgtcatcc caaagtggat                                    30

<210> SEQ ID NO 8
<211> LENGTH: 30
<212> TYPE: DNA
<213> ORGANISM: Artificial Sequence
<220> FEATURE:
<223> OTHER INFORMATION: Forward primer for amplifying DNA fragment
      containing aminotransferase gene derived from Bacillus altitudinis
      (1616AT-Nde-f)

<400> SEQUENCE: 8
ggaattccat atgagcggtt ttacagcgtt                                    30

<210> SEQ ID NO 9
<211> LENGTH: 40
<212> TYPE: DNA
<213> ORGANISM: Artificial Sequence
<220> FEATURE:
<223> OTHER INFORMATION: Reverse primer for amplifying DNA fragment
      containing aminotransferase gene derived from Bacillus altitudinis
      (1616-xho-r)

<400> SEQUENCE: 9
gtcaaggagt ttttctcgag taccgttggt gctgattgac                         40

<210> SEQ ID NO 10
<211> LENGTH: 29
<212> TYPE: DNA
<213> ORGANISM: Artificial Sequence
<220> FEATURE:
<223> OTHER INFORMATION: Forward primer for converting DNA sequence
      recognized by NdeI, which is found on aminotransferase gene
      derived from Bacillus altitudinis (1616-delNde-f)

<400> SEQUENCE: 10
ggattgaagg aacacatgaa aaagcatgc                                     29

<210> SEQ ID NO 11
<211> LENGTH: 29
<212> TYPE: DNA
<213> ORGANISM: Artificial Sequence
<220> FEATURE:
<223> OTHER INFORMATION: Reverse primer for converting DNA sequence
      recognized by NdeI, which is found on aminotransferase gene
      derived from Bacillus altitudinis (1616-delNde-r)

<400> SEQUENCE: 11
gcatgctttt tcatgtgttc cttcaatcc                                     29

<210> SEQ ID NO 12
<211> LENGTH: 30
<212> TYPE: DNA
<213> ORGANISM: Artificial Sequence
<220> FEATURE:
<223> OTHER INFORMATION: Forward primer for amplifying DNA fragment
      containing SpAld gene (SpAld-f-NdeI)

<400> SEQUENCE: 12
ggaattccat atgacccaga cgcgcctcaa                                    30

<210> SEQ ID NO 13
<211> LENGTH: 30
<212> TYPE: DNA
<213> ORGANISM: Artificial Sequence
<220> FEATURE:
<223> OTHER INFORMATION: Reverse primer for amplifying DNA fragment
      containing SpAld gene (SpAld-r-HindIII)

<400> SEQUENCE: 13
gcccaagctt tcagtacccc gccagttcgc                                    30

<210> SEQ ID NO 14
<211> LENGTH: 29
<212> TYPE: DNA
<213> ORGANISM: Artificial Sequence
<220> FEATURE:
<223> OTHER INFORMATION: Forward primer for converting rare codon 6L in
      SpAld gene (6L-f)

<400> SEQUENCE: 14
acccagacgc gcctgaacgg catcatccg                                     29

<210> SEQ ID NO 15
<211> LENGTH: 29
<212> TYPE: DNA
<213> ORGANISM: Artificial Sequence
<220> FEATURE:
<223> OTHER INFORMATION: Reverse primer for converting rare codon 6L in
      SpAld gene (6L-r)

<400> SEQUENCE: 15
cggatgatgc cgttcaggcg cgtctgggt                                     29

<210> SEQ ID NO 16
<211> LENGTH: 29
<212> TYPE: DNA
<213> ORGANISM: Artificial Sequence
<220> FEATURE:
<223> OTHER INFORMATION: Forward primer for converting rare codon 13L in
      SpAld gene (13L-f)

<400> SEQUENCE: 16
atcatccgcg ctctggaagc cggcaagcc                                     29

<210> SEQ ID NO 17
<211> LENGTH: 29
<212> TYPE: DNA
<213> ORGANISM: Artificial Sequence
<220> FEATURE:
<223> OTHER INFORMATION: Reverse primer for converting rare codon 13L in
      SpAld gene (13L-r)

<400> SEQUENCE: 17
ggcttgccgg cttccagagc gcggatgat                                     29

<210> SEQ ID NO 18
<211> LENGTH: 29
<212> TYPE: DNA
<213> ORGANISM: Artificial Sequence
<220> FEATURE:
<223> OTHER INFORMATION: Forward primer for converting rare codon 18P in
      SpAld gene (18P-f)

<400> SEQUENCE: 18
gaagccggca agccggcttt cacctgctt                                            29

<210> SEQ ID NO 19
<211> LENGTH: 29
<212> TYPE: DNA
<213> ORGANISM: Artificial Sequence
<220> FEATURE:
<223> OTHER INFORMATION: Reverse primer for converting rare codon 18P in
      SpAld gene (18P-r)

<400> SEQUENCE: 19
aagcaggtga agccggcttt gccggcttc                                            29

<210> SEQ ID NO 20
<211> LENGTH: 29
<212> TYPE: DNA
<213> ORGANISM: Artificial Sequence
<220> FEATURE:
<223> OTHER INFORMATION: Forward primer for converting rare codon 38P in
      SpAld gene (38P-f)

<400> SEQUENCE: 20
ctgaccgatg ccccgtatga cggcgtggt                                            29

<210> SEQ ID NO 21
<211> LENGTH: 29
<212> TYPE: DNA
<213> ORGANISM: Artificial Sequence
<220> FEATURE:
<223> OTHER INFORMATION: Reverse primer for converting rare codon 38P in
      SpAld gene (38P-r)

<400> SEQUENCE: 21
accacgccgt catacggggc atcggtcag                                            29

<210> SEQ ID NO 22
<211> LENGTH: 29
<212> TYPE: DNA
<213> ORGANISM: Artificial Sequence
<220> FEATURE:
<223> OTHER INFORMATION: Forward primer for converting rare codon 50P in
      SpAld gene (50P-f)

<400> SEQUENCE: 22
atggagcaca acccgtacga tgtcgcggc                                            29

<210> SEQ ID NO 23
<211> LENGTH: 29
<212> TYPE: DNA
<213> ORGANISM: Artificial Sequence
<220> FEATURE:
<223> OTHER INFORMATION: Reverse primer for converting rare codon 50P in
      SpAld gene (50P-r)

<400> SEQUENCE: 23
gccgcgacat cgtacgggtt gtgctccat                                            29

<210> SEQ ID NO 24
<211> LENGTH: 42
<212> TYPE: DNA
<213> ORGANISM: Artificial Sequence
<220> FEATURE:
<223> OTHER INFORMATION: Forward primer for converting rare codons 77P,
      81P and 84R in SpAld gene (77P-81P-84R-f)

<400> SEQUENCE: 24

```
cggtcgcgcc gtcggtcacc ccgatcgcgc gcatcccggc ca                    42
```

<210> SEQ ID NO 25
<211> LENGTH: 42
<212> TYPE: DNA
<213> ORGANISM: Artificial Sequence
<220> FEATURE:
<223> OTHER INFORMATION: Reverse primer for converting rare codons 77P,
      81P and 84R in SpAld gene (77P-81P-84R-r)

<400> SEQUENCE: 25

```
tggccgggat gcgcgcgatc ggggtgaccg acggcgcgac cg                    42
```

<210> SEQ ID NO 26
<211> LENGTH: 33
<212> TYPE: DNA
<213> ORGANISM: Artificial Sequence
<220> FEATURE:
<223> OTHER INFORMATION: Forward primer for preparing the
      aminotransferase mutant K39R derived from Bacillus altitudinis
      AJ1616 (K39R_FW)

<400> SEQUENCE: 26

```
gacatgtcta gagggcgtcc ttcaccaaaa cag                              33
```

<210> SEQ ID NO 27
<211> LENGTH: 33
<212> TYPE: DNA
<213> ORGANISM: Artificial Sequence
<220> FEATURE:
<223> OTHER INFORMATION: Reverse primer for preparing the
      aminotransferase mutant K39R derived from Bacillus altitudinis
      AJ1616 (K39R_RV)

<400> SEQUENCE: 27

```
ctgttttggt gaaggacgcc ctctagacat gtc                              33
```

<210> SEQ ID NO 28
<211> LENGTH: 30
<212> TYPE: DNA
<213> ORGANISM: Artificial Sequence
<220> FEATURE:
<223> OTHER INFORMATION: Forward primer for preparing the
      aminotransferase mutant S258G derived from Bacillus altitudinis
      AJ1616 (S258G_FW)

<400> SEQUENCE: 28

```
gttcgcctct actggtaaaa ttacgttccc                                  30
```

<210> SEQ ID NO 29
<211> LENGTH: 30
<212> TYPE: DNA
<213> ORGANISM: Artificial Sequence
<220> FEATURE:
<223> OTHER INFORMATION: Reverse primer for preparing the
      aminotransferase mutant S258G derived from Bacillus altitudinis
      AJ1616 (S258G_RV)

<400> SEQUENCE: 29

```
gggaacgtaa ttttaccagt agaggcgaac                                  30
```

<210> SEQ ID NO 30
<211> LENGTH: 36
<212> TYPE: DNA
<213> ORGANISM: Artificial Sequence
<220> FEATURE:
<223> OTHER INFORMATION: Forward primer for preparing the aminotransferase mutant T288G derived from Bacillus altitudinis
AJ1616 (T288G_FW)

<400> SEQUENCE: 30
cagctatcag ttcaaggcat tgggccagat aaaatc        36

<210> SEQ ID NO 31
<211> LENGTH: 36
<212> TYPE: DNA
<213> ORGANISM: Artificial Sequence
<220> FEATURE:
<223> OTHER INFORMATION: Reverse primer for preparing the
      aminotransferase mutant T288G derived from Bacillus altitudinis
      AJ1616 (T288G_RV)

<400> SEQUENCE: 31
gattttatct ggcccaatgc cttgaactga tagctg        36

<210> SEQ ID NO 32
<211> LENGTH: 33
<212> TYPE: DNA
<213> ORGANISM: Artificial Sequence
<220> FEATURE:
<223> OTHER INFORMATION: Forward primer for preparing the
      aminotransferase mutant I289A derived from Bacillus altitudinis
      AJ1616 (I289A_FW)

<400> SEQUENCE: 32
ctatcagttc aaaccgctgg gccagataaa atc        33

<210> SEQ ID NO 33
<211> LENGTH: 33
<212> TYPE: DNA
<213> ORGANISM: Artificial Sequence
<220> FEATURE:
<223> OTHER INFORMATION: Reverse primer for preparing the
      aminotransferase mutant I289A derived from Bacillus altitudinis
      AJ1616 (I289A_RV)

<400> SEQUENCE: 33
gattttatct ggcccagcgg tttgaactga tag        33

<210> SEQ ID NO 34
<211> LENGTH: 28
<212> TYPE: DNA
<213> ORGANISM: Artificial Sequence
<220> FEATURE:
<223> OTHER INFORMATION: Forward primer for preparing the
      aminotransferase mutant Q287E/T288G derived from Bacillus
      altitudinis AJ1616 (Q287E/T288G_FW)

<400> SEQUENCE: 34
cagctatcag ttgaaggcat tgggccag        28

<210> SEQ ID NO 35
<211> LENGTH: 28
<212> TYPE: DNA
<213> ORGANISM: Artificial Sequence
<220> FEATURE:
<223> OTHER INFORMATION: Reverse primer for preparing the
      aminotransferase mutant Q287E/T288G derived from Bacillus
      altitudinis AJ1616 (Q287E/T288G_RV)

<400> SEQUENCE: 35
ctggcccaat gccttcaact gatagctg        28

<210> SEQ ID NO 36

```
<211> LENGTH: 60
<212> TYPE: DNA
<213> ORGANISM: Artificial Sequence
<220> FEATURE:
<223> OTHER INFORMATION: Primer for preparing a DNA fragment for
      destroying aspC gene (aspC-L1)

<400> SEQUENCE: 36
tttgagaaca ttaccgccgc tcctgccgac ccgattctgg gctgaagcct gctttttat       60

<210> SEQ ID NO 37
<211> LENGTH: 60
<212> TYPE: DNA
<213> ORGANISM: Artificial Sequence
<220> FEATURE:
<223> OTHER INFORMATION: Primer for preparing a DNA fragment for
      destroying aspC gene (aspC-R1)

<400> SEQUENCE: 37
cagcactgcc acaatcgctt cgcacagcgg agccatgtta tccgctcaag ttagtataaa       60

<210> SEQ ID NO 38
<211> LENGTH: 30
<212> TYPE: DNA
<213> ORGANISM: Artificial Sequence
<220> FEATURE:
<223> OTHER INFORMATION: Primer for confirming the insertion of attL-
      cat-attR in the region of aspC gene (aspC-up)

<400> SEQUENCE: 38
aacctcttgg caacggtaaa aaagctgaac                                        30

<210> SEQ ID NO 39
<211> LENGTH: 18
<212> TYPE: DNA
<213> ORGANISM: Artificial Sequence
<220> FEATURE:
<223> OTHER INFORMATION: Primer for confirming the insertion of attL-
      cat-attR in the region of aspC gene (attL-1)

<400> SEQUENCE: 39
tagtgacctg ttcgttgc                                                     18

<210> SEQ ID NO 40
<211> LENGTH: 30
<212> TYPE: DNA
<213> ORGANISM: Artificial Sequence
<220> FEATURE:
<223> OTHER INFORMATION: Primer for confirming the insertion of attL-
      cat-attR in the region of aspC gene (aspC-down)

<400> SEQUENCE: 40
gcctgcgcaa agtcgtatgt ttggtctgga                                        30

<210> SEQ ID NO 41
<211> LENGTH: 18
<212> TYPE: DNA
<213> ORGANISM: Artificial Sequence
<220> FEATURE:
<223> OTHER INFORMATION: Primer for confirming the insertion of attL-
      cat-attR in the region of aspC gene (attR-1)

<400> SEQUENCE: 41
ttacgtttct cgttcagc                                                     18

<210> SEQ ID NO 42
<211> LENGTH: 882
```

<210> 42
<211> 882
<212> TYPE: DNA
<213> ORGANISM: Pseudomonas putida
<220> FEATURE:
<221> NAME/KEY: CDS
<222> LOCATION: (1)..(882)

<400> SEQUENCE: 42

```
atg att atg ccg aaa gcc tcc cat cag gat ctg cgt ttt gcg ttc cgt      48
Met Ile Met Pro Lys Ala Ser His Gln Asp Leu Arg Phe Ala Phe Arg
1               5                   10                  15 gaa ctg ctg gcc tct ggt agc tgt ttc cac acc gcg tca gtt ttt gat      96
Glu Leu Leu Ala Ser Gly Ser Cys Phe His Thr Ala Ser Val Phe Asp
            20                  25                  30 ccg atg agc gca cgt att gcg gcc gac ctg ggc ttc gaa gtc ggt atc     144
Pro Met Ser Ala Arg Ile Ala Ala Asp Leu Gly Phe Glu Val Gly Ile
        35                  40                  45 ctg ggc ggt agt gtc gcg tcc ctg caa gtg ctg gca gct ccg gat ttt     192
Leu Gly Gly Ser Val Ala Ser Leu Gln Val Leu Ala Ala Pro Asp Phe
    50                  55                  60 gcc ctg att acg ctg tct gaa ttc gtg gaa cag gca acc cgt atc ggt     240
Ala Leu Ile Thr Leu Ser Glu Phe Val Glu Gln Ala Thr Arg Ile Gly
65                  70                  75                  80 cgt gtt gct caa ctg ccg gtc ctg gca gat gca gac cat ggt tat ggt     288
Arg Val Ala Gln Leu Pro Val Leu Ala Asp Ala Asp His Gly Tyr Gly
                85                  90                  95 aac gca ctg aat gtt atg cgt acc gtc att gaa ctg gaa cgt gct ggt     336
Asn Ala Leu Asn Val Met Arg Thr Val Ile Glu Leu Glu Arg Ala Gly
            100                 105                 110 gtg gca gca ctg acc atc gaa gat acg ctg ctg ccg gcg cag ttt ggt     384
Val Ala Ala Leu Thr Ile Glu Asp Thr Leu Leu Pro Ala Gln Phe Gly
        115                 120                 125 cgc aaa agt acc gac ctg att ccg gtg gaa gaa ggc gtt ggt aaa atc     432
Arg Lys Ser Thr Asp Leu Ile Pro Val Glu Glu Gly Val Gly Lys Ile
    130                 135                 140 cgt gca gct ctg gaa gcc cgc gtt gat agc tct ctg tcc att atc gcg     480
Arg Ala Ala Leu Glu Ala Arg Val Asp Ser Ser Leu Ser Ile Ile Ala
145                 150                 155                 160 cgt acc aac gcc ggt gtc ctg agc acg gaa gaa att atc gtg cgc acc     528
Arg Thr Asn Ala Gly Val Leu Ser Thr Glu Glu Ile Ile Val Arg Thr
                165                 170                 175 cag tct tat caa aaa gca ggc gct gat ggt att tgc atg gtc ggc gtg     576
Gln Ser Tyr Gln Lys Ala Gly Ala Asp Gly Ile Cys Met Val Gly Val
            180                 185                 190 aaa gac ttt gaa cag ctg gaa caa atc gcg gaa cat ctg acg gtg ccg     624
Lys Asp Phe Glu Gln Leu Glu Gln Ile Ala Glu His Leu Thr Val Pro
        195                 200                 205 ctg atg ctg gtt acc tac ggt aac ccg aat ctg cgt gat gac gaa cgt     672
Leu Met Leu Val Thr Tyr Gly Asn Pro Asn Leu Arg Asp Asp Glu Arg
    210                 215                 220 ctg gca cgt ctg ggt gtt cgt att gtg gtt gat ggt cac gcg gcc tat     720
Leu Ala Arg Leu Gly Val Arg Ile Val Val Asp Gly His Ala Ala Tyr
225                 230                 235                 240 ttc gca gct atc aaa gcc acg tac gac tgt ctg cgt ctg caa cgt ggc     768
Phe Ala Ala Ile Lys Ala Thr Tyr Asp Cys Leu Arg Leu Gln Arg Gly
                245                 250                 255 cgc caa aac aaa tca gaa aat ctg tcg gca acc gaa ctg agc cac acc     816
Arg Gln Asn Lys Ser Glu Asn Leu Ser Ala Thr Glu Leu Ser His Thr
            260                 265                 270 tac acc cag ccg gaa gac tac att cgt tgg gca aaa gaa tac atg agc     864
Tyr Thr Gln Pro Glu Asp Tyr Ile Arg Trp Ala Lys Glu Tyr Met Ser
        275                 280                 285
```

```
gtt gaa gaa ctc gag tga                                                   882
Val Glu Glu Leu Glu
    290

<210> SEQ ID NO 43
<211> LENGTH: 293
<212> TYPE: PRT
<213> ORGANISM: Pseudomonas putida

<400> SEQUENCE: 43

Met Ile Met Pro Lys Ala Ser His Gln Asp Leu Arg Phe Ala Phe Arg
1               5                   10                  15

Glu Leu Leu Ala Ser Gly Ser Cys Phe His Thr Ala Ser Val Phe Asp
            20                  25                  30

Pro Met Ser Ala Arg Ile Ala Ala Asp Leu Gly Phe Glu Val Gly Ile
        35                  40                  45

Leu Gly Gly Ser Val Ala Ser Leu Gln Val Leu Ala Ala Pro Asp Phe
    50                  55                  60

Ala Leu Ile Thr Leu Ser Glu Phe Val Glu Gln Ala Thr Arg Ile Gly
65                  70                  75                  80

Arg Val Ala Gln Leu Pro Val Leu Ala Asp Ala Asp His Gly Tyr Gly
                85                  90                  95

Asn Ala Leu Asn Val Met Arg Thr Val Ile Glu Leu Glu Arg Ala Gly
            100                 105                 110

Val Ala Ala Leu Thr Ile Glu Asp Thr Leu Leu Pro Ala Gln Phe Gly
        115                 120                 125

Arg Lys Ser Thr Asp Leu Ile Pro Val Glu Glu Gly Val Gly Lys Ile
    130                 135                 140

Arg Ala Ala Leu Glu Ala Arg Val Asp Ser Ser Leu Ser Ile Ile Ala
145                 150                 155                 160

Arg Thr Asn Ala Gly Val Leu Ser Thr Glu Glu Ile Ile Val Arg Thr
                165                 170                 175

Gln Ser Tyr Gln Lys Ala Gly Ala Asp Gly Ile Cys Met Val Gly Val
            180                 185                 190

Lys Asp Phe Glu Gln Leu Glu Gln Ile Ala Glu His Leu Thr Val Pro
        195                 200                 205

Leu Met Leu Val Thr Tyr Gly Asn Pro Asn Leu Arg Asp Asp Glu Arg
    210                 215                 220

Leu Ala Arg Leu Gly Val Arg Ile Val Val Asp Gly His Ala Ala Tyr
225                 230                 235                 240

Phe Ala Ala Ile Lys Ala Thr Tyr Asp Cys Leu Arg Leu Gln Arg Gly
                245                 250                 255

Arg Gln Asn Lys Ser Glu Asn Leu Ser Ala Thr Glu Leu Ser His Thr
            260                 265                 270

Tyr Thr Gln Pro Glu Asp Tyr Ile Arg Trp Ala Lys Glu Tyr Met Ser
        275                 280                 285

Val Glu Glu Leu Glu
    290

<210> SEQ ID NO 44
<211> LENGTH: 20
<212> TYPE: PRT
<213> ORGANISM: Rhizobium radiobacter

<400> SEQUENCE: 44

Ala Phe Leu Ala Asp Ile Leu Ser Arg Val Lys Pro Ser Ala Thr Ile
```

```
1               5               10              15
Ala Val Thr Gln
        20
```

<210> SEQ ID NO 45
<211> LENGTH: 27
<212> TYPE: DNA
<213> ORGANISM: Artificial Sequence
<220> FEATURE:
<223> OTHER INFORMATION: Forward primer which is designed based on the
      genomic DNA sequence from Agrobacterium tumefaciens str. C58
      (Ag-u100-f)

<400> SEQUENCE: 45
ctggtgcaga taagccggct tttgacc                                          27

<210> SEQ ID NO 46
<211> LENGTH: 27
<212> TYPE: DNA
<213> ORGANISM: Artificial Sequence
<220> FEATURE:
<223> OTHER INFORMATION: Reverse primer which is designed based on the
      genomic DNA sequence from Agrobacterium tumefaciens str. C58
      (Ag-d100-r)

<400> SEQUENCE: 46
ccaccttcat catgctgctg tttctcg                                          27

<210> SEQ ID NO 47
<211> LENGTH: 1203
<212> TYPE: DNA
<213> ORGANISM: Rhizobium radiobacter
<220> FEATURE:
<221> NAME/KEY: CDS
<222> LOCATION: (1)..(1203)

<400> SEQUENCE: 47

```
atg gcc ttc ctt gcc gac att ctc tcc cgc gta aag cca tcc gcc acc        48
Met Ala Phe Leu Ala Asp Ile Leu Ser Arg Val Lys Pro Ser Ala Thr
1               5                   10                  15 atc gcc gtt acc cag aaa gcc cgt gag ctg aaa gcg aag ggc cgc gat        96
Ile Ala Val Thr Gln Lys Ala Arg Glu Leu Lys Ala Lys Gly Arg Asp
            20                  25                  30 gtg atc agc ctt ggc gcc ggc gag ccg gat ttc gat acg ccc gat aat       144
Val Ile Ser Leu Gly Ala Gly Glu Pro Asp Phe Asp Thr Pro Asp Asn
        35                  40                  45 atc aag gaa gcg gcc atc gac gcc atc aag cgc ggc gaa acg aaa tac       192
Ile Lys Glu Ala Ala Ile Asp Ala Ile Lys Arg Gly Glu Thr Lys Tyr
    50                  55                  60 acg ccc gtt tcc ggc att ccg gaa ctg cgc aag gcc att gct gac aag       240
Thr Pro Val Ser Gly Ile Pro Glu Leu Arg Lys Ala Ile Ala Asp Lys
65                  70                  75                  80 ttc aag cgc gaa aac ggc ctc gac tac aag ccg gag cag acg att gtc       288
Phe Lys Arg Glu Asn Gly Leu Asp Tyr Lys Pro Glu Gln Thr Ile Val
                85                  90                  95 ggc acc ggc ggc aag cag ata ctt ttc aac gcc ttc atg gcc acc ctc       336
Gly Thr Gly Gly Lys Gln Ile Leu Phe Asn Ala Phe Met Ala Thr Leu
            100                 105                 110 aac ccg ggt gac gaa gtc gtc att ccc gcg cct tac tgg gtc agc tac       384
Asn Pro Gly Asp Glu Val Val Ile Pro Ala Pro Tyr Trp Val Ser Tyr
        115                 120                 125 ccg gaa atg gtg gcg atc tgc ggc ggc acg cct gta ttc gtc gac acc       432
Pro Glu Met Val Ala Ile Cys Gly Gly Thr Pro Val Phe Val Asp Thr
    130                 135                 140
```

```
acg ctt gaa gac aat ttc aag ctg acg ccg gaa gcg ctg gaa aag gcg      480
Thr Leu Glu Asp Asn Phe Lys Leu Thr Pro Glu Ala Leu Glu Lys Ala
145                 150                 155                 160 atc aca ccg aag aca aag tgg ttc gtc ttc aac tcg cct tca aac ccc      528
Ile Thr Pro Lys Thr Lys Trp Phe Val Phe Asn Ser Pro Ser Asn Pro
                165                 170                 175 tcg ggt gcc gcc tat tcg cat gac gaa ctg aag gcg ctg acg gac gtg      576
Ser Gly Ala Ala Tyr Ser His Asp Glu Leu Lys Ala Leu Thr Asp Val
            180                 185                 190 ctg gtc aag cat ccg caa gtc tgg gtg ctg acg gac atg tac gag          624
Leu Val Lys His Pro Gln Val Trp Val Leu Thr Asp Asp Met Tyr Glu
        195                 200                 205 cac ctc acc tat ggc gat ttc aaa ttc gtc acc ccg gtt gag gtt gag      672
His Leu Thr Tyr Gly Asp Phe Lys Phe Val Thr Pro Val Glu Val Glu
    210                 215                 220 cct gcg ctc tat gat cgc acg ctg acg atg aac ggc gtc tcc aag gcc      720
Pro Ala Leu Tyr Asp Arg Thr Leu Thr Met Asn Gly Val Ser Lys Ala
225                 230                 235                 240 tat gcc atg acc ggc tgg cgt atc ggt tac gcg gcc ggc ccg ctg ccg      768
Tyr Ala Met Thr Gly Trp Arg Ile Gly Tyr Ala Ala Gly Pro Leu Pro
                245                 250                 255 ctg atc aag gcc atg gac atg atc cag ggc cag cag acc tcg ggc gcc      816
Leu Ile Lys Ala Met Asp Met Ile Gln Gly Gln Gln Thr Ser Gly Ala
            260                 265                 270 agc tcg atc gcg caa tgg gcg gct gtt gaa gcg ctg aac ggc acg cag      864
Ser Ser Ile Ala Gln Trp Ala Ala Val Glu Ala Leu Asn Gly Thr Gln
        275                 280                 285 gat ttc att ccg acc aac aag aaa atc ttc gaa ggt cgc cgt gat ctc      912
Asp Phe Ile Pro Thr Asn Lys Lys Ile Phe Glu Gly Arg Arg Asp Leu
    290                 295                 300 gtc gtc tcc atg ctc aac cag gcc aag ggc atc aat tgc ccg tca ccg      960
Val Val Ser Met Leu Asn Gln Ala Lys Gly Ile Asn Cys Pro Ser Pro
305                 310                 315                 320 gaa ggc gca ttc tac gtc tac ccg tcc tgc gcc ggc ctg att ggc aag     1008
Glu Gly Ala Phe Tyr Val Tyr Pro Ser Cys Ala Gly Leu Ile Gly Lys
                325                 330                 335 acc gcg cca tct ggc aag gtc atc gag tcg gat gtg gac ttc gtc tcc     1056
Thr Ala Pro Ser Gly Lys Val Ile Glu Ser Asp Val Asp Phe Val Ser
            340                 345                 350 gag ctt ctg gaa gcc gaa ggc gtc gcc gtc gtg cag gga tcg gct ttc     1104
Glu Leu Leu Glu Ala Glu Gly Val Ala Val Val Gln Gly Ser Ala Phe
        355                 360                 365 ggc ctc ggc ccg aac ttc cgc att tcc tac gcc acg tcg gaa agc ctg     1152
Gly Leu Gly Pro Asn Phe Arg Ile Ser Tyr Ala Thr Ser Glu Ser Leu
    370                 375                 380 ctg gaa gaa gcc tgc aag cgc att cag cgt ttc tgc gcc gat tgc cgt     1200
Leu Glu Glu Ala Cys Lys Arg Ile Gln Arg Phe Cys Ala Asp Cys Arg
385                 390                 395                 400 tga                                                                  1203

<210> SEQ ID NO 48
<211> LENGTH: 400
<212> TYPE: PRT
<213> ORGANISM: Rhizobium radiobacter

<400> SEQUENCE: 48

Met Ala Phe Leu Ala Asp Ile Leu Ser Arg Val Lys Pro Ser Ala Thr
1               5                   10                  15

Ile Ala Val Thr Gln Lys Ala Arg Glu Leu Lys Ala Lys Gly Arg Asp
```

```
            20                  25                  30
Val Ile Ser Leu Gly Ala Gly Glu Pro Asp Phe Asp Thr Pro Asp Asn
            35                  40                  45
Ile Lys Glu Ala Ala Ile Asp Ala Ile Lys Arg Gly Glu Thr Lys Tyr
        50                  55                  60
Thr Pro Val Ser Gly Ile Pro Glu Leu Arg Lys Ala Ile Ala Asp Lys
65                  70                  75                  80
Phe Lys Arg Glu Asn Gly Leu Asp Tyr Lys Pro Glu Gln Thr Ile Val
                85                  90                  95
Gly Thr Gly Gly Lys Gln Ile Leu Phe Asn Ala Phe Met Ala Thr Leu
            100                 105                 110
Asn Pro Gly Asp Glu Val Val Ile Pro Ala Pro Tyr Trp Val Ser Tyr
            115                 120                 125
Pro Glu Met Val Ala Ile Cys Gly Gly Thr Pro Val Phe Val Asp Thr
            130                 135                 140
Thr Leu Glu Asp Asn Phe Lys Leu Thr Pro Glu Ala Leu Glu Lys Ala
145                 150                 155                 160
Ile Thr Pro Lys Thr Lys Trp Phe Val Phe Asn Ser Pro Ser Asn Pro
                165                 170                 175
Ser Gly Ala Ala Tyr Ser His Asp Glu Leu Lys Ala Leu Thr Asp Val
            180                 185                 190
Leu Val Lys His Pro Gln Val Trp Val Leu Thr Asp Asp Met Tyr Glu
            195                 200                 205
His Leu Thr Tyr Gly Asp Phe Lys Phe Val Thr Pro Val Glu Val Glu
            210                 215                 220
Pro Ala Leu Tyr Asp Arg Thr Leu Thr Met Asn Gly Val Ser Lys Ala
225                 230                 235                 240
Tyr Ala Met Thr Gly Trp Arg Ile Gly Tyr Ala Ala Gly Pro Leu Pro
                245                 250                 255
Leu Ile Lys Ala Met Asp Met Ile Gln Gly Gln Gln Thr Ser Gly Ala
            260                 265                 270
Ser Ser Ile Ala Gln Trp Ala Ala Val Glu Ala Leu Asn Gly Thr Gln
            275                 280                 285
Asp Phe Ile Pro Thr Asn Lys Lys Ile Phe Glu Gly Arg Arg Asp Leu
            290                 295                 300
Val Val Ser Met Leu Asn Gln Ala Lys Gly Ile Asn Cys Pro Ser Pro
305                 310                 315                 320
Glu Gly Ala Phe Tyr Val Tyr Pro Ser Cys Ala Gly Leu Ile Gly Lys
                325                 330                 335
Thr Ala Pro Ser Gly Lys Val Ile Glu Ser Asp Val Asp Phe Val Ser
            340                 345                 350
Glu Leu Leu Glu Ala Glu Gly Val Ala Val Gln Gly Ser Ala Phe
            355                 360                 365
Gly Leu Gly Pro Asn Phe Arg Ile Ser Tyr Ala Thr Ser Glu Ser Leu
            370                 375                 380
Leu Glu Glu Ala Cys Lys Arg Ile Gln Arg Phe Cys Ala Asp Cys Arg
385                 390                 395                 400
```

<210> SEQ ID NO 49
<211> LENGTH: 35
<212> TYPE: DNA
<213> ORGANISM: Artificial Sequence
<220> FEATURE:
<223> OTHER INFORMATION: Forward primer for amplifying DNA fragment
      containing aminotransferase gene derived from Rhizobium radiobacter (3976AT-Nde-f)

<400> SEQUENCE: 49
ggaattccat atggccttcc ttgccgacat tctct                                      35

<210> SEQ ID NO 50
<211> LENGTH: 37
<212> TYPE: DNA
<213> ORGANISM: Artificial Sequence
<220> FEATURE:
<223> OTHER INFORMATION: Reverse primer for amplifying DNA fragment
      containing aminotransferase gene derived from Rhizobium
      radiobacter (3976-xho-r)

<400> SEQUENCE: 50
actccgctcg agacggcaat cggcgcagaa acgctga                                    37

<210> SEQ ID NO 51
<211> LENGTH: 20
<212> TYPE: PRT
<213> ORGANISM: Rhizobium sp.

<400> SEQUENCE: 51

Ala Phe Leu Ala Asp Ile Leu Ser Arg Val Lys Pro Ser Ala Thr Ile
 1               5                  10                  15

Ala Val Thr Gln
            20

<210> SEQ ID NO 52
<211> LENGTH: 1203
<212> TYPE: DNA
<213> ORGANISM: Rhizobium sp.
<220> FEATURE:
<221> NAME/KEY: CDS
<222> LOCATION: (1)..(1203)

<400> SEQUENCE: 52

| atg | gcc | ttc | ctt | gcc | gac | att | ctc | tcc | cgc | gta | aag | cca | tcc | gcc | acc | 48 |
| Met | Ala | Phe | Leu | Ala | Asp | Ile | Leu | Ser | Arg | Val | Lys | Pro | Ser | Ala | Thr | |
| 1 | | | | 5 | | | | | 10 | | | | | 15 | | |

| atc | gcc | gtt | acc | cag | aaa | gcc | cgt | gag | ctg | aaa | gcc | aag | ggt | cgc | gat | 96 |
| Ile | Ala | Val | Thr | Gln | Lys | Ala | Arg | Glu | Leu | Lys | Ala | Lys | Gly | Arg | Asp | |
| | | | 20 | | | | | 25 | | | | | 30 | | | |

| gtg | att | agc | ctt | ggc | gcc | ggc | gag | ccg | gat | ttc | gat | acg | ccc | gat | aat | 144 |
| Val | Ile | Ser | Leu | Gly | Ala | Gly | Glu | Pro | Asp | Phe | Asp | Thr | Pro | Asp | Asn | |
| | | 35 | | | | | 40 | | | | | 45 | | | | |

| atc | aag | gaa | gcg | gcc | att | gac | gcc | atc | aag | cgc | ggc | gaa | acc | aaa | tac | 192 |
| Ile | Lys | Glu | Ala | Ala | Ile | Asp | Ala | Ile | Lys | Arg | Gly | Glu | Thr | Lys | Tyr | |
| 50 | | | | | 55 | | | | | 60 | | | | | | |

| acg | ccg | gtt | tcc | ggc | att | cct | gaa | ctg | cgc | aag | gcg | att | gcc | gac | aag | 240 |
| Thr | Pro | Val | Ser | Gly | Ile | Pro | Glu | Leu | Arg | Lys | Ala | Ile | Ala | Asp | Lys | |
| 65 | | | | 70 | | | | | 75 | | | | | 80 | | |

| ttc | aag | cgt | gaa | aac | ggc | ctc | gac | tac | aag | ccg | gaa | cag | acc | atc | gtc | 288 |
| Phe | Lys | Arg | Glu | Asn | Gly | Leu | Asp | Tyr | Lys | Pro | Glu | Gln | Thr | Ile | Val | |
| | | | 85 | | | | | 90 | | | | | 95 | | | |

| ggc | acc | ggc | ggc | aag | cag | atc | ctc | ttc | aac | gcc | ttc | atg | gcg | acg | ctg | 336 |
| Gly | Thr | Gly | Gly | Lys | Gln | Ile | Leu | Phe | Asn | Ala | Phe | Met | Ala | Thr | Leu | |
| | | 100 | | | | | 105 | | | | | 110 | | | | |

| aac | ccc | ggt | gat | gag | gtc | gtc | att | ccc | gcg | cct | tac | tgg | gtc | agc | tac | 384 |
| Asn | Pro | Gly | Asp | Glu | Val | Val | Ile | Pro | Ala | Pro | Tyr | Trp | Val | Ser | Tyr | |
| | | 115 | | | | | 120 | | | | | 125 | | | | |

| ccg | gaa | atg | gtg | gcg | atc | tgc | ggc | ggt | acg | ccg | gtt | ttc | gtc | aac | gcc | 432 |
| Pro | Glu | Met | Val | Ala | Ile | Cys | Gly | Gly | Thr | Pro | Val | Phe | Val | Asn | Ala | |

```
            130                 135                 140
acg ctc gaa gac aat ttc aag ctg aag ccg gaa gcg ctg gaa aag gct      480
Thr Leu Glu Asp Asn Phe Lys Leu Lys Pro Glu Ala Leu Glu Lys Ala
145                 150                 155                 160 atc acg ccg aag aca aag tgg ttc gtc ttc aac tcg cct tcc aac ccc      528
Ile Thr Pro Lys Thr Lys Trp Phe Val Phe Asn Ser Pro Ser Asn Pro
                165                 170                 175 tcg ggt gcg gcc tat tcg cat gag gag ttg aag gcg ctg acg gac gtg      576
Ser Gly Ala Ala Tyr Ser His Glu Glu Leu Lys Ala Leu Thr Asp Val
            180                 185                 190 ctg gtc aag cat ccg cat gtc tgg gtg ctg acg gac gac atg tat gag      624
Leu Val Lys His Pro His Val Trp Val Leu Thr Asp Asp Met Tyr Glu
        195                 200                 205 cac ctg acc tat ggc gat ttc aaa ttc gtc acc cct gtg gaa gtc gag      672
His Leu Thr Tyr Gly Asp Phe Lys Phe Val Thr Pro Val Glu Val Glu
    210                 215                 220 cct tcg ctc tat gac cgg acg ttg acg atg aac ggc gtc tcc aag gcc      720
Pro Ser Leu Tyr Asp Arg Thr Leu Thr Met Asn Gly Val Ser Lys Ala
225                 230                 235                 240 tat gcc atg acc ggc tgg cgt atc ggt tac gct gcc ggc ccg ctg ccg      768
Tyr Ala Met Thr Gly Trp Arg Ile Gly Tyr Ala Ala Gly Pro Leu Pro
                245                 250                 255 ctg atc aag gcc atg gac atg atc cag ggc cag cag acc tcg ggc gca      816
Leu Ile Lys Ala Met Asp Met Ile Gln Gly Gln Gln Thr Ser Gly Ala
            260                 265                 270 agc tcg atc gca cag tgg gcc gct gtc gaa gct ctg aac ggc acg cag      864
Ser Ser Ile Ala Gln Trp Ala Ala Val Glu Ala Leu Asn Gly Thr Gln
        275                 280                 285 gat ttc att ccg gcg aac aag aag atc ttc gaa ggc cgt cgc gat ctc      912
Asp Phe Ile Pro Ala Asn Lys Lys Ile Phe Glu Gly Arg Arg Asp Leu
    290                 295                 300 gtc gtt tcc atg ctc aac cag gcc aag ggc atc agc tgc ccg tca ccg      960
Val Val Ser Met Leu Asn Gln Ala Lys Gly Ile Ser Cys Pro Ser Pro
305                 310                 315                 320 gaa ggt gca ttc tac gtc tac ccg tcc tgc gcc ggc ttg atc ggc aag     1008
Glu Gly Ala Phe Tyr Val Tyr Pro Ser Cys Ala Gly Leu Ile Gly Lys
                325                 330                 335 acc gcg cct tcg ggc aag gtc atc gag acg gat acg gat ttc gtt tcc     1056
Thr Ala Pro Ser Gly Lys Val Ile Glu Thr Asp Thr Asp Phe Val Ser
            340                 345                 350 gag ctt ctg gaa gcc gaa ggc gtt gcc gtc gtg cag gga tcg gct ttc     1104
Glu Leu Leu Glu Ala Glu Gly Val Ala Val Val Gln Gly Ser Ala Phe
        355                 360                 365 ggc ctt ggc ccg aac ttc cgc atc tcc tac gcc acg tcg gaa act ctt     1152
Gly Leu Gly Pro Asn Phe Arg Ile Ser Tyr Ala Thr Ser Glu Thr Leu
    370                 375                 380 ctc gaa gag gcc tgc aag cgc att cag cgt ttc tgc gcc gat tgc cgc     1200
Leu Glu Glu Ala Cys Lys Arg Ile Gln Arg Phe Cys Ala Asp Cys Arg
385                 390                 395                 400 taa                                                                  1203

<210> SEQ ID NO 53
<211> LENGTH: 400
<212> TYPE: PRT
<213> ORGANISM: Rhizobium sp.

<400> SEQUENCE: 53

Met Ala Phe Leu Ala Asp Ile Leu Ser Arg Val Lys Pro Ser Ala Thr
1               5                   10                  15
```

Ile Ala Val Thr Gln Lys Ala Arg Glu Leu Lys Ala Lys Gly Arg Asp
            20                  25                  30

Val Ile Ser Leu Gly Ala Gly Glu Pro Asp Phe Asp Thr Pro Asp Asn
        35                  40                  45

Ile Lys Glu Ala Ala Ile Asp Ala Ile Lys Arg Gly Glu Thr Lys Tyr
    50                  55                  60

Thr Pro Val Ser Gly Ile Pro Glu Leu Arg Lys Ala Ile Ala Asp Lys
65                  70                  75                  80

Phe Lys Arg Glu Asn Gly Leu Asp Tyr Lys Pro Glu Gln Thr Ile Val
                85                  90                  95

Gly Thr Gly Gly Lys Gln Ile Leu Phe Asn Ala Phe Met Ala Thr Leu
            100                 105                 110

Asn Pro Gly Asp Glu Val Val Ile Pro Ala Pro Tyr Trp Val Ser Tyr
        115                 120                 125

Pro Glu Met Val Ala Ile Cys Gly Gly Thr Pro Val Phe Val Asn Ala
    130                 135                 140

Thr Leu Glu Asp Asn Phe Lys Leu Lys Pro Glu Ala Leu Glu Lys Ala
145                 150                 155                 160

Ile Thr Pro Lys Thr Lys Trp Phe Val Phe Asn Ser Pro Ser Asn Pro
                165                 170                 175

Ser Gly Ala Ala Tyr Ser His Glu Glu Leu Lys Ala Leu Thr Asp Val
            180                 185                 190

Leu Val Lys His Pro His Val Trp Val Leu Thr Asp Asp Met Tyr Glu
        195                 200                 205

His Leu Thr Tyr Gly Asp Phe Lys Phe Val Thr Pro Val Glu Val Glu
    210                 215                 220

Pro Ser Leu Tyr Asp Arg Thr Leu Thr Met Asn Gly Val Ser Lys Ala
225                 230                 235                 240

Tyr Ala Met Thr Gly Trp Arg Ile Gly Tyr Ala Ala Gly Pro Leu Pro
                245                 250                 255

Leu Ile Lys Ala Met Asp Met Ile Gln Gly Gln Thr Ser Gly Ala
            260                 265                 270

Ser Ser Ile Ala Gln Trp Ala Ala Val Glu Ala Leu Asn Gly Thr Gln
        275                 280                 285

Asp Phe Ile Pro Ala Asn Lys Lys Ile Phe Glu Gly Arg Arg Asp Leu
    290                 295                 300

Val Val Ser Met Leu Asn Gln Ala Lys Gly Ile Ser Cys Pro Ser Pro
305                 310                 315                 320

Glu Gly Ala Phe Tyr Val Tyr Pro Ser Cys Ala Gly Leu Ile Gly Lys
                325                 330                 335

Thr Ala Pro Ser Gly Lys Val Ile Glu Thr Asp Thr Asp Phe Val Ser
            340                 345                 350

Glu Leu Leu Glu Ala Glu Gly Val Ala Val Val Gln Gly Ser Ala Phe
        355                 360                 365

Gly Leu Gly Pro Asn Phe Arg Ile Ser Tyr Ala Thr Ser Glu Thr Leu
    370                 375                 380

Leu Glu Glu Ala Cys Lys Arg Ile Gln Arg Phe Cys Ala Asp Cys Arg
385                 390                 395                 400

<210> SEQ ID NO 54
<211> LENGTH: 35
<212> TYPE: DNA
<213> ORGANISM: Artificial Sequence
<220> FEATURE:
<223> OTHER INFORMATION: Forward primer for amplifying DNA fragment containing aminotransferase gene derived from Rhizobium sp.
(12469AT-Nde-f)

<400> SEQUENCE: 54
ggaattccat atggccttcc ttgccgacat tctct                                35

<210> SEQ ID NO 55
<211> LENGTH: 37
<212> TYPE: DNA
<213> ORGANISM: Artificial Sequence
<220> FEATURE:
<223> OTHER INFORMATION: Reverse primer for amplifying DNA fragment
      containing aminotransferase gene derived from Rhizobium sp.
      (12469-xho-r)

<400> SEQUENCE: 55
actccgctcg aggcggcaat cggcgcagaa acgctga                              37

<210> SEQ ID NO 56
<211> LENGTH: 26
<212> TYPE: DNA
<213> ORGANISM: Artificial Sequence
<220> FEATURE:
<223> OTHER INFORMATION: Forward primer which is designed based on the
      genomic DNA sequence from Corynebacterium ammoniagenes DSM20306
      (Co-d50-r)

<400> SEQUENCE: 56
cttccttgga acaagtcgag gaagac                                          26

<210> SEQ ID NO 57
<211> LENGTH: 26
<212> TYPE: DNA
<213> ORGANISM: Artificial Sequence
<220> FEATURE:
<223> OTHER INFORMATION: Reverse primer which is designed based on a
      homologus region between the genomic DNA sequences corresponding
      to the aspartate aminotransferases from Corynebacterium striatum
      ATCC6940 (ZP_03935516) and from Corynebacterium ammoniagenes
      DSM20306

<400> SEQUENCE: 57
gctatcgcac aattccaccg caccttt                                         26

<210> SEQ ID NO 58
<211> LENGTH: 26
<212> TYPE: DNA
<213> ORGANISM: Artificial Sequence
<220> FEATURE:
<223> OTHER INFORMATION: Forward primer for amplifying DNA fragment
      containing aminotransferase gene derived from Corynebacterium
      ammoniagenes (Co-890-r)

<400> SEQUENCE: 58
acatcgttaa gcaagcgaac caccag                                          26

<210> SEQ ID NO 59
<211> LENGTH: 25
<212> TYPE: DNA
<213> ORGANISM: Artificial Sequence
<220> FEATURE:
<223> OTHER INFORMATION: Reverse primer for amplifying DNA fragment
      containing aminotransferase gene derived from Corynebacterium
      ammoniagenes (Co-1060-r)

<400> SEQUENCE: 59
gaaagacaag cgaatgtggt gctcg                                           25

<210> SEQ ID NO 60
<211> LENGTH: 1134
<212> TYPE: DNA
<213> ORGANISM: Corynebacterium ammoniagenes
<220> FEATURE:
<221> NAME/KEY: CDS
<222> LOCATION: (1)..(1134)

<400> SEQUENCE: 60

| | | | | | | | | | | | | | | | | |
|---|---|---|---|---|---|---|---|---|---|---|---|---|---|---|---|---|
| atg | agc | cac | atc | gct | caa | cgc | atc | ctt | gac | cag | cgt | caa | gca | tct | ctt | 48 |
| Met | Ser | His | Ile | Ala | Gln | Arg | Ile | Leu | Asp | Gln | Arg | Gln | Ala | Ser | Leu | |
| 1 | | | | 5 | | | | | 10 | | | | | 15 | | |
| cgc | ccg | ccg | ctt | ggg | gtg | gtg | ccg | ccc | ggc | gcg | gtg | tcg | ttg | gcg | ttg | 96 |
| Arg | Pro | Pro | Leu | Gly | Val | Val | Pro | Pro | Gly | Ala | Val | Ser | Leu | Ala | Leu | |
| | | | 20 | | | | | 25 | | | | | 30 | | | |
| ggc | gag | ccg | gac | ttt | gcc | cca | ccg | cag | gcg | gtt | atc | gat | gcc | acc | acg | 144 |
| Gly | Glu | Pro | Asp | Phe | Ala | Pro | Pro | Gln | Ala | Val | Ile | Asp | Ala | Thr | Thr | |
| | | 35 | | | | | 40 | | | | | 45 | | | | |
| caa | gca | gtc | gcc | caa | ggc | cgc | acc | aac | tac | acg | gat | cag | cac | ggt | atc | 192 |
| Gln | Ala | Val | Ala | Gln | Gly | Arg | Thr | Asn | Tyr | Thr | Asp | Gln | His | Gly | Ile | |
| | 50 | | | | | 55 | | | | | 60 | | | | | |
| gct | gag | ctt | cgc | gat | gcc | ctc | ctc | gcc | gcc | ctt | ccc | acc | cgc | ccc | tct | 240 |
| Ala | Glu | Leu | Arg | Asp | Ala | Leu | Leu | Ala | Ala | Leu | Pro | Thr | Arg | Pro | Ser | |
| 65 | | | | | 70 | | | | | 75 | | | | | 80 | |
| aac | tgg | gac | cgc | gac | aat | att | gtg | gtg | aca | cac | ggt | gca | acc | gcg | gga | 288 |
| Asn | Trp | Asp | Arg | Asp | Asn | Ile | Val | Val | Thr | His | Gly | Ala | Thr | Ala | Gly | |
| | | | | 85 | | | | | 90 | | | | | 95 | | |
| ctg | ggt | gcg | ctg | ttt | ttc | gcg | ctg | att | gaa | ccc | ggt | gac | aag | gtc | gtt | 336 |
| Leu | Gly | Ala | Leu | Phe | Phe | Ala | Leu | Ile | Glu | Pro | Gly | Asp | Lys | Val | Val | |
| | | | 100 | | | | | 105 | | | | | 110 | | | |
| atc | cca | cag | cct | gcg | tat | tct | ttg | tac | gcc | gac | cag | gtg | gtt | tta | gcc | 384 |
| Ile | Pro | Gln | Pro | Ala | Tyr | Ser | Leu | Tyr | Ala | Asp | Gln | Val | Val | Leu | Ala | |
| | | 115 | | | | | 120 | | | | | 125 | | | | |
| ggc | ggc | acc | gtg | gaa | ttt | gtt | ccc | atg | ggc | aag | gac | ctc | cac | ttt | gat | 432 |
| Gly | Gly | Thr | Val | Glu | Phe | Val | Pro | Met | Gly | Lys | Asp | Leu | His | Phe | Asp | |
| | 130 | | | | | 135 | | | | | 140 | | | | | |
| ttt | gac | cag | ctt | gcc | acg | gcg | ctt | gac | ggc | gca | aag | atg | gtg | gtc | ttt | 480 |
| Phe | Asp | Gln | Leu | Ala | Thr | Ala | Leu | Asp | Gly | Ala | Lys | Met | Val | Val | Phe | |
| 145 | | | | | 150 | | | | | 155 | | | | | 160 | |
| tct | aat | cct | tct | aat | ccc | aat | gga | atc | gtg | cat | acc | cgc | gat | gag | ctg | 528 |
| Ser | Asn | Pro | Ser | Asn | Pro | Asn | Gly | Ile | Val | His | Thr | Arg | Asp | Glu | Leu | |
| | | | | 165 | | | | | 170 | | | | | 175 | | |
| gaa | agg | ctt | gca | cag | ctt | ctc | gat | gcc | acc | gat | acc | ctc | gtc | gtt | tcc | 576 |
| Glu | Arg | Leu | Ala | Gln | Leu | Leu | Asp | Ala | Thr | Asp | Thr | Leu | Val | Val | Ser | |
| | | | 180 | | | | | 185 | | | | | 190 | | | |
| gac | gaa | gcc | tac | tcg | gcc | ctc | acc | tat | acc | gcc | gaa | cca | ttc | acc | tcc | 624 |
| Asp | Glu | Ala | Tyr | Ser | Ala | Leu | Thr | Tyr | Thr | Ala | Glu | Pro | Phe | Thr | Ser | |
| | | 195 | | | | | 200 | | | | | 205 | | | | |
| gct | tta | gag | gtt | ccc | ggc | ttg | cag | gag | cgc | acg | tta | tac | gtg | cag | acc | 672 |
| Ala | Leu | Glu | Val | Pro | Gly | Leu | Gln | Glu | Arg | Thr | Leu | Tyr | Val | Gln | Thr | |
| | 210 | | | | | 215 | | | | | 220 | | | | | |
| ttt | tcc | aag | aaa | tac | tgc | atg | acg | ggc | ttc | cgc | gtc | ggc | tac | gtc | gcg | 720 |
| Phe | Ser | Lys | Lys | Tyr | Cys | Met | Thr | Gly | Phe | Arg | Val | Gly | Tyr | Val | Ala | |
| 225 | | | | | 230 | | | | | 235 | | | | | 240 | |
| ggc | gcg | aga | gat | ttg | atc | gct | gcg | att | gcg | cag | atg | cac | cgc | acc | ttc | 768 |
| Gly | Ala | Arg | Asp | Leu | Ile | Ala | Ala | Ile | Ala | Gln | Met | His | Arg | Thr | Phe | |
| | | | | 245 | | | | | 250 | | | | | 255 | | |
| aac | ggc | tca | gtg | tcg | gag | cag | gcg | cag | ctg | gca | gcg | ctc | gcc | gcg | gta | 816 |
| Asn | Gly | Ser | Val | Ser | Glu | Gln | Ala | Gln | Leu | Ala | Ala | Leu | Ala | Ala | Val | |
| | | | 260 | | | | | 265 | | | | | 270 | | | |

```
tct ctg ccg gag tct gtg gtc aca ccg atg ttg gaa gaa tac gcc cag      864
Ser Leu Pro Glu Ser Val Val Thr Pro Met Leu Glu Glu Tyr Ala Gln
        275                 280                 285 cgc cgc gac ctg gtg gtt cgc ttg ctt aac gat gtc ccc cac gtc caa      912
Arg Arg Asp Leu Val Val Arg Leu Leu Asn Asp Val Pro His Val Gln
    290                 295                 300 ctc ttc gag ccc gaa ggc gcg ttt tat gca ttc ttc tct tat gac ttg      960
Leu Phe Glu Pro Glu Gly Ala Phe Tyr Ala Phe Phe Ser Tyr Asp Leu
305                 310                 315                 320 gac aag ccc tct tcc cag gta gca gcc gag ctg gcc gaa cgc ggt gta     1008
Asp Lys Pro Ser Ser Gln Val Ala Ala Glu Leu Ala Glu Arg Gly Val
            325                 330                 335 cta gtg cgc gct ggt gcc gaa tat ggc ccc gcc gcc gag cac cac att     1056
Leu Val Arg Ala Gly Ala Glu Tyr Gly Pro Ala Ala Glu His His Ile
        340                 345                 350 cgc ttg tct ttc gca gcc tcg caa gca gat atc gaa cgt ggc att gga     1104
Arg Leu Ser Phe Ala Ala Ser Gln Ala Asp Ile Glu Arg Gly Ile Gly
    355                 360                 365 atc att cgc caa tac ttc gaa aag tcc tag                             1134
Ile Ile Arg Gln Tyr Phe Glu Lys Ser
        370                 375

<210> SEQ ID NO 61
<211> LENGTH: 377
<212> TYPE: PRT
<213> ORGANISM: Corynebacterium ammoniagenes

<400> SEQUENCE: 61

Met Ser His Ile Ala Gln Arg Ile Leu Asp Gln Arg Gln Ala Ser Leu
1               5                   10                  15

Arg Pro Pro Leu Gly Val Val Pro Pro Gly Ala Val Ser Leu Ala Leu
            20                  25                  30

Gly Glu Pro Asp Phe Ala Pro Pro Gln Ala Val Ile Asp Ala Thr Thr
        35                  40                  45

Gln Ala Val Ala Gln Gly Arg Thr Asn Tyr Thr Asp Gln His Gly Ile
    50                  55                  60

Ala Glu Leu Arg Asp Ala Leu Leu Ala Ala Leu Pro Thr Arg Pro Ser
65                  70                  75                  80

Asn Trp Asp Arg Asp Asn Ile Val Val Thr His Gly Ala Thr Ala Gly
                85                  90                  95

Leu Gly Ala Leu Phe Phe Ala Leu Ile Glu Pro Gly Asp Lys Val Val
            100                 105                 110

Ile Pro Gln Pro Ala Tyr Ser Leu Tyr Ala Asp Gln Val Val Leu Ala
        115                 120                 125

Gly Gly Thr Val Glu Phe Val Pro Met Gly Lys Asp Leu His Phe Asp
    130                 135                 140

Phe Asp Gln Leu Ala Thr Ala Leu Asp Gly Ala Lys Met Val Val Phe
145                 150                 155                 160

Ser Asn Pro Ser Asn Pro Asn Gly Ile Val His Thr Arg Asp Glu Leu
                165                 170                 175

Glu Arg Leu Ala Gln Leu Leu Asp Ala Thr Asp Thr Leu Val Val Ser
            180                 185                 190

Asp Glu Ala Tyr Ser Ala Leu Thr Tyr Thr Ala Glu Pro Phe Thr Ser
        195                 200                 205

Ala Leu Glu Val Pro Gly Leu Gln Glu Arg Thr Leu Tyr Val Gln Thr
    210                 215                 220

Phe Ser Lys Lys Tyr Cys Met Thr Gly Phe Arg Val Gly Tyr Val Ala
```

```
                225                 230                 235                 240
        Gly Ala Arg Asp Leu Ile Ala Ala Ile Ala Gln Met His Arg Thr Phe
                        245                 250                 255

Asn Gly Ser Val Ser Glu Gln Ala Gln Leu Ala Ala Leu Ala Ala Val
                        260                 265                 270

Ser Leu Pro Glu Ser Val Val Thr Pro Met Leu Glu Tyr Ala Gln
                        275                 280                 285

Arg Arg Asp Leu Val Val Arg Leu Leu Asn Asp Val Pro His Val Gln
                        290                 295                 300

Leu Phe Glu Pro Glu Gly Ala Phe Tyr Ala Phe Phe Ser Tyr Asp Leu
        305                 310                 315                 320

Asp Lys Pro Ser Ser Gln Val Ala Ala Glu Leu Ala Glu Arg Gly Val
                        325                 330                 335

Leu Val Arg Ala Gly Ala Glu Tyr Gly Pro Ala Ala Glu His His Ile
                        340                 345                 350

Arg Leu Ser Phe Ala Ala Ser Gln Ala Asp Ile Glu Arg Gly Ile Gly
                        355                 360                 365

Ile Ile Arg Gln Tyr Phe Glu Lys Ser
                370                 375

<210> SEQ ID NO 62
<211> LENGTH: 35
<212> TYPE: DNA
<213> ORGANISM: Artificial Sequence
<220> FEATURE:
<223> OTHER INFORMATION: Forward primer for amplifying DNA fragment
      containing aminotransferase gene derived from Corynebacterium
      ammoniagenes (1444AT-Nde-f)

<400> SEQUENCE: 62
ggaattccat atgagccaca tcgctcaacg catcc                              35

<210> SEQ ID NO 63
<211> LENGTH: 37
<212> TYPE: DNA
<213> ORGANISM: Artificial Sequence
<220> FEATURE:
<223> OTHER INFORMATION: Reverse primer for amplifying DNA fragment
      containing aminotransferase gene derived from Corynebacterium
      ammoniagenes (1444-xho-r)

<400> SEQUENCE: 63
actccgctcg agggactttt cgaagtattg gcgaatg                            37

<210> SEQ ID NO 64
<211> LENGTH: 1275
<212> TYPE: DNA
<213> ORGANISM: Deinococcus geothermalis
<220> FEATURE:
<221> NAME/KEY: CDS
<222> LOCATION: (1)..(1275)

<400> SEQUENCE: 64 atg acc aaa gaa gca tcc cgc ccg gca ctg gac ctg gct cgt caa gcg     48
Met Thr Lys Glu Ala Ser Arg Pro Ala Leu Asp Leu Ala Arg Gln Ala
1               5                   10                  15 tat gaa gca ttt aaa gct cgt ggc ctg aat ctg aat atg cag cgt ggt     96
Tyr Glu Ala Phe Lys Ala Arg Gly Leu Asn Leu Asn Met Gln Arg Gly
                20                  25                  30 caa ccg gct gat gcg gac ttt gat ctg tct aac ggc ctg ctg acc gtt    144
Gln Pro Ala Asp Ala Asp Phe Asp Leu Ser Asn Gly Leu Leu Thr Val
            35                  40                  45
```

-continued

| | |
|---|---|
| ctg ggt gcc gaa gac gtc cgt atg gac ggc ctg gat ctg cgc aat tat<br>Leu Gly Ala Glu Asp Val Arg Met Asp Gly Leu Asp Leu Arg Asn Tyr<br>50            55              60 | 192 |
| ccg ggc ggt gtg gca ggt ctg ccg agc gcc cgc gca ctg ttt gcc ggt<br>Pro Gly Gly Val Ala Gly Leu Pro Ser Ala Arg Ala Leu Phe Ala Gly<br>65             70              75             80 | 240 |
| tac ctg gat gtt aaa gca gaa aac gtt ctg gtc tgg aac aat agc tct<br>Tyr Leu Asp Val Lys Ala Glu Asn Val Leu Val Trp Asn Asn Ser Ser<br>            85              90             95 | 288 |
| ctg gaa ctg caa ggt ctg gtt ctg acc ttc gcc ctg cat ggt gtc<br>Leu Glu Leu Gln Gly Leu Val Leu Thr Phe Ala Leu Leu His Gly Val<br>        100            105            110 | 336 |
| cgt ggt agc acg ggt ccg tgg ctg tct caa acc ccg aaa atg att gtg<br>Arg Gly Ser Thr Gly Pro Trp Leu Ser Gln Thr Pro Lys Met Ile Val<br>    115            120            125 | 384 |
| acg gtt ccg ggc tat gat cgc cac ttt ctg ctg caa acc ctg ggt<br>Thr Val Pro Gly Tyr Asp Arg His Phe Leu Leu Gln Thr Leu Gly<br>130            135            140 | 432 |
| ttc gaa ctg ctg acg gtg gac atg caa agc gat ggc ccg gac gtc gat<br>Phe Glu Leu Leu Thr Val Asp Met Gln Ser Asp Gly Pro Asp Val Asp<br>145            150            155            160 | 480 |
| gcc gtg gaa cgt ctg gca ggc acc gat ccg tct gtg aaa ggt att ctg<br>Ala Val Glu Arg Leu Ala Gly Thr Asp Pro Ser Val Lys Gly Ile Leu<br>            165            170            175 | 528 |
| ttt gtt ccg acc tac tca aac ccg ggc ggt gaa acg atc tcg ctg gaa<br>Phe Val Pro Thr Tyr Ser Asn Pro Gly Gly Glu Thr Ile Ser Leu Glu<br>        180            185            190 | 576 |
| aaa gct cgt cgc ctg gca ggt ctg caa gcg gcc gca ccg gac ttt acg<br>Lys Ala Arg Arg Leu Ala Gly Leu Gln Ala Ala Ala Pro Asp Phe Thr<br>    195            200            205 | 624 |
| att ttc gct gat gac gcg tat cgt gtc cat cac ctg gtg gaa gaa gat<br>Ile Phe Ala Asp Asp Ala Tyr Arg Val His His Leu Val Glu Glu Asp<br>210            215            220 | 672 |
| cgc gcc gaa ccg gtg aat ttc gtg gtt ctg gcc cgt gac gca ggt tac<br>Arg Ala Glu Pro Val Asn Phe Val Val Leu Ala Arg Asp Ala Gly Tyr<br>225            230            235            240 | 720 |
| ccg gat cgt gcc ttt gtt ttc gca tca acc tcg aaa atc acg ttt gct<br>Pro Asp Arg Ala Phe Val Phe Ala Ser Thr Ser Lys Ile Thr Phe Ala<br>            245            250            255 | 768 |
| ggt gca ggt ctg ggt ttc gtg gcg agt tcc gaa gat aac att cgt tgg<br>Gly Ala Gly Leu Gly Phe Val Ala Ser Ser Glu Asp Asn Ile Arg Trp<br>        260            265            270 | 816 |
| ctg agt aaa tat ctg ggc gcg cag tcc atc ggt ccg aat aaa gtc gaa<br>Leu Ser Lys Tyr Leu Gly Ala Gln Ser Ile Gly Pro Asn Lys Val Glu<br>    275            280            285 | 864 |
| caa gcc cgt cat gtg aaa ttt ctg acc gaa tac ccg ggc ggt ctg gaa<br>Gln Ala Arg His Val Lys Phe Leu Thr Glu Tyr Pro Gly Gly Leu Glu<br>290            295            300 | 912 |
| ggt ctg atg cgc gac cac gct gcg att atc gct ccg aaa ttc cgt gcg<br>Gly Leu Met Arg Asp His Ala Ala Ile Ile Ala Pro Lys Phe Arg Ala<br>305            310            315            320 | 960 |
| gtt gat gaa gtc ctg cgc gct gaa ctg ggc gaa ggt gaa tat gca<br>Val Asp Glu Val Leu Arg Ala Glu Leu Gly Glu Gly Glu Tyr Ala<br>            325            330            335 | 1008 |
| acc tgg acg ctg ccg aaa ggc ggt tac ttt atc agt ctg gac acc gct<br>Thr Trp Thr Leu Pro Lys Gly Gly Tyr Phe Ile Ser Leu Asp Thr Ala<br>        340            345            350 | 1056 |
| gaa ccg gtg gcg gat cgc gtc gtg aaa ctg gcg gaa gcc gca ggc gtt<br>Glu Pro Val Ala Asp Arg Val Val Lys Leu Ala Glu Ala Ala Gly Val | 1104 |

-continued

|     |     |     | 355 |     |     |     | 360 |     |     |     | 365 |     |     |      |
|-----|-----|-----|-----|-----|-----|-----|-----|-----|-----|-----|-----|-----|-----|------|
| agc | ctg | acc | ccg | gcg | ggt | gca | acg | tat | ccg | gca | ggt | caa | gat | ccg cat | 1152 |
| Ser | Leu | Thr | Pro | Ala | Gly | Ala | Thr | Tyr | Pro | Ala | Gly | Gln | Asp | Pro His |
|     | 370 |     |     |     |     | 375 |     |     |     |     | 380 |     |     |      |

```
agc ctg acc ccg gcg ggt gca acg tat ccg gca ggt caa gat ccg cat    1152
Ser Leu Thr Pro Ala Gly Ala Thr Tyr Pro Ala Gly Gln Asp Pro His
        370                 375                 380 aac cgt aat ctg cgt ctg gca ccg acc cgt ccg ccg gtg gaa gaa gtt    1200
Asn Arg Asn Leu Arg Leu Ala Pro Thr Arg Pro Pro Val Glu Glu Val
385                 390                 395                 400 cgc acg gca atg caa gtg gtc gcc gcg tgt atc cgc ctg gca acc gaa    1248
Arg Thr Ala Met Gln Val Val Ala Ala Cys Ile Arg Leu Ala Thr Glu
                    405                 410                 415 gaa tat cgt gct ggt cat ctc gag tga                                1275
Glu Tyr Arg Ala Gly His Leu Glu
                420
```

<210> SEQ ID NO 65
<211> LENGTH: 424
<212> TYPE: PRT
<213> ORGANISM: Deinococcus geothermalis

<400> SEQUENCE: 65

```
Met Thr Lys Glu Ala Ser Arg Pro Ala Leu Asp Leu Ala Arg Gln Ala
1               5                   10                  15

Tyr Glu Ala Phe Lys Ala Arg Gly Leu Asn Leu Asn Met Gln Arg Gly
                20                  25                  30

Gln Pro Ala Asp Ala Asp Phe Asp Leu Ser Asn Gly Leu Leu Thr Val
            35                  40                  45

Leu Gly Ala Glu Asp Val Arg Met Asp Gly Leu Asp Leu Arg Asn Tyr
        50                  55                  60

Pro Gly Gly Val Ala Gly Leu Pro Ser Ala Arg Ala Leu Phe Ala Gly
65                  70                  75                  80

Tyr Leu Asp Val Lys Ala Glu Asn Val Leu Val Trp Asn Asn Ser Ser
                85                  90                  95

Leu Glu Leu Gln Gly Leu Val Leu Thr Phe Ala Leu Leu His Gly Val
            100                 105                 110

Arg Gly Ser Thr Gly Pro Trp Leu Ser Gln Thr Pro Lys Met Ile Val
        115                 120                 125

Thr Val Pro Gly Tyr Asp Arg His Phe Leu Leu Gln Thr Leu Gly
        130                 135                 140

Phe Glu Leu Leu Thr Val Asp Met Gln Ser Asp Gly Pro Asp Val Asp
145                 150                 155                 160

Ala Val Glu Arg Leu Ala Gly Thr Asp Pro Ser Val Lys Gly Ile Leu
                165                 170                 175

Phe Val Pro Thr Tyr Ser Asn Pro Gly Gly Glu Thr Ile Ser Leu Glu
            180                 185                 190

Lys Ala Arg Arg Leu Ala Gly Leu Gln Ala Ala Ala Pro Asp Phe Thr
        195                 200                 205

Ile Phe Ala Asp Asp Ala Tyr Arg Val His His Leu Val Glu Glu Asp
    210                 215                 220

Arg Ala Glu Pro Val Asn Phe Val Leu Ala Arg Asp Ala Gly Tyr
225                 230                 235                 240

Pro Asp Arg Ala Phe Val Phe Ala Ser Thr Ser Lys Ile Thr Phe Ala
                245                 250                 255

Gly Ala Gly Leu Gly Phe Val Ala Ser Ser Glu Asp Asn Ile Arg Trp
            260                 265                 270

Leu Ser Lys Tyr Leu Gly Ala Gln Ser Ile Gly Pro Asn Lys Val Glu
        275                 280                 285
```

```
Gln Ala Arg His Val Lys Phe Leu Thr Glu Tyr Pro Gly Gly Leu Glu
    290                 295                 300

Gly Leu Met Arg Asp His Ala Ala Ile Ile Ala Pro Lys Phe Arg Ala
305                 310                 315                 320

Val Asp Glu Val Leu Arg Ala Glu Leu Gly Glu Gly Gly Glu Tyr Ala
                325                 330                 335

Thr Trp Thr Leu Pro Lys Gly Gly Tyr Phe Ile Ser Leu Asp Thr Ala
            340                 345                 350

Glu Pro Val Ala Asp Arg Val Val Lys Leu Ala Glu Ala Ala Gly Val
        355                 360                 365

Ser Leu Thr Pro Ala Gly Ala Thr Tyr Pro Ala Gly Gln Asp Pro His
    370                 375                 380

Asn Arg Asn Leu Arg Leu Ala Pro Thr Arg Pro Val Glu Val
385                 390                 395                 400

Arg Thr Ala Met Gln Val Val Ala Ala Cys Ile Arg Leu Ala Thr Glu
                405                 410                 415

Glu Tyr Arg Ala Gly His Leu Glu
            420

<210> SEQ ID NO 66
<211> LENGTH: 1287
<212> TYPE: DNA
<213> ORGANISM: Corynebacterium glutamicum
<220> FEATURE:
<221> NAME/KEY: CDS
<222> LOCATION: (1)..(1287)

<400> SEQUENCE: 66 atg agc tcg gtg tcg ctg caa gac ttt gac gct gaa cgc att ggc ctg      48
Met Ser Ser Val Ser Leu Gln Asp Phe Asp Ala Glu Arg Ile Gly Leu
1               5                   10                  15 ttc cac gaa gat att aaa cgt aaa ttt gat gaa ctg aaa tct aaa aac      96
Phe His Glu Asp Ile Lys Arg Lys Phe Asp Glu Leu Lys Ser Lys Asn
                20                  25                  30 ctg aaa ctg gat ctg acc cgt ggt aaa ccg agc tct gaa cag ctg gat     144
Leu Lys Leu Asp Leu Thr Arg Gly Lys Pro Ser Ser Glu Gln Leu Asp
            35                  40                  45 ttt gcg gac gaa ctg ctg gcc ctg ccg ggc aag ggt gat ttc aaa gcg     192
Phe Ala Asp Glu Leu Leu Ala Leu Pro Gly Lys Gly Asp Phe Lys Ala
        50                  55                  60 gcc gat ggc acc gac gtt cgt aac tat ggc ggt ctg gat ggt att gtc     240
Ala Asp Gly Thr Asp Val Arg Asn Tyr Gly Gly Leu Asp Gly Ile Val
65                  70                  75                  80 gac atc cgc cag att tgg gcg gat ctg ctg ggc gtg ccg gtt gaa caa     288
Asp Ile Arg Gln Ile Trp Ala Asp Leu Leu Gly Val Pro Val Glu Gln
                85                  90                  95 gtg ctg gca ggt gat gct agt tcc ctg aat atc atg ttt gac gtg att     336
Val Leu Ala Gly Asp Ala Ser Ser Leu Asn Ile Met Phe Asp Val Ile
            100                 105                 110 agc tgg tct tat atc ttc ggc aac aat gat tca gtt cag ccg tgg tcg     384
Ser Trp Ser Tyr Ile Phe Gly Asn Asn Asp Ser Val Gln Pro Trp Ser
        115                 120                 125 aaa gaa gaa acg gtg aaa tgg att tgc ccg gtt ccg ggc tac gac cgt     432
Lys Glu Glu Thr Val Lys Trp Ile Cys Pro Val Pro Gly Tyr Asp Arg
    130                 135                 140 cat ttt tct att acc gaa cgc ttt ggt ttc gaa atg atc agt gtt ccg     480
His Phe Ser Ile Thr Glu Arg Phe Gly Phe Glu Met Ile Ser Val Pro
145                 150                 155                 160
```

```
atg aac gaa gat ggc ccg gat atg gac gca gtt gaa gaa ctg gtc aaa      528
Met Asn Glu Asp Gly Pro Asp Met Asp Ala Val Glu Glu Leu Val Lys
                165                 170                 175 gac ccg caa gtc aaa ggc atg tgg gtg gtt ccg gtg ttt agt aat ccg      576
Asp Pro Gln Val Lys Gly Met Trp Val Val Pro Val Phe Ser Asn Pro
        180                 185                 190 acc ggc ttc acg gtg tcc gaa gat gtt gcc aaa cgt ctg tca acc atg      624
Thr Gly Phe Thr Val Ser Glu Asp Val Ala Lys Arg Leu Ser Thr Met
            195                 200                 205 gaa acg gca gct ccg gat ttt cgc gtc gtg tgg gac aat gcg tac gcc      672
Glu Thr Ala Ala Pro Asp Phe Arg Val Val Trp Asp Asn Ala Tyr Ala
    210                 215                 220 gtg cac acc ctg acg gat gaa ttc ccg gaa gtc att gac atc gtg ggt      720
Val His Thr Leu Thr Asp Glu Phe Pro Glu Val Ile Asp Ile Val Gly
225                 230                 235                 240 ctg ggt gaa gcg gcc ggt aac ccg aat cgt ttt tgg gcg ttc acc agt      768
Leu Gly Glu Ala Ala Gly Asn Pro Asn Arg Phe Trp Ala Phe Thr Ser
                245                 250                 255 acg tcc aaa att acc ctg gca ggc gct ggt gtc agc ttt ttc atg acg      816
Thr Ser Lys Ile Thr Leu Ala Gly Ala Gly Val Ser Phe Phe Met Thr
            260                 265                 270 agc gcg gaa aac cgt aaa tgg tat agc ggc cat gct ggt atc cgc ggc      864
Ser Ala Glu Asn Arg Lys Trp Tyr Ser Gly His Ala Gly Ile Arg Gly
        275                 280                 285 att ggt ccg aac aaa gtt aat cag ctg gcg cac gcc cgc tac ttt ggc      912
Ile Gly Pro Asn Lys Val Asn Gln Leu Ala His Ala Arg Tyr Phe Gly
    290                 295                 300 gat gca gaa ggt gtc cgt gct gtg atg cgc aaa cat gca gct tcc ctg      960
Asp Ala Glu Gly Val Arg Ala Val Met Arg Lys His Ala Ala Ser Leu
305                 310                 315                 320 gcg ccg aaa ttc aat aaa gtg ctg gaa atc ctg gat agt cgt ctg gcg     1008
Ala Pro Lys Phe Asn Lys Val Leu Glu Ile Leu Asp Ser Arg Leu Ala
                325                 330                 335 gaa tat ggt gtt gca cag tgg acc gtc ccg gcc ggc ggt tac ttt att     1056
Glu Tyr Gly Val Ala Gln Trp Thr Val Pro Ala Gly Gly Tyr Phe Ile
            340                 345                 350 tcg ctg gac gtt gtc ccg ggt acg gca agc cgc gtt gcg gaa ctg gcc     1104
Ser Leu Asp Val Val Pro Gly Thr Ala Ser Arg Val Ala Glu Leu Ala
        355                 360                 365 aaa gaa gca ggc atc gct ctg acc ggc gcg ggt tca tcg tat ccg ctg     1152
Lys Glu Ala Gly Ile Ala Leu Thr Gly Ala Gly Ser Ser Tyr Pro Leu
    370                 375                 380 cgt caa gat ccg gaa aac aaa aat ctg cgt ctg gca ccg agc ctg ccg     1200
Arg Gln Asp Pro Glu Asn Lys Asn Leu Arg Leu Ala Pro Ser Leu Pro
385                 390                 395                 400 ccg gtg gaa gaa ctg gaa gtt gcg atg gat ggt gtg gct acc tgc gtg     1248
Pro Val Glu Glu Leu Glu Val Ala Met Asp Gly Val Ala Thr Cys Val
                405                 410                 415 ctg ctg gct gcc gcc gaa cat tat gct tct ctc gag tga                 1287
Leu Leu Ala Ala Ala Glu His Tyr Ala Ser Leu Glu
            420                 425
```

<210> SEQ ID NO 67
<211> LENGTH: 428
<212> TYPE: PRT
<213> ORGANISM: Corynebacterium glutamicum

<400> SEQUENCE: 67

```
Met Ser Ser Val Ser Leu Gln Asp Phe Asp Ala Glu Arg Ile Gly Leu
1               5                   10                  15
```

-continued

```
Phe His Glu Asp Ile Lys Arg Lys Phe Asp Glu Leu Lys Ser Lys Asn
             20                  25                  30

Leu Lys Leu Asp Leu Thr Arg Gly Lys Pro Ser Ser Glu Gln Leu Asp
         35                  40                  45

Phe Ala Asp Glu Leu Leu Ala Leu Pro Gly Lys Gly Asp Phe Lys Ala
     50                  55                  60

Ala Asp Gly Thr Asp Val Arg Asn Tyr Gly Gly Leu Asp Gly Ile Val
 65                  70                  75                  80

Asp Ile Arg Gln Ile Trp Ala Asp Leu Leu Gly Val Pro Val Glu Gln
                 85                  90                  95

Val Leu Ala Gly Asp Ala Ser Ser Leu Asn Ile Met Phe Asp Val Ile
             100                 105                 110

Ser Trp Ser Tyr Ile Phe Gly Asn Asn Asp Ser Val Gln Pro Trp Ser
         115                 120                 125

Lys Glu Glu Thr Val Lys Trp Ile Cys Pro Val Pro Gly Tyr Asp Arg
     130                 135                 140

His Phe Ser Ile Thr Glu Arg Phe Gly Phe Glu Met Ile Ser Val Pro
145                 150                 155                 160

Met Asn Glu Asp Gly Pro Asp Met Asp Ala Val Glu Glu Leu Val Lys
                 165                 170                 175

Asp Pro Gln Val Lys Gly Met Trp Val Val Pro Val Phe Ser Asn Pro
             180                 185                 190

Thr Gly Phe Thr Val Ser Glu Asp Val Ala Lys Arg Leu Ser Thr Met
         195                 200                 205

Glu Thr Ala Ala Pro Asp Phe Arg Val Val Trp Asp Asn Ala Tyr Ala
     210                 215                 220

Val His Thr Leu Thr Asp Glu Phe Pro Glu Val Ile Asp Ile Val Gly
225                 230                 235                 240

Leu Gly Glu Ala Ala Gly Asn Pro Asn Arg Phe Trp Ala Phe Thr Ser
                 245                 250                 255

Thr Ser Lys Ile Thr Leu Ala Gly Ala Gly Val Ser Phe Phe Met Thr
             260                 265                 270

Ser Ala Glu Asn Arg Lys Trp Tyr Ser Gly His Ala Gly Ile Arg Gly
         275                 280                 285

Ile Gly Pro Asn Lys Val Asn Gln Leu Ala His Ala Arg Tyr Phe Gly
     290                 295                 300

Asp Ala Glu Gly Val Arg Ala Val Met Arg Lys His Ala Ala Ser Leu
305                 310                 315                 320

Ala Pro Lys Phe Asn Lys Val Leu Glu Ile Leu Asp Ser Arg Leu Ala
                 325                 330                 335

Glu Tyr Gly Val Ala Gln Trp Thr Val Pro Ala Gly Gly Tyr Phe Ile
             340                 345                 350

Ser Leu Asp Val Val Pro Gly Thr Ala Ser Arg Val Ala Glu Leu Ala
         355                 360                 365

Lys Glu Ala Gly Ile Ala Leu Thr Gly Ala Gly Ser Ser Tyr Pro Leu
     370                 375                 380

Arg Gln Asp Pro Glu Asn Lys Asn Leu Arg Leu Ala Pro Ser Leu Pro
385                 390                 395                 400

Pro Val Glu Glu Leu Glu Val Ala Met Asp Gly Val Ala Thr Cys Val
                 405                 410                 415

Leu Leu Ala Ala Ala Glu His Tyr Ala Ser Leu Glu
             420                 425
```

<210> SEQ ID NO 68
<211> LENGTH: 1200
<212> TYPE: DNA
<213> ORGANISM: Thermus thermophilus
<220> FEATURE:
<221> NAME/KEY: CDS
<222> LOCATION: (1)..(1200)

<400> SEQUENCE: 68

| | | | | | | | | | | | | | | | | |
|---|---|---|---|---|---|---|---|---|---|---|---|---|---|---|---|---|
| atg | aaa | ccg | ctg | tcc | tgg | tct | gaa | gcg | ttc | ggc | aaa | ggt | gct | ggt | cgt | 48 |
| Met | Lys | Pro | Leu | Ser | Trp | Ser | Glu | Ala | Phe | Gly | Lys | Gly | Ala | Gly | Arg | |
| 1 | | | | 5 | | | | | 10 | | | | | 15 | | |
| atc | caa | gcc | tct | acc | att | cgt | gaa | ctg | ctg | aaa | ctg | acg | cag | cgc | ccg | 96 |
| Ile | Gln | Ala | Ser | Thr | Ile | Arg | Glu | Leu | Leu | Lys | Leu | Thr | Gln | Arg | Pro | |
| | | | 20 | | | | | 25 | | | | | 30 | | | |
| ggt | att | ctg | agc | ttt | gca | ggc | ggt | ctg | ccg | gct | ccg | gaa | ctg | ttc | ccg | 144 |
| Gly | Ile | Leu | Ser | Phe | Ala | Gly | Gly | Leu | Pro | Ala | Pro | Glu | Leu | Phe | Pro | |
| | | 35 | | | | | 40 | | | | | 45 | | | | |
| aaa | gaa | gaa | gcg | gcc | gaa | gca | gct | gcg | cgt | atc | ctg | cgt | gaa | aaa | ggt | 192 |
| Lys | Glu | Glu | Ala | Ala | Glu | Ala | Ala | Ala | Arg | Ile | Leu | Arg | Glu | Lys | Gly | |
| 50 | | | | | 55 | | | | | 60 | | | | | | |
| gaa | gtt | gca | ctg | caa | tat | agc | ccg | acc | gaa | ggt | tac | gct | ccg | ctg | cgt | 240 |
| Glu | Val | Ala | Leu | Gln | Tyr | Ser | Pro | Thr | Glu | Gly | Tyr | Ala | Pro | Leu | Arg | |
| 65 | | | | | 70 | | | | | 75 | | | | | 80 | |
| gca | ttt | gtc | gct | gaa | tgg | att | ggt | gtt | cgt | ccg | gaa | gaa | gtc | ctg | atc | 288 |
| Ala | Phe | Val | Ala | Glu | Trp | Ile | Gly | Val | Arg | Pro | Glu | Glu | Val | Leu | Ile | |
| | | | | 85 | | | | | 90 | | | | | 95 | | |
| acc | acg | ggc | tct | cag | caa | gcg | ctg | gat | ctg | gtg | ggt | aaa | gtt | ttc | ctg | 336 |
| Thr | Thr | Gly | Ser | Gln | Gln | Ala | Leu | Asp | Leu | Val | Gly | Lys | Val | Phe | Leu | |
| | | | 100 | | | | | 105 | | | | | 110 | | | |
| gac | gaa | ggc | agt | ccg | gtt | ctg | ctg | gaa | gcc | ccg | tcc | tat | atg | ggt | gcg | 384 |
| Asp | Glu | Gly | Ser | Pro | Val | Leu | Leu | Glu | Ala | Pro | Ser | Tyr | Met | Gly | Ala | |
| | | | 115 | | | | | 120 | | | | | 125 | | | |
| att | cag | gcc | ttt | cgc | ctg | caa | ggt | ccg | cgt | ttc | ctg | acc | gtc | ccg | gca | 432 |
| Ile | Gln | Ala | Phe | Arg | Leu | Gln | Gly | Pro | Arg | Phe | Leu | Thr | Val | Pro | Ala | |
| | | 130 | | | | | 135 | | | | | 140 | | | | |
| ggt | gaa | gaa | ggc | ccg | gat | ctg | gac | gct | ctg | gaa | gaa | gtg | ctg | aaa | cgt | 480 |
| Gly | Glu | Glu | Gly | Pro | Asp | Leu | Asp | Ala | Leu | Glu | Glu | Val | Leu | Lys | Arg | |
| 145 | | | | | 150 | | | | | 155 | | | | | 160 | |
| gaa | cgc | ccg | cgt | ttt | ctg | tac | ctg | atc | ccg | agc | ttc | cag | aac | ccg | acc | 528 |
| Glu | Arg | Pro | Arg | Phe | Leu | Tyr | Leu | Ile | Pro | Ser | Phe | Gln | Asn | Pro | Thr | |
| | | | | 165 | | | | | 170 | | | | | 175 | | |
| ggc | ggt | ctg | acg | ccg | ctg | ccg | gca | cgt | aaa | cgt | ctg | ctg | caa | atg | gtg | 576 |
| Gly | Gly | Leu | Thr | Pro | Leu | Pro | Ala | Arg | Lys | Arg | Leu | Leu | Gln | Met | Val | |
| | | | 180 | | | | | 185 | | | | | 190 | | | |
| atg | gaa | cgt | ggt | ctg | gtg | gtt | gtc | gaa | gat | gac | gcg | tat | cgc | gaa | ctg | 624 |
| Met | Glu | Arg | Gly | Leu | Val | Val | Val | Glu | Asp | Asp | Ala | Tyr | Arg | Glu | Leu | |
| | | | 195 | | | | | 200 | | | | | 205 | | | |
| tac | ttt | ggc | gaa | gcc | cgt | ctg | ccg | tca | ctg | ttc | gaa | ctg | gca | cgc | gaa | 672 |
| Tyr | Phe | Gly | Glu | Ala | Arg | Leu | Pro | Ser | Leu | Phe | Glu | Leu | Ala | Arg | Glu | |
| | | 210 | | | | | 215 | | | | | 220 | | | | |
| gct | ggt | tat | ccg | ggc | gtg | att | tac | ctg | ggt | agc | ttt | tct | aaa | gtt | ctg | 720 |
| Ala | Gly | Tyr | Pro | Gly | Val | Ile | Tyr | Leu | Gly | Ser | Phe | Ser | Lys | Val | Leu | |
| 225 | | | | | 230 | | | | | 235 | | | | | 240 | |
| tcg | ccg | ggt | ctg | cgt | gtg | gca | ttc | gca | gtt | gct | cat | ccg | gaa | gcg | ctg | 768 |
| Ser | Pro | Gly | Leu | Arg | Val | Ala | Phe | Ala | Val | Ala | His | Pro | Glu | Ala | Leu | |
| | | | | 245 | | | | | 250 | | | | | 255 | | |
| caa | aaa | ctg | gtt | cag | gcg | aaa | caa | ggt | gcc | gat | ctg | cat | acc | ccg | atg | 816 |
| Gln | Lys | Leu | Val | Gln | Ala | Lys | Gln | Gly | Ala | Asp | Leu | His | Thr | Pro | Met | |
| | | | 260 | | | | | 265 | | | | | 270 | | | |
| ctg | aac | caa | atg | ctg | gtg | cac | gaa | ctg | ctg | aaa | gaa | ggc | ttt | tct | gaa | 864 |

```
                Leu Asn Gln Met Leu Val His Glu Leu Leu Lys Gly Phe Ser Glu
                            275                 280                 285 cgt ctg gaa cgt gtc cgt cgc gtg tat cgc gaa aaa gcg cag gcc atg         912
Arg Leu Glu Arg Val Arg Arg Val Tyr Arg Glu Lys Ala Gln Ala Met
290                 295                 300 ctg cac gca ctg gac cgt gaa gtc ccg aaa gaa gtg cgc tac acg cgt         960
Leu His Ala Leu Asp Arg Glu Val Pro Lys Glu Val Arg Tyr Thr Arg
305                 310                 315                 320 ccg aaa ggc ggt atg ttt gtg tgg atg gaa ctg ccg aaa ggt ctg agt        1008
Pro Lys Gly Gly Met Phe Val Trp Met Glu Leu Pro Lys Gly Leu Ser
                325                 330                 335 gcc gaa ggc ctg ttt cgt cgc gcg ctg gaa gaa aat gtt gcc ttc gtc        1056
Ala Glu Gly Leu Phe Arg Arg Ala Leu Glu Glu Asn Val Ala Phe Val
            340                 345                 350 ccg ggc ggt ccg ttt ttc gca aac ggc ggt ggc gaa aat acc ctg cgc        1104
Pro Gly Gly Pro Phe Phe Ala Asn Gly Gly Gly Glu Asn Thr Leu Arg
        355                 360                 365 ctg tcc tat gca acg ctg gat cgt gaa ggc atc gcc gaa ggt gtc cgc        1152
Leu Ser Tyr Ala Thr Leu Asp Arg Glu Gly Ile Ala Glu Gly Val Arg
370                 375                 380 cgc ctg ggt cgt gct ctg aaa ggt ctg ctg gcc ctg gtt ctc gag tga        1200
Arg Leu Gly Arg Ala Leu Lys Gly Leu Leu Ala Leu Val Leu Glu
385                 390                 395

<210> SEQ ID NO 69
<211> LENGTH: 399
<212> TYPE: PRT
<213> ORGANISM: Thermus thermophilus

<400> SEQUENCE: 69

Met Lys Pro Leu Ser Trp Ser Glu Ala Phe Gly Lys Gly Ala Gly Arg
1               5                   10                  15

Ile Gln Ala Ser Thr Ile Arg Glu Leu Leu Lys Leu Thr Gln Arg Pro
            20                  25                  30

Gly Ile Leu Ser Phe Ala Gly Gly Leu Pro Ala Pro Glu Leu Phe Pro
        35                  40                  45

Lys Glu Glu Ala Ala Glu Ala Ala Arg Ile Leu Arg Glu Lys Gly
    50                  55                  60

Glu Val Ala Leu Gln Tyr Ser Pro Thr Glu Gly Tyr Ala Pro Leu Arg
65                  70                  75                  80

Ala Phe Val Ala Glu Trp Ile Gly Val Arg Pro Glu Glu Val Leu Ile
                85                  90                  95

Thr Thr Gly Ser Gln Gln Ala Leu Asp Leu Val Gly Lys Val Phe Leu
            100                 105                 110

Asp Glu Gly Ser Pro Val Leu Leu Glu Ala Pro Ser Tyr Met Gly Ala
        115                 120                 125

Ile Gln Ala Phe Arg Leu Gln Gly Pro Arg Phe Leu Thr Val Pro Ala
    130                 135                 140

Gly Glu Glu Gly Pro Asp Leu Asp Ala Leu Glu Glu Val Leu Lys Arg
145                 150                 155                 160

Glu Arg Pro Arg Phe Leu Tyr Leu Ile Pro Ser Phe Gln Asn Pro Thr
                165                 170                 175

Gly Gly Leu Thr Pro Leu Pro Ala Arg Lys Arg Leu Leu Gln Met Val
            180                 185                 190

Met Glu Arg Gly Leu Val Val Val Glu Asp Asp Ala Tyr Arg Glu Leu
        195                 200                 205

Tyr Phe Gly Glu Ala Arg Leu Pro Ser Leu Phe Glu Leu Ala Arg Glu
```

```
                  210                 215                 220
Ala Gly Tyr Pro Gly Val Ile Tyr Leu Gly Ser Phe Ser Lys Val Leu
225                 230                 235                 240

Ser Pro Gly Leu Arg Val Ala Phe Ala Val Ala His Pro Glu Ala Leu
                245                 250                 255

Gln Lys Leu Val Gln Ala Lys Gln Gly Ala Asp Leu His Thr Pro Met
            260                 265                 270

Leu Asn Gln Met Leu Val His Glu Leu Lys Glu Gly Phe Ser Glu
        275                 280                 285

Arg Leu Glu Arg Val Arg Val Tyr Arg Glu Lys Ala Gln Ala Met
290                 295                 300

Leu His Ala Leu Asp Arg Glu Val Pro Lys Glu Val Arg Tyr Thr Arg
305                 310                 315                 320

Pro Lys Gly Gly Met Phe Val Trp Met Glu Leu Pro Lys Gly Leu Ser
                325                 330                 335

Ala Glu Gly Leu Phe Arg Arg Ala Leu Glu Glu Asn Val Ala Phe Val
            340                 345                 350

Pro Gly Gly Pro Phe Phe Ala Asn Gly Gly Glu Asn Thr Leu Arg
        355                 360                 365

Leu Ser Tyr Ala Thr Leu Asp Arg Glu Gly Ile Ala Glu Gly Val Arg
370                 375                 380

Arg Leu Gly Arg Ala Leu Lys Gly Leu Leu Ala Leu Val Leu Glu
385                 390                 395

<210> SEQ ID NO 70
<211> LENGTH: 1248
<212> TYPE: DNA
<213> ORGANISM: Thermotoga maritima
<220> FEATURE:
<221> NAME/KEY: CDS
<222> LOCATION: (1)..(1248)

<400> SEQUENCE: 70 atg gtc gtc aat ctg gaa ggt aaa atc tct aaa atc ggt caa aat atg      48
Met Val Val Asn Leu Glu Gly Lys Ile Ser Lys Ile Gly Gln Asn Met
1               5                   10                  15 aaa tcg agc att atc cgt gaa atc ctg aaa ttc gct gcg gat aaa gac      96
Lys Ser Ser Ile Ile Arg Glu Ile Leu Lys Phe Ala Ala Asp Lys Asp
            20                  25                  30 gcg att agc ttt ggc ggt ggc gtg ccg gat ccg gaa acc ttc ccg cgt     144
Ala Ile Ser Phe Gly Gly Gly Val Pro Asp Pro Glu Thr Phe Pro Arg
        35                  40                  45 aaa gaa ctg gca gaa atc gct aaa gaa atc atc gaa aaa gaa tac cat     192
Lys Glu Leu Ala Glu Ile Ala Lys Glu Ile Ile Glu Lys Glu Tyr His
    50                  55                  60 tac acc ctg caa tac tct acc acg gaa ggc gat ccg gtt ctg aaa cag     240
Tyr Thr Leu Gln Tyr Ser Thr Thr Glu Gly Asp Pro Val Leu Lys Gln
65                  70                  75                  80 caa att ctg aaa ctg ctg gaa cgt atg tac ggt att acc ggc ctg gat     288
Gln Ile Leu Lys Leu Leu Glu Arg Met Tyr Gly Ile Thr Gly Leu Asp
                85                  90                  95 gaa gac aac ctg atc ttt acg gtc ggc tca cag caa gcc ctg gat ctg     336
Glu Asp Asn Leu Ile Phe Thr Val Gly Ser Gln Gln Ala Leu Asp Leu
            100                 105                 110 att ggt aaa ctg ttc ctg gat gac gaa tcg tat tgc gtt ctg gat gac     384
Ile Gly Lys Leu Phe Leu Asp Asp Glu Ser Tyr Cys Val Leu Asp Asp
        115                 120                 125 ccg gca tac ctg ggt gca atc aac gca ttt cgc cag tat ctg gcc aat     432
```

```
                  Pro Ala Tyr Leu Gly Ala Ile Asn Ala Phe Arg Gln Tyr Leu Ala Asn
                      130                 135                 140 ttc gtg gtt gtc ccg ctg gaa gat gac ggc atg gat ctg aac gtg ctg            480
Phe Val Val Val Pro Leu Glu Asp Asp Gly Met Asp Leu Asn Val Leu
145                 150                 155                 160 gaa cgt aaa ctg tca gaa ttt gac aaa aac ggt aaa atc aaa caa gtt            528
Glu Arg Lys Leu Ser Glu Phe Asp Lys Asn Gly Lys Ile Lys Gln Val
                165                 170                 175 aaa ttc atc tac gtg gtt agc aac ttc cat aat ccg gca ggt gtg acc            576
Lys Phe Ile Tyr Val Val Ser Asn Phe His Asn Pro Ala Gly Val Thr
            180                 185                 190 acg tct ctg gaa aaa cgc aaa gcg ctg gtt gaa att gcc gaa aaa tac            624
Thr Ser Leu Glu Lys Arg Lys Ala Leu Val Glu Ile Ala Glu Lys Tyr
        195                 200                 205 gac ctg ttt atc gtc gaa gat gac ccg tat ggc gct ctg cgc tac gaa            672
Asp Leu Phe Ile Val Glu Asp Asp Pro Tyr Gly Ala Leu Arg Tyr Glu
    210                 215                 220 ggt gaa acc gtg gac ccg att ttt aaa atc ggt ggc ccg gaa cgt gtc            720
Gly Glu Thr Val Asp Pro Ile Phe Lys Ile Gly Gly Pro Glu Arg Val
225                 230                 235                 240 gtg ctg ctg aac acg ttc agt aaa gtt ctg gca ccg ggt ctg cgc att            768
Val Leu Leu Asn Thr Phe Ser Lys Val Leu Ala Pro Gly Leu Arg Ile
                245                 250                 255 ggc atg gtc gct ggt tcc aaa gaa ttc atc cgt aaa atc gtt cag gca            816
Gly Met Val Ala Gly Ser Lys Glu Phe Ile Arg Lys Ile Val Gln Ala
            260                 265                 270 aaa caa agt gct gat ctg tgc tcc ccg gca att acc cac cgt ctg gca            864
Lys Gln Ser Ala Asp Leu Cys Ser Pro Ala Ile Thr His Arg Leu Ala
        275                 280                 285 gca cgc tat ctg gaa cgt tac gac ctg ctg gaa cag ctg aaa ccg acc            912
Ala Arg Tyr Leu Glu Arg Tyr Asp Leu Leu Glu Gln Leu Lys Pro Thr
    290                 295                 300 atc gaa ctg tat cgt cgc aaa cgc acg gtg atg ctg aat gca ctg gaa            960
Ile Glu Leu Tyr Arg Arg Lys Arg Thr Val Met Leu Asn Ala Leu Glu
305                 310                 315                 320 gaa tac ttt tca gat att ccg ggc gtt aaa tgg gtc aaa tcg gaa ggt           1008
Glu Tyr Phe Ser Asp Ile Pro Gly Val Lys Trp Val Lys Ser Glu Gly
                325                 330                 335 ggc ctg ttc atc tgg ctg acc ctg ccg gaa ggt ttt gat acg tgg gaa           1056
Gly Leu Phe Ile Trp Leu Thr Leu Pro Glu Gly Phe Asp Thr Trp Glu
            340                 345                 350 atg ttc gaa tat gcc aaa cgc aaa aaa gtg ttt tac gtt ccg ggt cgt           1104
Met Phe Glu Tyr Ala Lys Arg Lys Lys Val Phe Tyr Val Pro Gly Arg
        355                 360                 365 gtc ttc aaa gtg tat gat gaa ccg agc ccg tct atg cgt ctg tcc ttt           1152
Val Phe Lys Val Tyr Asp Glu Pro Ser Pro Ser Met Arg Leu Ser Phe
    370                 375                 380 tgt ctg ccg ccg gac gaa aaa atc gtg gaa ggc atc aaa cgt ctg cgt           1200
Cys Leu Pro Pro Asp Glu Lys Ile Val Glu Gly Ile Lys Arg Leu Arg
385                 390                 395                 400 gaa gtt gtg ctg gaa tac ggt aaa gaa aaa cat ctg ctg ctc gag tga           1248
Glu Val Val Leu Glu Tyr Gly Lys Glu Lys His Leu Leu Leu Glu
                405                 410                 415
```

<210> SEQ ID NO 71
<211> LENGTH: 415
<212> TYPE: PRT
<213> ORGANISM: Thermotoga maritima

<400> SEQUENCE: 71

```
Met Val Val Asn Leu Glu Gly Lys Ile Ser Lys Ile Gly Gln Asn Met
1               5                   10                  15

Lys Ser Ser Ile Ile Arg Glu Ile Leu Lys Phe Ala Ala Asp Lys Asp
            20                  25                  30

Ala Ile Ser Phe Gly Gly Val Pro Asp Pro Glu Thr Phe Pro Arg
            35              40                  45

Lys Glu Leu Ala Glu Ile Ala Lys Glu Ile Ile Glu Lys Glu Tyr His
        50                  55                  60

Tyr Thr Leu Gln Tyr Ser Thr Thr Glu Gly Asp Pro Val Leu Lys Gln
65                  70                  75                  80

Gln Ile Leu Lys Leu Leu Glu Arg Met Tyr Gly Ile Thr Gly Leu Asp
                85                  90                  95

Glu Asp Asn Leu Ile Phe Thr Val Gly Ser Gln Gln Ala Leu Asp Leu
            100                 105                 110

Ile Gly Lys Leu Phe Leu Asp Asp Glu Ser Tyr Cys Val Leu Asp Asp
            115                 120                 125

Pro Ala Tyr Leu Gly Ala Ile Asn Ala Phe Arg Gln Tyr Leu Ala Asn
    130                 135                 140

Phe Val Val Pro Leu Glu Asp Asp Gly Met Asp Leu Asn Val Leu
145                 150                 155                 160

Glu Arg Lys Leu Ser Glu Phe Asp Lys Asn Gly Lys Ile Lys Gln Val
                165                 170                 175

Lys Phe Ile Tyr Val Val Ser Asn Phe His Asn Pro Ala Gly Val Thr
                180                 185                 190

Thr Ser Leu Glu Lys Arg Lys Ala Leu Val Glu Ile Ala Glu Lys Tyr
        195                 200                 205

Asp Leu Phe Ile Val Glu Asp Asp Pro Tyr Gly Ala Leu Arg Tyr Glu
    210                 215                 220

Gly Glu Thr Val Asp Pro Ile Phe Lys Ile Gly Gly Pro Glu Arg Val
225                 230                 235                 240

Val Leu Leu Asn Thr Phe Ser Lys Val Leu Ala Pro Gly Leu Arg Ile
                245                 250                 255

Gly Met Val Ala Gly Ser Lys Glu Phe Ile Arg Lys Ile Val Gln Ala
            260                 265                 270

Lys Gln Ser Ala Asp Leu Cys Ser Pro Ala Ile Thr His Arg Leu Ala
        275                 280                 285

Ala Arg Tyr Leu Glu Arg Tyr Asp Leu Leu Glu Gln Leu Lys Pro Thr
    290                 295                 300

Ile Glu Leu Tyr Arg Arg Lys Arg Thr Val Met Leu Asn Ala Leu Glu
305                 310                 315                 320

Glu Tyr Phe Ser Asp Ile Pro Gly Val Lys Trp Val Lys Ser Glu Gly
                325                 330                 335

Gly Leu Phe Ile Trp Leu Thr Leu Pro Glu Gly Phe Asp Thr Trp Glu
            340                 345                 350

Met Phe Glu Tyr Ala Lys Arg Lys Lys Val Phe Tyr Val Pro Gly Arg
        355                 360                 365

Val Phe Lys Val Tyr Asp Glu Pro Ser Pro Ser Met Arg Leu Ser Phe
    370                 375                 380

Cys Leu Pro Pro Asp Glu Lys Ile Val Glu Gly Ile Lys Arg Leu Arg
385                 390                 395                 400

Glu Val Val Leu Glu Tyr Gly Lys Glu Lys His Leu Leu Leu Glu
                405                 410                 415
```

<210> SEQ ID NO 72
<211> LENGTH: 1218
<212> TYPE: DNA
<213> ORGANISM: Pyrococcus horikoshii
<220> FEATURE:
<221> NAME/KEY: CDS
<222> LOCATION: (1)..(1218)

<400> SEQUENCE: 72

```
atg ctg ggc gat gtg gaa cgc ttc ttc tcg aaa aaa gct ctg gaa atg      48
Met Leu Gly Asp Val Glu Arg Phe Phe Ser Lys Lys Ala Leu Glu Met
 1               5                  10                  15 cgt gcg tct gaa gtc cgt gaa ctg ctg aaa ctg gtg gaa acc agt gat      96
Arg Ala Ser Glu Val Arg Glu Leu Leu Lys Leu Val Glu Thr Ser Asp
             20                  25                  30 att atc tcc ctg gcg ggc ggt ctg ccg aac ccg aaa acg ttc ccg aaa     144
Ile Ile Ser Leu Ala Gly Gly Leu Pro Asn Pro Lys Thr Phe Pro Lys
         35                  40                  45 gaa att atc cgt gat atc ctg gtt gaa atc atg gaa aaa tat gca gac     192
Glu Ile Ile Arg Asp Ile Leu Val Glu Ile Met Glu Lys Tyr Ala Asp
     50                  55                  60 aaa gct ctg caa tac ggc acc acg aaa ggt ttt acc ccg ctg cgt gaa     240
Lys Ala Leu Gln Tyr Gly Thr Thr Lys Gly Phe Thr Pro Leu Arg Glu
 65                  70                  75                  80 acg ctg atg aaa tgg ctg ggc aaa cgc tat ggt att tcc cag gat aat     288
Thr Leu Met Lys Trp Leu Gly Lys Arg Tyr Gly Ile Ser Gln Asp Asn
                 85                  90                  95 gac att atg atc acc agc ggt tct cag caa gcc ctg gat ctg att ggc     336
Asp Ile Met Ile Thr Ser Gly Ser Gln Gln Ala Leu Asp Leu Ile Gly
            100                 105                 110 cgc gtg ttc ctg aac ccg ggt gac atc gtg gtt gtc gaa gca ccg acc     384
Arg Val Phe Leu Asn Pro Gly Asp Ile Val Val Val Glu Ala Pro Thr
        115                 120                 125 tac ctg gcg gcc ctg caa gct ttt aat ttc tat gaa ccg cag tac att     432
Tyr Leu Ala Ala Leu Gln Ala Phe Asn Phe Tyr Glu Pro Gln Tyr Ile
    130                 135                 140 caa atc ccg ctg gat gac gaa ggc atg aaa gtt gaa atc ctg gaa gaa     480
Gln Ile Pro Leu Asp Asp Glu Gly Met Lys Val Glu Ile Leu Glu Glu
145                 150                 155                 160 aaa ctg aaa gaa ctg aaa agc cag ggt aaa aaa gtc aaa gtg gtt tat     528
Lys Leu Lys Glu Leu Lys Ser Gln Gly Lys Lys Val Lys Val Val Tyr
                165                 170                 175 acc gtg ccg acg ttc caa aac ccg gcg ggt gtg acc atg aat gaa gat     576
Thr Val Pro Thr Phe Gln Asn Pro Ala Gly Val Thr Met Asn Glu Asp
            180                 185                 190 cgt cgc aaa tat ctg ctg gaa ctg gcc tca gaa tac gac ttt atc gtc     624
Arg Arg Lys Tyr Leu Leu Glu Leu Ala Ser Glu Tyr Asp Phe Ile Val
        195                 200                 205 gtg gaa gat gac ccg tat ggc gaa ctg cgt tac tcg ggt aac ccg gaa     672
Val Glu Asp Asp Pro Tyr Gly Glu Leu Arg Tyr Ser Gly Asn Pro Glu
    210                 215                 220 aag aaa att aaa gcc ctg gat aat gaa ggc cgc gtt atc tac ctg ggt     720
Lys Lys Ile Lys Ala Leu Asp Asn Glu Gly Arg Val Ile Tyr Leu Gly
225                 230                 235                 240 acc ttt agc aaa att ctg gca ccg ggc ttc cgt atc ggt tgg atg gtc     768
Thr Phe Ser Lys Ile Leu Ala Pro Gly Phe Arg Ile Gly Trp Met Val
                245                 250                 255 ggc gat ccg ggt att atc cgc aaa atg gaa att gca aaa cag tct acc     816
Gly Asp Pro Gly Ile Ile Arg Lys Met Glu Ile Ala Lys Gln Ser Thr
            260                 265                 270 gac ctg tgc acg aac gtt ttt ggc caa gtt gtc gct tgg cgt tat gtc     864
Asp Leu Cys Thr Asn Val Phe Gly Gln Val Val Ala Trp Arg Tyr Val
```

```
Asp Leu Cys Thr Asn Val Phe Gly Gln Val Val Ala Trp Arg Tyr Val
            275                 280                 285 gat ggc ggt tac ctg gaa aaa cat att ccg gaa atc cgc aaa ttt tat      912
Asp Gly Gly Tyr Leu Glu Lys His Ile Pro Glu Ile Arg Lys Phe Tyr
        290                 295                 300 aaa ccg cgt cgc gat gca atg ctg gaa gct ctg gaa gaa ttc atg ccg      960
Lys Pro Arg Arg Asp Ala Met Leu Glu Ala Leu Glu Glu Phe Met Pro
305                 310                 315                 320 gaa ggt gtc aaa tgg acc aaa ccg gaa ggc ggt atg ttt att tgg gtg     1008
Glu Gly Val Lys Trp Thr Lys Pro Glu Gly Gly Met Phe Ile Trp Val
                325                 330                 335 acg ctg ccg gat ggc atc gac agc aag aaa atg ctg gaa cgt gcg atc     1056
Thr Leu Pro Asp Gly Ile Asp Ser Lys Lys Met Leu Glu Arg Ala Ile
            340                 345                 350 aaa aaa ggc gtg gcc tat gtt ccg ggt gaa gcg ttt tac gcc cac cgt     1104
Lys Lys Gly Val Ala Tyr Val Pro Gly Glu Ala Phe Tyr Ala His Arg
        355                 360                 365 gat gtg aaa aac acc atg cgc ctg aat ttc acg tat gtt gac gaa gac     1152
Asp Val Lys Asn Thr Met Arg Leu Asn Phe Thr Tyr Val Asp Glu Asp
370                 375                 380 aaa atc atg gaa ggt atc aaa cgc ctg gca gaa acg atc aaa gaa gaa     1200
Lys Ile Met Glu Gly Ile Lys Arg Leu Ala Glu Thr Ile Lys Glu Glu
385                 390                 395                 400 ctg aaa gcg ctc gag tga                                             1218
Leu Lys Ala Leu Glu
            405

<210> SEQ ID NO 73
<211> LENGTH: 405
<212> TYPE: PRT
<213> ORGANISM: Pyrococcus horikoshii

<400> SEQUENCE: 73

Met Leu Gly Asp Val Glu Arg Phe Phe Ser Lys Lys Ala Leu Glu Met
1               5                   10                  15

Arg Ala Ser Glu Val Arg Glu Leu Leu Lys Leu Val Glu Thr Ser Asp
            20                  25                  30

Ile Ile Ser Leu Ala Gly Gly Leu Pro Asn Pro Lys Thr Phe Pro Lys
        35                  40                  45

Glu Ile Ile Arg Asp Ile Leu Val Glu Ile Met Glu Lys Tyr Ala Asp
    50                  55                  60

Lys Ala Leu Gln Tyr Gly Thr Thr Lys Gly Phe Thr Pro Leu Arg Glu
65                  70                  75                  80

Thr Leu Met Lys Trp Leu Gly Lys Arg Tyr Gly Ile Ser Gln Asp Asn
                85                  90                  95

Asp Ile Met Ile Thr Ser Gly Ser Gln Gln Ala Leu Asp Leu Ile Gly
            100                 105                 110

Arg Val Phe Leu Asn Pro Gly Asp Ile Val Val Glu Ala Pro Thr
        115                 120                 125

Tyr Leu Ala Ala Leu Gln Ala Phe Asn Phe Tyr Glu Pro Gln Tyr Ile
    130                 135                 140

Gln Ile Pro Leu Asp Asp Glu Gly Met Lys Val Glu Ile Leu Glu Glu
145                 150                 155                 160

Lys Leu Lys Glu Leu Lys Ser Gln Gly Lys Lys Val Lys Val Val Tyr
                165                 170                 175

Thr Val Pro Thr Phe Gln Asn Pro Ala Gly Val Thr Met Asn Glu Asp
            180                 185                 190
```

```
Arg Arg Lys Tyr Leu Leu Glu Leu Ala Ser Glu Tyr Asp Phe Ile Val
        195                 200                 205

Val Glu Asp Asp Pro Tyr Gly Glu Leu Arg Tyr Ser Gly Asn Pro Glu
210                 215                 220

Lys Lys Ile Lys Ala Leu Asp Asn Glu Gly Arg Val Ile Tyr Leu Gly
225                 230                 235                 240

Thr Phe Ser Lys Ile Leu Ala Pro Gly Phe Arg Ile Gly Trp Met Val
                245                 250                 255

Gly Asp Pro Gly Ile Ile Arg Lys Met Glu Ile Ala Lys Gln Ser Thr
            260                 265                 270

Asp Leu Cys Thr Asn Val Phe Gly Gln Val Val Ala Trp Arg Tyr Val
        275                 280                 285

Asp Gly Gly Tyr Leu Glu Lys His Ile Pro Glu Ile Arg Lys Phe Tyr
290                 295                 300

Lys Pro Arg Arg Asp Ala Met Leu Glu Ala Leu Glu Glu Phe Met Pro
305                 310                 315                 320

Glu Gly Val Lys Trp Thr Lys Pro Glu Gly Met Phe Ile Trp Val
                325                 330                 335

Thr Leu Pro Asp Gly Ile Asp Ser Lys Lys Met Leu Glu Arg Ala Ile
            340                 345                 350

Lys Lys Gly Val Ala Tyr Val Pro Gly Glu Ala Phe Tyr Ala His Arg
        355                 360                 365

Asp Val Lys Asn Thr Met Arg Leu Asn Phe Thr Tyr Val Asp Glu Asp
370                 375                 380

Lys Ile Met Glu Gly Ile Lys Arg Leu Ala Glu Thr Ile Lys Glu Glu
385                 390                 395                 400

Leu Lys Ala Leu Glu
                405

<210> SEQ ID NO 74
<211> LENGTH: 1173
<212> TYPE: DNA
<213> ORGANISM: Phormidium lapideum
<220> FEATURE:
<221> NAME/KEY: CDS
<222> LOCATION: (1)..(1173)

<400> SEQUENCE: 74 atg aaa ctg gct gcc cgt gtt gaa agt gtg tcc ccg agt atg acc ctg      48
Met Lys Leu Ala Ala Arg Val Glu Ser Val Ser Pro Ser Met Thr Leu
1               5                   10                  15 att att gat gcg aaa gca aaa gcg atg aaa gcg gaa ggc att gat gtg      96
Ile Ile Asp Ala Lys Ala Lys Ala Met Lys Ala Glu Gly Ile Asp Val
            20                  25                  30 tgc agt ttt tcc gcc ggt gaa ccg gac ttc aac acg ccg aaa cat atc     144
Cys Ser Phe Ser Ala Gly Glu Pro Asp Phe Asn Thr Pro Lys His Ile
        35                  40                  45 gtt gaa gcg gcc aaa gca gct ctg gaa cag ggt aaa acc cgt tat ggt     192
Val Glu Ala Ala Lys Ala Ala Leu Glu Gln Gly Lys Thr Arg Tyr Gly
    50                  55                  60 ccg gcg gcc ggt gaa ccg cgt ctg cgt gaa gcg att gcc cag aaa ctg     240
Pro Ala Ala Gly Glu Pro Arg Leu Arg Glu Ala Ile Ala Gln Lys Leu
65                  70                  75                  80 caa cgt gat aac ggc ctg tgt tac ggt gcg gac aac atc ctg gtt acc     288
Gln Arg Asp Asn Gly Leu Cys Tyr Gly Ala Asp Asn Ile Leu Val Thr
                85                  90                  95 aat ggc ggt aaa cag agt att ttt aat ctg atg ctg gcg atg atc gaa     336
Asn Gly Gly Lys Gln Ser Ile Phe Asn Leu Met Leu Ala Met Ile Glu
```

```
              100                 105                 110
ccg ggt gat gaa gtg att atc ccg gcc ccg ttc tgg gtc tcc tat ccg     384
Pro Gly Asp Glu Val Ile Ile Pro Ala Pro Phe Trp Val Ser Tyr Pro
        115                 120                 125 gaa atg gtg aaa ctg gcc gaa ggc acg ccg gtt att ctg ccg acc acg     432
Glu Met Val Lys Leu Ala Glu Gly Thr Pro Val Ile Leu Pro Thr Thr
130                 135                 140 gtc gaa acc cag ttt aaa gtg agc ccg gaa cag att cgc caa gcg atc     480
Val Glu Thr Gln Phe Lys Val Ser Pro Glu Gln Ile Arg Gln Ala Ile
145                 150                 155                 160 acc ccg aaa acg aaa ctg ctg gtt ttc aac acc ccg tct aat ccg acg     528
Thr Pro Lys Thr Lys Leu Leu Val Phe Asn Thr Pro Ser Asn Pro Thr
                165                 170                 175 ggt atg gtt tac acc ccg gat gaa gtc cgt gca att gct cag gtc gca     576
Gly Met Val Tyr Thr Pro Asp Glu Val Arg Ala Ile Ala Gln Val Ala
                180                 185                 190 gtg gaa gca ggt ctg tgg gtg ctg agt gat gaa atc tac gaa aaa atc     624
Val Glu Ala Gly Leu Trp Val Leu Ser Asp Glu Ile Tyr Glu Lys Ile
                195                 200                 205 ctg tac gat gac gca caa cat ctg agt atc ggt gca gct tcc ccg gaa     672
Leu Tyr Asp Asp Ala Gln His Leu Ser Ile Gly Ala Ala Ser Pro Glu
210                 215                 220 gcg tat gaa cgc agc gtg gtt tgc tct ggc ttt gcg aaa acc tac gcc     720
Ala Tyr Glu Arg Ser Val Val Cys Ser Gly Phe Ala Lys Thr Tyr Ala
225                 230                 235                 240 atg acg ggt tgg cgt gtt ggt ttc ctg gca ggt ccg gtt ccg ctg gtc     768
Met Thr Gly Trp Arg Val Gly Phe Leu Ala Gly Pro Val Pro Leu Val
                245                 250                 255 aaa gca gcc acc aaa att cag ggt cac tca acg tcg aac gtc tgc acc     816
Lys Ala Ala Thr Lys Ile Gln Gly His Ser Thr Ser Asn Val Cys Thr
                260                 265                 270 ttt gca caa tat ggc gct atc gca gct tac gaa aat tct cag gat tgt     864
Phe Ala Gln Tyr Gly Ala Ile Ala Ala Tyr Glu Asn Ser Gln Asp Cys
                275                 280                 285 gtg caa gaa atg ctg gcg gcc ttt gcg gaa cgt cgc cgt tat atg ctg     912
Val Gln Glu Met Leu Ala Ala Phe Ala Glu Arg Arg Arg Tyr Met Leu
290                 295                 300 gat gca ctg aat gct atg ccg ggt ctg gaa tgt ccg aaa ccg gac ggc     960
Asp Ala Leu Asn Ala Met Pro Gly Leu Glu Cys Pro Lys Pro Asp Gly
305                 310                 315                 320 gcg ttt tac atg ttc ccg tca att gcc aaa acc ggt cgc agc tct ctg    1008
Ala Phe Tyr Met Phe Pro Ser Ile Ala Lys Thr Gly Arg Ser Ser Leu
                325                 330                 335 gat ttt tgc tcg gaa ctg ctg gac cag cac caa gtg gca acg gtt ccg    1056
Asp Phe Cys Ser Glu Leu Leu Asp Gln His Gln Val Ala Thr Val Pro
                340                 345                 350 ggt gca gct ttc ggc gct gat gac tgt atc cgt ctg agc tat gca acc    1104
Gly Ala Ala Phe Gly Ala Asp Asp Cys Ile Arg Leu Ser Tyr Ala Thr
                355                 360                 365 gac ctg gac acg atc aaa cgc ggt atg gaa cgc ctg gaa aaa ttt ctg    1152
Asp Leu Asp Thr Ile Lys Arg Gly Met Glu Arg Leu Glu Lys Phe Leu
                370                 375                 380 cac ggc att ctg ctc gag tga                                        1173
His Gly Ile Leu Leu Glu
385                 390

<210> SEQ ID NO 75
<211> LENGTH: 390
<212> TYPE: PRT
<213> ORGANISM: Phormidium lapideum
```

<400> SEQUENCE: 75

```
Met Lys Leu Ala Ala Arg Val Glu Ser Val Pro Ser Met Thr Leu
1               5                   10                  15

Ile Ile Asp Ala Lys Ala Lys Ala Met Lys Ala Glu Gly Ile Asp Val
                20                  25                  30

Cys Ser Phe Ser Ala Gly Glu Pro Asp Phe Asn Thr Pro Lys His Ile
            35                  40                  45

Val Glu Ala Ala Lys Ala Ala Leu Glu Gln Gly Lys Thr Arg Tyr Gly
        50                  55                  60

Pro Ala Ala Gly Glu Pro Arg Leu Arg Glu Ala Ile Ala Gln Lys Leu
65                  70                  75                  80

Gln Arg Asp Asn Gly Leu Cys Tyr Gly Ala Asp Asn Ile Leu Val Thr
                85                  90                  95

Asn Gly Gly Lys Gln Ser Ile Phe Asn Leu Met Leu Ala Met Ile Glu
            100                 105                 110

Pro Gly Asp Glu Val Ile Ile Pro Ala Pro Phe Trp Val Ser Tyr Pro
        115                 120                 125

Glu Met Val Lys Leu Ala Glu Gly Thr Pro Val Ile Leu Pro Thr Thr
130                 135                 140

Val Glu Thr Gln Phe Lys Val Ser Pro Glu Gln Ile Arg Gln Ala Ile
145                 150                 155                 160

Thr Pro Lys Thr Lys Leu Leu Val Phe Asn Thr Pro Ser Asn Pro Thr
                165                 170                 175

Gly Met Val Tyr Thr Pro Asp Glu Val Arg Ala Ile Ala Gln Val Ala
            180                 185                 190

Val Glu Ala Gly Leu Trp Val Leu Ser Asp Glu Ile Tyr Glu Lys Ile
        195                 200                 205

Leu Tyr Asp Asp Ala Gln His Leu Ser Ile Gly Ala Ala Ser Pro Glu
210                 215                 220

Ala Tyr Glu Arg Ser Val Val Cys Ser Gly Phe Ala Lys Thr Tyr Ala
225                 230                 235                 240

Met Thr Gly Trp Arg Val Gly Phe Leu Ala Gly Pro Val Pro Leu Val
                245                 250                 255

Lys Ala Ala Thr Lys Ile Gln Gly His Ser Thr Ser Asn Val Cys Thr
            260                 265                 270

Phe Ala Gln Tyr Gly Ala Ile Ala Ala Tyr Glu Asn Ser Gln Asp Cys
        275                 280                 285

Val Gln Glu Met Leu Ala Ala Phe Ala Glu Arg Arg Arg Tyr Met Leu
    290                 295                 300

Asp Ala Leu Asn Ala Met Pro Gly Leu Glu Cys Pro Lys Pro Asp Gly
305                 310                 315                 320

Ala Phe Tyr Met Phe Pro Ser Ile Ala Lys Thr Gly Arg Ser Ser Leu
                325                 330                 335

Asp Phe Cys Ser Glu Leu Leu Asp Gln His Gln Val Ala Thr Val Pro
            340                 345                 350

Gly Ala Ala Phe Gly Ala Asp Asp Cys Ile Arg Leu Ser Tyr Ala Thr
        355                 360                 365

Asp Leu Asp Thr Ile Lys Arg Gly Met Glu Arg Leu Glu Lys Phe Leu
370                 375                 380

His Gly Ile Leu Glu
385                 390
```

<210> SEQ ID NO 76
<211> LENGTH: 1164
<212> TYPE: DNA
<213> ORGANISM: Thermus thermophilus
<220> FEATURE:
<221> NAME/KEY: CDS
<222> LOCATION: (1)..(1164)

<400> SEQUENCE: 76

| | | | | | | | | | | | | | | | | |
|---|---|---|---|---|---|---|---|---|---|---|---|---|---|---|---|---|
| atg | cgt | ggt | ctg | tcg | cgt | cgt | gtc | caa | gca | atg | aaa | ccg | tca | gca | acc | 48 |
| Met | Arg | Gly | Leu | Ser | Arg | Arg | Val | Gln | Ala | Met | Lys | Pro | Ser | Ala | Thr | |
| 1 | | | | 5 | | | | | 10 | | | | | 15 | | |
| gtc | gcc | gtt | aat | gcc | aaa | gcc | ctg | gaa | ctg | cgt | cgt | cag | ggt | gtc | gat | 96 |
| Val | Ala | Val | Asn | Ala | Lys | Ala | Leu | Glu | Leu | Arg | Arg | Gln | Gly | Val | Asp | |
| | | 20 | | | | | 25 | | | | | 30 | | | | |
| ctg | gtg | gca | ctg | acc | gct | ggc | gaa | ccg | gat | ttt | gac | acg | ccg | gaa | cat | 144 |
| Leu | Val | Ala | Leu | Thr | Ala | Gly | Glu | Pro | Asp | Phe | Asp | Thr | Pro | Glu | His | |
| | 35 | | | | | 40 | | | | | 45 | | | | | |
| gtt | aaa | gaa | gcg | gca | cgt | cgc | gca | ctg | gca | caa | ggt | aaa | acc | aaa | tat | 192 |
| Val | Lys | Glu | Ala | Ala | Arg | Arg | Ala | Leu | Ala | Gln | Gly | Lys | Thr | Lys | Tyr | |
| 50 | | | | | 55 | | | | | 60 | | | | | | |
| gca | ccg | ccg | gcg | ggt | att | ccg | gaa | ctg | cgt | gaa | gca | ctg | gct | gaa | aaa | 240 |
| Ala | Pro | Pro | Ala | Gly | Ile | Pro | Glu | Leu | Arg | Glu | Ala | Leu | Ala | Glu | Lys | |
| 65 | | | | | 70 | | | | | 75 | | | | | 80 | |
| ttc | cgt | cgc | gaa | aac | ggt | ctg | agc | gtg | acg | ccg | gaa | gaa | acc | atc | gtt | 288 |
| Phe | Arg | Arg | Glu | Asn | Gly | Leu | Ser | Val | Thr | Pro | Glu | Glu | Thr | Ile | Val | |
| | | | | 85 | | | | | 90 | | | | | 95 | | |
| acg | gtc | ggc | ggt | aaa | cag | gcg | ctg | ttt | aac | ctg | ttt | caa | gcc | att | ctg | 336 |
| Thr | Val | Gly | Gly | Lys | Gln | Ala | Leu | Phe | Asn | Leu | Phe | Gln | Ala | Ile | Leu | |
| | | | 100 | | | | | 105 | | | | | 110 | | | |
| gat | ccg | ggc | gac | gaa | gtg | atc | gtt | ctg | tca | ccg | tat | tgg | gtg | tcg | tac | 384 |
| Asp | Pro | Gly | Asp | Glu | Val | Ile | Val | Leu | Ser | Pro | Tyr | Trp | Val | Ser | Tyr | |
| | 115 | | | | | 120 | | | | | 125 | | | | | |
| ccg | gaa | atg | gtt | cgt | ttt | gcg | ggc | ggt | gtg | gtt | gtc | gaa | gtg | gaa | acc | 432 |
| Pro | Glu | Met | Val | Arg | Phe | Ala | Gly | Gly | Val | Val | Val | Glu | Val | Glu | Thr | |
| 130 | | | | | 135 | | | | | 140 | | | | | | |
| ctg | ccg | gaa | gaa | ggt | ttc | gtc | ccg | gat | ccg | gaa | cgt | gtg | cgt | cgc | gca | 480 |
| Leu | Pro | Glu | Glu | Gly | Phe | Val | Pro | Asp | Pro | Glu | Arg | Val | Arg | Arg | Ala | |
| 145 | | | | | 150 | | | | | 155 | | | | | 160 | |
| att | acc | ccg | cgc | acg | aaa | gct | ctg | gtg | gtt | aac | tct | ccg | aac | aat | ccg | 528 |
| Ile | Thr | Pro | Arg | Thr | Lys | Ala | Leu | Val | Val | Asn | Ser | Pro | Asn | Asn | Pro | |
| | | | | 165 | | | | | 170 | | | | | 175 | | |
| acc | ggc | gca | gtt | tat | ccg | aaa | gaa | gtc | ctg | gaa | gca | ctg | gca | cgt | ctg | 576 |
| Thr | Gly | Ala | Val | Tyr | Pro | Lys | Glu | Val | Leu | Glu | Ala | Leu | Ala | Arg | Leu | |
| | | | 180 | | | | | 185 | | | | | 190 | | | |
| gca | gtt | gaa | cat | gat | ttt | tac | ctg | gtc | agc | gac | gaa | atc | tat | gaa | cat | 624 |
| Ala | Val | Glu | His | Asp | Phe | Tyr | Leu | Val | Ser | Asp | Glu | Ile | Tyr | Glu | His | |
| | | 195 | | | | | 200 | | | | | 205 | | | | |
| ctg | ctg | tac | gaa | ggt | gaa | cac | ttc | tcc | ccg | ggt | cgt | gtc | gca | ccg | gaa | 672 |
| Leu | Leu | Tyr | Glu | Gly | Glu | His | Phe | Ser | Pro | Gly | Arg | Val | Ala | Pro | Glu | |
| 210 | | | | | 215 | | | | | 220 | | | | | | |
| cac | acc | ctg | acg | gtg | aac | ggt | gca | gct | aaa | gca | ttt | gct | atg | acc | ggc | 720 |
| His | Thr | Leu | Thr | Val | Asn | Gly | Ala | Ala | Lys | Ala | Phe | Ala | Met | Thr | Gly | |
| 225 | | | | | 230 | | | | | 235 | | | | | 240 | |
| tgg | cgc | att | ggt | tat | gca | tgc | ggc | ccg | aaa | gaa | gtg | atc | aaa | gcg | atg | 768 |
| Trp | Arg | Ile | Gly | Tyr | Ala | Cys | Gly | Pro | Lys | Glu | Val | Ile | Lys | Ala | Met | |
| | | | | 245 | | | | | 250 | | | | | 255 | | |
| gcc | tca | gtt | agc | tct | cag | agt | acc | acg | tcc | ccg | gat | acg | att | gca | caa | 816 |
| Ala | Ser | Val | Ser | Ser | Gln | Ser | Thr | Thr | Ser | Pro | Asp | Thr | Ile | Ala | Gln | |
| | | | 260 | | | | | 265 | | | | | 270 | | | |
| tgg | gct | acc | ctg | gaa | gcg | ctg | acg | aat | cag | gaa | gcg | tcg | cgt | gcc | ttt | 864 |

-continued

```
                    Trp Ala Thr Leu Glu Ala Leu Thr Asn Gln Glu Ala Ser Arg Ala Phe
                            275                 280                 285 gtt gaa atg gca cgc gaa gct tat cgt cgc cgt cgc gac ctg ctg ctg        912
Val Glu Met Ala Arg Glu Ala Tyr Arg Arg Arg Arg Asp Leu Leu Leu
    290                 295                 300 gaa ggt ctg acc gca ctg ggc ctg aaa gct gtt cgt ccg agc ggt gcg        960
Glu Gly Leu Thr Ala Leu Gly Leu Lys Ala Val Arg Pro Ser Gly Ala
305                 310                 315                 320 ttc tac gtc ctg atg gat acg tct ccg atc gca ccg gac gaa gtt cgt       1008
Phe Tyr Val Leu Met Asp Thr Ser Pro Ile Ala Pro Asp Glu Val Arg
                325                 330                 335 gcg gcc gaa cgt ctg ctg gaa gcc ggt gtg gca gtc gtg ccg ggc acc       1056
Ala Ala Glu Arg Leu Leu Glu Ala Gly Val Ala Val Val Pro Gly Thr
            340                 345                 350 gat ttt gca gct ttc ggc cac gtg cgc ctg tca tac gcc acc tcc gaa       1104
Asp Phe Ala Ala Phe Gly His Val Arg Leu Ser Tyr Ala Thr Ser Glu
        355                 360                 365 gaa aat ctg cgt aaa gcc ctg gaa cgt ttt gct cgt gtc ctg ggt cgt       1152
Glu Asn Leu Arg Lys Ala Leu Glu Arg Phe Ala Arg Val Leu Gly Arg
    370                 375                 380 gcg ctc gag tga                                                       1164
Ala Leu Glu
385
```

<210> SEQ ID NO 77
<211> LENGTH: 387
<212> TYPE: PRT
<213> ORGANISM: Thermus thermophilus

<400> SEQUENCE: 77

```
Met Arg Gly Leu Ser Arg Val Gln Ala Met Lys Pro Ser Ala Thr
1               5                   10                  15

Val Ala Val Asn Ala Lys Ala Leu Glu Leu Arg Arg Gln Gly Val Asp
                20                  25                  30

Leu Val Ala Leu Thr Ala Gly Glu Pro Asp Phe Asp Thr Pro Glu His
            35                  40                  45

Val Lys Glu Ala Ala Arg Arg Ala Leu Ala Gln Gly Lys Thr Lys Tyr
        50                  55                  60

Ala Pro Pro Ala Gly Ile Pro Glu Leu Arg Glu Ala Leu Ala Glu Lys
65                  70                  75                  80

Phe Arg Arg Glu Asn Gly Leu Ser Val Thr Pro Glu Glu Thr Ile Val
                85                  90                  95

Thr Val Gly Gly Lys Gln Ala Leu Phe Asn Leu Phe Gln Ala Ile Leu
            100                 105                 110

Asp Pro Gly Asp Glu Val Ile Val Leu Ser Pro Tyr Trp Val Ser Tyr
        115                 120                 125

Pro Glu Met Val Arg Phe Ala Gly Gly Val Val Glu Val Glu Thr
    130                 135                 140

Leu Pro Glu Glu Gly Phe Val Pro Asp Pro Glu Arg Val Arg Arg Ala
145                 150                 155                 160

Ile Thr Pro Arg Thr Lys Ala Leu Val Val Asn Ser Pro Asn Asn Pro
                165                 170                 175

Thr Gly Ala Val Tyr Pro Lys Glu Val Leu Glu Ala Leu Ala Arg Leu
            180                 185                 190

Ala Val Glu His Asp Phe Tyr Leu Val Ser Asp Glu Ile Tyr Glu His
        195                 200                 205

Leu Leu Tyr Glu Gly Glu His Phe Ser Pro Gly Arg Val Ala Pro Glu
```

```
                210                 215                 220
His Thr Leu Thr Val Asn Gly Ala Ala Lys Ala Phe Ala Met Thr Gly
225                 230                 235                 240

Trp Arg Ile Gly Tyr Ala Cys Gly Pro Lys Glu Val Ile Lys Ala Met
                245                 250                 255

Ala Ser Val Ser Ser Gln Ser Thr Thr Ser Pro Asp Thr Ile Ala Gln
                260                 265                 270

Trp Ala Thr Leu Glu Ala Leu Thr Asn Gln Glu Ala Ser Arg Ala Phe
            275                 280                 285

Val Glu Met Ala Arg Glu Ala Tyr Arg Arg Arg Asp Leu Leu Leu
        290                 295                 300

Glu Gly Leu Thr Ala Leu Gly Leu Lys Ala Val Arg Pro Ser Gly Ala
305                 310                 315                 320

Phe Tyr Val Leu Met Asp Thr Ser Pro Ile Ala Pro Asp Glu Val Arg
                325                 330                 335

Ala Ala Glu Arg Leu Leu Glu Ala Gly Val Ala Val Pro Gly Thr
                340                 345                 350

Asp Phe Ala Ala Phe Gly His Val Arg Leu Ser Tyr Ala Thr Ser Glu
            355                 360                 365

Glu Asn Leu Arg Lys Ala Leu Glu Arg Phe Ala Arg Val Leu Gly Arg
        370                 375                 380

Ala Leu Glu
385

<210> SEQ ID NO 78
<211> LENGTH: 1176
<212> TYPE: DNA
<213> ORGANISM: Pyrococcus horikoshii
<220> FEATURE:
<221> NAME/KEY: CDS
<222> LOCATION: (1)..(1176)

<400> SEQUENCE: 78 atg gcc ctg tcg gac cgt ctg gaa ctg gtg tcg gcg agt gaa att cgt      48
Met Ala Leu Ser Asp Arg Leu Glu Leu Val Ser Ala Ser Glu Ile Arg
1               5                   10                  15 aaa ctg ttt gat att gcc gct ggt atg aaa gat gtt att agt ctg ggc      96
Lys Leu Phe Asp Ile Ala Ala Gly Met Lys Asp Val Ile Ser Leu Gly
            20                  25                  30 att ggt gaa ccg gat ttc gac acc ccg cag cat atc aaa gaa tat gct     144
Ile Gly Glu Pro Asp Phe Asp Thr Pro Gln His Ile Lys Glu Tyr Ala
        35                  40                  45 aaa gaa gcg ctg gat aaa ggt ctg acg cac tac ggc ccg aac att ggt     192
Lys Glu Ala Leu Asp Lys Gly Leu Thr His Tyr Gly Pro Asn Ile Gly
    50                  55                  60 ctg ctg gaa ctg cgc gaa gcc atc gca gaa aaa ctg aaa aaa cag aac     240
Leu Leu Glu Leu Arg Glu Ala Ile Ala Glu Lys Leu Lys Lys Gln Asn
65                  70                  75                  80 ggc att gaa gct gat ccg aaa acc gaa atc atg gtt ctg ctg ggc gcc     288
Gly Ile Glu Ala Asp Pro Lys Thr Glu Ile Met Val Leu Leu Gly Ala
                85                  90                  95 aat caa gca ttt ctg atg ggt ctg agt gcc ttc ctg aaa gac ggc gaa     336
Asn Gln Ala Phe Leu Met Gly Leu Ser Ala Phe Leu Lys Asp Gly Glu
            100                 105                 110 gaa gtg ctg att ccg acc ccg gct ttc gtc tcc tat gct ccg gcg gtg     384
Glu Val Leu Ile Pro Thr Pro Ala Phe Val Ser Tyr Ala Pro Ala Val
        115                 120                 125 atc ctg gcg ggc ggt aaa ccg gtt gaa gtc ccg acg tat gaa gaa gat     432
```

```
                 Ile Leu Ala Gly Gly Lys Pro Val Glu Val Pro Thr Tyr Glu Glu Asp
                     130                 135                 140 gaa ttt cgc ctg aat gtt gac gaa ctg aaa aaa tac gtc acc gat aaa         480
Glu Phe Arg Leu Asn Val Asp Glu Leu Lys Lys Tyr Val Thr Asp Lys
145                 150                 155                 160 acg cgt gcc ctg att atc aac tca ccg tgc aat ccg acc ggt gcc gtt         528
Thr Arg Ala Leu Ile Ile Asn Ser Pro Cys Asn Pro Thr Gly Ala Val
                    165                 170                 175 ctg acg aaa aaa gat ctg gaa gaa att gca gac ttt gtg gtt gaa cat         576
Leu Thr Lys Lys Asp Leu Glu Glu Ile Ala Asp Phe Val Val Glu His
            180                 185                 190 gat ctg att gtg atc tcg gac gaa gtt tat gaa cat ttc att tac gat         624
Asp Leu Ile Val Ile Ser Asp Glu Val Tyr Glu His Phe Ile Tyr Asp
        195                 200                 205 gac gct cgc cac tac agc atc gcg tct ctg gat ggc atg ttt gaa cgt         672
Asp Ala Arg His Tyr Ser Ile Ala Ser Leu Asp Gly Met Phe Glu Arg
    210                 215                 220 acc atc acg gtg aac ggc ttt agc aaa acc ttc gca atg acg ggt tgg         720
Thr Ile Thr Val Asn Gly Phe Ser Lys Thr Phe Ala Met Thr Gly Trp
225                 230                 235                 240 cgt ctg ggt ttt gtg gca gca ccg tct tgg att atc gaa cgt atg gtt         768
Arg Leu Gly Phe Val Ala Ala Pro Ser Trp Ile Ile Glu Arg Met Val
                    245                 250                 255 aaa ttc cag atg tac aac gcg acc tgt ccg gtc acg ttc att caa tac         816
Lys Phe Gln Met Tyr Asn Ala Thr Cys Pro Val Thr Phe Ile Gln Tyr
                260                 265                 270 gca gct gcg aaa gcc ctg aaa gat gaa cgc tct tgg aaa gca gtt gaa         864
Ala Ala Ala Lys Ala Leu Lys Asp Glu Arg Ser Trp Lys Ala Val Glu
            275                 280                 285 gaa atg cgt aaa gaa tat gac cgt cgc cgt aaa ctg gtg tgg aaa cgt         912
Glu Met Arg Lys Glu Tyr Asp Arg Arg Arg Lys Leu Val Trp Lys Arg
        290                 295                 300 ctg aac gaa atg ggt ctg ccg acc gtt aaa ccg aaa ggc gcg ttt tac         960
Leu Asn Glu Met Gly Leu Pro Thr Val Lys Pro Lys Gly Ala Phe Tyr
305                 310                 315                 320 att ttc ccg cgc atc cgt gat acc ggc ctg acg agt aaa aaa ttc tcc        1008
Ile Phe Pro Arg Ile Arg Asp Thr Gly Leu Thr Ser Lys Lys Phe Ser
                    325                 330                 335 gaa ctg atg ctg aaa gaa gct cgc gtc gca gtc gtg ccg ggt tca gca        1056
Glu Leu Met Leu Lys Glu Ala Arg Val Ala Val Val Pro Gly Ser Ala
                340                 345                 350 ttt ggt aaa gca ggc gaa ggt tat gtg cgt att tcg tat gcc acc gca        1104
Phe Gly Lys Ala Gly Glu Gly Tyr Val Arg Ile Ser Tyr Ala Thr Ala
            355                 360                 365 tac gaa aaa ctg gaa gaa gcg atg gac cgt atg gaa cgt gtg ctg aaa        1152
Tyr Glu Lys Leu Glu Glu Ala Met Asp Arg Met Glu Arg Val Leu Lys
        370                 375                 380 gaa cgc aaa ctg gtg ctc gag tga                                        1176
Glu Arg Lys Leu Val Leu Glu
385                 390

<210> SEQ ID NO 79
<211> LENGTH: 391
<212> TYPE: PRT
<213> ORGANISM: Pyrococcus horikoshii

<400> SEQUENCE: 79

Met Ala Leu Ser Asp Arg Leu Glu Leu Val Ser Ala Ser Glu Ile Arg
1               5                   10                  15

Lys Leu Phe Asp Ile Ala Ala Gly Met Lys Asp Val Ile Ser Leu Gly
```

```
            20                  25                  30
Ile Gly Glu Pro Asp Phe Asp Thr Pro Gln His Ile Lys Glu Tyr Ala
         35                  40                  45

Lys Glu Ala Leu Asp Lys Gly Leu Thr His Tyr Gly Pro Asn Ile Gly
 50                  55                  60

Leu Leu Glu Leu Arg Glu Ala Ile Ala Glu Lys Leu Lys Lys Gln Asn
 65                  70                  75                  80

Gly Ile Glu Ala Asp Pro Lys Thr Glu Ile Met Val Leu Leu Gly Ala
             85                  90                  95

Asn Gln Ala Phe Leu Met Gly Leu Ser Ala Phe Leu Lys Asp Gly Glu
         100                 105                 110

Glu Val Leu Ile Pro Thr Pro Ala Phe Val Ser Tyr Ala Pro Ala Val
     115                 120                 125

Ile Leu Ala Gly Gly Lys Pro Val Glu Val Pro Thr Tyr Glu Glu Asp
 130                 135                 140

Glu Phe Arg Leu Asn Val Asp Glu Leu Lys Lys Tyr Val Thr Asp Lys
145                 150                 155                 160

Thr Arg Ala Leu Ile Ile Asn Ser Pro Cys Asn Pro Thr Gly Ala Val
             165                 170                 175

Leu Thr Lys Lys Asp Leu Glu Ile Ala Asp Phe Val Val Glu His
         180                 185                 190

Asp Leu Ile Val Ile Ser Asp Glu Val Tyr Glu His Phe Ile Tyr Asp
     195                 200                 205

Asp Ala Arg His Tyr Ser Ile Ala Ser Leu Asp Gly Met Phe Glu Arg
 210                 215                 220

Thr Ile Thr Val Asn Gly Phe Ser Lys Thr Phe Ala Met Thr Gly Trp
225                 230                 235                 240

Arg Leu Gly Phe Val Ala Ala Pro Ser Trp Ile Ile Glu Arg Met Val
             245                 250                 255

Lys Phe Gln Met Tyr Asn Ala Thr Cys Pro Val Thr Phe Ile Gln Tyr
         260                 265                 270

Ala Ala Ala Lys Ala Leu Lys Asp Glu Arg Ser Trp Lys Ala Val Glu
     275                 280                 285

Glu Met Arg Lys Glu Tyr Asp Arg Arg Lys Leu Val Trp Lys Arg
 290                 295                 300

Leu Asn Glu Met Gly Leu Pro Thr Val Lys Pro Lys Gly Ala Phe Tyr
305                 310                 315                 320

Ile Phe Pro Arg Ile Arg Asp Thr Gly Leu Thr Ser Lys Lys Phe Ser
             325                 330                 335

Glu Leu Met Leu Lys Glu Ala Arg Val Ala Val Val Pro Gly Ser Ala
         340                 345                 350

Phe Gly Lys Ala Gly Glu Gly Tyr Val Arg Ile Ser Tyr Ala Thr Ala
     355                 360                 365

Tyr Glu Lys Leu Glu Glu Ala Met Asp Arg Met Glu Arg Val Leu Lys
 370                 375                 380

Glu Arg Lys Leu Val Leu Glu
385                 390

<210> SEQ ID NO 80
<211> LENGTH: 1119
<212> TYPE: DNA
<213> ORGANISM: Methanococcus jannaschii
<220> FEATURE:
<221> NAME/KEY: CDS
<222> LOCATION: (1)..(1119)
```

<400> SEQUENCE: 80

```
atg ctg tct aaa cgc ctg ctg aat ttt gaa tct ttt gaa gtt atg gac      48
Met Leu Ser Lys Arg Leu Leu Asn Phe Glu Ser Phe Glu Val Met Asp
1               5                   10                  15 atc ctg gca ctg gca cag aaa ctg gaa tcg gaa ggt aaa aaa gtg att      96
Ile Leu Ala Leu Ala Gln Lys Leu Glu Ser Glu Gly Lys Lys Val Ile
                20                  25                  30 cat ctg gaa atc ggt gaa ccg gat ttt aac acc ccg aaa ccg att gtt     144
His Leu Glu Ile Gly Glu Pro Asp Phe Asn Thr Pro Lys Pro Ile Val
            35                  40                  45 gac gaa ggt atc aaa agc ctg aaa gaa ggc aaa acc cac tat acg gat     192
Asp Glu Gly Ile Lys Ser Leu Lys Glu Gly Lys Thr His Tyr Thr Asp
        50                  55                  60 tct cgt ggc att ctg gaa ctg cgc gaa aaa atc agt gaa ctg tac aaa     240
Ser Arg Gly Ile Leu Glu Leu Arg Glu Lys Ile Ser Glu Leu Tyr Lys
65                  70                  75                  80 gac aaa tac aaa gca gat atc atc ccg gac aat att atc att acg ggc     288
Asp Lys Tyr Lys Ala Asp Ile Ile Pro Asp Asn Ile Ile Ile Thr Gly
                85                  90                  95 ggt agc tct ctg ggt ctg ttt ttc gct ctg agt tcc atc att gat gac     336
Gly Ser Ser Leu Gly Leu Phe Phe Ala Leu Ser Ser Ile Ile Asp Asp
            100                 105                 110 ggc gat gaa gtg ctg att cag aac ccg tgc tat ccg tgt tac aaa aat     384
Gly Asp Glu Val Leu Ile Gln Asn Pro Cys Tyr Pro Cys Tyr Lys Asn
        115                 120                 125 ttt atc cgt ttc ctg ggt gca aaa ccg gtc ttt tgc gat ttc acc gtg     432
Phe Ile Arg Phe Leu Gly Ala Lys Pro Val Phe Cys Asp Phe Thr Val
130                 135                 140 gaa agt ctg gaa gaa gca ctg tcc gac aaa acg aaa gct atc att atc     480
Glu Ser Leu Glu Glu Ala Leu Ser Asp Lys Thr Lys Ala Ile Ile Ile
145                 150                 155                 160 aac tca ccg tcg aat ccg ctg ggc gaa gtc att gat cgc gaa atc tat     528
Asn Ser Pro Ser Asn Pro Leu Gly Glu Val Ile Asp Arg Glu Ile Tyr
                165                 170                 175 gaa ttt gcg tac gaa aac att ccg tac att atc tcc gac gaa atc tat     576
Glu Phe Ala Tyr Glu Asn Ile Pro Tyr Ile Ile Ser Asp Glu Ile Tyr
            180                 185                 190 aat ggt ctg gtg tac gaa ggc aaa tgt tat tct gcc att gaa ttc gat     624
Asn Gly Leu Val Tyr Glu Gly Lys Cys Tyr Ser Ala Ile Glu Phe Asp
        195                 200                 205 gaa aac ctg gaa aaa acc att ctg atc aat ggt ttt agc aaa ctg tac     672
Glu Asn Leu Glu Lys Thr Ile Leu Ile Asn Gly Phe Ser Lys Leu Tyr
210                 215                 220 gcg atg acg ggt tgg cgt att ggc tac gtt atc agt aac gat gaa atc     720
Ala Met Thr Gly Trp Arg Ile Gly Tyr Val Ile Ser Asn Asp Glu Ile
225                 230                 235                 240 atc gaa gcc att ctg aaa ctg caa caa aac ctg ttt att agc gca ccg     768
Ile Glu Ala Ile Leu Lys Leu Gln Gln Asn Leu Phe Ile Ser Ala Pro
                245                 250                 255 acc atc tct caa tat gcg gcc ctg aaa gct ttc gaa aaa gaa acg gaa     816
Thr Ile Ser Gln Tyr Ala Ala Leu Lys Ala Phe Glu Lys Glu Thr Glu
            260                 265                 270 cgc gaa att aac agc atg atc aaa gaa ttc gat cgt cgc cgt cgc ctg     864
Arg Glu Ile Asn Ser Met Ile Lys Glu Phe Asp Arg Arg Arg Arg Leu
        275                 280                 285 gtg ctg aaa tac gtt aaa gac ttt ggt tgg gaa gtt aac aat ccg att     912
Val Leu Lys Tyr Val Lys Asp Phe Gly Trp Glu Val Asn Asn Pro Ile
290                 295                 300
```

|  |  |
|---|---|
| ggc gcc tat tac gtc ttc ccg aac atc ggt gaa gat ggc cgt gaa ttc<br>Gly Ala Tyr Tyr Val Phe Pro Asn Ile Gly Glu Asp Gly Arg Glu Phe<br>305                      310                      315                    320 | 960 |
| gcg tac aaa ctg ctg aaa gaa aaa ttc gtc gcc ctg acc ccg ggc att<br>Ala Tyr Lys Leu Leu Lys Glu Lys Phe Val Ala Leu Thr Pro Gly Ile<br>                    325                      330                      335 | 1008 |
| ggt ttt ggc tca aaa ggc aaa aat tac att cgc atc tcg tat gcc aac<br>Gly Phe Gly Ser Lys Gly Lys Asn Tyr Ile Arg Ile Ser Tyr Ala Asn<br>                  340                      345                      350 | 1056 |
| agt tac gaa aac atc aaa gaa ggt ctg gaa cgc atc aaa gaa ttc ctg<br>Ser Tyr Glu Asn Ile Lys Glu Gly Leu Glu Arg Ile Lys Glu Phe Leu<br>355                      360                      365 | 1104 |
| aac aaa ctc gag tga<br>Asn Lys Leu Glu<br>    370 | 1119 |

<210> SEQ ID NO 81
<211> LENGTH: 372
<212> TYPE: PRT
<213> ORGANISM: Methanococcus jannaschii

<400> SEQUENCE: 81

Met Leu Ser Lys Arg Leu Leu Asn Phe Glu Ser Phe Glu Val Met Asp
1                 5                    10                  15

Ile Leu Ala Leu Ala Gln Lys Leu Glu Ser Glu Gly Lys Lys Val Ile
                20                    25                    30

His Leu Glu Ile Gly Glu Pro Asp Phe Asn Thr Pro Lys Pro Ile Val
                    35                    40                    45

Asp Glu Gly Ile Lys Ser Leu Lys Glu Gly Lys Thr His Tyr Thr Asp
   50                    55                    60

Ser Arg Gly Ile Leu Glu Leu Arg Glu Lys Ile Ser Glu Leu Tyr Lys
65                70                    75                    80

Asp Lys Tyr Lys Ala Asp Ile Ile Pro Asp Asn Ile Ile Ile Thr Gly
                      85                    90                    95

Gly Ser Ser Leu Gly Leu Phe Phe Ala Leu Ser Ser Ile Ile Asp Asp
                100                  105                  110

Gly Asp Glu Val Leu Ile Gln Asn Pro Cys Tyr Pro Cys Tyr Lys Asn
                115                  120                  125

Phe Ile Arg Phe Leu Gly Ala Lys Pro Val Phe Cys Asp Phe Thr Val
130                135                  140

Glu Ser Leu Glu Glu Ala Leu Ser Asp Lys Thr Lys Ala Ile Ile Ile
145                150                  155                  160

Asn Ser Pro Ser Asn Pro Leu Gly Glu Val Ile Asp Arg Glu Ile Tyr
                165                  170                  175

Glu Phe Ala Tyr Glu Asn Ile Pro Tyr Ile Ile Ser Asp Glu Ile Tyr
                  180                  185                  190

Asn Gly Leu Val Tyr Glu Gly Lys Cys Tyr Ser Ala Ile Glu Phe Asp
                195                  200                  205

Glu Asn Leu Glu Lys Thr Ile Leu Ile Asn Gly Phe Ser Lys Leu Tyr
         210                  215                  220

Ala Met Thr Gly Trp Arg Ile Gly Tyr Val Ile Ser Asn Asp Glu Ile
225                230                  235                  240

Ile Glu Ala Ile Leu Lys Leu Gln Gln Asn Leu Phe Ile Ser Ala Pro
                  245                  250                  255

Thr Ile Ser Gln Tyr Ala Ala Leu Lys Ala Phe Glu Lys Glu Thr Glu
                  260                  265                  270

```
Arg Glu Ile Asn Ser Met Ile Lys Glu Phe Asp Arg Arg Arg Leu
            275                 280                 285

Val Leu Lys Tyr Val Lys Asp Phe Gly Trp Glu Val Asn Asn Pro Ile
    290                 295                 300

Gly Ala Tyr Tyr Val Phe Pro Asn Ile Gly Glu Asp Gly Arg Glu Phe
305                 310                 315                 320

Ala Tyr Lys Leu Leu Lys Glu Lys Phe Val Ala Leu Thr Pro Gly Ile
                325                 330                 335

Gly Phe Gly Ser Lys Gly Lys Asn Tyr Ile Arg Ile Ser Tyr Ala Asn
                340                 345                 350

Ser Tyr Glu Asn Ile Lys Glu Gly Leu Glu Arg Ile Lys Glu Phe Leu
            355                 360                 365

Asn Lys Leu Glu
    370

<210> SEQ ID NO 82
<211> LENGTH: 1200
<212> TYPE: DNA
<213> ORGANISM: Thermotoga maritima
<220> FEATURE:
<221> NAME/KEY: CDS
<222> LOCATION: (1)..(1200)

<400> SEQUENCE: 82 atg gat gtc ttt agc gac cgt gtc ctg ctg acc gaa gaa tca ccg atc      48
Met Asp Val Phe Ser Asp Arg Val Leu Leu Thr Glu Glu Ser Pro Ile
1               5                   10                  15 cgc aaa ctg gtt ccg ttt gct gaa atg gcg aaa aaa cgc ggc gtc cgt      96
Arg Lys Leu Val Pro Phe Ala Glu Met Ala Lys Lys Arg Gly Val Arg
                20                  25                  30 att cat cac ctg aac atc ggt cag ccg gat ctg aaa acc ccg gaa gtg     144
Ile His His Leu Asn Ile Gly Gln Pro Asp Leu Lys Thr Pro Glu Val
            35                  40                  45 ttt ttc gaa cgc atc tat gaa aat aaa ccg gaa gtg gtt tat tac agc     192
Phe Phe Glu Arg Ile Tyr Glu Asn Lys Pro Glu Val Val Tyr Tyr Ser
        50                  55                  60 cat agc gcg ggc att tgg gaa ctg cgt gaa gcg ttt gcc agc tat tac     240
His Ser Ala Gly Ile Trp Glu Leu Arg Glu Ala Phe Ala Ser Tyr Tyr
65                  70                  75                  80 aaa cgt cgc caa cgc gtt gat gtc aaa ccg gaa aac gtg ctg gtt acc     288
Lys Arg Arg Gln Arg Val Asp Val Lys Pro Glu Asn Val Leu Val Thr
                85                  90                  95 aat ggc ggt tct gaa gcc att ctg ttt agt ttc gca gtc atc gct aac     336
Asn Gly Gly Ser Glu Ala Ile Leu Phe Ser Phe Ala Val Ile Ala Asn
            100                 105                 110 ccg ggt gac gaa att ctg gtg ctg gaa ccg ttt tat gcg aac tac aat     384
Pro Gly Asp Glu Ile Leu Val Leu Glu Pro Phe Tyr Ala Asn Tyr Asn
        115                 120                 125 gca ttc gct aaa att gcc ggc gtg aaa ctg atc ccg gtt acg cgt cgc     432
Ala Phe Ala Lys Ile Ala Gly Val Lys Leu Ile Pro Val Thr Arg Arg
    130                 135                 140 atg gaa gaa ggt ttt gcg atc ccg cag aac ctg gaa tcg ttc atc aat     480
Met Glu Glu Gly Phe Ala Ile Pro Gln Asn Leu Glu Ser Phe Ile Asn
145                 150                 155                 160 gaa cgt acc aaa ggc att gtt ctg agc aac ccg tgc aat ccg acg ggc     528
Glu Arg Thr Lys Gly Ile Val Leu Ser Asn Pro Cys Asn Pro Thr Gly
                165                 170                 175 gtc gtg tat ggt aaa gat gaa atg cgt tac ctg gtt gaa att gcc gaa     576
Val Val Tyr Gly Lys Asp Glu Met Arg Tyr Leu Val Glu Ile Ala Glu
            180                 185                 190
```

```
cgc cac ggc ctg ttt ctg atc gtc gac gaa gtg tac agt gaa att gtg      624
Arg His Gly Leu Phe Leu Ile Val Asp Glu Val Tyr Ser Glu Ile Val
        195                 200                 205 ttt cgc ggt gaa ttc gcg tca gcc ctg tcg atc gaa agc gat aaa gtt      672
Phe Arg Gly Glu Phe Ala Ser Ala Leu Ser Ile Glu Ser Asp Lys Val
    210                 215                 220 gtc gtg att gac agt gtt tcc aaa aaa ttc tct gcg tgc ggc gcc cgt      720
Val Val Ile Asp Ser Val Ser Lys Lys Phe Ser Ala Cys Gly Ala Arg
225                 230                 235                 240 gtc ggt tgt ctg atc acc cgc aac gaa gaa ctg att agt cat gca atg      768
Val Gly Cys Leu Ile Thr Arg Asn Glu Glu Leu Ile Ser His Ala Met
                245                 250                 255 aaa ctg gct cag ggt cgt ctg gca ccg ccg ctg ctg gaa caa atc ggc      816
Lys Leu Ala Gln Gly Arg Leu Ala Pro Pro Leu Leu Glu Gln Ile Gly
            260                 265                 270 tcc gtg ggt ctg ctg aat ctg gat gac tca ttt ttc gat ttt gtt cgt      864
Ser Val Gly Leu Leu Asn Leu Asp Asp Ser Phe Phe Asp Phe Val Arg
        275                 280                 285 gaa acc tat cgt gaa cgc gtt gaa acg gtc ctg aaa aaa ctg gaa gaa      912
Glu Thr Tyr Arg Glu Arg Val Glu Thr Val Leu Lys Lys Leu Glu Glu
    290                 295                 300 cac ggc ctg aaa cgc ttt acc aaa ccg tcc ggt gca ttc tac att acg      960
His Gly Leu Lys Arg Phe Thr Lys Pro Ser Gly Ala Phe Tyr Ile Thr
305                 310                 315                 320 gct gaa ctg ccg gtg gaa gac gcg gaa gaa ttt gcc cgc tgg atg ctg     1008
Ala Glu Leu Pro Val Glu Asp Ala Glu Glu Phe Ala Arg Trp Met Leu
                325                 330                 335 acc gat ttc aat atg gac ggc gaa acc acg atg gtt gca ccg ctg cgt     1056
Thr Asp Phe Asn Met Asp Gly Glu Thr Thr Met Val Ala Pro Leu Arg
            340                 345                 350 ggt ttt tat ctg acg ccg ggc ctg ggt aaa aaa gaa att cgc atc gct     1104
Gly Phe Tyr Leu Thr Pro Gly Leu Gly Lys Lys Glu Ile Arg Ile Ala
        355                 360                 365 tgt gtg ctg gaa aaa gat ctg tct cgt gcg att gat gtt ctg atg         1152
Cys Val Leu Glu Lys Asp Leu Ser Arg Ala Ile Asp Val Leu Met
    370                 375                 380 gaa ggt ctg aaa atg ttc tgt agc agc cgt atc tcc tgt ctc gag tga     1200
Glu Gly Leu Lys Met Phe Cys Ser Ser Arg Ile Ser Cys Leu Glu
385                 390                 395
```

<210> SEQ ID NO 83
<211> LENGTH: 399
<212> TYPE: PRT
<213> ORGANISM: Thermotoga maritima

<400> SEQUENCE: 83

Met Asp Val Phe Ser Asp Arg Val Leu Leu Thr Glu Glu Ser Pro Ile
1               5                   10                  15

Arg Lys Leu Val Pro Phe Ala Glu Met Ala Lys Lys Arg Gly Val Arg
            20                  25                  30

Ile His His Leu Asn Ile Gly Gln Pro Asp Leu Lys Thr Pro Glu Val
        35                  40                  45

Phe Phe Glu Arg Ile Tyr Glu Asn Lys Pro Glu Val Val Tyr Tyr Ser
    50                  55                  60

His Ser Ala Gly Ile Trp Glu Leu Arg Glu Ala Phe Ala Ser Tyr Tyr
65                  70                  75                  80

Lys Arg Arg Gln Arg Val Asp Val Lys Pro Glu Asn Val Leu Val Thr
                85                  90                  95

-continued

```
Asn Gly Gly Ser Glu Ala Ile Leu Phe Ser Phe Ala Val Ile Ala Asn
            100                 105                 110

Pro Gly Asp Glu Ile Leu Val Leu Glu Pro Phe Tyr Ala Asn Tyr Asn
        115                 120                 125

Ala Phe Ala Lys Ile Ala Gly Val Lys Leu Ile Pro Val Thr Arg Arg
    130                 135                 140

Met Glu Glu Gly Phe Ala Ile Pro Gln Asn Leu Glu Ser Phe Ile Asn
145                 150                 155                 160

Glu Arg Thr Lys Gly Ile Val Leu Ser Asn Pro Cys Asn Pro Thr Gly
                165                 170                 175

Val Val Tyr Gly Lys Asp Glu Met Arg Tyr Leu Val Glu Ile Ala Glu
            180                 185                 190

Arg His Gly Leu Phe Leu Ile Val Asp Glu Val Tyr Ser Glu Ile Val
        195                 200                 205

Phe Arg Gly Glu Phe Ala Ser Ala Leu Ser Ile Glu Ser Asp Lys Val
    210                 215                 220

Val Val Ile Asp Ser Val Ser Lys Lys Phe Ser Ala Cys Gly Ala Arg
225                 230                 235                 240

Val Gly Cys Leu Ile Thr Arg Asn Glu Glu Leu Ile Ser His Ala Met
                245                 250                 255

Lys Leu Ala Gln Gly Arg Leu Ala Pro Pro Leu Leu Glu Gln Ile Gly
            260                 265                 270

Ser Val Gly Leu Leu Asn Leu Asp Asp Ser Phe Phe Asp Phe Val Arg
        275                 280                 285

Glu Thr Tyr Arg Glu Arg Val Glu Thr Val Leu Lys Lys Leu Glu Glu
    290                 295                 300

His Gly Leu Lys Arg Phe Thr Lys Pro Ser Gly Ala Phe Tyr Ile Thr
305                 310                 315                 320

Ala Glu Leu Pro Val Glu Asp Ala Glu Phe Ala Arg Trp Met Leu
                325                 330                 335

Thr Asp Phe Asn Met Asp Gly Thr Thr Met Val Ala Pro Leu Arg
            340                 345                 350

Gly Phe Tyr Leu Thr Pro Gly Leu Gly Lys Lys Glu Ile Arg Ile Ala
        355                 360                 365

Cys Val Leu Glu Lys Asp Leu Leu Ser Arg Ala Ile Asp Val Leu Met
    370                 375                 380

Glu Gly Leu Lys Met Phe Cys Ser Ser Arg Ile Ser Cys Leu Glu
385                 390                 395

<210> SEQ ID NO 84
<211> LENGTH: 1263
<212> TYPE: DNA
<213> ORGANISM: Saccharomyces cerevisiae
<220> FEATURE:
<221> NAME/KEY: CDS
<222> LOCATION: (1)..(1263)

<400> SEQUENCE: 84 atg tca gcc acc ctg ttc aat aat atc gaa ctg ctg ccg ccg gac gcc    48
Met Ser Ala Thr Leu Phe Asn Asn Ile Glu Leu Leu Pro Pro Asp Ala
1               5                   10                  15 ctg ttt ggt atc aaa caa cgc tat ggt caa gat caa cgc gcc acc aaa    96
Leu Phe Gly Ile Lys Gln Arg Tyr Gly Gln Asp Gln Arg Ala Thr Lys
            20                  25                  30 gtt gac ctg ggc att ggt gca tat cgt gat gac aat ggc aaa ccg tgg   144
Val Asp Leu Gly Ile Gly Ala Tyr Arg Asp Asp Asn Gly Lys Pro Trp
        35                  40                  45
```

-continued

| | | |
|---|---|---|
| gtc ctg ccg agt gtg aaa gcg gcc gaa aaa ctg atc cat aac gat agc<br>Val Leu Pro Ser Val Lys Ala Ala Glu Lys Leu Ile His Asn Asp Ser<br>50                     55                     60 | | 192 |
| tct tac aat cac gaa tac ctg ggc atc acc ggt ctg ccg agc ctg acg<br>Ser Tyr Asn His Glu Tyr Leu Gly Ile Thr Gly Leu Pro Ser Leu Thr<br>65                   70                    75                   80 | | 240 |
| tct aac gca gct aaa att atc ttt ggt acc cag agc gac gcg ctg caa<br>Ser Asn Ala Ala Lys Ile Ile Phe Gly Thr Gln Ser Asp Ala Leu Gln<br>                    85                    90                   95 | | 288 |
| gaa gat cgc gtc att tct gtg cag tca ctg tcg ggc acg ggt gca ctg<br>Glu Asp Arg Val Ile Ser Val Gln Ser Leu Ser Gly Thr Gly Ala Leu<br>              100                   105                   110 | | 336 |
| cat atc agt gct aaa ttt ttc tcc aaa ttt ttc ccg gac aaa ctg gtt<br>His Ile Ser Ala Lys Phe Phe Ser Lys Phe Phe Pro Asp Lys Leu Val<br>              115                   120                   125 | | 384 |
| tac ctg tca aaa ccg acc tgg gca aac cac atg gct att ttc gaa aat<br>Tyr Leu Ser Lys Pro Thr Trp Ala Asn His Met Ala Ile Phe Glu Asn<br>130                    135                   140 | | 432 |
| cag ggc ctg aaa acc gct acg tat ccg tac tgg gcc aat gaa acg aaa<br>Gln Gly Leu Lys Thr Ala Thr Tyr Pro Tyr Trp Ala Asn Glu Thr Lys<br>145                    150                   155                   160 | | 480 |
| tcg ctg gat ctg aac ggc ttt ctg aat gcg att caa aaa gcc ccg gaa<br>Ser Leu Asp Leu Asn Gly Phe Leu Asn Ala Ile Gln Lys Ala Pro Glu<br>              165                   170                   175 | | 528 |
| ggt tca atc ttc gtg ctg cat tcg tgc gcg cac aat ccg acc ggt ctg<br>Gly Ser Ile Phe Val Leu His Ser Cys Ala His Asn Pro Thr Gly Leu<br>              180                   185                   190 | | 576 |
| gac ccg acg agt gaa cag tgg gtt caa att gtc gat gcg atc gcc tcc<br>Asp Pro Thr Ser Glu Gln Trp Val Gln Ile Val Asp Ala Ile Ala Ser<br>              195                   200                   205 | | 624 |
| aaa aac cat atc gcg ctg ttt gat acc gcc tat cag ggc ttc gca acg<br>Lys Asn His Ile Ala Leu Phe Asp Thr Ala Tyr Gln Gly Phe Ala Thr<br>210                    215                   220 | | 672 |
| ggt gat ctg gac aaa gat gca tac gct gtt cgt ctg ggc gtc gaa aaa<br>Gly Asp Leu Asp Lys Asp Ala Tyr Ala Val Arg Leu Gly Val Glu Lys<br>225                    230                   235                   240 | | 720 |
| ctg agt acc gtt tcc ccg gtg ttt gtt tgc caa tca ttc gcg aaa aac<br>Leu Ser Thr Val Ser Pro Val Phe Val Cys Gln Ser Phe Ala Lys Asn<br>              245                   250                   255 | | 768 |
| gcc ggc atg tat ggt gaa cgc gtc ggt tgt ttt cat ctg gct ctg acc<br>Ala Gly Met Tyr Gly Glu Arg Val Gly Cys Phe His Leu Ala Leu Thr<br>              260                   265                   270 | | 816 |
| aaa cag gcg caa aat aaa acc att aaa ccg gca gtg acg tct cag ctg<br>Lys Gln Ala Gln Asn Lys Thr Ile Lys Pro Ala Val Thr Ser Gln Leu<br>              275                   280                   285 | | 864 |
| gcg aaa att atc cgt tca gaa gtg tcg aac ccg ccg gca tac ggc gct<br>Ala Lys Ile Ile Arg Ser Glu Val Ser Asn Pro Pro Ala Tyr Gly Ala<br>290                    295                   300 | | 912 |
| aaa atc gtt gcc aaa ctg ctg gaa acc ccg gaa ctg acg gaa cag tgg<br>Lys Ile Val Ala Lys Leu Leu Glu Thr Pro Glu Leu Thr Glu Gln Trp<br>305                    310                   315                   320 | | 960 |
| cac aaa gat atg gtg acc atg agt tcc cgc att acg aaa atg cgt cat<br>His Lys Asp Met Val Thr Met Ser Ser Arg Ile Thr Lys Met Arg His<br>              325                   330                   335 | | 1008 |
| gcg ctg cgc gac cac ctg gtc aaa ctg ggc acc ccg ggt aac tgg gat<br>Ala Leu Arg Asp His Leu Val Lys Leu Gly Thr Pro Gly Asn Trp Asp<br>              340                   345                   350 | | 1056 |
| cat atc gtg aat cag tgt ggc atg ttt agc ttc acc ggt ctg acg ccg<br>His Ile Val Asn Gln Cys Gly Met Phe Ser Phe Thr Gly Leu Thr Pro | | 1104 |

-continued

```
                355                 360                 365
caa atg gtt aaa cgt ctg gaa gaa acc cac gcc gtg tat ctg gtt gca    1152
Gln Met Val Lys Arg Leu Glu Glu Thr His Ala Val Tyr Leu Val Ala
370                 375                 380 agc ggt cgc gcg tct att gcc ggc ctg aac cag ggt aat gtc gaa tat    1200
Ser Gly Arg Ala Ser Ile Ala Gly Leu Asn Gln Gly Asn Val Glu Tyr
385                 390                 395                 400 gtc gca aaa gcc att gac gaa gtg gtc cgt ttc tac gca acc gaa gca    1248
Val Ala Lys Ala Ile Asp Glu Val Val Arg Phe Tyr Ala Thr Glu Ala
            405                 410                 415 aaa ctg ctc gag tga                                                 1263
Lys Leu Leu Glu
        420
```

<210> SEQ ID NO 85
<211> LENGTH: 420
<212> TYPE: PRT
<213> ORGANISM: Saccharomyces cerevisiae

<400> SEQUENCE: 85

Met Ser Ala Thr Leu Phe Asn Asn Ile Glu Leu Leu Pro Pro Asp Ala
1               5                   10                  15

Leu Phe Gly Ile Lys Gln Arg Tyr Gly Gln Asp Gln Arg Ala Thr Lys
            20                  25                  30

Val Asp Leu Gly Ile Gly Ala Tyr Arg Asp Asp Asn Gly Lys Pro Trp
        35                  40                  45

Val Leu Pro Ser Val Lys Ala Ala Glu Lys Leu Ile His Asn Asp Ser
    50                  55                  60

Ser Tyr Asn His Glu Tyr Leu Gly Ile Thr Gly Leu Pro Ser Leu Thr
65                  70                  75                  80

Ser Asn Ala Ala Lys Ile Ile Phe Gly Thr Gln Ser Asp Ala Leu Gln
                85                  90                  95

Glu Asp Arg Val Ile Ser Val Gln Ser Leu Ser Gly Thr Gly Ala Leu
            100                 105                 110

His Ile Ser Ala Lys Phe Phe Ser Lys Phe Phe Pro Asp Lys Leu Val
        115                 120                 125

Tyr Leu Ser Lys Pro Thr Trp Ala Asn His Met Ala Ile Phe Glu Asn
    130                 135                 140

Gln Gly Leu Lys Thr Ala Thr Tyr Pro Tyr Trp Ala Asn Glu Thr Lys
145                 150                 155                 160

Ser Leu Asp Leu Asn Gly Phe Leu Asn Ala Ile Gln Lys Ala Pro Glu
                165                 170                 175

Gly Ser Ile Phe Val Leu His Ser Cys Ala His Asn Pro Thr Gly Leu
            180                 185                 190

Asp Pro Thr Ser Glu Gln Trp Val Gln Ile Val Asp Ala Ile Ala Ser
        195                 200                 205

Lys Asn His Ile Ala Leu Phe Asp Thr Ala Tyr Gln Gly Phe Ala Thr
    210                 215                 220

Gly Asp Leu Asp Lys Asp Ala Tyr Ala Val Arg Leu Gly Val Glu Lys
225                 230                 235                 240

Leu Ser Thr Val Ser Pro Val Phe Val Cys Gln Ser Phe Ala Lys Asn
                245                 250                 255

Ala Gly Met Tyr Gly Glu Arg Val Gly Cys Phe His Leu Ala Leu Thr
            260                 265                 270

Lys Gln Ala Gln Asn Lys Thr Ile Lys Pro Ala Val Thr Ser Gln Leu
        275                 280                 285

```
Ala Lys Ile Ile Arg Ser Glu Val Ser Asn Pro Ala Tyr Gly Ala
        290                 295                 300

Lys Ile Val Ala Lys Leu Leu Glu Thr Pro Glu Leu Thr Glu Gln Trp
305                 310                 315                 320

His Lys Asp Met Val Thr Met Ser Ser Arg Ile Thr Lys Met Arg His
                325                 330                 335

Ala Leu Arg Asp His Leu Val Lys Leu Gly Thr Pro Gly Asn Trp Asp
                340                 345                 350

His Ile Val Asn Gln Cys Gly Met Phe Ser Phe Thr Gly Leu Thr Pro
            355                 360                 365

Gln Met Val Lys Arg Leu Glu Glu Thr His Ala Val Tyr Leu Val Ala
        370                 375                 380

Ser Gly Arg Ala Ser Ile Ala Gly Leu Asn Gln Gly Asn Val Glu Tyr
385                 390                 395                 400

Val Ala Lys Ala Ile Asp Glu Val Val Arg Phe Tyr Ala Thr Glu Ala
                405                 410                 415

Lys Leu Leu Glu
        420

<210> SEQ ID NO 86
<211> LENGTH: 1200
<212> TYPE: DNA
<213> ORGANISM: Eubacterium rectale
<220> FEATURE:
<221> NAME/KEY: CDS
<222> LOCATION: (1)..(1200)

<400> SEQUENCE: 86 atg gtc gtc aat gaa tca atg tat caa ctg ggc tcg gtc cgc tcg gca      48
Met Val Val Asn Glu Ser Met Tyr Gln Leu Gly Ser Val Arg Ser Ala
1               5                   10                  15 atc cgt gaa ctg ttc gaa tat ggc aaa aaa cgt gct gcg att gtt ggc      96
Ile Arg Glu Leu Phe Glu Tyr Gly Lys Lys Arg Ala Ala Ile Val Gly
                20                  25                  30 aaa gaa aac gtc tat gat ttt agc att ggt aat ccg tct atc ccg gcc     144
Lys Glu Asn Val Tyr Asp Phe Ser Ile Gly Asn Pro Ser Ile Pro Ala
            35                  40                  45 ccg cag att gtt aac gac acc atc aaa gaa ctg gtg acg gat tat gac     192
Pro Gln Ile Val Asn Asp Thr Ile Lys Glu Leu Val Thr Asp Tyr Asp
        50                  55                  60 tct gtt gct ctg cat ggc tac acc agt gcg caa ggt gat gtg gaa acg     240
Ser Val Ala Leu His Gly Tyr Thr Ser Ala Gln Gly Asp Val Glu Thr
65                  70                  75                  80 cgt gcg gcc att gct gaa ttt ctg aac aat acc cat ggc acg cac ttc     288
Arg Ala Ala Ile Ala Glu Phe Leu Asn Asn Thr His Gly Thr His Phe
                85                  90                  95 aac gcc gac aat ctg tac atg acc atg ggt gca gct gcg agc ctg tct     336
Asn Ala Asp Asn Leu Tyr Met Thr Met Gly Ala Ala Ala Ser Leu Ser
            100                 105                 110 atc tgc ttt cgt gcc ctg acc agc gat gcg tat gat gaa ttc att acg     384
Ile Cys Phe Arg Ala Leu Thr Ser Asp Ala Tyr Asp Glu Phe Ile Thr
        115                 120                 125 atc gcg ccg tat ttt ccg gaa tac aaa gtg ttc gtt aat gcc gca ggc     432
Ile Ala Pro Tyr Phe Pro Glu Tyr Lys Val Phe Val Asn Ala Ala Gly
            130                 135                 140 gca cgc ctg gtc gaa gtg ccg gca gat acc gaa cat ttt cag att gat     480
Ala Arg Leu Val Glu Val Pro Ala Asp Thr Glu His Phe Gln Ile Asp
145                 150                 155                 160
```

```
ttc gac gct ctg gaa gaa cgt atc aac gcg cac acg cgc ggc gtt att      528
Phe Asp Ala Leu Glu Glu Arg Ile Asn Ala His Thr Arg Gly Val Ile
                165                 170                 175 atc aat agt ccg aac aat ccg tcc ggt acc gtc tat tca gaa gaa acg      576
Ile Asn Ser Pro Asn Asn Pro Ser Gly Thr Val Tyr Ser Glu Glu Thr
            180                 185                 190 atc aaa aaa ctg tcg gat ctg ctg gaa aag aaa agc aaa gaa att ggc      624
Ile Lys Lys Leu Ser Asp Leu Leu Glu Lys Lys Ser Lys Glu Ile Gly
        195                 200                 205 cgt ccg atc ttt att atc gcg gat gaa ccg tat cgc gaa att gtt tac      672
Arg Pro Ile Phe Ile Ile Ala Asp Glu Pro Tyr Arg Glu Ile Val Tyr
    210                 215                 220 gac ggt atc aaa gtg ccg ttc gtt acc aaa tat tac gat aac acg ctg      720
Asp Gly Ile Lys Val Pro Phe Val Thr Lys Tyr Tyr Asp Asn Thr Leu
225                 230                 235                 240 gtg tgc tat agt tac tcc aaa tca ctg tcg ctg ccg ggc gaa cgt atc      768
Val Cys Tyr Ser Tyr Ser Lys Ser Leu Ser Leu Pro Gly Glu Arg Ile
                245                 250                 255 ggt tac gtt ctg gtc ccg gat gaa gtt tat gac aaa gca gaa ctg tac      816
Gly Tyr Val Leu Val Pro Asp Glu Val Tyr Asp Lys Ala Glu Leu Tyr
            260                 265                 270 gct gcg gtc tgc ggt gct ggt cgt gca ctg ggt tat gtg tgt gcg ccg      864
Ala Ala Val Cys Gly Ala Gly Arg Ala Leu Gly Tyr Val Cys Ala Pro
        275                 280                 285 agt ctg ttc cag aaa atg atc gtt aaa tgt caa ggc gcc acc ggt gat      912
Ser Leu Phe Gln Lys Met Ile Val Lys Cys Gln Gly Ala Thr Gly Asp
    290                 295                 300 atc aac gca tat aaa gaa aat cgt gac ctg ctg tac gaa ggc ctg acc      960
Ile Asn Ala Tyr Lys Glu Asn Arg Asp Leu Leu Tyr Glu Gly Leu Thr
305                 310                 315                 320 cgc att ggt tat cac tgc ttc aaa ccg gat ggc gcc ttt tac atg ttc     1008
Arg Ile Gly Tyr His Cys Phe Lys Pro Asp Gly Ala Phe Tyr Met Phe
                325                 330                 335 gtg aaa gca ctg gaa gat gac tcc aat gct ttt tgt gaa aaa gcg aaa     1056
Val Lys Ala Leu Glu Asp Asp Ser Asn Ala Phe Cys Glu Lys Ala Lys
            340                 345                 350 gaa gaa gat gtc ctg att gtg gcc gca gac ggt ttc ggt tgc ccg ggt     1104
Glu Glu Asp Val Leu Ile Val Ala Ala Asp Gly Phe Gly Cys Pro Gly
        355                 360                 365 tgg gtc cgt atc tct tat tgt gtg gat cgt gaa atg att aaa cac agc     1152
Trp Val Arg Ile Ser Tyr Cys Val Asp Arg Glu Met Ile Lys His Ser
    370                 375                 380 atg ccg gcc ttt gaa aaa atc tat aaa aaa tac aat aaa ctc gag tga     1200
Met Pro Ala Phe Glu Lys Ile Tyr Lys Lys Tyr Asn Lys Leu Glu
385                 390                 395

<210> SEQ ID NO 87
<211> LENGTH: 399
<212> TYPE: PRT
<213> ORGANISM: Eubacterium rectale

<400> SEQUENCE: 87

Met Val Val Asn Glu Ser Met Tyr Gln Leu Gly Ser Val Arg Ser Ala
1               5                   10                  15

Ile Arg Glu Leu Phe Glu Tyr Gly Lys Lys Arg Ala Ala Ile Val Gly
            20                  25                  30

Lys Glu Asn Val Tyr Asp Phe Ser Ile Gly Asn Pro Ser Ile Pro Ala
        35                  40                  45

Pro Gln Ile Val Asn Asp Thr Ile Lys Glu Leu Val Thr Asp Tyr Asp
    50                  55                  60
```

Ser Val Ala Leu His Gly Tyr Thr Ser Ala Gln Gly Asp Val Glu Thr
65                  70                  75                  80

Arg Ala Ala Ile Ala Glu Phe Leu Asn Asn Thr His Gly Thr His Phe
                85                  90                  95

Asn Ala Asp Asn Leu Tyr Met Thr Met Gly Ala Ala Ser Leu Ser
            100                 105                 110

Ile Cys Phe Arg Ala Leu Thr Ser Asp Ala Tyr Asp Glu Phe Ile Thr
        115                 120                 125

Ile Ala Pro Tyr Phe Pro Glu Tyr Lys Val Phe Val Asn Ala Ala Gly
    130                 135                 140

Ala Arg Leu Val Glu Val Pro Ala Asp Thr His Phe Gln Ile Asp
145                 150                 155                 160

Phe Asp Ala Leu Glu Glu Arg Ile Asn Ala His Thr Arg Gly Val Ile
                165                 170                 175

Ile Asn Ser Pro Asn Asn Pro Ser Gly Thr Val Tyr Ser Glu Glu Thr
            180                 185                 190

Ile Lys Lys Leu Ser Asp Leu Leu Glu Lys Ser Lys Glu Ile Gly
        195                 200                 205

Arg Pro Ile Phe Ile Ile Ala Asp Glu Pro Tyr Arg Glu Ile Val Tyr
210                 215                 220

Asp Gly Ile Lys Val Pro Phe Val Thr Lys Tyr Tyr Asp Asn Thr Leu
225                 230                 235                 240

Val Cys Tyr Ser Tyr Ser Lys Ser Leu Ser Leu Pro Gly Glu Arg Ile
                245                 250                 255

Gly Tyr Val Leu Val Pro Asp Glu Val Tyr Asp Lys Ala Glu Leu Tyr
            260                 265                 270

Ala Ala Val Cys Gly Ala Gly Arg Ala Leu Gly Tyr Val Cys Ala Pro
        275                 280                 285

Ser Leu Phe Gln Lys Met Ile Val Lys Cys Gln Gly Ala Thr Gly Asp
    290                 295                 300

Ile Asn Ala Tyr Lys Glu Asn Arg Asp Leu Leu Tyr Glu Gly Leu Thr
305                 310                 315                 320

Arg Ile Gly Tyr His Cys Phe Lys Pro Asp Gly Ala Phe Tyr Met Phe
                325                 330                 335

Val Lys Ala Leu Glu Asp Asp Ser Asn Ala Phe Cys Gly Lys Ala Lys
            340                 345                 350

Glu Glu Asp Val Leu Ile Val Ala Ala Asp Gly Phe Gly Cys Pro Gly
        355                 360                 365

Trp Val Arg Ile Ser Tyr Cys Val Asp Arg Glu Met Ile Lys His Ser
    370                 375                 380

Met Pro Ala Phe Glu Lys Ile Tyr Lys Lys Tyr Asn Lys Leu Glu
385                 390                 395

<210> SEQ ID NO 88
<211> LENGTH: 1314
<212> TYPE: DNA
<213> ORGANISM: Bacillus pumilus
<220> FEATURE:
<221> NAME/KEY: CDS
<222> LOCATION: (1)..(1314)

<400> SEQUENCE: 88 atg tcg ggc ttt acg gca ctg tcg gaa gcg gaa ctg aat gac ctg tat     48
Met Ser Gly Phe Thr Ala Leu Ser Glu Ala Glu Leu Asn Asp Leu Tyr
1               5                   10                  15

```
gcg gca ctg caa gat gaa tat gaa acc tac aaa tcc aaa aac ctg cat      96
Ala Ala Leu Gln Asp Glu Tyr Glu Thr Tyr Lys Ser Lys Asn Leu His
             20                  25                  30 ctg gac atg agc cgt ggc aaa ccg tct ccg aaa cag ctg gat ctg agt     144
Leu Asp Met Ser Arg Gly Lys Pro Ser Pro Lys Gln Leu Asp Leu Ser
         35                  40                  45 atg ggt atg ctg gat gtg gtt acc tcc aaa gac gca atg acc gct gaa     192
Met Gly Met Leu Asp Val Val Thr Ser Lys Asp Ala Met Thr Ala Glu
     50                  55                  60 gat ggc acg gac gtg cgc aac tat ggc ggt ctg acg ggt ctg agc gaa     240
Asp Gly Thr Asp Val Arg Asn Tyr Gly Gly Leu Thr Gly Leu Ser Glu
 65                  70                  75                  80 acc aaa acg ttt ttc gcg gat gtt ctg aat ctg aaa ccg gaa caa att     288
Thr Lys Thr Phe Phe Ala Asp Val Leu Asn Leu Lys Pro Glu Gln Ile
                 85                  90                  95 atc att ggc ggt aac agc tct ctg aat atg atg cat gac acc atc gca     336
Ile Ile Gly Gly Asn Ser Ser Leu Asn Met Met His Asp Thr Ile Ala
            100                 105                 110 cgt gct atg acg cac ggc gtt tat gat tct aaa acc ccg tgg ggt aaa     384
Arg Ala Met Thr His Gly Val Tyr Asp Ser Lys Thr Pro Trp Gly Lys
        115                 120                 125 ctg ccg aaa gtc aaa ttt ctg gca ccg tca ccg ggt tac gat cgt cac     432
Leu Pro Lys Val Lys Phe Leu Ala Pro Ser Pro Gly Tyr Asp Arg His
130                 135                 140 ttt tcg att tgc gaa ctg ttc aac atc gaa atg att acc gtc gat atg     480
Phe Ser Ile Cys Glu Leu Phe Asn Ile Glu Met Ile Thr Val Asp Met
145                 150                 155                 160 aaa gcc gac ggt ccg gat atg gac cag gtg gaa aaa ctg gtt gcg gaa     528
Lys Ala Asp Gly Pro Asp Met Asp Gln Val Glu Lys Leu Val Ala Glu
                165                 170                 175 gac gaa gcc atc aaa ggc att tgg tgt gtt ccg aaa tat agc aat ccg     576
Asp Glu Ala Ile Lys Gly Ile Trp Cys Val Pro Lys Tyr Ser Asn Pro
            180                 185                 190 gat ggt att acc tac tct gat gaa gtc gtg gac cgt ctg gcg agc atg     624
Asp Gly Ile Thr Tyr Ser Asp Glu Val Val Asp Arg Leu Ala Ser Met
        195                 200                 205 aaa acg aaa gcc gat gac ttt cgc atc ttc tgg gat gac gcg tat gcc     672
Lys Thr Lys Ala Asp Asp Phe Arg Ile Phe Trp Asp Asp Ala Tyr Ala
210                 215                 220 gtg cat cac ctg acc gat acg ccg gac acc ctg aaa gat att ttt cag     720
Val His His Leu Thr Asp Thr Pro Asp Thr Leu Lys Asp Ile Phe Gln
225                 230                 235                 240 gca gtc gaa gaa gct ggc cat ccg cac cgt gtg ttt atg ttc gca tca     768
Ala Val Glu Glu Ala Gly His Pro His Arg Val Phe Met Phe Ala Ser
                245                 250                 255 acc tcg aaa atc acg ttt ccg ggc agc ggt att gcg ctg atg gcc agt     816
Thr Ser Lys Ile Thr Phe Pro Gly Ser Gly Ile Ala Leu Met Ala Ser
            260                 265                 270 tcc ctg gat aac gtt agt ttc acc cag aaa caa ctg tcc atc cag acg     864
Ser Leu Asp Asn Val Ser Phe Thr Gln Lys Gln Leu Ser Ile Gln Thr
        275                 280                 285 att ggc ccg gat aaa atc aac caa ctg cgt cat ctg cgc ttt ttc aaa     912
Ile Gly Pro Asp Lys Ile Asn Gln Leu Arg His Leu Arg Phe Phe Lys
290                 295                 300 aat ccg gaa ggt ctg aaa gaa cac atg cgc aaa cac gcg gcc atc att     960
Asn Pro Glu Gly Leu Lys Glu His Met Arg Lys His Ala Ala Ile Ile
305                 310                 315                 320 aaa ccg aaa ttt gat ctg gtg ctg tca atc ctg gac gaa acc ctg ggc    1008
Lys Pro Lys Phe Asp Leu Val Leu Ser Ile Leu Asp Glu Thr Leu Gly
                325                 330                 335
```

```
ggt aaa gat att gcc gaa tgg cat aaa ccg aac ggc ggt tac ttc att      1056
Gly Lys Asp Ile Ala Glu Trp His Lys Pro Asn Gly Gly Tyr Phe Ile
        340                 345                 350 tcg ctg aat acc ctg gat cac tgc gca aaa gct gtt gtc cag aaa gca      1104
Ser Leu Asn Thr Leu Asp His Cys Ala Lys Ala Val Val Gln Lys Ala
    355                 360                 365 aaa gaa gct ggt gtt acc atg acg ggt gca ggt gca acc tat ccg tac      1152
Lys Glu Ala Gly Val Thr Met Thr Gly Ala Gly Ala Thr Tyr Pro Tyr
370                 375                 380 ggt aaa gat ccg ctg gac cgt aat atc cgc att gca ccg acc ttt ccg      1200
Gly Lys Asp Pro Leu Asp Arg Asn Ile Arg Ile Ala Pro Thr Phe Pro
385                 390                 395                 400 agt ctg gaa gaa ctg gaa caa gct atc gat att ttc acg ctg tgt gtt      1248
Ser Leu Glu Glu Leu Glu Gln Ala Ile Asp Ile Phe Thr Leu Cys Val
            405                 410                 415 caa ctg gtg tct atc gaa aaa ctg ctg tcc aaa aaa tct caa tct gct      1296
Gln Leu Val Ser Ile Glu Lys Leu Leu Ser Lys Lys Ser Gln Ser Ala
            420                 425                 430 ccg acc gtg ctc gag tga                                              1314
Pro Thr Val Leu Glu
            435

<210> SEQ ID NO 89
<211> LENGTH: 437
<212> TYPE: PRT
<213> ORGANISM: Bacillus pumilus

<400> SEQUENCE: 89

Met Ser Gly Phe Thr Ala Leu Ser Glu Ala Glu Leu Asn Asp Leu Tyr
1               5                   10                  15

Ala Ala Leu Gln Asp Glu Tyr Glu Thr Tyr Lys Ser Lys Asn Leu His
            20                  25                  30

Leu Asp Met Ser Arg Gly Lys Pro Ser Pro Lys Gln Leu Asp Leu Ser
        35                  40                  45

Met Gly Met Leu Asp Val Val Thr Ser Lys Asp Ala Met Thr Ala Glu
    50                  55                  60

Asp Gly Thr Asp Val Arg Asn Tyr Gly Gly Leu Thr Gly Leu Ser Glu
65                  70                  75                  80

Thr Lys Thr Phe Phe Ala Asp Val Leu Asn Leu Lys Pro Glu Gln Ile
                85                  90                  95

Ile Ile Gly Gly Asn Ser Ser Leu Asn Met Met His Asp Thr Ile Ala
            100                 105                 110

Arg Ala Met Thr His Gly Val Tyr Asp Ser Lys Thr Pro Trp Gly Lys
        115                 120                 125

Leu Pro Lys Val Lys Phe Leu Ala Pro Ser Pro Gly Tyr Asp Arg His
    130                 135                 140

Phe Ser Ile Cys Glu Leu Phe Asn Ile Glu Met Ile Thr Val Asp Met
145                 150                 155                 160

Lys Ala Asp Gly Pro Asp Met Asp Gln Val Glu Lys Leu Val Ala Glu
                165                 170                 175

Asp Glu Ala Ile Lys Gly Ile Trp Cys Val Pro Lys Tyr Ser Asn Pro
            180                 185                 190

Asp Gly Ile Thr Tyr Ser Asp Glu Val Val Asp Arg Leu Ala Ser Met
        195                 200                 205

Lys Thr Lys Ala Asp Asp Phe Arg Ile Phe Trp Asp Asp Ala Tyr Ala
    210                 215                 220
```

```
Val His His Leu Thr Asp Thr Pro Asp Thr Leu Lys Asp Ile Phe Gln
225                 230                 235                 240

Ala Val Glu Glu Ala Gly His Pro His Arg Val Phe Met Phe Ala Ser
                245                 250                 255

Thr Ser Lys Ile Thr Phe Pro Gly Ser Gly Ile Ala Leu Met Ala Ser
            260                 265                 270

Ser Leu Asp Asn Val Ser Phe Thr Gln Lys Gln Leu Ser Ile Gln Thr
        275                 280                 285

Ile Gly Pro Asp Lys Ile Asn Gln Leu Arg His Leu Arg Phe Phe Lys
    290                 295                 300

Asn Pro Glu Gly Leu Lys Glu His Met Arg Lys His Ala Ala Ile Ile
305                 310                 315                 320

Lys Pro Lys Phe Asp Leu Val Leu Ser Ile Leu Asp Glu Thr Leu Gly
                325                 330                 335

Gly Lys Asp Ile Ala Glu Trp His Lys Pro Asn Gly Gly Tyr Phe Ile
            340                 345                 350

Ser Leu Asn Thr Leu Asp His Cys Ala Lys Ala Val Val Gln Lys Ala
        355                 360                 365

Lys Glu Ala Gly Val Thr Met Thr Gly Ala Gly Ala Thr Tyr Pro Tyr
    370                 375                 380

Gly Lys Asp Pro Leu Asp Arg Asn Ile Arg Ile Ala Pro Thr Phe Pro
385                 390                 395                 400

Ser Leu Glu Glu Leu Glu Gln Ala Ile Asp Ile Phe Thr Leu Cys Val
                405                 410                 415

Gln Leu Val Ser Ile Glu Lys Leu Leu Ser Lys Lys Ser Gln Ser Ala
            420                 425                 430

Pro Thr Val Leu Glu
        435

<210> SEQ ID NO 90
<211> LENGTH: 1296
<212> TYPE: DNA
<213> ORGANISM: Bacillus cellulosilyticus
<220> FEATURE:
<221> NAME/KEY: CDS
<222> LOCATION: (1)..(1296)

<400> SEQUENCE: 90 atg agc gat tac acc gtg ctg tca acg caa gaa ctg caa caa gtc cac    48
Met Ser Asp Tyr Thr Val Leu Ser Thr Gln Glu Leu Gln Gln Val His
1               5                   10                  15 atg gac ctg ctg gaa aaa ttc aac aaa ctg aaa gac gaa aat ctg gcg    96
Met Asp Leu Leu Glu Lys Phe Asn Lys Leu Lys Asp Glu Asn Leu Ala
            20                  25                  30 ctg gat atg agt cgt ggt aaa ccg tcc ccg gat caa ctg gac ctg tca   144
Leu Asp Met Ser Arg Gly Lys Pro Ser Pro Asp Gln Leu Asp Leu Ser
        35                  40                  45 aac ggc atg ctg gat att atc tcg gcg gac acc ccg ctg aaa gcc gaa   192
Asn Gly Met Leu Asp Ile Ile Ser Ala Asp Thr Pro Leu Lys Ala Glu
    50                  55                  60 gat ggt acg gac gtg cgc aat tat ggc ggt ctg gat ggc ctg ccg gaa   240
Asp Gly Thr Asp Val Arg Asn Tyr Gly Gly Leu Asp Gly Leu Pro Glu
65                  70                  75                  80 gcg aaa gcc ttt ttc agc aac att ctg aat gtt agc tct aac gaa att   288
Ala Lys Ala Phe Phe Ser Asn Ile Leu Asn Val Ser Ser Asn Glu Ile
                85                  90                  95 atc att ggc ggt aac agt tcc ctg aat ctg atg cat gat acc gtt gca   336
Ile Ile Gly Gly Asn Ser Ser Leu Asn Leu Met His Asp Thr Val Ala
```

```
              100                 105                 110
cgt gct atg ctg ttt ggt gtc aat gac ggc gaa acg gcg tgg gcc aaa      384
Arg Ala Met Leu Phe Gly Val Asn Asp Gly Glu Thr Ala Trp Ala Lys
        115                 120                 125 ctg ccg aaa gtc aaa ttc ctg tgc ccg agc ccg ggt tac gat cgt cac      432
Leu Pro Lys Val Lys Phe Leu Cys Pro Ser Pro Gly Tyr Asp Arg His
130                 135                 140 ttc tct att tgt gaa ctg ttc aac atc gaa atg att cgc gtt gat atg      480
Phe Ser Ile Cys Glu Leu Phe Asn Ile Glu Met Ile Arg Val Asp Met
145                 150                 155                 160 ctg gaa gac ggc ccg aac atg gat cag atc gaa aaa ctg gtg caa gaa      528
Leu Glu Asp Gly Pro Asn Met Asp Gln Ile Glu Lys Leu Val Gln Glu
                165                 170                 175 gac gaa agt atc aaa ggt att tgg tgc gtt ccg aaa tat agt aac ccg      576
Asp Glu Ser Ile Lys Gly Ile Trp Cys Val Pro Lys Tyr Ser Asn Pro
            180                 185                 190 gat ggc att acc tac tcc gat gaa gtg gtt gac cgt ttt gca agc atg      624
Asp Gly Ile Thr Tyr Ser Asp Glu Val Val Asp Arg Phe Ala Ser Met
        195                 200                 205 aaa acg aaa gct aaa gac ttt cgc att ttc tgg gat gac gcg tat acc      672
Lys Thr Lys Ala Lys Asp Phe Arg Ile Phe Trp Asp Asp Ala Tyr Thr
    210                 215                 220 gtg cat cac ctg acg gat aaa ccg gac gaa ctg aaa aat atc ctg acc      720
Val His His Leu Thr Asp Lys Pro Asp Glu Leu Lys Asn Ile Leu Thr
225                 230                 235                 240 gca tgt aaa cag gct ggc aac gaa gat cgc gtt ctg atc ttt tca tcg      768
Ala Cys Lys Gln Ala Gly Asn Glu Asp Arg Val Leu Ile Phe Ser Ser
                245                 250                 255 acc agc aaa att acg ttc gcg ggc ggt ggc atc ggt gtc ctg gcc agc      816
Thr Ser Lys Ile Thr Phe Ala Gly Gly Gly Ile Gly Val Leu Ala Ser
            260                 265                 270 tct gaa aac aac atc cag tac ttc aaa aaa ctg ctg gca atg caa acc      864
Ser Glu Asn Asn Ile Gln Tyr Phe Lys Lys Leu Leu Ala Met Gln Thr
        275                 280                 285 atc ggc ccg gat aaa ctg aat cag atc cgt cat att cgc ttt ttc aaa      912
Ile Gly Pro Asp Lys Leu Asn Gln Ile Arg His Ile Arg Phe Phe Lys
    290                 295                 300 aac gtg gaa aat ctg tca acc cac atg aaa aaa cac gcc tcg atc att      960
Asn Val Glu Asn Leu Ser Thr His Met Lys Lys His Ala Ser Ile Ile
305                 310                 315                 320 aaa ccg aaa ttt gat atg gtc ctg aac aaa ctg gaa agc gaa atc ggt     1008
Lys Pro Lys Phe Asp Met Val Leu Asn Lys Leu Glu Ser Glu Ile Gly
                325                 330                 335 ggc aaa aac att ggt tct tgg gtg gaa ccg aat ggt ggc tat ttt att     1056
Gly Lys Asn Ile Gly Ser Trp Val Glu Pro Asn Gly Gly Tyr Phe Ile
            340                 345                 350 agt ttc aac acc ctg gat ggt tgc gcc aaa acg gtc gtg tcc atg gcg     1104
Ser Phe Asn Thr Leu Asp Gly Cys Ala Lys Thr Val Val Ser Met Ala
        355                 360                 365 aaa gaa gcc ggt gtt aaa ctg acc ggt gca ggc gct acg ttt ccg tac     1152
Lys Glu Ala Gly Val Lys Leu Thr Gly Ala Gly Ala Thr Phe Pro Tyr
    370                 375                 380 ggt cac gat ccg cgt gac cgc aat atc cgt att gca ccg acc ttc ccg     1200
Gly His Asp Pro Arg Asp Arg Asn Ile Arg Ile Ala Pro Thr Phe Pro
385                 390                 395                 400 tct ctg atc gaa ctg gaa cgc gct atg gat gtc ttc tgc ctg tgt gtg     1248
Ser Leu Ile Glu Leu Glu Arg Ala Met Asp Val Phe Cys Leu Cys Val
                405                 410                 415 caa ctg gcg tcg gtg gaa aaa ctg ctg aaa gaa caa ctg ctc gag tga     1296
Gln Leu Ala Ser Val Glu Lys Leu Leu Lys Glu Gln Leu Leu Glu
```

```
Gln Leu Ala Ser Val Glu Lys Leu Leu Lys Gln Leu Leu Glu
            420                 425                 430
```

<210> SEQ ID NO 91
<211> LENGTH: 431
<212> TYPE: PRT
<213> ORGANISM: Bacillus cellulosilyticus

<400> SEQUENCE: 91

```
Met Ser Asp Tyr Thr Val Leu Ser Thr Gln Glu Leu Gln Gln Val His
1               5                   10                  15

Met Asp Leu Leu Glu Lys Phe Asn Lys Leu Lys Asp Glu Asn Leu Ala
            20                  25                  30

Leu Asp Met Ser Arg Gly Lys Pro Ser Pro Asp Gln Leu Asp Leu Ser
        35                  40                  45

Asn Gly Met Leu Asp Ile Ile Ser Ala Asp Thr Pro Leu Lys Ala Glu
50                  55                  60

Asp Gly Thr Asp Val Arg Asn Tyr Gly Gly Leu Asp Gly Leu Pro Glu
65                  70                  75                  80

Ala Lys Ala Phe Phe Ser Asn Ile Leu Asn Val Ser Ser Asn Glu Ile
                85                  90                  95

Ile Ile Gly Gly Asn Ser Ser Leu Asn Leu Met His Asp Thr Val Ala
            100                 105                 110

Arg Ala Met Leu Phe Gly Val Asn Asp Gly Glu Thr Ala Trp Ala Lys
        115                 120                 125

Leu Pro Lys Val Lys Phe Leu Cys Pro Ser Pro Gly Tyr Asp Arg His
    130                 135                 140

Phe Ser Ile Cys Glu Leu Phe Asn Ile Glu Met Ile Arg Val Asp Met
145                 150                 155                 160

Leu Glu Asp Gly Pro Asn Met Asp Gln Ile Lys Leu Val Gln Glu
                165                 170                 175

Asp Glu Ser Ile Lys Gly Ile Trp Cys Val Pro Lys Tyr Ser Asn Pro
            180                 185                 190

Asp Gly Ile Thr Tyr Ser Asp Glu Val Val Asp Arg Phe Ala Ser Met
        195                 200                 205

Lys Thr Lys Ala Lys Asp Phe Arg Ile Phe Trp Asp Asp Ala Tyr Thr
    210                 215                 220

Val His His Leu Thr Asp Lys Pro Asp Glu Leu Lys Asn Ile Leu Thr
225                 230                 235                 240

Ala Cys Lys Gln Ala Gly Asn Glu Asp Arg Val Leu Ile Phe Ser Ser
                245                 250                 255

Thr Ser Lys Ile Thr Phe Ala Gly Gly Gly Ile Gly Val Leu Ala Ser
            260                 265                 270

Ser Glu Asn Asn Ile Gln Tyr Phe Lys Lys Leu Leu Ala Met Gln Thr
        275                 280                 285

Ile Gly Pro Asp Lys Leu Asn Gln Ile Arg His Ile Arg Phe Lys
    290                 295                 300

Asn Val Glu Asn Leu Ser Thr His Met Lys Lys His Ala Ser Ile Ile
305                 310                 315                 320

Lys Pro Lys Phe Asp Met Val Leu Asn Lys Leu Glu Ser Glu Ile Gly
                325                 330                 335

Gly Lys Asn Ile Gly Ser Trp Val Glu Pro Asn Gly Gly Tyr Phe Ile
            340                 345                 350

Ser Phe Asn Thr Leu Asp Gly Cys Ala Lys Thr Val Val Ser Met Ala
        355                 360                 365
```

```
Lys Glu Ala Gly Val Lys Leu Thr Gly Ala Gly Ala Thr Phe Pro Tyr
        370                 375                 380

Gly His Asp Pro Arg Asp Arg Asn Ile Arg Ile Ala Pro Thr Phe Pro
385                 390                 395                 400

Ser Leu Ile Glu Leu Glu Arg Ala Met Asp Val Phe Cys Leu Cys Val
                405                 410                 415

Gln Leu Ala Ser Val Glu Lys Leu Leu Lys Glu Gln Leu Leu Glu
            420                 425                 430

<210> SEQ ID NO 92
<211> LENGTH: 1185
<212> TYPE: DNA
<213> ORGANISM: Bacillus sp.
<220> FEATURE:
<221> NAME/KEY: CDS
<222> LOCATION: (1)..(1185)

<400> SEQUENCE: 92 atg aaa gaa ctg ctg gca aac cgt gtg aaa acc ctg acc ccg tct acg      48
Met Lys Glu Leu Leu Ala Asn Arg Val Lys Thr Leu Thr Pro Ser Thr
1               5                   10                  15 acc ctg gcg att acc gca aaa gcg aaa gaa atg aaa gcg cag ggt att      96
Thr Leu Ala Ile Thr Ala Lys Ala Lys Glu Met Lys Ala Gln Gly Ile
            20                  25                  30 gat gtg atc ggt ctg ggt gca ggt gaa ccg gac ttt aac acc ccg cag     144
Asp Val Ile Gly Leu Gly Ala Gly Glu Pro Asp Phe Asn Thr Pro Gln
        35                  40                  45 aat att atg gat gcg gcc atc gac tcg atg cag caa ggc tat acc aaa     192
Asn Ile Met Asp Ala Ala Ile Asp Ser Met Gln Gln Gly Tyr Thr Lys
    50                  55                  60 tac acg ccg agc ggc ggt ctg ccg gca ctg aaa cag gct atc atc gaa     240
Tyr Thr Pro Ser Gly Gly Leu Pro Ala Leu Lys Gln Ala Ile Ile Glu
65                  70                  75                  80 aaa ttc aaa cgt gat aac caa ctg gaa tat aaa ccg aat gaa att atc     288
Lys Phe Lys Arg Asp Asn Gln Leu Glu Tyr Lys Pro Asn Glu Ile Ile
                85                  90                  95 gtc ggt gtg ggc gcg aaa cat gtg ctg tac acc ctg ttc cag gtt att     336
Val Gly Val Gly Ala Lys His Val Leu Tyr Thr Leu Phe Gln Val Ile
            100                 105                 110 ctg aac gaa ggt gac gaa gtt att atc ccg atc ccg tat tgg gtt tct     384
Leu Asn Glu Gly Asp Glu Val Ile Ile Pro Ile Pro Tyr Trp Val Ser
        115                 120                 125 tac ccg gaa cag gtc aaa ctg gcc ggc ggt gtt ccg gtc tat att gaa     432
Tyr Pro Glu Gln Val Lys Leu Ala Gly Gly Val Pro Val Tyr Ile Glu
    130                 135                 140 gca acc agt gaa cag aac tac aaa att acg gct gaa caa ctg aaa aat     480
Ala Thr Ser Glu Gln Asn Tyr Lys Ile Thr Ala Glu Gln Leu Lys Asn
145                 150                 155                 160 gcg atc acc gat aaa acg aaa gcc gtc att atc aac agc ccg tct aat     528
Ala Ile Thr Asp Lys Thr Lys Ala Val Ile Ile Asn Ser Pro Ser Asn
                165                 170                 175 ccg acc ggc atg gtg tat acg cgt gaa gaa ctg gaa gat att gca aaa     576
Pro Thr Gly Met Val Tyr Thr Arg Glu Glu Leu Glu Asp Ile Ala Lys
            180                 185                 190 atc gct ctg gaa aac aat att ctg atc gtg tcc gac gaa att tat gaa     624
Ile Ala Leu Glu Asn Asn Ile Leu Ile Val Ser Asp Glu Ile Tyr Glu
        195                 200                 205 aaa ctg ctg tac aac ggt gcc gaa cat ttc agt att gca cag atc tcc     672
Lys Leu Leu Tyr Asn Gly Ala Glu His Phe Ser Ile Ala Gln Ile Ser
    210                 215                 220
```

```
gaa gaa gtt aaa gca caa acc att gtc atc aat ggc gtg agt aaa tcc       720
Glu Glu Val Lys Ala Gln Thr Ile Val Ile Asn Gly Val Ser Lys Ser
225                 230                 235                 240 cac tca atg acg ggc tgg cgc att ggt tat gca gct ggc aac gcg gat       768
His Ser Met Thr Gly Trp Arg Ile Gly Tyr Ala Ala Gly Asn Ala Asp
            245                 250                 255 att atc aat gcc atg acc gac ctg gca tcg cac agc acg tct aac ccg       816
Ile Ile Asn Ala Met Thr Asp Leu Ala Ser His Ser Thr Ser Asn Pro
        260                 265                 270 acc acg gct agc cag tat gcg gcc atc gaa gcg tac aat ggt ccg caa       864
Thr Thr Ala Ser Gln Tyr Ala Ala Ile Glu Ala Tyr Asn Gly Pro Gln
    275                 280                 285 gat agt gtg gaa gaa atg cgt aaa gcg ttt gaa tcc cgc ctg gaa acc       912
Asp Ser Val Glu Glu Met Arg Lys Ala Phe Glu Ser Arg Leu Glu Thr
290                 295                 300 att tat ccg aaa ctg tca gct atc ccg ggt ttt aaa gtg gtt aaa ccg       960
Ile Tyr Pro Lys Leu Ser Ala Ile Pro Gly Phe Lys Val Val Lys Pro
305                 310                 315                 320 cag ggc gcc ttc tac ctg ctg ccg gat gtt tct gaa gca gct caa aaa      1008
Gln Gly Ala Phe Tyr Leu Leu Pro Asp Val Ser Glu Ala Ala Gln Lys
            325                 330                 335 acc ggc ttt gca agc gtc gac gaa ttc gcg tct gcc ctg ctg acg gaa      1056
Thr Gly Phe Ala Ser Val Asp Glu Phe Ala Ser Ala Leu Leu Thr Glu
        340                 345                 350 gcg aat gtg gcc gtt att ccg ggt agc ggt ttc ggt gca ccg tca acc      1104
Ala Asn Val Ala Val Ile Pro Gly Ser Gly Phe Gly Ala Pro Ser Thr
    355                 360                 365 att cgc atc tcg tac gca acc tct ctg aac ctg att gaa gaa gcg att      1152
Ile Arg Ile Ser Tyr Ala Thr Ser Leu Asn Leu Ile Glu Glu Ala Ile
370                 375                 380 gaa cgc att gac cgt ttt gtg aaa ctc gag tga                          1185
Glu Arg Ile Asp Arg Phe Val Lys Leu Glu
385                 390

<210> SEQ ID NO 93
<211> LENGTH: 394
<212> TYPE: PRT
<213> ORGANISM: Bacillus sp.

<400> SEQUENCE: 93

Met Lys Glu Leu Leu Ala Asn Arg Val Lys Thr Leu Thr Pro Ser Thr
1               5                   10                  15

Thr Leu Ala Ile Thr Ala Lys Ala Lys Glu Met Lys Ala Gln Gly Ile
            20                  25                  30

Asp Val Ile Gly Leu Gly Ala Gly Glu Pro Asp Phe Asn Thr Pro Gln
        35                  40                  45

Asn Ile Met Asp Ala Ala Ile Asp Ser Met Gln Gln Gly Tyr Thr Lys
    50                  55                  60

Tyr Thr Pro Ser Gly Gly Leu Pro Ala Leu Lys Gln Ala Ile Ile Glu
65                  70                  75                  80

Lys Phe Lys Arg Asp Asn Gln Leu Glu Tyr Lys Pro Asn Glu Ile Ile
                85                  90                  95

Val Gly Val Gly Ala Lys His Val Leu Tyr Thr Leu Phe Gln Val Ile
            100                 105                 110

Leu Asn Glu Gly Asp Glu Val Ile Ile Pro Ile Pro Tyr Trp Val Ser
        115                 120                 125

Tyr Pro Glu Gln Val Lys Leu Ala Gly Gly Val Pro Val Tyr Ile Glu
    130                 135                 140
```

Ala Thr Ser Glu Gln Asn Tyr Lys Ile Thr Ala Glu Gln Leu Lys Asn
145                 150                 155                 160

Ala Ile Thr Asp Lys Thr Lys Ala Val Ile Ile Asn Ser Pro Ser Asn
            165                 170                 175

Pro Thr Gly Met Val Tyr Thr Arg Glu Glu Leu Glu Asp Ile Ala Lys
        180                 185                 190

Ile Ala Leu Glu Asn Asn Ile Leu Ile Val Ser Asp Glu Ile Tyr Glu
    195                 200                 205

Lys Leu Leu Tyr Asn Gly Ala Glu His Phe Ser Ile Ala Gln Ile Ser
210                 215                 220

Glu Glu Val Lys Ala Gln Thr Ile Val Ile Asn Gly Val Ser Lys Ser
225                 230                 235                 240

His Ser Met Thr Gly Trp Arg Ile Gly Tyr Ala Ala Gly Asn Ala Asp
            245                 250                 255

Ile Ile Asn Ala Met Thr Asp Leu Ala Ser His Ser Thr Ser Asn Pro
        260                 265                 270

Thr Thr Ala Ser Gln Tyr Ala Ala Ile Glu Ala Tyr Asn Gly Pro Gln
    275                 280                 285

Asp Ser Val Glu Glu Met Arg Lys Ala Phe Glu Ser Arg Leu Glu Thr
290                 295                 300

Ile Tyr Pro Lys Leu Ser Ala Ile Pro Gly Phe Lys Val Val Lys Pro
305                 310                 315                 320

Gln Gly Ala Phe Tyr Leu Leu Pro Asp Val Ser Glu Ala Ala Gln Lys
            325                 330                 335

Thr Gly Phe Ala Ser Val Asp Glu Phe Ala Ser Ala Leu Leu Thr Glu
        340                 345                 350

Ala Asn Val Ala Val Ile Pro Gly Ser Gly Phe Gly Ala Pro Ser Thr
    355                 360                 365

Ile Arg Ile Ser Tyr Ala Thr Ser Leu Asn Leu Ile Glu Glu Ala Ile
370                 375                 380

Glu Arg Ile Asp Arg Phe Val Lys Leu Glu
385                 390

<210> SEQ ID NO 94
<211> LENGTH: 1239
<212> TYPE: DNA
<213> ORGANISM: Sinorhizobium meliloti
<220> FEATURE:
<221> NAME/KEY: CDS
<222> LOCATION: (1)..(1239)

<400> SEQUENCE: 94

| atg acc atc aat gcc acg gtt aaa gaa gcg ggt ttc cag ccg gcg tcg | 48 |
| Met Thr Ile Asn Ala Thr Val Lys Glu Ala Gly Phe Gln Pro Ala Ser | |
| 1               5                   10                  15 | |

| cgt att agt agt atc ggt gtg tct gaa atc ctg aaa atc ggt gcc cgc | 96 |
| Arg Ile Ser Ser Ile Gly Val Ser Glu Ile Leu Lys Ile Gly Ala Arg | |
|         20                  25                  30 | |

| gcg gcc gca atg aaa cgt gaa ggc aaa ccg gtt att atc ctg ggc gca | 144 |
| Ala Ala Ala Met Lys Arg Glu Gly Lys Pro Val Ile Ile Leu Gly Ala | |
|     35                  40                  45 | |

| ggt gaa ccg gat ttt gac acc ccg gaa cat gtc aaa caa gct gcg agc | 192 |
| Gly Glu Pro Asp Phe Asp Thr Pro Glu His Val Lys Gln Ala Ala Ser | |
| 50                  55                  60 | |

| gat gcc att cac cgc ggt gaa acc aaa tat acg gca ctg gac ggc acg | 240 |
| Asp Ala Ile His Arg Gly Glu Thr Lys Tyr Thr Ala Leu Asp Gly Thr | |
| 65                  70                  75                  80 | |

```
ccg gaa ctg aaa aaa gct atc cgc gaa aaa ttt caa cgt gaa aac ggt      288
Pro Glu Leu Lys Lys Ala Ile Arg Glu Lys Phe Gln Arg Glu Asn Gly
            85                  90                  95 ctg gcg tac gaa ctg gat gaa att acc gtg gct acg ggc gcg aaa cag      336
Leu Ala Tyr Glu Leu Asp Glu Ile Thr Val Ala Thr Gly Ala Lys Gln
        100                 105                 110 atc ctg ttc aat gcc atg atg gca tct ctg gat ccg ggt gac gaa gtt      384
Ile Leu Phe Asn Ala Met Met Ala Ser Leu Asp Pro Gly Asp Glu Val
        115                 120                 125 att atc ccg acc ccg tat tgg acg tca tac tcg gat att gtc cat atc      432
Ile Ile Pro Thr Pro Tyr Trp Thr Ser Tyr Ser Asp Ile Val His Ile
        130                 135                 140 tgc gaa ggt aaa ccg gtg ctg att gct tgt gac gcg agc tct ggc ttt      480
Cys Glu Gly Lys Pro Val Leu Ile Ala Cys Asp Ala Ser Ser Gly Phe
145                 150                 155                 160 cgt ctg acc gcc gaa aaa ctg gaa gca gca atc acc ccg cgt acg cgt      528
Arg Leu Thr Ala Glu Lys Leu Glu Ala Ala Ile Thr Pro Arg Thr Arg
                165                 170                 175 tgg gtc ctg ctg aac agc ccg tct aat ccg agc ggt gct gcg tat tct      576
Trp Val Leu Leu Asn Ser Pro Ser Asn Pro Ser Gly Ala Ala Tyr Ser
            180                 185                 190 gcc gca gat tac cgc ccg ctg ctg gaa gtt ctg ctg cgt cat ccg cac      624
Ala Ala Asp Tyr Arg Pro Leu Leu Glu Val Leu Leu Arg His Pro His
        195                 200                 205 gtc tgg ctg ctg gtt gat gac atg tat gaa cac atc gtg tac gat ggc      672
Val Trp Leu Leu Val Asp Asp Met Tyr Glu His Ile Val Tyr Asp Gly
210                 215                 220 ttt cgc ttc gtt acc ccg gcg cag ctg gaa ccg ggt ctg aaa aac cgt      720
Phe Arg Phe Val Thr Pro Ala Gln Leu Glu Pro Gly Leu Lys Asn Arg
225                 230                 235                 240 acc ctg acg gtg aat ggc gtt agc aaa gct tat gcg atg acg ggt tgg      768
Thr Leu Thr Val Asn Gly Val Ser Lys Ala Tyr Ala Met Thr Gly Trp
                245                 250                 255 cgt att ggt tac gcg ggt ggt ccg cgt gaa ctg atc aaa gcc atg gca      816
Arg Ile Gly Tyr Ala Gly Gly Pro Arg Glu Leu Ile Lys Ala Met Ala
            260                 265                 270 gtg gtt cag agt caa gcc acc tcc tgc ccg agt tcc att tca cag gct      864
Val Val Gln Ser Gln Ala Thr Ser Cys Pro Ser Ser Ile Ser Gln Ala
        275                 280                 285 gcg tcg gtg gca gca ctg aac ggt ccg caa gat ttt ctg aaa gaa cgc      912
Ala Ser Val Ala Ala Leu Asn Gly Pro Gln Asp Phe Leu Lys Glu Arg
        290                 295                 300 acc gaa agc ttc cag cgt cgc cgt gac ctg gtc gtg aac ggt ctg aat      960
Thr Glu Ser Phe Gln Arg Arg Arg Asp Leu Val Val Asn Gly Leu Asn
305                 310                 315                 320 gcg att gat ggc ctg gac tgc cgt gtt ccg gaa ggt gct ttt tat acc     1008
Ala Ile Asp Gly Leu Asp Cys Arg Val Pro Glu Gly Ala Phe Tyr Thr
                325                 330                 335 ttc tca ggc tgt gcg ggt gtt ctg ggc aaa gtc acg ccg tcg ggc aaa     1056
Phe Ser Gly Cys Ala Gly Val Leu Gly Lys Val Thr Pro Ser Gly Lys
            340                 345                 350 cgc atc aaa acc gat acg gac ttt tgt gcc tat ctg ctg gaa gat gcc     1104
Arg Ile Lys Thr Asp Thr Asp Phe Cys Ala Tyr Leu Leu Glu Asp Ala
        355                 360                 365 cat gtg gca gtt gtc ccg ggt agt gca ttc ggc ctg tcc ccg ttt ttc     1152
His Val Ala Val Val Pro Gly Ser Ala Phe Gly Leu Ser Pro Phe Phe
        370                 375                 380 cgt att agt tac gcg acc tcc gaa gcc gaa ctg aaa gaa gcc ctg gaa     1200
Arg Ile Ser Tyr Ala Thr Ser Glu Ala Glu Leu Lys Glu Ala Leu Glu
```

```
                385                 390                 395                 400
cgc att gct gcc gcc tgt gac cgt ctg tcg ctc gag tga                                1239
Arg Ile Ala Ala Ala Cys Asp Arg Leu Ser Leu Glu
                405                             410

<210> SEQ ID NO 95
<211> LENGTH: 412
<212> TYPE: PRT
<213> ORGANISM: Sinorhizobium meliloti

<400> SEQUENCE: 95

Met Thr Ile Asn Ala Thr Val Lys Glu Ala Gly Phe Gln Pro Ala Ser
1               5                   10                  15

Arg Ile Ser Ser Ile Gly Val Ser Glu Ile Leu Lys Ile Gly Ala Arg
                20                  25                  30

Ala Ala Ala Met Lys Arg Glu Gly Lys Pro Val Ile Ile Leu Gly Ala
            35                  40                  45

Gly Glu Pro Asp Phe Asp Thr Pro Glu His Val Lys Gln Ala Ala Ser
        50                  55                  60

Asp Ala Ile His Arg Gly Glu Thr Lys Tyr Thr Ala Leu Asp Gly Thr
65                  70                  75                  80

Pro Glu Leu Lys Lys Ala Ile Arg Glu Lys Phe Gln Arg Glu Asn Gly
                85                  90                  95

Leu Ala Tyr Glu Leu Asp Glu Ile Thr Val Ala Thr Gly Ala Lys Gln
            100                 105                 110

Ile Leu Phe Asn Ala Met Met Ala Ser Leu Asp Pro Gly Asp Glu Val
        115                 120                 125

Ile Ile Pro Thr Pro Tyr Trp Thr Ser Tyr Ser Asp Ile Val His Ile
130                 135                 140

Cys Glu Gly Lys Pro Val Leu Ile Ala Cys Asp Ala Ser Ser Gly Phe
145                 150                 155                 160

Arg Leu Thr Ala Glu Lys Leu Glu Ala Ala Ile Thr Pro Arg Thr Arg
                165                 170                 175

Trp Val Leu Leu Asn Ser Pro Ser Asn Pro Ser Gly Ala Ala Tyr Ser
            180                 185                 190

Ala Ala Asp Tyr Arg Pro Leu Leu Glu Val Leu Arg His Pro His
        195                 200                 205

Val Trp Leu Leu Val Asp Asp Met Tyr Glu His Ile Val Tyr Asp Gly
210                 215                 220

Phe Arg Phe Val Thr Pro Ala Gln Leu Glu Pro Gly Leu Lys Asn Arg
225                 230                 235                 240

Thr Leu Thr Val Asn Gly Val Ser Lys Ala Tyr Ala Met Thr Gly Trp
                245                 250                 255

Arg Ile Gly Tyr Ala Gly Gly Pro Arg Glu Leu Ile Lys Ala Met Ala
            260                 265                 270

Val Val Gln Ser Gln Ala Thr Ser Cys Pro Ser Ser Ile Ser Gln Ala
        275                 280                 285

Ala Ser Val Ala Ala Leu Asn Gly Pro Gln Asp Phe Leu Lys Glu Arg
        290                 295                 300

Thr Glu Ser Phe Gln Arg Arg Asp Leu Val Val Asn Gly Leu Asn
305                 310                 315                 320

Ala Ile Asp Gly Leu Asp Cys Arg Val Pro Glu Gly Ala Phe Tyr Thr
                325                 330                 335

Phe Ser Gly Cys Ala Gly Val Leu Gly Lys Val Thr Pro Ser Gly Lys
            340                 345                 350
```

```
Arg Ile Lys Thr Asp Thr Asp Phe Cys Ala Tyr Leu Leu Glu Asp Ala
        355                 360                 365

His Val Ala Val Val Pro Gly Ser Ala Phe Gly Leu Ser Pro Phe Phe
    370                 375                 380

Arg Ile Ser Tyr Ala Thr Ser Glu Ala Glu Leu Lys Glu Ala Leu Glu
385                 390                 395                 400

Arg Ile Ala Ala Ala Cys Asp Arg Leu Ser Leu Glu
        405                 410

<210> SEQ ID NO 96
<211> LENGTH: 999
<212> TYPE: DNA
<213> ORGANISM: Methanothermobacter thermautotrophicus
<220> FEATURE:
<221> NAME/KEY: CDS
<222> LOCATION: (1)..(999)

<400> SEQUENCE: 96
```

| | | | | | | | | | | | | | | | | |
|---|---|---|---|---|---|---|---|---|---|---|---|---|---|---|---|---|
| atg | cgt | ctg | tgg | cgt | gct | ctg | tat | cgc | ccg | ccg | acc | att | acc | tac | ccg | 48 |
| Met | Arg | Leu | Trp | Arg | Ala | Leu | Tyr | Arg | Pro | Pro | Thr | Ile | Thr | Tyr | Pro | |
| 1 | | | | 5 | | | | | 10 | | | | | 15 | | |
| tca | aaa | agc | ccg | gaa | gtc | att | att | atg | tct | tgt | gaa | gcg | tcc | ggc | aaa | 96 |
| Ser | Lys | Ser | Pro | Glu | Val | Ile | Ile | Met | Ser | Cys | Glu | Ala | Ser | Gly | Lys | |
| | | | 20 | | | | | 25 | | | | | 30 | | | |
| att | tgg | ctg | aac | ggt | gaa | atg | gtt | gaa | tgg | gaa | gaa | gca | acc | gtt | cat | 144 |
| Ile | Trp | Leu | Asn | Gly | Glu | Met | Val | Glu | Trp | Glu | Glu | Ala | Thr | Val | His | |
| | | | | 35 | | | | | 40 | | | | | 45 | | |
| gtc | ctg | tca | cat | gtg | gtt | cac | tat | ggc | agc | tct | gtg | ttt | gaa | ggt | att | 192 |
| Val | Leu | Ser | His | Val | Val | His | Tyr | Gly | Ser | Ser | Val | Phe | Glu | Gly | Ile | |
| | | 50 | | | | | 55 | | | | | 60 | | | | |
| cgt | tgc | tac | cgc | aat | tcg | aaa | ggt | agc | gcg | atc | ttt | cgt | ctg | cgc | gaa | 240 |
| Arg | Cys | Tyr | Arg | Asn | Ser | Lys | Gly | Ser | Ala | Ile | Phe | Arg | Leu | Arg | Glu | |
| 65 | | | | | 70 | | | | | 75 | | | | | 80 | |
| cac | gtt | aaa | cgt | ctg | ttc | gat | tcc | gcc | aaa | att | tat | cgc | atg | gac | atc | 288 |
| His | Val | Lys | Arg | Leu | Phe | Asp | Ser | Ala | Lys | Ile | Tyr | Arg | Met | Asp | Ile | |
| | | | | 85 | | | | | 90 | | | | | 95 | | |
| ccg | tac | acc | cag | gaa | caa | att | tgc | gat | gcc | atc | gtt | gaa | acg | gtc | cgt | 336 |
| Pro | Tyr | Thr | Gln | Glu | Gln | Ile | Cys | Asp | Ala | Ile | Val | Glu | Thr | Val | Arg | |
| | | | 100 | | | | | 105 | | | | | 110 | | | |
| gaa | aac | ggt | ctg | gaa | gaa | tgt | tat | atc | cgt | ccg | gtc | gtg | ttc | cgc | ggc | 384 |
| Glu | Asn | Gly | Leu | Glu | Glu | Cys | Tyr | Ile | Arg | Pro | Val | Val | Phe | Arg | Gly | |
| | | | | 115 | | | | | 120 | | | | | 125 | | |
| tac | ggt | gaa | atg | ggc | gtg | cat | ccg | gtt | aat | tgt | ccg | gtg | gac | gtt | gca | 432 |
| Tyr | Gly | Glu | Met | Gly | Val | His | Pro | Val | Asn | Cys | Pro | Val | Asp | Val | Ala | |
| | | 130 | | | | | 135 | | | | | 140 | | | | |
| gtc | gca | gca | tgg | gaa | tgg | ggt | gca | tat | ctg | ggt | gca | gaa | gca | ctg | gaa | 480 |
| Val | Ala | Ala | Trp | Glu | Trp | Gly | Ala | Tyr | Leu | Gly | Ala | Glu | Ala | Leu | Glu | |
| 145 | | | | | 150 | | | | | 155 | | | | | 160 | |
| gtg | ggc | gtt | gat | gca | ggt | gtt | tct | acc | tgg | cgt | cgc | atg | gct | ccg | aac | 528 |
| Val | Gly | Val | Asp | Ala | Gly | Val | Ser | Thr | Trp | Arg | Arg | Met | Ala | Pro | Asn | |
| | | | | 165 | | | | | 170 | | | | | 175 | | |
| acg | atg | ccg | aat | atg | gca | aaa | gct | ggc | ggt | aac | tat | ctg | aat | tca | cag | 576 |
| Thr | Met | Pro | Asn | Met | Ala | Lys | Ala | Gly | Gly | Asn | Tyr | Leu | Asn | Ser | Gln | |
| | | | 180 | | | | | 185 | | | | | 190 | | | |
| ctg | gca | aaa | atg | gaa | gct | gtg | cgc | cat | ggc | tac | gat | gaa | gcg | att | atg | 624 |
| Leu | Ala | Lys | Met | Glu | Ala | Val | Arg | His | Gly | Tyr | Asp | Glu | Ala | Ile | Met | |
| | | 195 | | | | | 200 | | | | | 205 | | | | |
| ctg | gac | tat | cac | ggt | tac | atc | tct | gaa | ggc | agt | ggt | gaa | aac | att | ttt | 672 |
| Leu | Asp | Tyr | His | Gly | Tyr | Ile | Ser | Glu | Gly | Ser | Gly | Glu | Asn | Ile | Phe | |
| 210 | | | | | 215 | | | | | 220 | | | | | | |

-continued

```
ctg gtc tcg gaa ggc gaa atc tat acc ccg cct gtg agt tcc tca ctg        720
Leu Val Ser Glu Gly Glu Ile Tyr Thr Pro Pro Val Ser Ser Ser Leu
225                 230                 235                 240 ctg cgt ggt att acg cgc gat agc gtg att aaa atc gca cgt acc gaa        768
Leu Arg Gly Ile Thr Arg Asp Ser Val Ile Lys Ile Ala Arg Thr Glu
                245                 250                 255 ggc gtc acg gtg cac gaa gaa ccg att acc cgc gaa atg ctg tac atc        816
Gly Val Thr Val His Glu Glu Pro Ile Thr Arg Glu Met Leu Tyr Ile
            260                 265                 270 gcg gat gaa gcc ttt ttc acc ggc acg gca gct gaa att acc ccg atc        864
Ala Asp Glu Ala Phe Phe Thr Gly Thr Ala Ala Glu Ile Thr Pro Ile
        275                 280                 285 cgt agc gtt gac ggc att gaa atc ggt gct ggt cgt cgc ggt ccg gtc        912
Arg Ser Val Asp Gly Ile Glu Ile Gly Ala Gly Arg Arg Gly Pro Val
    290                 295                 300 acg aaa ctg ctg caa gat gaa ttt ttc cgc atc atc cgt gcc gaa acc        960
Thr Lys Leu Leu Gln Asp Glu Phe Phe Arg Ile Ile Arg Ala Glu Thr
305                 310                 315                 320 gaa gat agc ttt ggc tgg ctg acc tac att ctc gag tga                    999
Glu Asp Ser Phe Gly Trp Leu Thr Tyr Ile Leu Glu
                325                 330

<210> SEQ ID NO 97
<211> LENGTH: 332
<212> TYPE: PRT
<213> ORGANISM: Methanothermobacter thermautotrophicus

<400> SEQUENCE: 97

Met Arg Leu Trp Arg Ala Leu Tyr Arg Pro Pro Thr Ile Thr Tyr Pro
1               5                   10                  15

Ser Lys Ser Pro Glu Val Ile Ile Met Ser Cys Glu Ala Ser Gly Lys
                20                  25                  30

Ile Trp Leu Asn Gly Glu Met Val Glu Trp Glu Glu Ala Thr Val His
            35                  40                  45

Val Leu Ser His Val Val His Tyr Gly Ser Ser Val Phe Glu Gly Ile
        50                  55                  60

Arg Cys Tyr Arg Asn Ser Lys Gly Ser Ala Ile Phe Arg Leu Arg Glu
65                  70                  75                  80

His Val Lys Arg Leu Phe Asp Ser Ala Lys Ile Tyr Arg Met Asp Ile
                85                  90                  95

Pro Tyr Thr Gln Glu Gln Ile Cys Asp Ala Ile Val Glu Thr Val Arg
                100                 105                 110

Glu Asn Gly Leu Glu Glu Cys Tyr Ile Arg Pro Val Val Phe Arg Gly
            115                 120                 125

Tyr Gly Glu Met Gly Val His Pro Val Asn Cys Pro Val Asp Val Ala
        130                 135                 140

Val Ala Ala Trp Glu Trp Gly Ala Tyr Leu Gly Ala Glu Ala Leu Glu
145                 150                 155                 160

Val Gly Val Asp Ala Gly Val Ser Thr Trp Arg Arg Met Ala Pro Asn
                165                 170                 175

Thr Met Pro Asn Met Ala Lys Ala Gly Gly Asn Tyr Leu Asn Ser Gln
            180                 185                 190

Leu Ala Lys Met Glu Ala Val Arg His Gly Tyr Asp Glu Ala Ile Met
        195                 200                 205

Leu Asp Tyr His Gly Tyr Ile Ser Glu Gly Ser Gly Glu Asn Ile Phe
    210                 215                 220
```

```
Leu Val Ser Glu Gly Glu Ile Tyr Thr Pro Pro Val Ser Ser Ser Leu
225                 230                 235                 240

Leu Arg Gly Ile Thr Arg Asp Ser Val Ile Lys Ile Ala Arg Thr Glu
            245                 250                 255

Gly Val Thr Val His Glu Glu Pro Ile Thr Arg Glu Met Leu Tyr Ile
            260                 265                 270

Ala Asp Glu Ala Phe Phe Thr Gly Thr Ala Ala Glu Ile Thr Pro Ile
        275                 280                 285

Arg Ser Val Asp Gly Ile Glu Ile Gly Ala Gly Arg Arg Gly Pro Val
        290                 295                 300

Thr Lys Leu Leu Gln Asp Glu Phe Phe Arg Ile Ile Arg Ala Glu Thr
305                 310                 315                 320

Glu Asp Ser Phe Gly Trp Leu Thr Tyr Ile Leu Glu
                325                 330

<210> SEQ ID NO 98
<211> LENGTH: 1605
<212> TYPE: DNA
<213> ORGANISM: Lactobacillus acidophilus
<220> FEATURE:
<221> NAME/KEY: CDS
<222> LOCATION: (1)..(1605)

<400> SEQUENCE: 98
```

| | | | | | | | | | | | | | | | | |
|---|---|---|---|---|---|---|---|---|---|---|---|---|---|---|---|---|
| atg | gac | aac | tcc | gaa | gaa | aaa | aaa | ctg | gaa | gcc | ctg | ggt | gcc | ttt | gaa | 48 |
| Met | Asp | Asn | Ser | Glu | Glu | Lys | Lys | Leu | Glu | Ala | Leu | Gly | Ala | Phe | Glu | |
| 1 | | | | 5 | | | | | 10 | | | | | 15 | | |
| atc | tca | cgt | aaa | atg | ctg | gcg | ctg | gcg | cag | aaa | aat | gaa | aaa | agc | aac | 96 |
| Ile | Ser | Arg | Lys | Met | Leu | Ala | Leu | Ala | Gln | Lys | Asn | Glu | Lys | Ser | Asn | |
| | | | 20 | | | | | 25 | | | | | 30 | | | |
| att | ttt | ctg | aat | gcg | ggc | cgt | ggt | aac | ccg | aat | tgg | atc | cag | acc | ctg | 144 |
| Ile | Phe | Leu | Asn | Ala | Gly | Arg | Gly | Asn | Pro | Asn | Trp | Ile | Gln | Thr | Leu | |
| | | | | 35 | | | | | 40 | | | | | 45 | | |
| gca | cgt | ctg | gca | ttt | gtg | cgt | ctg | gtt | caa | ttc | ggt | gtt | acg | gaa | tct | 192 |
| Ala | Arg | Leu | Ala | Phe | Val | Arg | Leu | Val | Gln | Phe | Gly | Val | Thr | Glu | Ser | |
| | | 50 | | | | | 55 | | | | | 60 | | | | |
| aaa | ctg | acc | att | aac | aat | ggt | atc | atg | gcc | ggc | tat | att | aac | acg | gat | 240 |
| Lys | Leu | Thr | Ile | Asn | Asn | Gly | Ile | Met | Ala | Gly | Tyr | Ile | Asn | Thr | Asp | |
| 65 | | | | | 70 | | | | | 75 | | | | | 80 | |
| ggc | atc | cgt | gaa | cgc | ctg | ttt | gca | ttc | ctg | gat | ccg | gac | aaa | aac | gat | 288 |
| Gly | Ile | Arg | Glu | Arg | Leu | Phe | Ala | Phe | Leu | Asp | Pro | Asp | Lys | Asn | Asp | |
| | | | | 85 | | | | | 90 | | | | | 95 | | |
| gaa | gac | aaa | ttc | ctg | atc | gat | gcc | gtg | aac | tac | tgc | cat | acc | gaa | ctg | 336 |
| Glu | Asp | Lys | Phe | Leu | Ile | Asp | Ala | Val | Asn | Tyr | Cys | His | Thr | Glu | Leu | |
| | | | 100 | | | | | 105 | | | | | 110 | | | |
| ggt | ctg | aat | cgt | gac | aaa | gtg | gtt | gca | gaa | tgg | gtt | aac | ggc | gca | gtc | 384 |
| Gly | Leu | Asn | Arg | Asp | Lys | Val | Val | Ala | Glu | Trp | Val | Asn | Gly | Ala | Val | |
| | | | 115 | | | | | 120 | | | | | 125 | | | |
| gct | aac | aat | tat | ccg | gtc | ccg | gat | cgc | tgt | ctg | gtg | aac | acg | gaa | aaa | 432 |
| Ala | Asn | Asn | Tyr | Pro | Val | Pro | Asp | Arg | Cys | Leu | Val | Asn | Thr | Glu | Lys | |
| | | 130 | | | | | 135 | | | | | 140 | | | | |
| atc | atc | aac | tat | ttt | ctg | caa | gaa | ctg | tca | tac | aaa | gat | gca | aat | ctg | 480 |
| Ile | Ile | Asn | Tyr | Phe | Leu | Gln | Glu | Leu | Ser | Tyr | Lys | Asp | Ala | Asn | Leu | |
| 145 | | | | | 150 | | | | | 155 | | | | | 160 | |
| gct | gaa | caa | acc | gac | ctg | ttt | ccg | acg | gaa | ggc | ggt | acc | gcg | gcc | att | 528 |
| Ala | Glu | Gln | Thr | Asp | Leu | Phe | Pro | Thr | Glu | Gly | Gly | Thr | Ala | Ala | Ile | |
| | | | | 165 | | | | | 170 | | | | | 175 | | |
| gtt | tac | gcg | ttc | cat | tcg | ctg | gcc | gaa | aac | cac | ctg | ctg | aaa | aaa | ggt | 576 |
| Val | Tyr | Ala | Phe | His | Ser | Leu | Ala | Glu | Asn | His | Leu | Leu | Lys | Lys | Gly | |
| | | | | 180 | | | | | 185 | | | | | 190 | | |

| | | |
|---|---|---|
| gat aaa atc gcc atc aac gaa ccg atc ttc acc ccg tac ctg cgt atc<br>Asp Lys Ile Ala Ile Asn Glu Pro Ile Phe Thr Pro Tyr Leu Arg Ile<br>      195                   200                 205 | | 624 |
| ccg gaa ctg aaa gat tat gaa ctg gtt gaa gtc gac ctg cac agc tat<br>Pro Glu Leu Lys Asp Tyr Glu Leu Val Glu Val Asp Leu His Ser Tyr<br>210                   215                   220 | | 672 |
| gag aaa aac gat tgg gaa att gaa ccg aat gaa atc gaa aaa ctg aaa<br>Glu Lys Asn Asp Trp Glu Ile Glu Pro Asn Glu Ile Glu Lys Leu Lys<br>225                   230                 235               240 | | 720 |
| gac ccg agc att aaa gcg ctg atc gtc gtg aac ccg acg aat ccg acc<br>Asp Pro Ser Ile Lys Ala Leu Ile Val Val Asn Pro Thr Asn Pro Thr<br>                245               250               255 | | 768 |
| tct aaa gaa ttt gat acc aac gcg ctg aat gcc att aaa cag gct gtc<br>Ser Lys Glu Phe Asp Thr Asn Ala Leu Asn Ala Ile Lys Gln Ala Val<br>         260                   265               270 | | 816 |
| gag aaa aac ccg aaa ctg atg att atc agc gac gaa gtg tat ggt gcc<br>Glu Lys Asn Pro Lys Leu Met Ile Ile Ser Asp Glu Val Tyr Gly Ala<br>275                   280                 285 | | 864 |
| ttt gtt ccg aac ttc aaa agc atc tat tct gtt gtc ccg tac aat acg<br>Phe Val Pro Asn Phe Lys Ser Ile Tyr Ser Val Val Pro Tyr Asn Thr<br>         290                   295               300 | | 912 |
| atg ctg gtt tat agt tac tcc aaa ctg ttt ggt tgc acc ggc tgg cgc<br>Met Leu Val Tyr Ser Tyr Ser Lys Leu Phe Gly Cys Thr Gly Trp Arg<br>305                   310                 315               320 | | 960 |
| ctg ggc gtt att gct ctg aac gag aaa aac gtc ttc gat gac aat atc<br>Leu Gly Val Ile Ala Leu Asn Glu Lys Asn Val Phe Asp Asp Asn Ile<br>                325               330               335 | | 1008 |
| gcg cat ctg gat aaa gtg gaa ctg cgt cag ctg cac aaa cgc tac agc<br>Ala His Leu Asp Lys Val Glu Leu Arg Gln Leu His Lys Arg Tyr Ser<br>                340               345               350 | | 1056 |
| tct gtg gtt ctg gat ccg gac aaa atg aaa ttt att gat cgt ctg tgt<br>Ser Val Val Leu Asp Pro Asp Lys Met Lys Phe Ile Asp Arg Leu Cys<br>355                   360                 365 | | 1104 |
| gcg gac tca cgc tcg atc ggt ctg tat cat acg gcc ggc ctg tca acc<br>Ala Asp Ser Arg Ser Ile Gly Leu Tyr His Thr Ala Gly Leu Ser Thr<br>         370                   375               380 | | 1152 |
| ccg cag caa att atg gaa gca ctg ttc tcg atg acc cac ctg ctg acc<br>Pro Gln Gln Ile Met Glu Ala Leu Phe Ser Met Thr His Leu Leu Thr<br>385                   390                 395               400 | | 1200 |
| agt acg aac ggc ggt tcc gat gac ccg tac att gat atc gca cgt aaa<br>Ser Thr Asn Gly Gly Ser Asp Asp Pro Tyr Ile Asp Ile Ala Arg Lys<br>                405               410               415 | | 1248 |
| ctg gtg tct gaa cgc tat gat cag ctg cat gac gca atg caa gct ccg<br>Leu Val Ser Glu Arg Tyr Asp Gln Leu His Asp Ala Met Gln Ala Pro<br>         420                   425               430 | | 1296 |
| aaa gat gaa acc gac acg aat acc cac tat tac tcc ctg att gat atc<br>Lys Asp Glu Thr Asp Thr Asn Thr His Tyr Tyr Ser Leu Ile Asp Ile<br>435                   440                 445 | | 1344 |
| tat cgt ctg gcg gaa aaa atc tac ggc aaa gaa ttt cgc gat tat ctg<br>Tyr Arg Leu Ala Glu Lys Ile Tyr Gly Lys Glu Phe Arg Asp Tyr Leu<br>         450                   455               460 | | 1392 |
| acg aac aat ttt gaa cag gtg gac ttc ctg ctg aaa ctg gct gag aaa<br>Thr Asn Asn Phe Glu Gln Val Asp Phe Leu Leu Lys Leu Ala Glu Lys<br>465                   470                 475               480 | | 1440 |
| aac ggt gtc gtg ctg gtc gat ggc gtg ggt ttc ggc gcg aaa ccg ggc<br>Asn Gly Val Val Leu Val Asp Gly Val Gly Phe Gly Ala Lys Pro Gly<br>                485               490               495 | | 1488 |
| gaa ctg cgc gtt agt caa gca aat ctg ccg acc gaa gat tat gct ctg<br>Glu Leu Arg Val Ser Gln Ala Asn Leu Pro Thr Glu Asp Tyr Ala Leu | | 1536 |

```
              500             505             510
att ggc aaa caa gtc ctg gaa ctg ctg aaa gaa tac tat gaa gaa ttt    1584
Ile Gly Lys Gln Val Leu Glu Leu Leu Lys Glu Tyr Tyr Glu Glu Phe
    515             520             525 aaa cag aat aat ctc gag taa                                         1605
Lys Gln Asn Asn Leu Glu
    530
```

<210> SEQ ID NO 99
<211> LENGTH: 534
<212> TYPE: PRT
<213> ORGANISM: Lactobacillus acidophilus

<400> SEQUENCE: 99

```
Met Asp Asn Ser Glu Glu Lys Lys Leu Glu Ala Leu Gly Ala Phe Glu
1               5                   10                  15

Ile Ser Arg Lys Met Leu Ala Leu Ala Gln Lys Asn Glu Lys Ser Asn
            20                  25                  30

Ile Phe Leu Asn Ala Gly Arg Gly Asn Pro Asn Trp Ile Gln Thr Leu
        35                  40                  45

Ala Arg Leu Ala Phe Val Arg Leu Val Gln Phe Gly Val Thr Glu Ser
    50                  55                  60

Lys Leu Thr Ile Asn Asn Gly Ile Met Ala Gly Tyr Ile Asn Thr Asp
65                  70                  75                  80

Gly Ile Arg Glu Arg Leu Phe Ala Phe Leu Asp Pro Asp Lys Asn Asp
                85                  90                  95

Glu Asp Lys Phe Leu Ile Asp Ala Val Asn Tyr Cys His Thr Glu Leu
            100                 105                 110

Gly Leu Asn Arg Asp Lys Val Val Ala Glu Trp Val Asn Gly Ala Val
        115                 120                 125

Ala Asn Asn Tyr Pro Val Pro Asp Arg Cys Leu Val Asn Thr Glu Lys
    130                 135                 140

Ile Ile Asn Tyr Phe Leu Gln Glu Leu Ser Tyr Lys Asp Ala Asn Leu
145                 150                 155                 160

Ala Glu Gln Thr Asp Leu Phe Pro Thr Glu Gly Gly Thr Ala Ala Ile
                165                 170                 175

Val Tyr Ala Phe His Ser Leu Ala Glu Asn His Leu Leu Lys Lys Gly
            180                 185                 190

Asp Lys Ile Ala Ile Asn Glu Pro Ile Phe Thr Pro Tyr Leu Arg Ile
        195                 200                 205

Pro Glu Leu Lys Asp Tyr Glu Leu Val Glu Val Asp Leu His Ser Tyr
    210                 215                 220

Glu Lys Asn Asp Trp Glu Ile Glu Pro Asn Glu Ile Glu Lys Leu Lys
225                 230                 235                 240

Asp Pro Ser Ile Lys Ala Leu Ile Val Val Asn Pro Thr Asn Pro Thr
                245                 250                 255

Ser Lys Glu Phe Asp Thr Asn Ala Leu Asn Ala Ile Lys Gln Ala Val
            260                 265                 270

Glu Lys Asn Pro Lys Leu Met Ile Ile Ser Asp Glu Val Tyr Gly Ala
        275                 280                 285

Phe Val Pro Asn Phe Lys Ser Ile Tyr Ser Val Pro Tyr Asn Thr
    290                 295                 300

Met Leu Val Tyr Ser Tyr Ser Lys Leu Phe Gly Cys Thr Gly Trp Arg
305                 310                 315                 320

Leu Gly Val Ile Ala Leu Asn Glu Lys Asn Val Phe Asp Asp Asn Ile
```

```
                325                 330                 335
Ala His Leu Asp Lys Val Glu Leu Arg Gln Leu His Lys Arg Tyr Ser
                340                 345                 350

Ser Val Val Leu Asp Pro Asp Lys Met Lys Phe Ile Asp Arg Leu Cys
                355                 360                 365

Ala Asp Ser Arg Ser Ile Gly Leu Tyr His Thr Ala Gly Leu Ser Thr
            370                 375                 380

Pro Gln Gln Ile Met Glu Ala Leu Phe Ser Met Thr His Leu Leu Thr
385                 390                 395                 400

Ser Thr Asn Gly Gly Ser Asp Asp Pro Tyr Ile Asp Ile Ala Arg Lys
                405                 410                 415

Leu Val Ser Glu Arg Tyr Asp Gln Leu His Asp Ala Met Gln Ala Pro
                420                 425                 430

Lys Asp Glu Thr Asp Thr Asn Thr His Tyr Tyr Ser Leu Ile Asp Ile
                435                 440                 445

Tyr Arg Leu Ala Glu Lys Ile Tyr Gly Lys Glu Phe Arg Asp Tyr Leu
            450                 455                 460

Thr Asn Asn Phe Glu Gln Val Asp Phe Leu Leu Lys Leu Ala Glu Lys
465                 470                 475                 480

Asn Gly Val Val Leu Val Asp Gly Val Gly Phe Gly Ala Lys Pro Gly
                485                 490                 495

Glu Leu Arg Val Ser Gln Ala Asn Leu Pro Thr Glu Asp Tyr Ala Leu
                500                 505                 510

Ile Gly Lys Gln Val Leu Glu Leu Leu Lys Glu Tyr Tyr Glu Glu Phe
            515                 520                 525

Lys Gln Asn Asn Leu Glu
    530

<210> SEQ ID NO 100
<211> LENGTH: 1209
<212> TYPE: DNA
<213> ORGANISM: Sinorhizobium meliloti
<220> FEATURE:
<221> NAME/KEY: CDS
<222> LOCATION: (1)..(1209)

<400> SEQUENCE: 100 atg gcc ttc ctg gcg gat gca ctg agt cgt gtt aaa ccg tcg gca acc    48
Met Ala Phe Leu Ala Asp Ala Leu Ser Arg Val Lys Pro Ser Ala Thr
1               5                   10                  15 atc gct gtg tcg cag aaa gcc cgt gaa ctg aaa gca aaa ggc cgt gat    96
Ile Ala Val Ser Gln Lys Ala Arg Glu Leu Lys Ala Lys Gly Arg Asp
                20                  25                  30 gtg att ggc ctg ggt gcg ggc gaa ccg gat ttt gac acc ccg gac aac   144
Val Ile Gly Leu Gly Ala Gly Glu Pro Asp Phe Asp Thr Pro Asp Asn
            35                  40                  45 atc aaa aaa gcg gcc att gat gcc atc gac cgc ggc gaa acc aaa tat   192
Ile Lys Lys Ala Ala Ile Asp Ala Ile Asp Arg Gly Glu Thr Lys Tyr
        50                  55                  60 acg cct gtg agc ggt att ccg gaa ctg cgt gaa gcg atc gcc aaa aaa   240
Thr Pro Val Ser Gly Ile Pro Glu Leu Arg Glu Ala Ile Ala Lys Lys
65                  70                  75                  80 ttc aaa cgc gaa aac aac ctg gat tac acc gca gct cag acg att gtt   288
Phe Lys Arg Glu Asn Asn Leu Asp Tyr Thr Ala Ala Gln Thr Ile Val
                85                  90                  95 ggc acc ggc ggt aaa caa atc ctg ttt aac gcg ttc atg gcc acc ctg   336
Gly Thr Gly Gly Lys Gln Ile Leu Phe Asn Ala Phe Met Ala Thr Leu
                100                 105                 110
```

```
aat ccg ggt gat gaa gtg gtt att ccg gca ccg tat tgg gtg tct tac      384
Asn Pro Gly Asp Glu Val Val Ile Pro Ala Pro Tyr Trp Val Ser Tyr
    115                 120                 125 ccg gaa atg gtt gct ctg tgc ggc ggt acg ccg gtg ttt gtt ccg acc      432
Pro Glu Met Val Ala Leu Cys Gly Gly Thr Pro Val Phe Val Pro Thr
130                 135                 140 cgt cag gaa aac aat ttc aaa ctg aaa gca gaa gat ctg gac cgc gct      480
Arg Gln Glu Asn Asn Phe Lys Leu Lys Ala Glu Asp Leu Asp Arg Ala
145                 150                 155                 160 atc acc ccg aaa acg aaa tgg ttt gtt ttc aac agc ccg tct aat ccg      528
Ile Thr Pro Lys Thr Lys Trp Phe Val Phe Asn Ser Pro Ser Asn Pro
                165                 170                 175 tca ggc gcg gcc tat tcg cat gaa gaa ctg aaa gca ctg acc gat gtc      576
Ser Gly Ala Ala Tyr Ser His Glu Glu Leu Lys Ala Leu Thr Asp Val
            180                 185                 190 ctg atg aaa cat ccg cac gtc tgg gtg ctg acg gat gac atg tat gaa      624
Leu Met Lys His Pro His Val Trp Val Leu Thr Asp Asp Met Tyr Glu
        195                 200                 205 cac ctg acc tac ggt gac ttt cgt ttc gcc acg ccg gtt gaa gtc gaa      672
His Leu Thr Tyr Gly Asp Phe Arg Phe Ala Thr Pro Val Glu Val Glu
    210                 215                 220 ccg ggc ctg tac gaa cgc acc ctg acg atg aat ggt gtg tca aaa gcg      720
Pro Gly Leu Tyr Glu Arg Thr Leu Thr Met Asn Gly Val Ser Lys Ala
225                 230                 235                 240 tat gcg atg acc ggt tgg cgt att ggc tac gca gct ggt ccg ctg cat      768
Tyr Ala Met Thr Gly Trp Arg Ile Gly Tyr Ala Ala Gly Pro Leu His
                245                 250                 255 ctg att aaa gcg atg gat atg atc caa ggc cag caa acg agt ggt gcg      816
Leu Ile Lys Ala Met Asp Met Ile Gln Gly Gln Gln Thr Ser Gly Ala
            260                 265                 270 gcc tcc atc gca cag tgg gca gct gtt gaa gct ctg aac ggc ccg caa      864
Ala Ser Ile Ala Gln Trp Ala Ala Val Glu Ala Leu Asn Gly Pro Gln
        275                 280                 285 gat ttc atc ggt cgc aac aaa gaa atc ttc cag ggc cgt cgc gac ctg      912
Asp Phe Ile Gly Arg Asn Lys Glu Ile Phe Gln Gly Arg Arg Asp Leu
    290                 295                 300 gtc gtg agc atg ctg aac cag gcc aaa ggc att tct tgc ccg acc ccg      960
Val Val Ser Met Leu Asn Gln Ala Lys Gly Ile Ser Cys Pro Thr Pro
305                 310                 315                 320 gaa ggt gca ttt tat gtc tac ccg agt tgt gcg ggt ctg att ggc aaa     1008
Glu Gly Ala Phe Tyr Val Tyr Pro Ser Cys Ala Gly Leu Ile Gly Lys
                325                 330                 335 acc gcc ccg tcc ggt aaa gtc atc gaa acg gat gaa gac ttc gtg tcc     1056
Thr Ala Pro Ser Gly Lys Val Ile Glu Thr Asp Glu Asp Phe Val Ser
            340                 345                 350 gaa ctg ctg gaa acc gaa ggc gtt gcg gtt gtc cac ggt tca gcc ttt     1104
Glu Leu Leu Glu Thr Glu Gly Val Ala Val Val His Gly Ser Ala Phe
        355                 360                 365 ggt ctg ggc ccg aat ttc cgt att tcg tat gcg acg tcc gaa gct ctg     1152
Gly Leu Gly Pro Asn Phe Arg Ile Ser Tyr Ala Thr Ser Glu Ala Leu
    370                 375                 380 ctg gaa gaa gcc tgc cgt cgc att cag cgt ttt tgt gcc gcc tgt cgt     1200
Leu Glu Glu Ala Cys Arg Arg Ile Gln Arg Phe Cys Ala Ala Cys Arg
385                 390                 395                 400 ctc gag taa                                                         1209
Leu Glu

<210> SEQ ID NO 101
<211> LENGTH: 402
```

<212> TYPE: PRT
<213> ORGANISM: Sinorhizobium meliloti

<400> SEQUENCE: 101

| | | | | | | | | | | | | | | |
|---|---|---|---|---|---|---|---|---|---|---|---|---|---|---|
| Met | Ala | Phe | Leu | Ala | Asp | Ala | Leu | Ser | Arg | Val | Lys | Pro | Ser | Ala | Thr |
| 1 | | | | 5 | | | | | 10 | | | | | 15 | |

Ile Ala Val Ser Gln Lys Ala Arg Glu Leu Lys Ala Lys Gly Arg Asp
            20                  25                  30

Val Ile Gly Leu Gly Ala Gly Glu Pro Asp Phe Asp Thr Pro Asp Asn
        35                  40                  45

Ile Lys Lys Ala Ala Ile Asp Ala Ile Asp Arg Gly Glu Thr Lys Tyr
    50                  55                  60

Thr Pro Val Ser Gly Ile Pro Glu Leu Arg Glu Ala Ile Ala Lys Lys
65                  70                  75                  80

Phe Lys Arg Glu Asn Asn Leu Asp Tyr Thr Ala Ala Gln Thr Ile Val
                85                  90                  95

Gly Thr Gly Gly Lys Gln Ile Leu Phe Asn Ala Phe Met Ala Thr Leu
            100                 105                 110

Asn Pro Gly Asp Glu Val Val Ile Pro Ala Pro Tyr Trp Val Ser Tyr
        115                 120                 125

Pro Glu Met Val Ala Leu Cys Gly Gly Thr Pro Val Phe Val Pro Thr
    130                 135                 140

Arg Gln Glu Asn Phe Lys Leu Lys Ala Glu Asp Leu Asp Arg Ala
145                 150                 155                 160

Ile Thr Pro Lys Thr Lys Trp Phe Val Phe Asn Ser Pro Ser Asn Pro
                165                 170                 175

Ser Gly Ala Ala Tyr Ser His Glu Glu Leu Lys Ala Leu Thr Asp Val
            180                 185                 190

Leu Met Lys His Pro His Val Trp Val Leu Thr Asp Asp Met Tyr Glu
        195                 200                 205

His Leu Thr Tyr Gly Asp Phe Arg Phe Ala Thr Pro Val Glu Val Glu
    210                 215                 220

Pro Gly Leu Tyr Glu Arg Thr Leu Thr Met Asn Gly Val Ser Lys Ala
225                 230                 235                 240

Tyr Ala Met Thr Gly Trp Arg Ile Gly Tyr Ala Ala Gly Pro Leu His
                245                 250                 255

Leu Ile Lys Ala Met Asp Met Ile Gln Gly Gln Thr Ser Gly Ala
            260                 265                 270

Ala Ser Ile Ala Gln Trp Ala Ala Val Glu Ala Leu Asn Gly Pro Gln
        275                 280                 285

Asp Phe Ile Gly Arg Asn Lys Glu Ile Phe Gln Gly Arg Arg Asp Leu
    290                 295                 300

Val Val Ser Met Leu Asn Gln Ala Lys Gly Ile Ser Cys Pro Thr Pro
305                 310                 315                 320

Glu Gly Ala Phe Tyr Val Tyr Pro Ser Cys Ala Gly Leu Ile Gly Lys
                325                 330                 335

Thr Ala Pro Ser Gly Lys Val Ile Glu Thr Asp Glu Asp Phe Val Ser
            340                 345                 350

Glu Leu Leu Glu Thr Glu Gly Val Ala Val His Gly Ser Ala Phe
        355                 360                 365

Gly Leu Gly Pro Asn Phe Arg Ile Ser Tyr Ala Thr Ser Glu Ala Leu
    370                 375                 380

Leu Glu Glu Ala Cys Arg Arg Ile Gln Arg Phe Cys Ala Ala Cys Arg
385                 390                 395                 400

Leu Glu

<210> SEQ ID NO 102
<211> LENGTH: 1167
<212> TYPE: DNA
<213> ORGANISM: Pyrococcus horikoshii
<220> FEATURE:
<221> NAME/KEY: CDS
<222> LOCATION: (1)..(1167)

<400> SEQUENCE: 102

| | | | | | | | | | | | | | | | | |
|---|---|---|---|---|---|---|---|---|---|---|---|---|---|---|---|---|
| atg | gaa | atc | atg | gaa | ttc | gaa | gaa | gcg | ttc | aaa | gaa | gtc | tac | gaa | atg | 48 |
| Met | Glu | Ile | Met | Glu | Phe | Glu | Glu | Ala | Phe | Lys | Glu | Val | Tyr | Glu | Met | |
| 1 | | | | 5 | | | | | 10 | | | | | 15 | | |
| gtc | aaa | ccg | aaa | tac | aaa | ctg | ttc | acg | gca | ggt | ccg | gtg | gct | tgc | ttt | 96 |
| Val | Lys | Pro | Lys | Tyr | Lys | Leu | Phe | Thr | Ala | Gly | Pro | Val | Ala | Cys | Phe | |
| | | | 20 | | | | | 25 | | | | | 30 | | | |
| ccg | gaa | gtc | ctg | gaa | att | atg | aaa | gtg | cag | atg | ttc | tcg | cat | cgt | agc | 144 |
| Pro | Glu | Val | Leu | Glu | Ile | Met | Lys | Val | Gln | Met | Phe | Ser | His | Arg | Ser | |
| | | | | 35 | | | | | 40 | | | | | 45 | | |
| aaa | gaa | tat | cgc | aaa | gtt | cac | atg | gat | acc | gtc | gaa | cgt | ctg | cgc | gaa | 192 |
| Lys | Glu | Tyr | Arg | Lys | Val | His | Met | Asp | Thr | Val | Glu | Arg | Leu | Arg | Glu | |
| | | 50 | | | | | 55 | | | | | 60 | | | | |
| ttt | ctg | gaa | gtc | gaa | aaa | ggt | gaa | gtt | ctg | ctg | gtc | ccg | agc | tct | ggc | 240 |
| Phe | Leu | Glu | Val | Glu | Lys | Gly | Glu | Val | Leu | Leu | Val | Pro | Ser | Ser | Gly | |
| 65 | | | | | 70 | | | | | 75 | | | | | 80 | |
| acc | ggt | att | atg | gaa | gca | tcc | atc | cgt | aac | ggc | gtt | tca | aaa | ggc | ggt | 288 |
| Thr | Gly | Ile | Met | Glu | Ala | Ser | Ile | Arg | Asn | Gly | Val | Ser | Lys | Gly | Gly | |
| | | | | 85 | | | | | 90 | | | | | 95 | | |
| aaa | gtg | ctg | gtt | acg | att | atc | ggc | gcc | ttc | ggt | aaa | cgt | tat | aaa | gaa | 336 |
| Lys | Val | Leu | Val | Thr | Ile | Ile | Gly | Ala | Phe | Gly | Lys | Arg | Tyr | Lys | Glu | |
| | | | 100 | | | | | 105 | | | | | 110 | | | |
| gtg | gtt | gaa | tcc | aat | ggt | cgc | aaa | gca | gtc | gtg | ctg | gaa | tac | gaa | ccg | 384 |
| Val | Val | Glu | Ser | Asn | Gly | Arg | Lys | Ala | Val | Val | Leu | Glu | Tyr | Glu | Pro | |
| | | | | 115 | | | | | 120 | | | | | 125 | | |
| ggc | aaa | gca | gtg | aaa | ccg | gaa | gat | ctg | gat | gac | gct | ctg | cgc | aaa | aac | 432 |
| Gly | Lys | Ala | Val | Lys | Pro | Glu | Asp | Leu | Asp | Asp | Ala | Leu | Arg | Lys | Asn | |
| | | 130 | | | | | 135 | | | | | 140 | | | | |
| ccg | gac | gtg | gaa | gcg | gtt | acc | att | acg | tac | aac | gaa | acc | tcg | acg | ggt | 480 |
| Pro | Asp | Val | Glu | Ala | Val | Thr | Ile | Thr | Tyr | Asn | Glu | Thr | Ser | Thr | Gly | |
| 145 | | | | | 150 | | | | | 155 | | | | | 160 | |
| gtt | ctg | aat | ccg | ctg | ccg | gaa | ctg | gcg | aaa | gtc | gcc | aaa | gaa | cat | gat | 528 |
| Val | Leu | Asn | Pro | Leu | Pro | Glu | Leu | Ala | Lys | Val | Ala | Lys | Glu | His | Asp | |
| | | | | 165 | | | | | 170 | | | | | 175 | | |
| aaa | ctg | gtc | ttt | gtg | gac | gca | gtg | agc | gct | atg | ggc | ggt | gct | gat | atc | 576 |
| Lys | Leu | Val | Phe | Val | Asp | Ala | Val | Ser | Ala | Met | Gly | Gly | Ala | Asp | Ile | |
| | | | 180 | | | | | 185 | | | | | 190 | | | |
| aaa | ttc | gac | aaa | tgg | ggc | ctg | gat | gtt | gtc | ttt | agt | tcc | tca | cag | aaa | 624 |
| Lys | Phe | Asp | Lys | Trp | Gly | Leu | Asp | Val | Val | Phe | Ser | Ser | Ser | Gln | Lys | |
| | | | | 195 | | | | | 200 | | | | | 205 | | |
| gcg | ttc | ggt | gtt | ccg | ccg | ggt | ctg | gca | att | ggt | gcc | ttt | agc | gaa | cgt | 672 |
| Ala | Phe | Gly | Val | Pro | Pro | Gly | Leu | Ala | Ile | Gly | Ala | Phe | Ser | Glu | Arg | |
| | | 210 | | | | | 215 | | | | | 220 | | | | |
| ttc | ctg | gaa | atc | gcc | gaa | aaa | atg | ccg | gaa | cgc | ggt | tgg | tat | ttt | gac | 720 |
| Phe | Leu | Glu | Ile | Ala | Glu | Lys | Met | Pro | Glu | Arg | Gly | Trp | Tyr | Phe | Asp | |
| 225 | | | | | 230 | | | | | 235 | | | | | 240 | |
| att | ccg | ctg | tac | gtg | aaa | tac | ctg | aaa | gaa | aaa | gaa | tct | acc | ccg | agt | 768 |
| Ile | Pro | Leu | Tyr | Val | Lys | Tyr | Leu | Lys | Glu | Lys | Glu | Ser | Thr | Pro | Ser | |
| | | | | 245 | | | | | 250 | | | | | 255 | | |
| acg | ccg | ccg | atg | ccg | caa | gtg | ttc | ggc | atc | aat | gtt | gcc | ctg | cgt | att | 816 |

```
Thr Pro Pro Met Pro Gln Val Phe Gly Ile Asn Val Ala Leu Arg Ile
            260             265                 270 atc gaa aaa atg ggc ggt aaa gaa aaa tgg ctg gaa atg tac gaa aaa     864
Ile Glu Lys Met Gly Gly Lys Glu Lys Trp Leu Glu Met Tyr Glu Lys
        275                 280                 285 cgc gca aaa atg gtc cgt gaa ggt gtg cgc gaa att ggc ctg gat atc     912
Arg Ala Lys Met Val Arg Glu Gly Val Arg Glu Ile Gly Leu Asp Ile
    290                 295                 300 ctg gct gaa ccg ggt cat gaa tct ccg acc att acg gcg gtg ctg acc     960
Leu Ala Glu Pro Gly His Glu Ser Pro Thr Ile Thr Ala Val Leu Thr
305                 310                 315                 320 ccg ccg ggt atc aaa ggt gac gaa gtt tat gaa gcc atg cgt aaa cgc    1008
Pro Pro Gly Ile Lys Gly Asp Glu Val Tyr Glu Ala Met Arg Lys Arg
                325                 330                 335 ggc ttt gaa ctg gca aaa ggc tac ggt tca gtt aaa gaa aaa acc ttt    1056
Gly Phe Glu Leu Ala Lys Gly Tyr Gly Ser Val Lys Glu Lys Thr Phe
            340                 345                 350 cgt att ggc cac atg ggt tat atg aaa ttc gaa gat atc caa gaa atg    1104
Arg Ile Gly His Met Gly Tyr Met Lys Phe Glu Asp Ile Gln Glu Met
        355                 360                 365 ctg gac aat ctg cgt gaa gtc atc aac gaa ctg aaa aaa caa aaa ggt    1152
Leu Asp Asn Leu Arg Glu Val Ile Asn Glu Leu Lys Lys Gln Lys Gly
    370                 375                 380 atc aac ctc gag taa                                                 1167
Ile Asn Leu Glu
385
```

<210> SEQ ID NO 103
<211> LENGTH: 388
<212> TYPE: PRT
<213> ORGANISM: Pyrococcus horikoshii

<400> SEQUENCE: 103

```
Met Glu Ile Met Glu Phe Glu Glu Ala Phe Lys Glu Val Tyr Glu Met
1               5                   10                  15

Val Lys Pro Lys Tyr Lys Leu Phe Thr Ala Gly Pro Val Ala Cys Phe
            20                  25                  30

Pro Glu Val Leu Glu Ile Met Lys Val Gln Met Phe Ser His Arg Ser
        35                  40                  45

Lys Glu Tyr Arg Lys Val His Met Asp Thr Val Glu Arg Leu Arg Glu
    50                  55                  60

Phe Leu Glu Val Glu Lys Gly Glu Val Leu Leu Val Pro Ser Ser Gly
65                  70                  75                  80

Thr Gly Ile Met Glu Ala Ser Ile Arg Asn Gly Val Ser Lys Gly Gly
                85                  90                  95

Lys Val Leu Val Thr Ile Ile Gly Ala Phe Gly Lys Tyr Lys Tyr Glu
            100                 105                 110

Val Val Glu Ser Asn Gly Arg Lys Ala Val Val Leu Glu Tyr Glu Pro
        115                 120                 125

Gly Lys Ala Val Lys Pro Glu Asp Leu Asp Ala Leu Arg Lys Asn
    130                 135                 140

Pro Asp Val Glu Ala Val Thr Ile Thr Tyr Asn Glu Thr Ser Thr Gly
145                 150                 155                 160

Val Leu Asn Pro Leu Pro Glu Leu Ala Lys Val Ala Lys Glu His Asp
                165                 170                 175

Lys Leu Val Phe Val Asp Ala Val Ser Ala Met Gly Gly Ala Asp Ile
            180                 185                 190
```

```
Lys Phe Asp Lys Trp Gly Leu Asp Val Val Phe Ser Ser Ser Gln Lys
            195                 200                 205

Ala Phe Gly Val Pro Pro Gly Leu Ala Ile Gly Ala Phe Ser Glu Arg
210                 215                 220

Phe Leu Glu Ile Ala Glu Lys Met Pro Glu Arg Gly Trp Tyr Phe Asp
225                 230                 235                 240

Ile Pro Leu Tyr Val Lys Tyr Leu Lys Glu Lys Ser Thr Pro Ser
                245                 250                 255

Thr Pro Pro Met Pro Gln Val Phe Gly Ile Asn Val Ala Leu Arg Ile
            260                 265                 270

Ile Glu Lys Met Gly Gly Lys Glu Lys Trp Leu Glu Met Tyr Glu Lys
        275                 280                 285

Arg Ala Lys Met Val Arg Glu Gly Val Arg Glu Ile Gly Leu Asp Ile
    290                 295                 300

Leu Ala Glu Pro Gly His Glu Ser Pro Thr Ile Thr Ala Val Leu Thr
305                 310                 315                 320

Pro Pro Gly Ile Lys Gly Asp Glu Val Tyr Glu Ala Met Arg Lys Arg
                325                 330                 335

Gly Phe Glu Leu Ala Lys Gly Tyr Gly Ser Val Lys Glu Lys Thr Phe
            340                 345                 350

Arg Ile Gly His Met Gly Tyr Met Lys Phe Glu Asp Ile Gln Glu Met
        355                 360                 365

Leu Asp Asn Leu Arg Glu Val Ile Asn Glu Leu Lys Lys Gln Lys Gly
    370                 375                 380

Ile Asn Leu Glu
385

<210> SEQ ID NO 104
<211> LENGTH: 1194
<212> TYPE: DNA
<213> ORGANISM: Thermoanaerobacter tengcongensis
<220> FEATURE:
<221> NAME/KEY: CDS
<222> LOCATION: (1)..(1194)

<400> SEQUENCE: 104 atg aac ctg agc caa aac gca ctg caa atc acg ccg agt atg acc ctg      48
Met Asn Leu Ser Gln Asn Ala Leu Gln Ile Thr Pro Ser Met Thr Leu
1               5                   10                  15 gaa atc acc gcc aaa gcc cgc caa ctg aaa gcc gaa ggc gtc gat gtg      96
Glu Ile Thr Ala Lys Ala Arg Gln Leu Lys Ala Glu Gly Val Asp Val
                20                  25                  30 att gac ttt ggc gtg ggt gaa ccg gat ttc gac acc ccg gat tat atc     144
Ile Asp Phe Gly Val Gly Glu Pro Asp Phe Asp Thr Pro Asp Tyr Ile
            35                  40                  45 aaa gaa gcg gcc att gaa gcc atc aaa aaa ggt tat acc aaa tac acg     192
Lys Glu Ala Ala Ile Glu Ala Ile Lys Lys Gly Tyr Thr Lys Tyr Thr
        50                  55                  60 ccg gca tct ggc att ctg gaa ctg aaa aaa gct atc tgc gaa aaa ctg     240
Pro Ala Ser Gly Ile Leu Glu Leu Lys Lys Ala Ile Cys Glu Lys Leu
65                  70                  75                  80 aaa cgt gaa aac ggt ctg ttt tat gaa ccg gaa cag att gtg gtt tct     288
Lys Arg Glu Asn Gly Leu Phe Tyr Glu Pro Glu Gln Ile Val Val Ser
                85                  90                  95 aat ggc gca aaa cat agt att tac aac gca ctg tcc gct atc ctg aat     336
Asn Gly Ala Lys His Ser Ile Tyr Asn Ala Leu Ser Ala Ile Leu Asn
            100                 105                 110 ccg ggt gat gaa gtt att atc ccg gtc ccg tat tgg ctg agc tac ccg     384
```

```
            Pro Gly Asp Glu Val Ile Ile Pro Val Pro Tyr Trp Leu Ser Tyr Pro
                    115                 120                 125 gaa atg gtg cgc ctg gcg tat ggc aaa ccg gtt ttt gtc cag acc aaa         432
Glu Met Val Arg Leu Ala Tyr Gly Lys Pro Val Phe Val Gln Thr Lys
        130                 135                 140 gaa gaa aac aac ttc aaa atc acc gca gaa gaa ctg acg gca gct att         480
Glu Glu Asn Asn Phe Lys Ile Thr Ala Glu Glu Leu Thr Ala Ala Ile
145                 150                 155                 160 aac ccg aaa acg aaa gct ctg atc ctg aat tca ccg aac aat ccg acc         528
Asn Pro Lys Thr Lys Ala Leu Ile Leu Asn Ser Pro Asn Asn Pro Thr
                165                 170                 175 ggt gcg gtg tat acg cgt aaa gaa ctg caa gat atc gcc gaa gtc gtg         576
Gly Ala Val Tyr Thr Arg Lys Glu Leu Gln Asp Ile Ala Glu Val Val
            180                 185                 190 gaa gaa acc ggc att ttt gtc atc tcg gac gaa gtg tat gaa aaa ctg         624
Glu Glu Thr Gly Ile Phe Val Ile Ser Asp Glu Val Tyr Glu Lys Leu
        195                 200                 205 att tac gaa ggt gaa cat gtt agt atc gct tcc ctg ggc gaa aaa att         672
Ile Tyr Glu Gly Glu His Val Ser Ile Ala Ser Leu Gly Glu Lys Ile
    210                 215                 220 aaa gaa ctg acc atc gtt gtc aac ggt atg agt aaa gcg tat gcc atg         720
Lys Glu Leu Thr Ile Val Val Asn Gly Met Ser Lys Ala Tyr Ala Met
225                 230                 235                 240 acc ggc tgg cgt att ggt tac acg gcc agc tct ctg gat gtc gcg aaa         768
Thr Gly Trp Arg Ile Gly Tyr Thr Ala Ser Ser Leu Asp Val Ala Lys
                245                 250                 255 gtg atg gcc aat att cag tca cac acc acg tcg aac ccg aat agc atc         816
Val Met Ala Asn Ile Gln Ser His Thr Thr Ser Asn Pro Asn Ser Ile
            260                 265                 270 gcg caa tat gcc agc gtg acc gca ctg acg ggt gac ggt gtt gcc att         864
Ala Gln Tyr Ala Ser Val Thr Ala Leu Thr Gly Asp Gly Val Ala Ile
        275                 280                 285 aaa cgc atg gtc gaa gaa ttc aac aaa cgt cgc ctg tac gcg gtg gaa         912
Lys Arg Met Val Glu Glu Phe Asn Lys Arg Arg Leu Tyr Ala Val Glu
    290                 295                 300 cgt atc tct aaa atg aaa ggt ctg aaa gca gtt cgc ccg caa ggc gct         960
Arg Ile Ser Lys Met Lys Gly Leu Lys Ala Val Arg Pro Gln Gly Ala
305                 310                 315                 320 ttc tac gtg ttc gtt aac atc gaa gaa tac gtg ggc aaa aaa gtt aac        1008
Phe Tyr Val Phe Val Asn Ile Glu Glu Tyr Val Gly Lys Lys Val Asn
                325                 330                 335 ggt cgt aaa atc aaa ggc agt ctg gat ttt gcg acc ctg ctg atc gaa        1056
Gly Arg Lys Ile Lys Gly Ser Leu Asp Phe Ala Thr Leu Leu Ile Glu
            340                 345                 350 gaa gca aac gtt gct gtg gtt ccg gcc ctg ccg ttc ggc atg gac aat        1104
Glu Ala Asn Val Ala Val Val Pro Ala Leu Pro Phe Gly Met Asp Asn
        355                 360                 365 tat att cgc atc tcc tac gca acg agt atg gaa aac att gaa aaa ggt        1152
Tyr Ile Arg Ile Ser Tyr Ala Thr Ser Met Glu Asn Ile Glu Lys Gly
    370                 375                 380 ctg gat cgc att gaa aac ttc ctg aat aaa atc ctc gag taa               1194
Leu Asp Arg Ile Glu Asn Phe Leu Asn Lys Ile Leu Glu
385                 390                 395

<210> SEQ ID NO 105
<211> LENGTH: 397
<212> TYPE: PRT
<213> ORGANISM: Thermoanaerobacter tengcongensis

<400> SEQUENCE: 105
```

```
Met Asn Leu Ser Gln Asn Ala Leu Gln Ile Thr Pro Ser Met Thr Leu
1               5                   10                  15

Glu Ile Thr Ala Lys Ala Arg Gln Leu Lys Ala Glu Gly Val Asp Val
            20                  25                  30

Ile Asp Phe Gly Val Gly Glu Pro Asp Phe Asp Thr Pro Asp Tyr Ile
            35                  40                  45

Lys Glu Ala Ala Ile Glu Ala Ile Lys Lys Gly Tyr Thr Lys Tyr Thr
50                  55                  60

Pro Ala Ser Gly Ile Leu Glu Leu Lys Lys Ala Ile Cys Glu Lys Leu
65                  70                  75                  80

Lys Arg Glu Asn Gly Leu Phe Tyr Glu Pro Glu Gln Ile Val Val Ser
                85                  90                  95

Asn Gly Ala Lys His Ser Ile Tyr Asn Ala Leu Ser Ala Ile Leu Asn
            100                 105                 110

Pro Gly Asp Glu Val Ile Ile Pro Val Pro Tyr Trp Leu Ser Tyr Pro
            115                 120                 125

Glu Met Val Arg Leu Ala Tyr Gly Lys Pro Val Phe Val Gln Thr Lys
            130                 135                 140

Glu Glu Asn Asn Phe Lys Ile Thr Ala Glu Leu Thr Ala Ala Ile
145                 150                 155                 160

Asn Pro Lys Thr Lys Ala Leu Ile Leu Asn Ser Pro Asn Asn Pro Thr
                165                 170                 175

Gly Ala Val Tyr Thr Arg Lys Glu Leu Gln Asp Ile Ala Glu Val Val
            180                 185                 190

Glu Glu Thr Gly Ile Phe Val Ile Ser Asp Glu Val Tyr Glu Lys Leu
            195                 200                 205

Ile Tyr Glu Gly Glu His Val Ser Ile Ala Ser Leu Gly Glu Lys Ile
210                 215                 220

Lys Glu Leu Thr Ile Val Val Asn Gly Met Ser Lys Ala Tyr Ala Met
225                 230                 235                 240

Thr Gly Trp Arg Ile Gly Tyr Thr Ala Ser Ser Leu Asp Val Ala Lys
                245                 250                 255

Val Met Ala Asn Ile Gln Ser His Thr Thr Ser Asn Pro Asn Ser Ile
            260                 265                 270

Ala Gln Tyr Ala Ser Val Thr Ala Leu Thr Gly Asp Gly Val Ala Ile
            275                 280                 285

Lys Arg Met Val Glu Glu Phe Asn Lys Arg Leu Tyr Ala Val Glu
            290                 295                 300

Arg Ile Ser Lys Met Lys Gly Leu Lys Ala Val Arg Pro Gln Gly Ala
305                 310                 315                 320

Phe Tyr Val Phe Val Asn Ile Glu Glu Tyr Val Gly Lys Lys Val Asn
                325                 330                 335

Gly Arg Lys Ile Lys Gly Ser Leu Asp Phe Ala Thr Leu Leu Ile Glu
            340                 345                 350

Glu Ala Asn Val Ala Val Val Pro Ala Leu Pro Phe Gly Met Asp Asn
            355                 360                 365

Tyr Ile Arg Ile Ser Tyr Ala Thr Ser Met Glu Asn Ile Glu Lys Gly
            370                 375                 380

Leu Asp Arg Ile Glu Asn Phe Leu Asn Lys Ile Leu Glu
385                 390                 395
```

<210> SEQ ID NO 106
<211> LENGTH: 1284
<212> TYPE: DNA

<213> ORGANISM: Clostridium cellulolyticum
<220> FEATURE:
<221> NAME/KEY: CDS
<222> LOCATION: (1)..(1284)

<400> SEQUENCE: 106

| | | | | | | | | | | | | | | | | |
|---|---|---|---|---|---|---|---|---|---|---|---|---|---|---|---|---|
| atg | aaa | agc | tac | aaa | gac | ctg | agc | aaa | gaa | gaa | ctg | aaa | tcc | gaa | atc | 48 |
| Met | Lys | Ser | Tyr | Lys | Asp | Leu | Ser | Lys | Glu | Glu | Leu | Lys | Ser | Glu | Ile | |
| 1 | | | | 5 | | | | | 10 | | | | | 15 | | |

| gaa | atc | ctg | gaa | aaa | cgc | tac | aac | gaa | ttc | aaa | gca | caa | aac | ctg | aaa | 96 |
|---|---|---|---|---|---|---|---|---|---|---|---|---|---|---|---|---|
| Glu | Ile | Leu | Glu | Lys | Arg | Tyr | Asn | Glu | Phe | Lys | Ala | Gln | Asn | Leu | Lys | |
| | | | 20 | | | | | 25 | | | | | 30 | | | |

| ctg | gat | atg | acc | cgt | ggt | aaa | ccg | tgc | gct | gaa | cag | ctg | gac | ctg | tct | 144 |
|---|---|---|---|---|---|---|---|---|---|---|---|---|---|---|---|---|
| Leu | Asp | Met | Thr | Arg | Gly | Lys | Pro | Cys | Ala | Glu | Gln | Leu | Asp | Leu | Ser | |
| | | 35 | | | | | 40 | | | | | 45 | | | | |

| atg | gat | atg | ctg | gac | att | ccg | gcg | gtt | gaa | ctg | cgc | aaa | gcg | gcc | gat | 192 |
|---|---|---|---|---|---|---|---|---|---|---|---|---|---|---|---|---|
| Met | Asp | Met | Leu | Asp | Ile | Pro | Ala | Val | Glu | Leu | Arg | Lys | Ala | Ala | Asp | |
| 50 | | | | | 55 | | | | | 60 | | | | | | |

| ggc | acc | gac | tgt | ttt | aat | tat | ggc | gtt | ctg | gat | ggt | att | ccg | gaa | gca | 240 |
|---|---|---|---|---|---|---|---|---|---|---|---|---|---|---|---|---|
| Gly | Thr | Asp | Cys | Phe | Asn | Tyr | Gly | Val | Leu | Asp | Gly | Ile | Pro | Glu | Ala | |
| 65 | | | | 70 | | | | | 75 | | | | | 80 | | |

| aaa | gct | ctg | ttc | gcc | caa | atg | ctg | gaa | gtg | agc | acg | gat | gaa | atc | atg | 288 |
|---|---|---|---|---|---|---|---|---|---|---|---|---|---|---|---|---|
| Lys | Ala | Leu | Phe | Ala | Gln | Met | Leu | Glu | Val | Ser | Thr | Asp | Glu | Ile | Met | |
| | | | | 85 | | | | | 90 | | | | | 95 | | |

| gtt | ggc | ggt | aac | agc | tct | ctg | aat | ctg | atg | tat | gac | acc | att | gcg | cgt | 336 |
|---|---|---|---|---|---|---|---|---|---|---|---|---|---|---|---|---|
| Val | Gly | Gly | Asn | Ser | Ser | Leu | Asn | Leu | Met | Tyr | Asp | Thr | Ile | Ala | Arg | |
| | | | 100 | | | | | 105 | | | | | 110 | | | |

| gcc | atg | tcg | ctg | ggc | atc | ctg | ggt | agc | acg | ccg | tgg | tct | aaa | ctg | aac | 384 |
|---|---|---|---|---|---|---|---|---|---|---|---|---|---|---|---|---|
| Ala | Met | Ser | Leu | Gly | Ile | Leu | Gly | Ser | Thr | Pro | Trp | Ser | Lys | Leu | Asn | |
| | | 115 | | | | | 120 | | | | | 125 | | | | |

| agt | gtg | aaa | ttt | ctg | tgc | ccg | agc | ccg | ggc | tac | gat | cgc | cat | ttt | gca | 432 |
|---|---|---|---|---|---|---|---|---|---|---|---|---|---|---|---|---|
| Ser | Val | Lys | Phe | Leu | Cys | Pro | Ser | Pro | Gly | Tyr | Asp | Arg | His | Phe | Ala | |
| 130 | | | | | 135 | | | | | 140 | | | | | | |

| att | tgt | gaa | ctg | ttc | ggt | atc | gaa | atg | att | acc | atc | gat | atg | aaa | cag | 480 |
|---|---|---|---|---|---|---|---|---|---|---|---|---|---|---|---|---|
| Ile | Cys | Glu | Leu | Phe | Gly | Ile | Glu | Met | Ile | Thr | Ile | Asp | Met | Lys | Gln | |
| 145 | | | | 150 | | | | | 155 | | | | | 160 | | |

| gac | ggc | ccg | gat | atg | gac | acg | gtt | gaa | aaa | ctg | gtc | tcc | gaa | gat | gac | 528 |
|---|---|---|---|---|---|---|---|---|---|---|---|---|---|---|---|---|
| Asp | Gly | Pro | Asp | Met | Asp | Thr | Val | Glu | Lys | Leu | Val | Ser | Glu | Asp | Asp | |
| | | | | 165 | | | | | 170 | | | | | 175 | | |

| tca | att | aaa | ggt | atc | tgg | tgc | gtg | ccg | aaa | tat | tcc | aat | ccg | gat | ggc | 576 |
|---|---|---|---|---|---|---|---|---|---|---|---|---|---|---|---|---|
| Ser | Ile | Lys | Gly | Ile | Trp | Cys | Val | Pro | Lys | Tyr | Ser | Asn | Pro | Asp | Gly | |
| | | | 180 | | | | | 185 | | | | | 190 | | | |

| att | acc | tac | acg | gat | gaa | gtg | gtt | gac | cgt | ttc | tca | aac | ctg | aaa | ccg | 624 |
|---|---|---|---|---|---|---|---|---|---|---|---|---|---|---|---|---|
| Ile | Thr | Tyr | Thr | Asp | Glu | Val | Val | Asp | Arg | Phe | Ser | Asn | Leu | Lys | Pro | |
| | | | | 195 | | | | | 200 | | | | | 205 | | |

| aaa | gcc | aaa | gat | ttt | cgc | atc | ttc | tgg | gac | aat | gca | tat | tgc | gtt | cat | 672 |
|---|---|---|---|---|---|---|---|---|---|---|---|---|---|---|---|---|
| Lys | Ala | Lys | Asp | Phe | Arg | Ile | Phe | Trp | Asp | Asn | Ala | Tyr | Cys | Val | His | |
| | | 210 | | | | | 215 | | | | | 220 | | | | |

| cac | ctg | acc | gaa | aac | ccg | gat | aaa | ctg | aaa | aac | atc | ctg | aaa | gct | tgt | 720 |
|---|---|---|---|---|---|---|---|---|---|---|---|---|---|---|---|---|
| His | Leu | Thr | Glu | Asn | Pro | Asp | Lys | Leu | Lys | Asn | Ile | Leu | Lys | Ala | Cys | |
| 225 | | | | | 230 | | | | | 235 | | | | | 240 | |

| aaa | gat | gcg | ggt | aac | gac | aat | atg | gtc | tac | atc | ttt | agt | tcc | acg | tca | 768 |
|---|---|---|---|---|---|---|---|---|---|---|---|---|---|---|---|---|
| Lys | Asp | Ala | Gly | Asn | Asp | Asn | Met | Val | Tyr | Ile | Phe | Ser | Ser | Thr | Ser | |
| | | | | 245 | | | | | 250 | | | | | 255 | | |

| aaa | gtg | tcg | ttc | ccg | ggt | gca | ggt | gtc | gca | gtg | atg | gca | acc | tcg | acg | 816 |
|---|---|---|---|---|---|---|---|---|---|---|---|---|---|---|---|---|
| Lys | Val | Ser | Phe | Pro | Gly | Ala | Gly | Val | Ala | Val | Met | Ala | Thr | Ser | Thr | |
| | | | 260 | | | | | 265 | | | | | 270 | | | |

| gaa | aac | atc | aaa | ggc | att | aaa | aaa | tct | ctg | acc | atc | cag | acg | atc | ggt | 864 |
|---|---|---|---|---|---|---|---|---|---|---|---|---|---|---|---|---|
| Glu | Asn | Ile | Lys | Gly | Ile | Lys | Lys | Ser | Leu | Thr | Ile | Gln | Thr | Ile | Gly | |
| | | 275 | | | | | 280 | | | | | 285 | | | | |

```
cat gat aaa att aat caa ctg cgt cac gcc aaa tac ttc aaa aac ctg      912
His Asp Lys Ile Asn Gln Leu Arg His Ala Lys Tyr Phe Lys Asn Leu
    290                 295                 300 gat ggt atc aac agc cac atg aaa aaa cac gca gac atc ctg aaa ccg      960
Asp Gly Ile Asn Ser His Met Lys Lys His Ala Asp Ile Leu Lys Pro
305                 310                 315                 320 aaa ttt aac acc gtc ctg gaa att ttc gaa ggc gaa ctg ggc ggt aaa     1008
Lys Phe Asn Thr Val Leu Glu Ile Phe Glu Gly Glu Leu Gly Gly Lys
                325                 330                 335 gat atc gct tct tgg aac aaa ccg aat ggc ggt tat ttt gtt agt ctg     1056
Asp Ile Ala Ser Trp Asn Lys Pro Asn Gly Gly Tyr Phe Val Ser Leu
            340                 345                 350 aac acc atg gat aat tgt gcg aaa gaa gtt gct aaa ctg gcg agt gaa     1104
Asn Thr Met Asp Asn Cys Ala Lys Glu Val Ala Lys Leu Ala Ser Glu
        355                 360                 365 gcc ggc gtc gca ctg acc aaa gca ggc gct acg ttc ccg tac ggt aac     1152
Ala Gly Val Ala Leu Thr Lys Ala Gly Ala Thr Phe Pro Tyr Gly Asn
    370                 375                 380 gat ccg cgt gac cgc aat ctg cgc att gcc ccg acc atg ccg ccg atc     1200
Asp Pro Arg Asp Arg Asn Leu Arg Ile Ala Pro Thr Met Pro Pro Ile
385                 390                 395                 400 gaa gaa ctg aaa aaa gcc att gaa gtc ctg gtc att tgt gtc caa ctg     1248
Glu Glu Leu Lys Lys Ala Ile Glu Val Leu Val Ile Cys Val Gln Leu
                405                 410                 415 gtc tcc gct aat aaa ctg ctg aat caa ctc gag taa                     1284
Val Ser Ala Asn Lys Leu Leu Asn Gln Leu Glu
            420                 425

<210> SEQ ID NO 107
<211> LENGTH: 427
<212> TYPE: PRT
<213> ORGANISM: Clostridium cellulolyticum

<400> SEQUENCE: 107

Met Lys Ser Tyr Lys Asp Leu Ser Lys Glu Glu Leu Lys Ser Glu Ile
1               5                   10                  15

Glu Ile Leu Glu Lys Arg Tyr Asn Glu Phe Lys Ala Gln Asn Leu Lys
            20                  25                  30

Leu Asp Met Thr Arg Gly Lys Pro Cys Ala Glu Gln Leu Asp Leu Ser
        35                  40                  45

Met Asp Met Leu Asp Ile Pro Ala Val Glu Leu Arg Lys Ala Ala Asp
    50                  55                  60

Gly Thr Asp Cys Phe Asn Tyr Gly Val Leu Asp Gly Ile Pro Glu Ala
65                  70                  75                  80

Lys Ala Leu Phe Ala Gln Met Leu Glu Val Ser Thr Asp Glu Ile Met
                85                  90                  95

Val Gly Gly Asn Ser Ser Leu Asn Leu Met Tyr Asp Thr Ile Ala Arg
            100                 105                 110

Ala Met Ser Leu Gly Ile Leu Gly Ser Thr Pro Trp Ser Lys Leu Asn
        115                 120                 125

Ser Val Lys Phe Leu Cys Pro Ser Pro Gly Tyr Asp Arg His Phe Ala
    130                 135                 140

Ile Cys Glu Leu Phe Gly Ile Glu Met Ile Thr Ile Asp Met Lys Gln
145                 150                 155                 160

Asp Gly Pro Asp Met Asp Thr Val Glu Lys Leu Val Ser Glu Asp Asp
                165                 170                 175

Ser Ile Lys Gly Ile Trp Cys Val Pro Lys Tyr Ser Asn Pro Asp Gly
            180                 185                 190
```

```
Ile Thr Tyr Thr Asp Glu Val Val Asp Arg Phe Ser Asn Leu Lys Pro
        195                 200                 205

Lys Ala Lys Asp Phe Arg Ile Phe Trp Asp Asn Ala Tyr Cys Val His
    210                 215                 220

His Leu Thr Glu Asn Pro Asp Lys Leu Lys Asn Ile Leu Lys Ala Cys
225                 230                 235                 240

Lys Asp Ala Gly Asn Asp Asn Met Val Tyr Ile Phe Ser Ser Thr Ser
                245                 250                 255

Lys Val Ser Phe Pro Gly Ala Gly Val Ala Val Met Ala Thr Ser Thr
                260                 265                 270

Glu Asn Ile Lys Gly Ile Lys Lys Ser Leu Thr Ile Gln Thr Ile Gly
            275                 280                 285

His Asp Lys Ile Asn Gln Leu Arg His Ala Lys Tyr Phe Lys Asn Leu
        290                 295                 300

Asp Gly Ile Asn Ser His Met Lys Lys His Ala Asp Ile Leu Lys Pro
305                 310                 315                 320

Lys Phe Asn Thr Val Leu Glu Ile Phe Glu Gly Leu Gly Gly Lys
                325                 330                 335

Asp Ile Ala Ser Trp Asn Lys Pro Asn Gly Gly Tyr Phe Val Ser Leu
                340                 345                 350

Asn Thr Met Asp Asn Cys Ala Lys Glu Val Ala Lys Leu Ala Ser Glu
            355                 360                 365

Ala Gly Val Ala Leu Thr Lys Ala Gly Ala Thr Phe Pro Tyr Gly Asn
        370                 375                 380

Asp Pro Arg Asp Arg Asn Leu Arg Ile Ala Pro Thr Met Pro Pro Ile
385                 390                 395                 400

Glu Glu Leu Lys Lys Ala Ile Glu Val Leu Val Ile Cys Val Gln Leu
                405                 410                 415

Val Ser Ala Asn Lys Leu Leu Asn Gln Leu Glu
                420                 425

<210> SEQ ID NO 108
<211> LENGTH: 1299
<212> TYPE: DNA
<213> ORGANISM: Rhodococcus erythropolis
<220> FEATURE:
<221> NAME/KEY: CDS
<222> LOCATION: (1)..(1299)

<400> SEQUENCE: 108 atg ccg att caa acc cag att ggt ctg atg agc cac gaa gaa ctg acg      48
Met Pro Ile Gln Thr Gln Ile Gly Leu Met Ser His Glu Glu Leu Thr
1               5                   10                  15 agc gaa cac gaa agc caa agc gca aaa tac acg caa ctg caa gct caa      96
Ser Glu His Glu Ser Gln Ser Ala Lys Tyr Thr Gln Leu Gln Ala Gln
            20                  25                  30 aaa ctg gcg ctg gat ctg acc cgt ggt aaa ccg agc ccg gaa cag ctg     144
Lys Leu Ala Leu Asp Leu Thr Arg Gly Lys Pro Ser Pro Glu Gln Leu
        35                  40                  45 gac ctg tct gcc gaa ctg ctg acg ctg ccg ggc gat ggt gac ttt cgt     192
Asp Leu Ser Ala Glu Leu Leu Thr Leu Pro Gly Asp Gly Asp Phe Arg
    50                  55                  60 gat ggc agc ggt acc gac tgc cgc aat tat ggt ggt ctg acg ggt ctg     240
Asp Gly Ser Gly Thr Asp Cys Arg Asn Tyr Gly Gly Leu Thr Gly Leu
65                  70                  75                  80 ccg gaa ctg cgt gcg att ttc ggc gaa ctg ctg ggt atc ccg gtg gcc     288
Pro Glu Leu Arg Ala Ile Phe Gly Glu Leu Leu Gly Ile Pro Val Ala
```

-continued

```
                85                 90                  95
aac ctg ctg gcc ggt aac aat gct tcc ctg gaa atc atg cat gat aac      336
Asn Leu Leu Ala Gly Asn Asn Ala Ser Leu Glu Ile Met His Asp Asn
            100                 105                 110 gtg gtt ttt agt ctg ctg cac ggt acc ccg gac tcc gca cgt ccg tgg      384
Val Val Phe Ser Leu Leu His Gly Thr Pro Asp Ser Ala Arg Pro Trp
            115                 120                 125 gcc cag gaa gaa aaa att aaa ttt ctg tgt ccg gct ccg ggc tac gat      432
Ala Gln Glu Glu Lys Ile Lys Phe Leu Cys Pro Ala Pro Gly Tyr Asp
130                 135                 140 cgc cat ttc gcg atc acg gaa agt ctg ggt att gaa atg atc gcc gtg      480
Arg His Phe Ala Ile Thr Glu Ser Leu Gly Ile Glu Met Ile Ala Val
145                 150                 155                 160 ccg atg aac cac gat ggc ccg gac gtc gtg aaa att gca gaa ctg gtt      528
Pro Met Asn His Asp Gly Pro Asp Val Val Lys Ile Ala Glu Leu Val
            165                 170                 175 gct tct gat ccg caa atc aaa ggc atg tgg gcg gtg ccg gtt tat gcc      576
Ala Ser Asp Pro Gln Ile Lys Gly Met Trp Ala Val Pro Val Tyr Ala
            180                 185                 190 aat ccg acc ggc gca gtt tac tca gaa gaa att gtc cgt acc ctg gca      624
Asn Pro Thr Gly Ala Val Tyr Ser Glu Glu Ile Val Arg Thr Leu Ala
            195                 200                 205 tcg atg ccg acg gcg gcc ccg gat ttt cgt ctg tat tgg gac aac gca      672
Ser Met Pro Thr Ala Ala Pro Asp Phe Arg Leu Tyr Trp Asp Asn Ala
210                 215                 220 tac gct gtc cat ccg ctg gtt ggc gaa acc gcg ccg agt tat gat att      720
Tyr Ala Val His Pro Leu Val Gly Glu Thr Ala Pro Ser Tyr Asp Ile
225                 230                 235                 240 ctg tcc atg gca gct gaa gca ggt cac ccg aac cgt ccg ctg gtc ttt      768
Leu Ser Met Ala Ala Glu Ala Gly His Pro Asn Arg Pro Leu Val Phe
            245                 250                 255 gca agt acc tcc aaa atc acg ttc gcg ggc gcc ggt gtg agc ttt ttc      816
Ala Ser Thr Ser Lys Ile Thr Phe Ala Gly Ala Gly Val Ser Phe Phe
            260                 265                 270 ggt agc tct gcg gaa aat ctg gcc tgg tac cag aaa ttc ctg ggc aaa      864
Gly Ser Ser Ala Glu Asn Leu Ala Trp Tyr Gln Lys Phe Leu Gly Lys
            275                 280                 285 aaa tct atc ggt ccg gat aaa gtt aac caa ctg cgt cat ctg cgc ttt      912
Lys Ser Ile Gly Pro Asp Lys Val Asn Gln Leu Arg His Leu Arg Phe
290                 295                 300 ttc ggc aat gct gac ggt gtc cgt gcg cac atg gaa aaa cac cgc gca      960
Phe Gly Asn Ala Asp Gly Val Arg Ala His Met Glu Lys His Arg Ala
305                 310                 315                 320 ttt ctg gct ccg aaa ttc gaa ctg gtg ctg cgt att ctg gaa gat cgc     1008
Phe Leu Ala Pro Lys Phe Glu Leu Val Leu Arg Ile Leu Glu Asp Arg
            325                 330                 335 ctg ggt gca agc aaa gtt gct tct tgg acc gaa ccg aaa ggc ggt tat     1056
Leu Gly Ala Ser Lys Val Ala Ser Trp Thr Glu Pro Lys Gly Gly Tyr
            340                 345                 350 ttt atc agc ctg gat gtt gtc gac ggc acg gcg aaa cgc gtg att gaa     1104
Phe Ile Ser Leu Asp Val Val Asp Gly Thr Ala Lys Arg Val Ile Glu
            355                 360                 365 ctg gcg aaa aac gca ggt atc gca ctg acc gcg gcc ggt tca gcg ttt     1152
Leu Ala Lys Asn Ala Gly Ile Ala Leu Thr Ala Ala Gly Ser Ala Phe
370                 375                 380 ccg tac tcg acg gat ccg gat gac cgt aat att cgt ctg gca ccg tca     1200
Pro Tyr Ser Thr Asp Pro Asp Asp Arg Asn Ile Arg Leu Ala Pro Ser
385                 390                 395                 400 ttc ccg tcg acc gcc gaa ctg gaa gtt gca atg gat ggt gtc gca acc     1248
```

```
Phe Pro Ser Thr Ala Glu Leu Glu Val Ala Met Asp Gly Val Ala Thr
                    405                 410                 415 tgt gtc ctg ctg gcc gca acg gaa tca cgc ctg tca gaa atc ctc gag   1296
Cys Val Leu Leu Ala Ala Thr Glu Ser Arg Leu Ser Glu Ile Leu Glu
                420                 425                 430 taa                                                                1299

<210> SEQ ID NO 109
<211> LENGTH: 432
<212> TYPE: PRT
<213> ORGANISM: Rhodococcus erythropolis

<400> SEQUENCE: 109

Met Pro Ile Gln Thr Gln Ile Gly Leu Met Ser His Glu Glu Leu Thr
1               5                   10                  15

Ser Glu His Glu Ser Gln Ser Ala Lys Tyr Thr Gln Leu Gln Ala Gln
            20                  25                  30

Lys Leu Ala Leu Asp Leu Thr Arg Gly Lys Pro Ser Pro Glu Gln Leu
        35                  40                  45

Asp Leu Ser Ala Glu Leu Leu Thr Leu Pro Gly Asp Gly Asp Phe Arg
    50                  55                  60

Asp Gly Ser Gly Thr Asp Cys Arg Asn Tyr Gly Gly Leu Thr Gly Leu
65                  70                  75                  80

Pro Glu Leu Arg Ala Ile Phe Gly Glu Leu Gly Ile Pro Val Ala
                85                  90                  95

Asn Leu Leu Ala Gly Asn Asn Ala Ser Leu Glu Ile Met His Asp Asn
            100                 105                 110

Val Val Phe Ser Leu Leu His Gly Thr Pro Asp Ser Ala Arg Pro Trp
        115                 120                 125

Ala Gln Glu Glu Lys Ile Lys Phe Leu Cys Pro Ala Pro Gly Tyr Asp
    130                 135                 140

Arg His Phe Ala Ile Thr Glu Ser Leu Gly Ile Glu Met Ile Ala Val
145                 150                 155                 160

Pro Met Asn His Asp Gly Pro Asp Val Val Lys Ile Ala Glu Leu Val
                165                 170                 175

Ala Ser Asp Pro Gln Ile Lys Gly Met Trp Ala Val Pro Val Tyr Ala
            180                 185                 190

Asn Pro Thr Gly Ala Val Tyr Ser Glu Glu Ile Val Arg Thr Leu Ala
        195                 200                 205

Ser Met Pro Thr Ala Ala Pro Asp Phe Arg Leu Tyr Trp Asp Asn Ala
    210                 215                 220

Tyr Ala Val His Pro Leu Val Gly Glu Thr Ala Pro Ser Tyr Asp Ile
225                 230                 235                 240

Leu Ser Met Ala Ala Glu Ala Gly His Pro Asn Arg Pro Leu Val Phe
                245                 250                 255

Ala Ser Thr Ser Lys Ile Thr Phe Ala Gly Ala Gly Val Ser Phe Phe
            260                 265                 270

Gly Ser Ser Ala Glu Asn Leu Ala Trp Tyr Gln Lys Phe Leu Gly Lys
        275                 280                 285

Lys Ser Ile Gly Pro Asp Lys Val Asn Gln Leu Arg His Leu Arg Phe
    290                 295                 300

Phe Gly Asn Ala Asp Gly Val Arg Ala His Met Glu Lys His Arg Ala
305                 310                 315                 320

Phe Leu Ala Pro Lys Phe Glu Leu Val Leu Arg Ile Leu Glu Asp Arg
                325                 330                 335
```

```
Leu Gly Ala Ser Lys Val Ala Ser Trp Thr Glu Pro Lys Gly Gly Tyr
            340                 345                 350

Phe Ile Ser Leu Asp Val Val Asp Gly Thr Ala Lys Arg Val Ile Glu
            355                 360                 365

Leu Ala Lys Asn Ala Gly Ile Ala Leu Thr Ala Ala Gly Ser Ala Phe
            370                 375                 380

Pro Tyr Ser Thr Asp Pro Asp Arg Asn Ile Arg Leu Ala Pro Ser
385                 390                 395                 400

Phe Pro Ser Thr Ala Glu Leu Glu Val Ala Met Asp Gly Val Ala Thr
                405                 410                 415

Cys Val Leu Leu Ala Ala Thr Glu Ser Arg Leu Ser Glu Ile Leu Glu
            420                 425                 430

<210> SEQ ID NO 110
<211> LENGTH: 1356
<212> TYPE: DNA
<213> ORGANISM: Saccharophagus degradans
<220> FEATURE:
<221> NAME/KEY: CDS
<222> LOCATION: (1)..(1356)

<400> SEQUENCE: 110
```

| | | | | | | | | | | | | | | | | |
|---|---|---|---|---|---|---|---|---|---|---|---|---|---|---|---|---|
| atg | caa | gct | ccg | tac | acc | aat | ctg | aaa | acg | cac | cac | aaa | tgg | gtc | gaa | 48 |
| Met | Gln | Ala | Pro | Tyr | Thr | Asn | Leu | Lys | Thr | His | His | Lys | Trp | Val | Glu | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ttc | tcc | gcc | gaa | gac | acc | acg | ctg | aac | ctg | agt | aac | gcc | tca | gtc | gaa | 96 |
| Phe | Ser | Ala | Glu | Asp | Thr | Thr | Leu | Asn | Leu | Ser | Asn | Ala | Ser | Val | Glu | |
| | | | | 20 | | | | | 25 | | | | | 30 | | |

| | | | | | | | | | | | | | | | | |
|---|---|---|---|---|---|---|---|---|---|---|---|---|---|---|---|---|
| cag | ctg | caa | gaa | tgg | aaa | cag | caa | ctg | tcg | gcg | gaa | tat | gat | aac | gtt | 144 |
| Gln | Leu | Gln | Glu | Trp | Lys | Gln | Gln | Leu | Ser | Ala | Glu | Tyr | Asp | Asn | Val | |
| | | | 35 | | | | | 40 | | | | | 45 | | | |

| | | | | | | | | | | | | | | | | |
|---|---|---|---|---|---|---|---|---|---|---|---|---|---|---|---|---|
| ctg | gcc | cgt | aaa | ctg | aat | ctg | gac | ctg | acc | cgc | ggc | aaa | ccg | agt | gcg | 192 |
| Leu | Ala | Arg | Lys | Leu | Asn | Leu | Asp | Leu | Thr | Arg | Gly | Lys | Pro | Ser | Ala | |
| | | 50 | | | | | 55 | | | | | 60 | | | | |

| | | | | | | | | | | | | | | | | |
|---|---|---|---|---|---|---|---|---|---|---|---|---|---|---|---|---|
| gaa | cag | ctg | agt | ctg | tcc | gat | gct | atg | gac | ggc | att | ctg | gcg | ggt | gat | 240 |
| Glu | Gln | Leu | Ser | Leu | Ser | Asp | Ala | Met | Asp | Gly | Ile | Leu | Ala | Gly | Asp | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| tat | att | acg | gcc | agt | ggc | atc | gac | gtg | cgt | aac | tac | ggc | ggt | ctg | gaa | 288 |
| Tyr | Ile | Thr | Ala | Ser | Gly | Ile | Asp | Val | Arg | Asn | Tyr | Gly | Gly | Leu | Glu | |
| | | | | 85 | | | | | 90 | | | | | 95 | | |

| | | | | | | | | | | | | | | | | |
|---|---|---|---|---|---|---|---|---|---|---|---|---|---|---|---|---|
| ggt | atc | ccg | gaa | gcg | cgt | gcg | att | ggc | tcc | gat | atc | ctg | ggt | gtt | ccg | 336 |
| Gly | Ile | Pro | Glu | Ala | Arg | Ala | Ile | Gly | Ser | Asp | Ile | Leu | Gly | Val | Pro | |
| | | | | 100 | | | | | 105 | | | | | 110 | | |

| | | | | | | | | | | | | | | | | |
|---|---|---|---|---|---|---|---|---|---|---|---|---|---|---|---|---|
| gtc | gaa | aac | gtt | ctg | gcc | ggc | ggt | aat | agc | tct | ctg | acc | ctg | atg | tac | 384 |
| Val | Glu | Asn | Val | Leu | Ala | Gly | Gly | Asn | Ser | Ser | Leu | Thr | Leu | Met | Tyr | |
| | | | 115 | | | | | 120 | | | | | 125 | | | |

| | | | | | | | | | | | | | | | | |
|---|---|---|---|---|---|---|---|---|---|---|---|---|---|---|---|---|
| cag | acg | atg | gca | att | gct | cat | caa | ttc | ggt | ctg | gct | ggc | gaa | ggt | agc | 432 |
| Gln | Thr | Met | Ala | Ile | Ala | His | Gln | Phe | Gly | Leu | Ala | Gly | Glu | Gly | Ser | |
| | | 130 | | | | | 135 | | | | | 140 | | | | |

| | | | | | | | | | | | | | | | | |
|---|---|---|---|---|---|---|---|---|---|---|---|---|---|---|---|---|
| gcg | tgg | tct | cag | gaa | ggc | acc | gtg | aaa | ttt | ctg | tgc | ccg | gtt | ccg | ggt | 480 |
| Ala | Trp | Ser | Gln | Glu | Gly | Thr | Val | Lys | Phe | Leu | Cys | Pro | Val | Pro | Gly | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| tat | gat | cgt | cat | tac | agc | gtt | tgt | gaa | cac | ctg | ggc | atc | gaa | atg | ctg | 528 |
| Tyr | Asp | Arg | His | Tyr | Ser | Val | Cys | Glu | His | Leu | Gly | Ile | Glu | Met | Leu | |
| | | | | 165 | | | | | 170 | | | | | 175 | | |

| | | | | | | | | | | | | | | | | |
|---|---|---|---|---|---|---|---|---|---|---|---|---|---|---|---|---|
| acc | gtc | gcg | atg | acc | tct | acg | ggt | ccg | gat | atg | gac | caa | gtg | gaa | aaa | 576 |
| Thr | Val | Ala | Met | Thr | Ser | Thr | Gly | Pro | Asp | Met | Asp | Gln | Val | Glu | Lys | |
| | | | | 180 | | | | | 185 | | | | | 190 | | |

| | | | | | | | | | | | | | | | | |
|---|---|---|---|---|---|---|---|---|---|---|---|---|---|---|---|---|
| atg | att | gcg | gcc | gat | ccg | agc | atc | aaa | ggc | atg | tgg | tgc | gtt | ccg | aaa | 624 |

|   |   |   |   |   |   |   |   |   |   |   |   |   |
|---|---|---|---|---|---|---|---|---|---|---|---|---|
|   | Met | Ile | Ala | Ala | Asp | Pro | Ser | Ile | Lys | Gly | Met | Trp | Cys | Val | Pro | Lys |   |
|   |     |     | 195 |     |     |     | 200 |     |     |     |     | 205 |     |     |     |     |   |

```
tat agt aat ccg acc ggt gtg gtt tac tcc gac gaa acg gtc gaa cgt    672
Tyr Ser Asn Pro Thr Gly Val Val Tyr Ser Asp Glu Thr Val Glu Arg
210                 215                 220 att gca aac ctg ggc aat atc gct ggt aaa aac ttt cgc gtg ttc tgg    720
Ile Ala Asn Leu Gly Asn Ile Ala Gly Lys Asn Phe Arg Val Phe Trp
225                 230                 235                 240 gat aat gcg tat gcc att cat gat ctg tca gac aac ccg gtt gca ctg    768
Asp Asn Ala Tyr Ala Ile His Asp Leu Ser Asp Asn Pro Val Ala Leu
                245                 250                 255 gct aat atc ttt gaa gcc tgt aaa gca gct ggc acc gaa gat tcg gtg    816
Ala Asn Ile Phe Glu Ala Cys Lys Ala Ala Gly Thr Glu Asp Ser Val
    260                 265                 270 att cag ttc gca tca acc tcg aaa gtc acg cac gcc ggc agc ggt gtg    864
Ile Gln Phe Ala Ser Thr Ser Lys Val Thr His Ala Gly Ser Gly Val
275                 280                 285 gca ttt atc gcg gcc tcg gat acc aac ctg aaa ttt ttc aaa ctg gca    912
Ala Phe Ile Ala Ala Ser Asp Thr Asn Leu Lys Phe Phe Lys Leu Ala
290                 295                 300 ctg ggc ttc atg acg att ggt ccg gat aaa gtg aat cag ctg cgt cat    960
Leu Gly Phe Met Thr Ile Gly Pro Asp Lys Val Asn Gln Leu Arg His
305                 310                 315                 320 gcc aaa ttt ttc gca gct gac ggt gca ctg tca gct cac atg gcg aaa   1008
Ala Lys Phe Phe Ala Ala Asp Gly Ala Leu Ser Ala His Met Ala Lys
                325                 330                 335 cac gcg gcc att atc aaa ccg cgc ttt gcg agt gtt ctg aaa cac ctg   1056
His Ala Ala Ile Ile Lys Pro Arg Phe Ala Ser Val Leu Lys His Leu
    340                 345                 350 gaa gca gct ttc tcc gat aac gac ctg ggc gaa tgg gaa agc gcg gat   1104
Glu Ala Ala Phe Ser Asp Asn Asp Leu Gly Glu Trp Glu Ser Ala Asp
355                 360                 365 ggc ggt tat ttt att tct ttc gac acc cgt ccg ggt ctg gcc cag aaa   1152
Gly Gly Tyr Phe Ile Ser Phe Asp Thr Arg Pro Gly Leu Ala Gln Lys
370                 375                 380 gtc gtg aaa ctg gcc ggc gat gca ggt gtg aaa ctg acc ccg gcg ggt   1200
Val Val Lys Leu Ala Gly Asp Ala Gly Val Lys Leu Thr Pro Ala Gly
385                 390                 395                 400 gca acg ttt ccg tac ggt aaa gat ccg cag gac tct aat att cgc atc   1248
Ala Thr Phe Pro Tyr Gly Lys Asp Pro Gln Asp Ser Asn Ile Arg Ile
                405                 410                 415 gca ccg acc gtg ccg acg gtt gat caa gtc gaa gaa gct atg caa gtc   1296
Ala Pro Thr Val Pro Thr Val Asp Gln Val Glu Glu Ala Met Gln Val
    420                 425                 430 ttc gtc ctg tgt gtg aaa ctg gcg tcg gtg gaa caa gca ctg gca aat   1344
Phe Val Leu Cys Val Lys Leu Ala Ser Val Glu Gln Ala Leu Ala Asn
435                 440                 445 tcg ctc gag taa                                                   1356
Ser Leu Glu
    450

<210> SEQ ID NO 111
<211> LENGTH: 451
<212> TYPE: PRT
<213> ORGANISM: Saccharophagus degradans

<400> SEQUENCE: 111

Met Gln Ala Pro Tyr Thr Asn Leu Lys Thr His His Lys Trp Val Glu
1               5                   10                  15

Phe Ser Ala Glu Asp Thr Thr Leu Asn Leu Ser Asn Ala Ser Val Glu
```

```
                20                  25                  30
Gln Leu Gln Glu Trp Lys Gln Gln Leu Ser Ala Glu Tyr Asp Asn Val
            35                  40                  45
Leu Ala Arg Lys Leu Asn Leu Asp Leu Thr Arg Gly Lys Pro Ser Ala
 50                  55                  60
Glu Gln Leu Ser Leu Ser Asp Ala Met Asp Gly Ile Leu Ala Gly Asp
 65                  70                  75                  80
Tyr Ile Thr Ala Ser Gly Ile Asp Val Arg Asn Tyr Gly Gly Leu Glu
                85                  90                  95
Gly Ile Pro Glu Ala Arg Ala Ile Gly Ser Asp Ile Leu Gly Val Pro
            100                 105                 110
Val Glu Asn Val Leu Ala Gly Gly Asn Ser Ser Leu Thr Leu Met Tyr
            115                 120                 125
Gln Thr Met Ala Ile Ala His Gln Phe Gly Leu Ala Gly Glu Gly Ser
            130                 135                 140
Ala Trp Ser Gln Glu Gly Thr Val Lys Phe Leu Cys Pro Val Pro Gly
145                 150                 155                 160
Tyr Asp Arg His Tyr Ser Val Cys Glu His Leu Gly Ile Glu Met Leu
                165                 170                 175
Thr Val Ala Met Thr Ser Thr Gly Pro Asp Met Asp Gln Val Glu Lys
            180                 185                 190
Met Ile Ala Ala Asp Pro Ser Ile Lys Gly Met Trp Cys Val Pro Lys
            195                 200                 205
Tyr Ser Asn Pro Thr Gly Val Val Tyr Ser Asp Glu Thr Val Glu Arg
            210                 215                 220
Ile Ala Asn Leu Gly Asn Ile Ala Gly Lys Asn Phe Arg Val Phe Trp
225                 230                 235                 240
Asp Asn Ala Tyr Ala Ile His Asp Leu Ser Asp Asn Pro Val Ala Leu
                245                 250                 255
Ala Asn Ile Phe Glu Ala Cys Lys Ala Ala Gly Thr Glu Asp Ser Val
            260                 265                 270
Ile Gln Phe Ala Ser Thr Ser Lys Val Thr His Ala Gly Ser Gly Val
            275                 280                 285
Ala Phe Ile Ala Ala Ser Asp Thr Asn Leu Lys Phe Phe Lys Leu Ala
            290                 295                 300
Leu Gly Phe Met Thr Ile Gly Pro Asp Lys Val Asn Gln Leu Arg His
305                 310                 315                 320
Ala Lys Phe Phe Ala Asp Gly Ala Leu Ser Ala His Met Ala Lys
                325                 330                 335
His Ala Ala Ile Ile Lys Pro Arg Phe Ala Ser Val Leu Lys His Leu
            340                 345                 350
Glu Ala Ala Phe Ser Asp Asn Asp Leu Gly Glu Trp Glu Ser Ala Asp
            355                 360                 365
Gly Gly Tyr Phe Ile Ser Phe Asp Thr Arg Pro Gly Leu Ala Gln Lys
            370                 375                 380
Val Val Lys Leu Ala Gly Asp Ala Gly Val Lys Leu Thr Pro Ala Gly
385                 390                 395                 400
Ala Thr Phe Pro Tyr Gly Lys Asp Pro Gln Asp Ser Asn Ile Arg Ile
                405                 410                 415
Ala Pro Thr Val Pro Thr Val Asp Gln Val Glu Glu Ala Met Gln Val
            420                 425                 430
Phe Val Leu Cys Val Lys Leu Ala Ser Val Glu Gln Ala Leu Ala Asn
            435                 440                 445
```

```
Ser Leu Glu
    450

<210> SEQ ID NO 112
<211> LENGTH: 11
<212> TYPE: PRT
<213> ORGANISM: Corynebacterium ammoniagenes
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 112

Met Ser Xaa Ile Ala Gln Xaa Ile Leu Asp Gln
1               5                   10
```

METHOD FOR PRODUCING MONATIN USING AN L-AMINO ACID AMINOTRANSFERASE

CROSS-REFERENCE TO RELATED APPLICATIONS

This application claims the benefit of priority from U.S. provisional Patent Application No. 61/477,402, filed on Apr. 20, 2011, the entire contents of which are incorporated herein by reference.

TECHNICAL FIELD

The present invention relates to a method for producing Monatin using an L-amino acid aminotransferase, and the like.

BACKGROUND ART

Monatin [4-(indole-3-yl-methyl)-4-hydroxy-glutamic acid] is a compound that is one of amino acids contained in roots of Schlerochitom ilicifolius that is a shrub in South Africa and is particularly expected as a low calorie sweetener because of having sweetness one thousand and several hundreds times sweeter than sucrose (see Patent Document 1). The Monatin has asymmetric carbon atoms at positions 2 and 4, and a naturally occurring stereoisomer of Monatin is a 2S,4S-isomer. Naturally non-occurring three stereoisomers have been synthesized by organic chemistry processes. All of these stereoisomers are excellent in sweetness, and expected to be used as the sweeteners.

Several methods have been reported as the methods for producing the Monatin (e.g., see Patent Document 2). However, all of the reported methods require a step of multiple stages, and thus, it is required to improve a synthetic yield of the Monatin.

Specifically, for the method for producing the Monatin, the following method for producing 2R,4R-Monatin by synthesizing indole-3-pyruvate (hereinafter referred to as "IPA" as needed) from L-tryptophan (L-Trp), synthesizing 4R form of 4-(indole-3-yl-methyl)-4-hydroxy-2-oxoglutaric acid (hereinafter referred to as "4R-IHOG" as needed) from the resulting IPA and pyruvate, and subsequently subjecting the obtained 4R-IHOG to an oximation reaction, a reduction reaction and an epimerization-crystallization method has been known (conventional method (1)) (see Patent Document 2).

However, an aldolase step (second step) is an equilibrium reaction, and thus, a satisfactory yield is not always obtained in this reaction.

Conventional method (1) for producing 2R,4R-Monatin

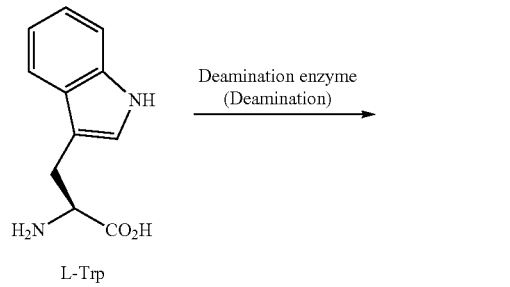

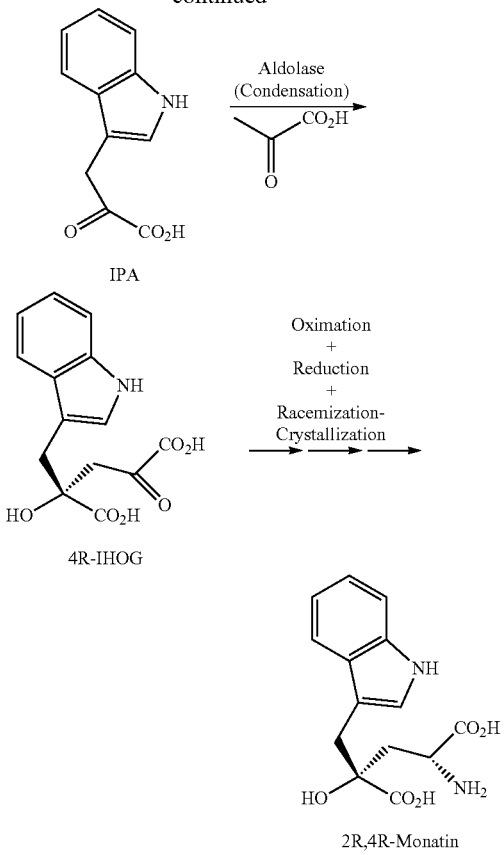

In order to improve the yield of the 2R,4R-Monatin, the method for producing the 2R,4R-Monatin by a one-pot enzymatic reaction has been invented (conventional method (2)) (see Patent Documents 3 to 6).

Patent Document 1: JP Sho-64-25757-A
Patent Document 2: International Publication WO2003/059865
Patent Document 3: International Publication WO2007/133184
Patent Document 4: International Publication WO2005/042756
Patent Document 5: US Patent Application Publication No. 2006/0252135 Specification
Patent Document 6: US Patent Application Publication No. 2008/020434 Specification

SUMMARY OF INVENTION

Problem to be Solved by the Invention

The object of the present invention is to provide a method for producing Monatin with a good yield.

Means for Solving Problem

As a result of an extensive study, the present inventors have found that the above problem can be solved by using an L-amino acid aminotransferase, and completed the present invention. No L-amino acid aminotransferase that acts upon 4R-IHOG has been known so far.

Accordingly, the present invention is as follows.

[1] A method for producing 2S,4R-Monatin or a salt thereof, comprising contacting 4R-IHOG with an L-amino acid aminotransferase in the presence of an L-amino acid to form the 2S,4R-Monatin.

[2] The production method of [1], further comprising contacting a keto acid with a decarboxylase to degrade the keto acid, wherein the keto acid is formed from the L-amino acid due to action of the L-amino acid aminotransferase.

[3] The production method of [1], wherein the L-amino acid is L-aspartate.

[4] The production method of [3], further comprising contacting oxaloacetate with an oxaloacetate decarboxylase to irreversibly form pyruvate, wherein the oxaloacetate is formed from the L-aspartate by action of the L-amino acid aminotransferase.

[5] The production method of [1], wherein the L-amino acid aminotransferase is derived from a microorganism belonging to genus *Arthrobacter*, genus *Bacillus*, genus *Candida*, genus *Corynebacterium*, genus *Lodderomyces*, genus *Micrococcus*, genus *Microbacterium*, genus *Nocardia*, genus *Pseudomonas*, genus *Rhizobium*, genus *Stenotrophomonas*, genus *Dietzia*, genus *Ochrobactrum*, genus *Brevundimonas*, genus *Burkholderia*, genus *Carnimonas*, genus *Yarrowia*, genus *Clostridium*, genus *Deinococcus*, genus *Eubacterium*, genus *Lactobacillus*, genus *Methanothermobacter*, genus *Phormidium*, genus *Pyrococcus*, genus *Rhodococcus*, genus *Saccharomyces*, genus *Saccharophagus*, genus *Sinorhizobium*, genus *Thermoanaerobacter*, genus *Thermotoga* or genus *Thermus*.

[6] The production method of [5], wherein the L-amino acid aminotransferase is derived from a microorganism belonging to *Arthrobacter* sp., *Bacillus altitudinis*, *Bacillus cellulosilyticus*, *Bacillus pumilus*, *Bacillus* sp., *Candida norvegensis*, *Candida inconspicua*, *Corynebacterium ammoniagenes*, *Corynebacterium glutamicum*, *Lodderomyces elongisporus*, *Micrococcus luteus*, *Microbacterium* sp., *Nocardia globerula*, *Pseudomonas chlororaphis*, *Pseudomonas citronocllolis*, *Pseudomonas fragi*, *Pseudomonas putida*, *Pseudomonas synxantha*, *Pseudomonas taetrolens*, *Pseudomonas* sp., *Rhizobium radiobacter*, *Rhizobium* sp., *Stenotrophomonas* sp., *Dietzia maris*, *Ochrobactrum pseudogrignonense*, *Brevundimonas diminuta*, *Burkholderia* sp., *Carnimonas* sp., *Yarrowia lypolytica*, *Clostridium cellulolyticum*, *Deinococcus geothermalis*, *Eubacterium rectale*, *Lactobacillus acidophilus*, *Methanothermobacter thermautotrophicus*, *Phormidium lapideum*, *Pyrococcus horikoshii*, *Rhodococcus erythropolis*, *Saccharomyces cerevisiae*, *Saccharophagus degradans*, *Sinorhizobium meliloti*, *Thermoanaerobacter tengcongensis*, *Thermotoga maritime*, or *Thermus thermophilus*.

[7] The production method of [1], wherein the L-amino acid aminotransferase consists of an amino acid sequence showing 90% or more identity to the amino acid sequence represented by SEQ ID NO:2, SEQ ID NO:48, SEQ ID NO:53, SEQ ID NO:61, SEQ ID NO:65, SEQ ID NO:67, SEQ ID NO:69, SEQ ID NO:73, SEQ ID NO:75, SEQ ID NO:77, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, or SEQ ID NO:111.

[8] The production method of [7], wherein the L-amino acid aminotransferase comprises one or more mutations of amino acid residues selected from the group consisting of the amino acid residues at position 39, position 109, position 128, position 150, position 258, position 287, position 288, position 289, position 303, position 358 and position 431 in the amino acid sequence represented by SEQ ID NO:2.

[9] The production method of [8], wherein the one or more mutations of amino acid residues are selected from the group consisting of:
i) substitution of the lysine at position 39 with an arginine;
ii) substitution of the serine at position 258 with a glycine;
iii) substitution of the glutamine at position 287 with a glutamic acid;
iv) substitution of the threonine at position 288 with a glycine;
v) substitution of the isoleucine at position 289 with an alanine;
vi) substitution of the aspartic acid at position 109 with a glycine;
vii) substitution of the histidine at position 150 with a tyrosine;
viii) substitution of the phenylalanine at position 303 with a leucine;
ix) substitution of the aspartic acid at position 358 with a tyrosine;
x) substitution of the serine at position 431 with a threonine; and
xi) substitution of the glutamic acid at position 128 with a glycine.

[10] The production method of [1], wherein the 4R-IHOG is contacted with the L-amino acid aminotransferase using a transformant that expresses the L-amino acid aminotransferase.

[11] The production method of [1], further comprising condensing indole-3-pyruvate and pyruvate to form the 4R-IHOG.

[12] The production method of [11], the indole-3-pyruvate and the pyruvate are condensed by contacting the indole-3-pyruvate and the pyruvate with an aldolase.

[13] The production method of [11], wherein at least part of the pyruvate used in the formation of the 4R-IHOG is from pyruvate formed from the oxaloacetate due to action of the oxaloacetate decarboxylase.

[14] The production method of [11], further comprising deaminating a tryptophan to form the indole-3-pyruvate.

[15] The production method of [14], wherein the tryptophan is deaminated by contacting the tryptophan with a deamination enzyme.

[16] The production method of [11] or [14], wherein the production of the 2S,4R-Monatin or the salt thereof is carried out in one reactor.

[17] A method for producing 2R,4R-Monatin or a salt thereof, comprising the following (I) and (II):
(I) performing the method of [1] to form the 2S,4R-Monatin; and
(II) isomerizing the 2S,4R-Monatin to form the 2R,4R-Monatin.

[18] The production method of [17], wherein the 2S,4R-Monatin is isomerized in the presence of an aromatic aldehyde.

[19] The production method of [17], wherein the salt is a sodium salt or a potassium salt.

[20] An L-amino acid aminotransferase that is a protein selected form the group consisting of the following (A)-(D):
(A) a protein consisting of the amino acid sequence represented by SEQ ID NO:2, SEQ ID NO:48, SEQ ID NO:53, or SEQ ID NO:61;
(B) a protein comprising the amino acid sequence represented by SEW ID NO:2, SEQ ID NO:48, SEQ ID NO:53, or SEQ ID NO:61;
(C) a protein consisting of an amino acid sequence showing 90% or more identity to the amino acid sequence represented by SEQ ID NO:2, SEQ ID NO:48, SEQ ID NO:53, or SEQ ID NO:61, and having an L-amino acid aminotransferase activity; and
(D) a protein consisting of an amino acid sequence comprising mutation of one or several amino acid residues, which is selected from the group consisting of deletion, substitution, addition and insertion of the amino acid residues in the amino acid sequence represented by SEQ ID NO:2, SEQ ID NO:48, SEQ ID NO:53, or SEQ ID NO:61, and having an L-amino acid aminotransferase activity.
[21] The L-amino acid aminotransferase of [20], wherein the L-amino acid aminotransferase comprises one or more mutations of amino acid residues selected from the group consisting of the amino acid residues at position 39, position 109, position 128, position 150, position 258, position 287, position 288 and position 289, position 303, position 358 and position 431 in the amino acid sequence represented by SEQ ID NO:2.
[22] The L-amino acid aminotransferase of [21], wherein the one or more mutations of amino acid residues are selected from the group consisting of:
i) substitution of the lysine at position 39 with an arginine;
ii) substitution of the serine at position 258 with a glycine;
iii) substitution of the glutamine at position 287 with a glutamic acid;
iv) substitution of the threonine at position 288 with a glycine;
v) substitution of the isoleucine at position 289 with an alanine;
vi) substitution of the aspartic acid at position 109 with a glycine;
vii) substitution of the histidine at position 150 with a tyrosine;
viii) substitution of the phenylalanine at position 303 with a leucine;
ix) substitution of the aspartic acid at position 358 with a tyrosine;
x) substitution of the serine at position 431 with a threonine; and
xi) substitution of the glutamic acid at position 128 with a glycine.
[23] A polynucleotide selected from the group consisting of the following (a)-(e):
(a) a polynucleotide consisting of the nucleotide sequence represented by SEQ ID NO:1, SEQ ID NO:47, SEQ ID NO:52, or SEQ ID NO:60;
(b) a polynucleotide comprising the nucleotide sequence represented by SEQ ID NO:1, SEQ ID NO:47, SEQ ID NO:52, or SEQ ID NO:60;
(c) a polynucleotide consisting of a nucleotide sequence showing 90% or more identity to the amino acid sequence represented by SEQ ID NO:1, SEQ ID NO:47, SEQ ID NO:52, or SEQ ID NO:60, and encoding a protein having an L-amino acid aminotransferase activity;
(d) a polynucleotide that hybridizes under a stringent condition with a polynucleotide consisting of the nucleotide sequence complementary to the nucleotide sequence represented by SEQ ID NO:1, SEQ ID NO:47, SEQ ID NO:52, or SEQ ID NO:60, and encodes a protein having an L-amino acid aminotransferase activity; and
(e) a polynucleotide encoding the L-amino acid aminotransferase of [20].
[24] An expression vector comprising the polynucleotide of [23].
[25] A transformant introduced with the expression vector of [24].

[26] A method for producing an L-aminotransfearase, comprising culturing the transformant of [25] in a medium to obtain the L-amino acid aminotransferase.
[27] A method of producing 2S,4R-Monatin or a salt thereof, comprising contacting 4R-IHOG with the L-amino acid aminotransferase of [20] in the presence of an L-amino acid to form the 2S,4R-Monatin.
[28] A method for producing 2R,4R-Monatin or a salt thereof, comprising the following (I') and (II'):
(I') performing the method of [27] to form the 2S,4R-Monatin; and
(II') isomerizing the 2S,4R-Monatin to form the 2R,4R-Monatin.
[29] The production method of [28], wherein the 2S,4R-Monatin is isomerized in the presence of an aromatic aldehyde.
[30] The production method of [28], wherein the salt is a sodium salt or a potassium salt.

Effect of the Invention

The method of the present invention can contribute to improvement of the yield of the Monatin by producing the 2S,4R-Monatin with a good yield from 4R-IHOG using the L-amino acid aminotransferase. The method of the present invention has an advantage that it is not necessary to use an expensive D-amino acid (D-Asp and the like) as a substrate when the 2S,4R-Monatin is formed from IHOG or that it is not necessary to add an enzyme such as racemase to form the D-amino acid from an L-amino acid. In the method of the present invention, when performing not only the reaction to form the 2S,4R-Monatin from 4R-IHOG (third step) but also the reaction to form IPA from L-Trp (first step) and the reaction to form 4R-IHOG from IPA (second step), whole reaction equilibrium can be defined in the third step and the reaction equilibrium in the second step can be largely shifted to a direction to form 4R-IHOG. In this case, the method of the present invention makes it possible to produce the 2S,4R-Monatin with a very good yield by avoiding a by-product of L-Trp (progress of a reverse reaction of the first step).

BEST MODES FOR CARRYING OUT THE INVENTION

Figure 1:
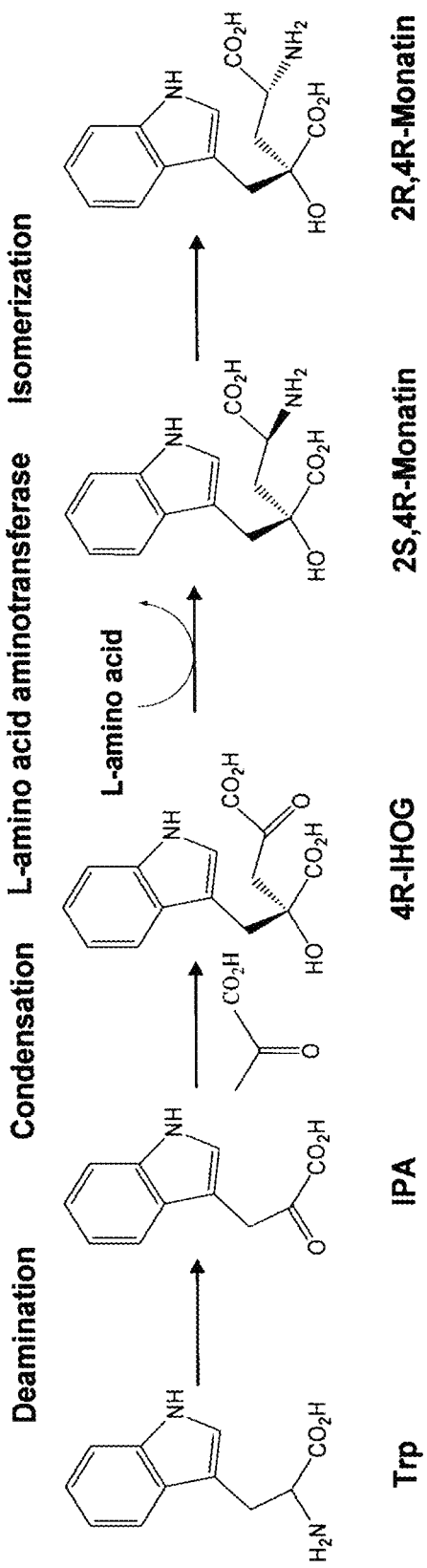
FIG. 1 is a view showing one example of the production method of the present invention. Trp: tryptophan; IPA: indole-3-pyruvate; IHOG: 4-(indole-3-yl-methyl)-4-hydroxy-2-oxoglutaric acid; Monatin: 4-(indole-3-yl-methyl)-4-hydroxy-glutamic acid.
Figure 2:
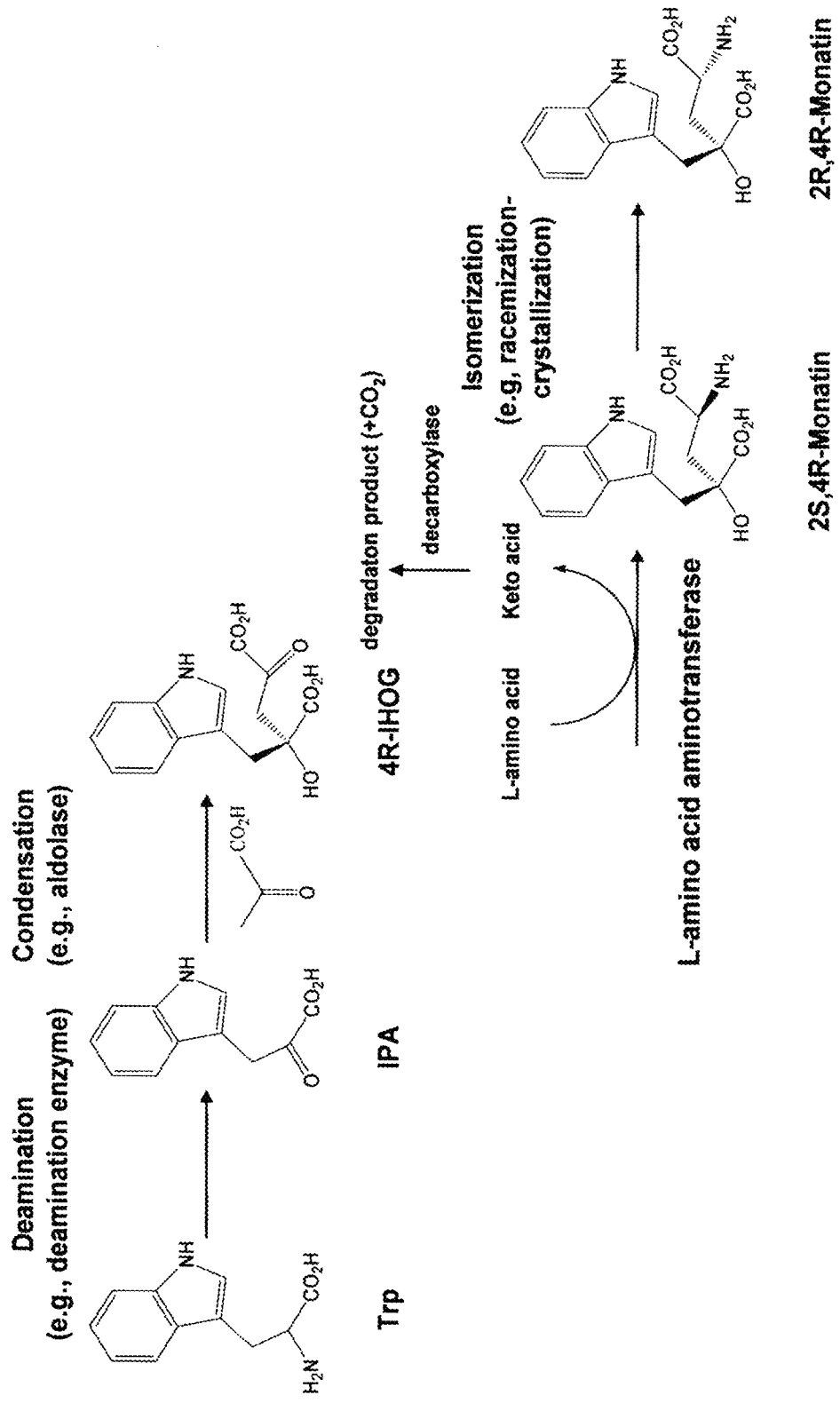
FIG. 2 is a view showing one example of the production method of the present invention. Abbreviations are the same as in FIG. 1.
Figure 3:
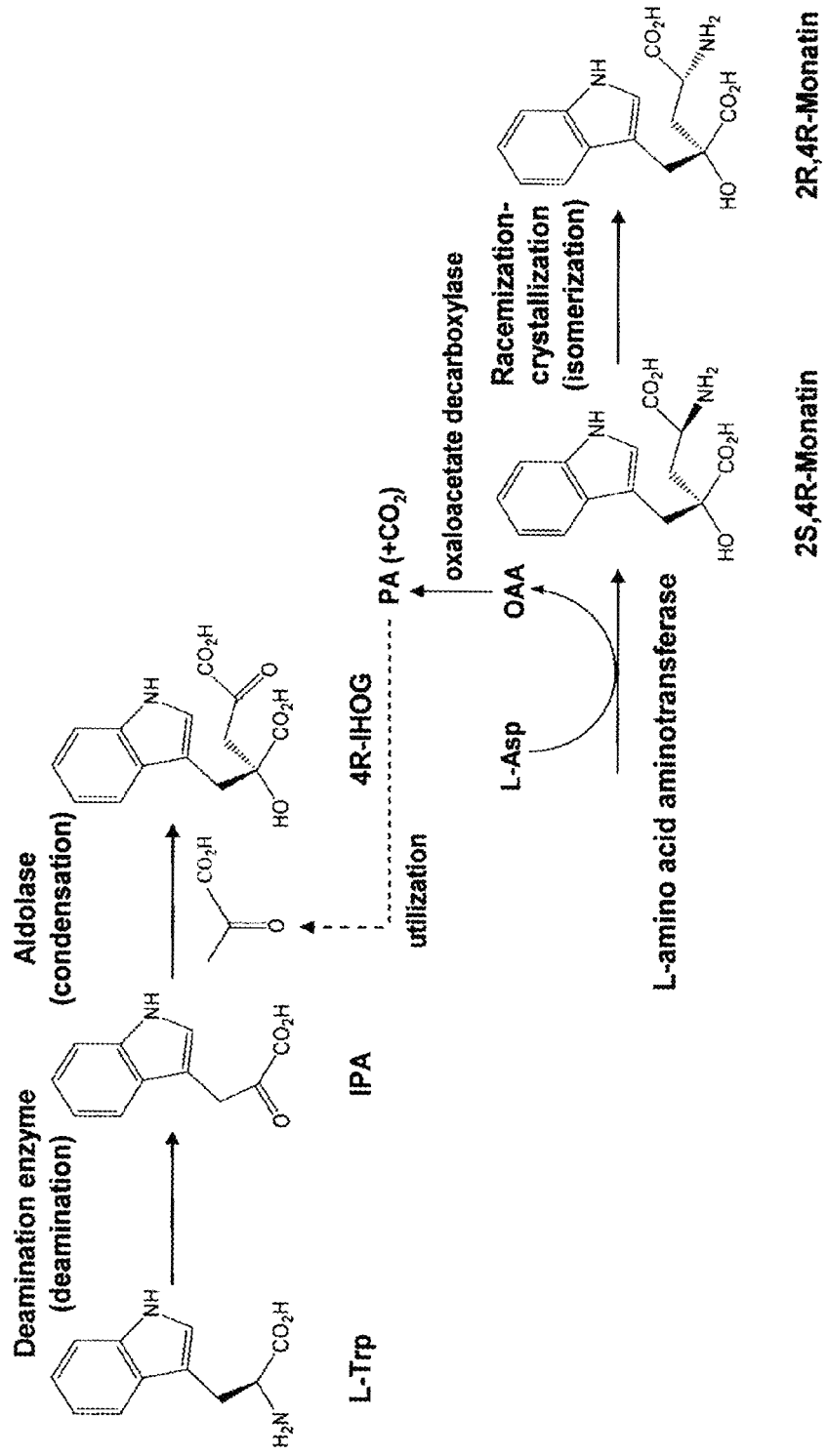
FIG. 3 is a view showing a preferable example of the production method of the present invention. L-Trp: L-tryptophan; L-Asp: L-aspartic acid; OAA: oxaloacetate; PA: pyruvate; and the other abbreviations are the same as in FIG. 1.

(1) Method for Producing 2S,4R-Monatin or a Salt Thereof

The present invention provides a method (1) for producing 2S,4R-Monatin or a salt thereof. The production method of the present invention can be classified into (1-1) a method for producing the 2S,4R-Monatin from 4R-IHOG, (1-2) a method for producing the 2S,4R-Monatin from IPA and pyruvate, and (1-3) a method for producing the 2S,4R-Monatin from tryptophan. The methods (1-1), (1-2) and (1-3) are common in contacting 4R-IHOG with an L-amino acid aminotransferase in the presence of the L-amino acid to form the 2S,4R-Monatin.

(1-1) Method for Producing 2S,4R-Monatin from 4R-IHOG

This method comprises contacting 4R-IHOG with the L-amino acid aminotransferase in the presence of the L-amino acid to form the 2S,4R-Monatin (reaction 1). By contacting 4R-IHOG with the L-amino acid aminotransferase in the presence of the L-amino acid, an amino group in the L-amino acid can be transferred to 4R-IHOG to form the 2S,4R-Monatin.

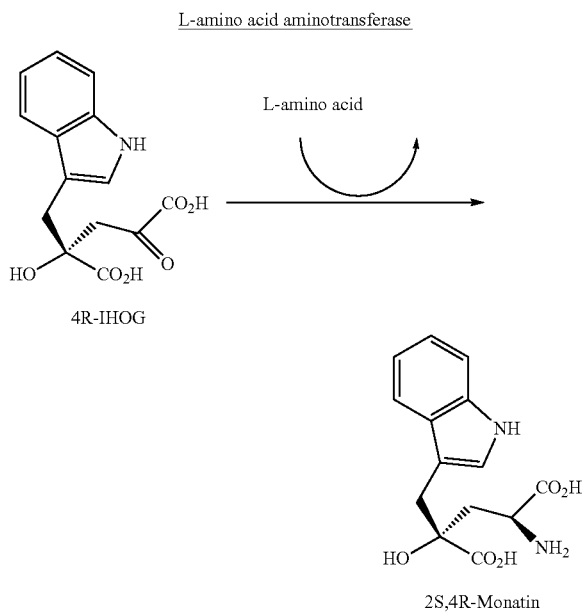

The kinds of the L-amino acid is not particularly limited as long as the amino group in the L-amino acid can be transferred to 4R-IHOG that is an objective substrate by the L-amino acid aminotransferase. Various L-amino acids such as L-α-amino acids are known as such an L-amino acid. Specifically, such an L-amino acid includes L-aspartic acid, L-alanine, L-lysine, L-arginine, L-histidine, L-glutamic acid, L-asparagine, L-glutamine, L-serine, L-threonine, L-tyrosine, L-cysteine, L-valine, L-leucine, L-isoleucine, L-proline, L-phenylalanine, L-methionine and L-tryptophan. A solt form of the L-amino acid may be added to a reaction solution.

The concentration of the L-amino acid in a reaction solution is, for example, 1 mM to 3 M, preferably 20 mM to 1 M, more preferably 100 mM to 500 mM.

In one embodiment, the L-amino acid aminotransferase may be a protein derived from a microorganism such as a bacterium, actinomycete or yeast. The classification of the microorganisms can be carried out by a classification method well-known in the art, e.g., a classification method used in the database of NCBI (National Center for Biotechnology Information). Examples of the microorganisms from which the L-amino acid aminotransferase is derived include microorganisms belonging to genus *Arthrobacter*, genus *Bacillus*, genus *Candida*, genus *Corynebacterium*, genus *Lodderomyces*, genus *Micrococcus*, genus *Microbacterium*, genus *Nocardia*, genus *Pseudomonas*, genus *Rhizobium*, genus *Stenotrophomonas*, genus *Dietzia*, genus *Ochrobactrum*, genus *Brevundimonas*, genus *Burkholderia*, genus *Carnimonas*, genus *Yarrowia*, genus *Clostridium*, genus *Deinococcus*, genus *Eubacterium*, genus *Lactobacillus*, genus *Methanococcus*, genus *Methanothermobacter*, genus *Phormidium*, genus *Pyrococcus*, genus *Rhodococcus*, genus *Saccharomyces*, genus *Saccharophagus*, genus *Sinorhizobium*, genus *Thermoanaerobacter*, genus *Thermotoga*, and genus *Thermus*.

Specifically, examples of the microorganisms belonging to genus *Arthrobacter* include *Arthrobacter* sp.

Examples of the microorganisms belonging to genus *Bacillus* include *Bacillus altitudinis*, *Bacillus cellulosilyticus*, *Bacillus pumilus*, and *Bacillus* sp. Examples of the microorganisms belonging to genus *Candida* include *Candida norvegensis* and *Candida inconspicua*. Examples of the microorganisms belonging to genus *Corynebacterium* include *Corynebacterium ammoniagenes*, and *Corynebacterium glutamicum*. Examples of the microorganisms belonging to genus *Lodderomyces* include *Lodderomyces elongisporus*. Examples of the microorganisms belonging to genus *Micrococcus* include *Micrococcus luteus*. Examples of the microorganisms belonging to genus *Microbacterium* include *Microbacterium* sp. Examples of the microorganisms belonging to genus *Nocardia* include *Nocardia globerula*.

Examples of the microorganisms belonging to genus *Pseudomonas* include *Pseudomonas chlororaphis* (e.g., *Pseudomonas chlororaphis* subsp. *chlororaphis*), *Pseudomonas citronocllolis*, *Pseudomonas fragi*, *Pseudomonas putida*, *Pseudomonas synxantha*, *Pseudomonas taetrolens*, and *Pseudomonas* sp.

Examples of the microorganisms belonging to genus *Rhizobium* include *Rhizobium* radiobacter and *Rhizobium* sp. Examples of the microorganisms belonging to genus *Stenotrophomonas* include *Stenotrophomonas* sp. Examples of the microorganisms belonging to genus *Dietzia* include *Dietzia maris*. Examples of the microorganisms belonging to genus *Ochrobactrum* include *Ochrobactrum pseudogrignonense*. Examples of the microorganisms belonging to genus *Brevundimonas* include *Brevundimonas diminuta*. Examples of the microorganisms belonging to genus *Burkholderia* include *Burkholderia* sp. Examples of the microorganisms belonging to genus *Carnimonas* include *Carnimonas* sp. Examples of the microorganisms belonging to genus *Yarrowia* include *Yarrowia lypolytica*.

Examples of the microorganisms belonging to genus *Clostridium* include *Clostridium cellulolyticum*. Examples of the microorganisms belonging to genus *Deinococcus* include *Deinococcus geothermalis*. Examples of the microorganisms belonging to genus *Eubacterium* include *Eubacterium rectale*. Examples of the microorganisms belonging to genus *Lactobacillus* include *Lactobacillus acidophilus*. Examples of the microorganisms belonging to genus *Methanococcus* include *Methanococcus jannaschii*. Examples of the microorganisms belonging to genus *Methanothermobacter* include *Methanothermobacter thermautotrophicus*. Examples of the microorganisms belonging to genus *Phormidium* include *Phormidium lapideum*. Examples of the microorganisms belonging to genus *Pyrococcus* include *Pyrococcus horikoshii*. Examples of the microorganisms belonging to genus *Rhodococcus* include *Rhodococcus erythropolis*. Examples of the microorganisms belonging to genus *Saccharomyces* include *Saccharomyces cerevisiae*. Examples of the microorganisms belonging to genus *Saccharophagus* include *Saccharophagus degradans*.

Examples of the microorganisms belonging to genus *Sinorhizobium* include *Sinorhizobium meliloti*. Examples of the microorganisms belonging to genus *Thermoanaerobacter* include *Thermoanaerobacter tengcongensis*. Examples of the microorganisms belonging to genus *Thermotoga* include *Thermotoga maritima*. Examples of the microorganisms belonging to genus *Thermus* include *Thermus thermophilus*.

In another embodiment, the L-amino acid aminotransferase may be a naturally occurring protein or an artificial mutant protein. Such an L-amino acid aminotransferase includes those consisting of an amino acid sequence having high homology (e.g., similarity, identity) to an amino acid sequence represented by SEQ ID NO:2, SEQ ID NO:48, SEQ ID NO:53, SEQ ID NO:61, SEQ ID NO:65, SEQ ID NO:67, SEQ ID NO:69, SEQ ID NO:73, SEQ ID NO:75, SEQ ID NO:77, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, or SEQ ID NO:111, and having an L-amino acid aminotransferase activity. The term "L-amino acid aminotransferase activity" refers to an activity of transferring the amino group in the L-amino acid to 4R-IHOG that is the objective substrate for forming the 2S,4R Monatin that is an objective compound having the amino group. Specifically, the L-amino acid aminotransferase includes a protein consisting of the amino acid sequence showing 80% or more, preferably 90% or more, more preferably 95% or more and particularly preferably 98% or more or 99% or more homology (e.g., similarity, identity) to the amino acid sequence represented by SEQ ID NO:2, and having the L-amino acid aminotransferase activity.

The homology of the amino acid sequences and nucleotide sequences can be determined using algorithm BLAST by Karlin and Altschul (Pro. Natl. Acad. Sci. USA, 90, 5873 (1993)) or FASTA by Pearson (Methods Enzymol., 183, 63 (1990)). Programs referred to as BLASTP and BLASTN have been developed based on this algorithm BLAST. Thus, the homology of the amino acid sequences and the nucleotide sequences may be calculated using these programs with default setting. A numerical value obtained when matching count is calculated as a percentage by using GENETYX Ver. 7.0.9 that is software from GENETYX Corporation and using full length polypeptide chains encoded in ORF with setting of Unit Size to Compare=2 may be used as the homology of the amino acid sequences. The lowest value among the values derived from these calculations may be employed as the homology of the amino acid sequences and the nucleotide sequences.

In further another embodiment, the L-amino acid aminotransferase may be a protein consisting of an amino acid sequence comprising mutation (e.g., deletion, substitution, addition and insertion) of one or several amino acid residues in the amino acid sequence represented by SEQ ID NO:2, SEQ ID NO:48, SEQ ID NO:53, SEQ ID NO:61, SEQ ID NO:65, SEQ ID NO:67, SEQ ID NO:69, SEQ ID NO:73, SEQ ID NO:75, SEQ ID NO:77, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, or SEQ ID NO:111, and having the L-amino acid aminotransferase activity. The mutation of one or several amino acid residues may be introduced into one region or multiple different regions in the amino acid sequence. The term "one or several amino acid residues" indicate a range in which a three dimensional structure and the activity of the protein are not largely impaired. The term "one or several amino acid residues" in the case of the protein denote, for example, 1 to 100, preferably 1 to 80, more preferably 1 to 50, 1 to 30, 1 to 20, 1 to 10 or 1 to 5 amino acid residues. Such mutation may be attributed to naturally occurring mutation (mutant or variant) based on individual difference, species difference and the like of the microorganism carrying a gene encoding the L-amino acid aminotransferase.

A position of the amino acid residue to be mutated in the amino acid sequence is apparent to those skilled in the art. Specifically, a person skilled in the art can recognize the correlation between the structure and the function by 1) comparing the amino acid sequences of the multiple proteins having the same kind of activity (e.g., the amino acid sequence represented by SEQ ID NO:2, and amino acid sequences of other L-amino acid aminotransferase), 2) clarifying relatively conserved regions and relatively non-conserved regions, and then 3) predicting a region capable of playing an important role for its function and a region incapable of playing the important role for its function from the relatively conserved regions and the relatively non-conserved regions, respectively. Therefore, a person skilled in the art can specify the position of the amino acid residue to be mutated in the amino acid sequence of the L-amino acid aminotransferase.

When an amino acid residue is mutated by the substitution, the substitution of the amino acid may be conservative substitution. As used herein, the term "conservative substitution" means that a certain amino acid residue is substituted with an amino acid residue having an analogous side chain. Families of the amino acid residues having the analogous side chain are well-known in the art. Examples of such families include an amino acid having a basic side chain (e.g., lysine, arginine or histidine), an amino acid having an acidic side chain (e.g., aspartic acid or glutamic acid), an amino acid having a non-charged polar side chain (e.g., asparagine, glutamine, serine, threonine, tyrosine or cysteine), an amino acid having a non-polar side chain (e.g., glycine, alanine, valine, leucine, isoleucine, proline, phenylalanine, methionine or tryptophan), an amino acid having a β-position branched side chain (e.g., threonine, valine or isoleucine), an amino acid having an aromatic side chain (e.g., tyrosine, phenylalanine, tryptophan or histidine), an amino acid having a hydroxyl group (e.g., alcoholic or phenolic)-containing side chain (e.g., serine, threonine or tyrosine), and an amino acid having a sulfur-containing side chain (e.g., cysteine or methionine). Preferably, the conservative substitution of the amino acids may be the substitution between aspartic acid and glutamic acid, the substitution among arginine, lysine and histidine, the substitution between tryptophan and phenylalanine, the substitution between phenylalanine and valine, the substitution among leucine, isoleucine and alanine, and the substitution between glycine and alanine.

In further another embodiment, the L-amino acid aminotransferase may be a protein encoded by DNA that hybridizes under a stringent condition with a nucleotide sequence complementary to a nucleotide sequence represented by SEQ ID NO:2, SEQ ID NO:47, SEQ ID NO:52, SEQ ID NO:60, SEQ ID NO:64, SEQ ID NO:66, SEQ ID NO:68, SEQ ID NO:72, SEQ ID NO:74, SEQ ID NO:76, SEQ ID NO:83, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, or SEQ ID NO:110, and having the L-amino acid aminotransferase activity. The "stringent condition" refers to the condition where a so-called specific hybrid is formed whereas no non-specific hybrid is formed. Although it is difficult to clearly quantify this condition, one example of this condition is the condition where a pair of polynucleotides with high homology (e.g., identity), for example, a pair of polynucleotides having the homology of 80% or more, preferably 90% or more, more preferably 95% or more, and particularly preferably 90% or more are hybridized whereas a pair of polynucleotides with lower homology than that are not hybridized. Specifically, such a condition includes hybridization in 6×SSC (sodium chloride/sodium citrate) at about 45° C. followed by one or two or more washings in 0.2×SSC and 0.1% SDS at 50 to 65° C.

In a preferred embodiment, the L-amino acid aminotransferase may be L-amino acid aminotransferase mutant in which one or more (e.g., one or two) of any amino acid residues selected from the group consisting of the amino acid residues at position 39, position 109, position 128, position 150, position 258, position 287, position 288, position 289, position 303, position 358, and position 431 in the amino acid sequence represented by SEQ ID NO:2 are mutated (e.g., substituted). Preferred examples of the L-amino acid aminotransferase mutant comprise one or more (e.g., one or two) substitutions selected from the group consisting of:
i) substitution of the lysine at position 39 with an arginine;
ii) substitution of the serine at position 258 with a glycine;
iii) substitution of the glutamine at position 287 with a glutamic acid;
iv) substitution of the threonine at position 288 with a glycine;
v) substitution of the isoleucine at position 289 with an alanine;
vi) substitution of the aspartic acid at position 109 with a glycine; vii) substitution of the histidine at position 150 with a tyrosine;
viii) substitution of the phenylalanine at position 303 with a leucine;
ix) substitution of the aspartic acid at position 358 with a tyrosine;
x) substitution of the serine at position 431 with a threonine; and
xi) substitution of the glutamic acid at position 128 with a glycine.

For the combination of the substitution of one or more (e.g., one or two) of any amino acid residues selected from the group consisting of the amino acid residues at position 39, position 109, position 128, position 150, position 258, position 287, position 288, position 289, position 303, position 358 and position 431 in the amino acid sequence represented by SEQ ID NO:2, the combined mutations as shown below can be introduced although the combination of the amino acid substitutions which can be utilized in the present invention is not limited to the following:
a) T288G
b) S258G/I289A
c) K39R/T288G
d) Q287E/T288G
e) K39R/D109R/T288G/S431T
f) K39R/D109R/T288G/F303L
g) D109R/Q287E/T288G/F303L
h) D109R/S258G/I289A/F303L
i) D109R/Q287E/T288G/S431T
j) D109R/S258G/I289A/S431T
k) K39R/D109R/E128G/T288G/F303L
l) K39R/D109G/E128G/T288G/F303L
m) D109R/E128G/Q287E/T288G/F303L
n) D109R/E128G/S258G/I289A/S431T
o) D109G/E128G/Q287E/T288G/F303L
p) D109G/E128G/S258G/I289A/F303L
q) K39R/D109G/H150Y/T288G/F303L/D358Y/S431T
r) K39R/D109G/E128G/H150Y/T288G/F303L/D358Y
s) D109G/H150Y/Q287E/T288G/F303L/D358Y/S431T
t) D109G/H150Y/S258G/I289A/F303L/D358Y/S431T
u) D109G/E128G/H150Y/Q287E/T288G/F303L/D358Y or
v) D109G/E128G/H150Y/S258G/I289A/F303L/D358Y In one embodiment, the contact of 4R-IHOG with the L-amino acid aminotransferase can be accomplished by allowing 4R-IHOG and the L-amino acid aminotransferase extracted from an L-amino acid aminotransferase-producing microorganism (extracted enzyme) to coexist in a reaction solution. Examples of the L-amino acid aminotransferase-producing microorganism include the microorganisms that naturally produce the L-amino acid aminotransferase (e.g., the aforementioned microorganisms), and transformants that express the L-amino acid aminotransferase. Specifically, examples of the extracted enzyme include a purified enzyme, a crude enzyme, an immobilized enzyme, a cuture broth, and a treated product of the culture broth (e.g., an L-amino acid aminotransferase-containing fraction prepared from the above enzyme-producing microorganism, and a disrupted product of and a lysate of the above enzyme-producing microorganism). Examples of the treatment for obtaining the treated product of the culture broth from the culture broth include a heat treatment (42° C. to 80° C., pH 3 to 12, 1 minute to 24 hours), a solvent treatment (e.g., xylene, toluene, ethanol, isopropylalcohol), a surfactant (e.g., Tween 20, Triton X-100), and a treatment with a bacteriolytic enzyme (e.g., lysozyme treatment). Alternatively, the culture broth is subjected to a reaction after retaining it with adjusting temperature, pH and the like to enhance an enzymatic activity detected in the broth. In this case, the temperature may be set at 4° C. to 60° C., preferably 20° C. to 37° C. In addition, the pH may be set at 3 to 12, preferably 7 to 9. The time may be set for about 5 minutes to 20 days, preferably about 1 hour to 7 days. During retaining the broth, aeration and agitation may be or may not be carried out.

In another embodiment, the contact of 4R-IHOG with the L-amino acid aminotransferase can be accomplished by allowing 4R-IHOG and the L-amino acid aminotransferase-producing microorganism to coexist in the reaction solution (e.g., culture medium).

The reaction solution used in the production method (1) of the present invention is not particularly limited as long as the objective reaction progresses, and for example, water and buffer are used. Examples of the reaction solution include Tris buffer, phosphate buffer (e.g., $KH_2PO_4$), carbonate buffer, borate buffer and acetate buffer. The concentration of the buffer may be, for example, 0.1 mM to 10 M, preferably 1 mM to 1 M. When the L-amino acid aminotransferase-producing microorganism is used in the production method of the present invention, the culture medium may be used as the reaction solution. Such a culture medium can be prepared using a medium described later. The reaction solution used in the production method of the present invention may further comprise pyridoxal phosphate (PLP) as a coenzyme. A salt form of PLP may be added to the reaction solution. The concentration of PLP in the reaction solution may be, for example, 1 µM to 100 mM, preferably 10 µM to 1 mM. When the reaction solution comprises PLP, an effect to form 2R,4R-Monatin from the 2S,4R-Monatin can be expected by an isomerization reaction which can be catalyzed by PLP (e.g., see Example 11).

A pH value of the reaction solution used in the production method (1) of the present invention is not particularly limited as long as the objective reaction progresses, and is, for example, pH 5 to 10, is preferably pH 6 to 9 and is more preferably pH 7 to 8.

A reaction temperature in the production method (1) of the present invention is not particularly limited as long as the objective reaction progresses, and is, for example, 10 to 50° C., is preferably 20 to 40° C. and is more preferably 25 to 35° C.

A reaction time period in the production method (1) of the present invention is not particularly limited as long as the time period is sufficient to form the 2S,4R-Monatin, and is, for example, 2 to 100 hours, is preferably 4 to 50 hours and is more preferably 8 to 25 hours.

When a transformant that expresses the L-amino acid aminotransferase is used as the L-amino acid aminotransferase-producing microorganism, this transformant can be made by, for example, making an expression vector of the L-amino acid aminotransferase, and then introducing this expression vector into a host. For example, the transformant that expresses the L-amino acid aminotransferase can be obtained by making the expression vector incorporating DNA having the nucleotide sequence represented by SEQ ID NO:1, and introducing it into an appropriate host. For example, various prokaryotic cells including bacteria belonging to genus *Escherichia* such as *Escherichia coli*, genus *Corynebacterium* (e.g., *Corynebacterium glutamicum*) and genes *Bacillus* (e.g., *Bacillus subtilis*), and various eukaryotic cells including genus *Saccharomyces* (e.g., *Saccharomyces cerevisiae*), genus *Pichia* (e.g., *Pichia stipitis*) and genus *Aspergillus* (e.g., *Aspergillus oryzae*) can be used as the host for expressing the L-amino acid aminotransferase. For the host, a strain having deletion of a certain gene may be used. Examples of such a gene which may be deleted include AspC, an L-amino acid aminotransferase derived from a host, an aldolase derived from a host, a deamination enzyme derived from a host. Examples of the transformants include a transformant carrying a vector in its cytoplasm, and a transformant introduced with a gene of interest into its genome.

An L-amino acid aminotransferase-producing microorganism can be cultured using certain culture apparatus (e.g., a test tube, a flask, or a jar fermenter) in a medium having the composition mentioned below. The culture condition can be set appropriately. Specifically, the culture temperature may be 25° C. to 37° C., pH may be 6.5 to 7.5, the culture time may be 1 hour to 100 hours. The cultivation may be carried out with controlling the concentration of dissolved oxygen. In this case, the concentration of dissolved oxygen (DO value) in the culture solution may be utilized as an indicator of the controlling. The condition on aeration and agitation can be controlled such that relative concentration of dissolved oxygen (DO value) in the case of the concentration of oxygen in air being considered 21% is not less than 1% to 10%, preferably 3% to 8%. The cultivation may be batch cultivation or fed-batch cultivation. In the case of the fed-batch cultivation, a sugar source solution and a solution containing phosphate can be continuously or discontinuously added in a sequential manner to continue the cultivation.

The hosts to be transformed are as described above. Describing *Escherichia coli* in detail, the host can be selected from *Escherichia coli* K12 strain subspecies, *Escherichia coli* JM109, DH5α, HB101, BL21 (DE3) strains and the like. Methods for performing the transformation and methods for selecting the transformant are described in Molecular Cloning: A Laboratory Manual, 3rd edition, Cold Spring Harbor press (2001/01/15) and the like. A method for making transformed *Escherichia coli* and producing a certain enzyme by the use thereof will be specifically described below as one example.

As a promoter for expressing DNA encoding the L-amino acid aminotransferase, the promoter typically used for producing a heterogeneous protein in *E. coli* can be used, and includes potent promoters such as PhoA, PhoC, T7 promoter, lac promoter, trp promoter, trc promoter, tac promoter, PR and PL promoters of lambda phage, and T5 promoter. PhoA, PhoC and lac are preferred. As the vector, pUC (e.g., pUC19, pUC18), pSTV, pBR (e.g., pBR322), pHSG (e.g., pHSG299, pHSG298, pHSG399, pHSG398), RSF (e.g., RSF1010), pACYC (e.g., pACYC177, pACYC184), pMW (e.g., pMW119, pMW118, pMW219, pMW218), pQE (e.g., pQE30) and derivatives thereof, and the like may be used. The vectors of phage DNA may also be utilized as the other vectors. Further, the expression vector containing the promoter and capable of expressing the inserted DNA sequence may be used. Preferably, the vector may be pUC, pSTV or pMW.

A terminator that is a transcription termination sequence may be ligated to downstream of an L-amino acid aminotransferase gene. Examples of such a terminator include T7 terminator, fd phage terminator, T4 terminator, a terminator of a tetracycline resistant gene, and a terminator of an *E. coli* trpA gene.

So-called multiple copy types are preferable as the vector for introducing the L-amino acid aminotransferase gene into *E. coli*, and include plasmids having a replication origin derived from ColE1, such as pUC type plasmids, pBR322 type plasmids or derivatives thereof. Here, the "derivatives" means those in which modification is given to the plasmids by substitution, deletion, insertion, addition and/or inversion of nucleotides. The "modification" as referred to here also includes the modification by mutagenic treatments by mutagenic agents and UV irradiation, or natural mutation, or the like.

For selecting the transformant, it is preferable that the vector has a marker such as an ampicillin resistant gene. As such a plasmid, the expression vectors carrying the strong promoter are commercially available (e.g., pUC types (supplied from TAKARA BIO Inc.), pPROK types (supplied from Clontech), pKK233-2 (supplied from Clontech)).

The L-amino acid aminotransferase is expressed by transforming *E. coli* with the obtained expression vector and culturing this *E. coli*.

A medium such as M9-casamino acid medium and LB medium typically used for culturing *E. coli* may be used as the medium. The medium may contain a certain carbon source, a nitrogen source, and a coenzyme (e.g., pyridoxine hydrochloride). Specifically, peptone, yeast extract, NaCl, glucose, $MgSO_4$, ammonium sulfate, potassium dihydrogen phosphate, ferric sulfate, manganese sulfate, thiamine, hydrolysate of soy with hydrochloric acid, Disfoam GD113-K (NOF Corporation) and the like may be used. Culture conditions and production induction conditions are appropriately selected depending on types of the marker and the promoter in the used vector, the host bacterium and the like.

The following methods and the like are available for recovering the L-amino acid aminotransferase. The L-amino acid aminotransferase can be obtained as a disrupted product or a lysate by collecting the L-amino acid aminotransferase-producing microorganism followed by disrupting (e.g., sonication, homogenization) or lysing (e.g., lysozyme treatment) the microbial cells. Also, the purified enzyme, the crude enzyme, the L-amino acid aminotransferase-containing fraction, or the like can be obtained by subjecting such a disrupted product or lysate to techniques such as extraction, precipitation, filtration and column chromatography.

In a preferred embodiment, the production method of the present invention further comprises contacting a keto acid (R—COCOOH) formed from the L-amino acid (e.g., L-α-amino acid) by action of the L-amino acid aminotransferase with a decarboxylase to degrade the keto acid (see the reaction 1'). By promoting the degradation of the keto acid formed from the L-amino acid by an amino group transfer reaction, it is possible to shift the equilibrium of the reaction to form the 2S,4R-Monatin from 4R-IHOG so that the 2S,4R-Monatin is formed in a larger amount.
(Reaction 1')

the oxaloacetate, it is possible to shift the equilibrium of the reaction to form the 2S,4R-Monatin from 4R-IHOG so that the 2S,4R-Monatin is formed in a larger amount. A salt form of L-aspartic acid may be added to the reaction solution. The concentration of L-aspartate in the reaction solution is 1 mM to 3 M, preferably 20 mM to 1 M, more preferably 100 mM to 500 mM.
(Reaction 1")

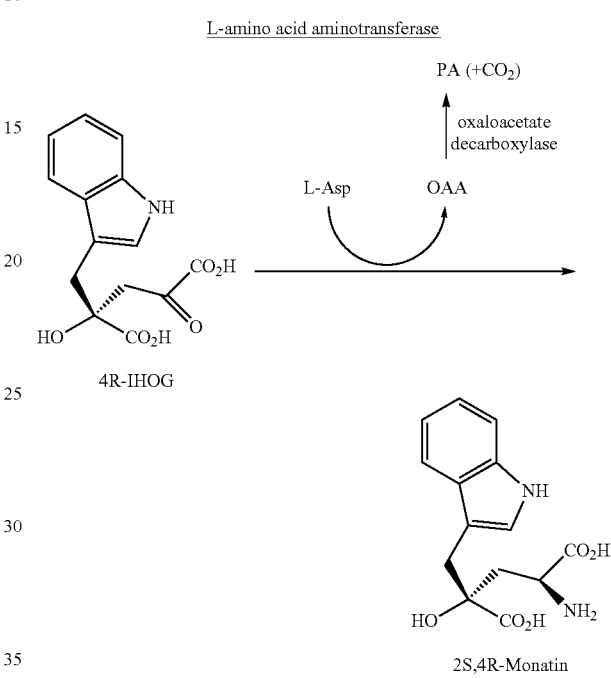

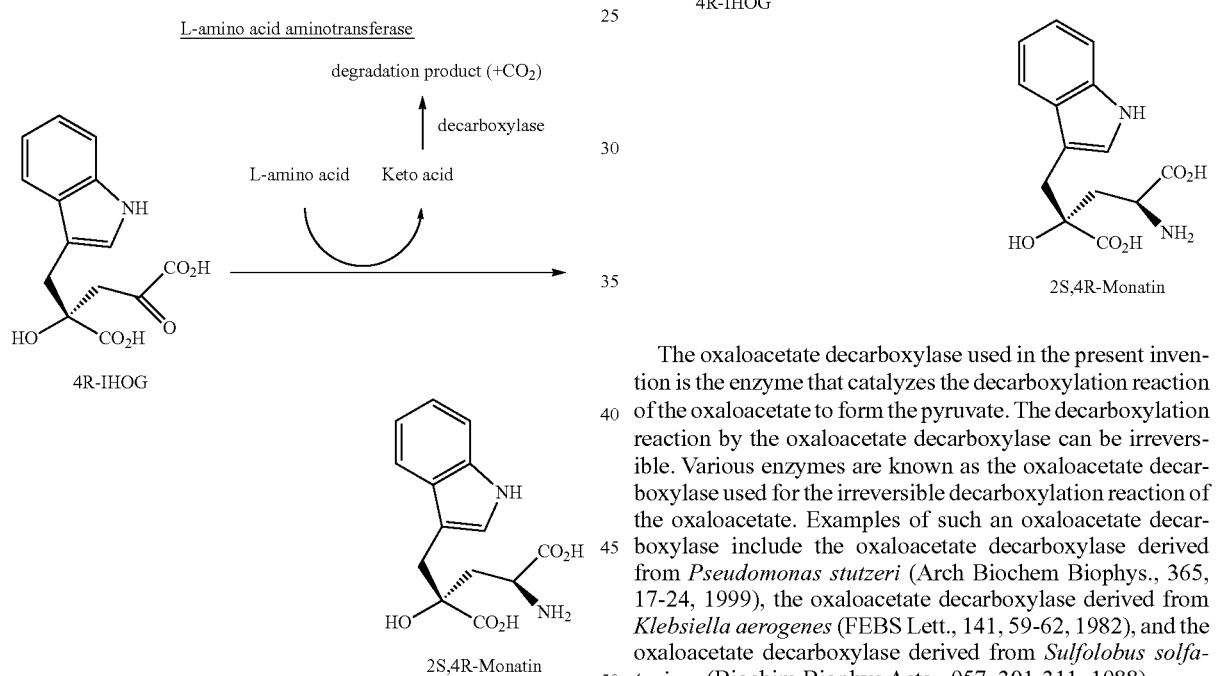

The decarboxylase used in the present invention is the enzyme that catalyzes a decarboxylation reaction of the keto acid. The decarboxylation reaction by the decarboxylase can be irreversible. Various enzymes are known as the decarboxylase used for the irreversible decarboxylation reaction of the keto acid, and examples thereof include an oxaloacetate decarboxylase derived from *Pseudomonas stutzeri* (Arch Biochem Biophys., 365, 17-24, 1999) and a pyruvate decarboxylase derived from *Zymomonas mobilis* (Applied Microbiology and Biotechnology, 17, 152-157, 1983).

In a particularly preferred embodiment, the production method of the present invention comprises contacting oxaloacetate (OAA) formed from L-aspartic acid (L-Asp) by action of the L-amino acid aminotransferase with the oxaloacetate decarboxylase to form the pyruvate (PA) (see the reaction 1"). By promoting the irreversible formation of the pyruvate from The oxaloacetate decarboxylase used in the present invention is the enzyme that catalyzes the decarboxylation reaction of the oxaloacetate to form the pyruvate. The decarboxylation reaction by the oxaloacetate decarboxylase can be irreversible. Various enzymes are known as the oxaloacetate decarboxylase used for the irreversible decarboxylation reaction of the oxaloacetate. Examples of such an oxaloacetate decarboxylase include the oxaloacetate decarboxylase derived from *Pseudomonas stutzeri* (Arch Biochem Biophys., 365, 17-24, 1999), the oxaloacetate decarboxylase derived from *Klebsiella aerogenes* (FEBS Lett., 141, 59-62, 1982), and the oxaloacetate decarboxylase derived from *Sulfolobus solfataricus* (Biochim Biophys Acta., 957, 301-311, 1988).

When the decarboxylase is used in the production of the 2S,4R-Monatin from 4R-IHOG, the contact of the keto acid formed from the L-amino acid with the decarboxylase can be accomplished by allowing the keto acid and the decarboxylase extracted from a decarboxylase-producing microorganism (extracted enzyme) or the decarboxylase-producing microorganism to coexist in the reaction solution (e.g., culture medium). Examples of the decarboxylase-producing microorganism include microorganisms that naturally produce the decarboxylase and transformants that express the decarboxylase. Examples of the extracted enzyme include a purified enzyme, a crude enzyme, an immobilized enzyme, a culture broth, and a treated product of the culture broth (e.g., a decarboxylase-containing fraction prepared from the above decarboxylase-producing microorganism, and a disrupted product of and a lysate of the above decarboxylase-producing microorganism). Examples of the treatment for obtaining the treated product of the culture broth from the culture broth include a heat treatment (42° C. to 80° C., pH 3 to 12, 1 minute to 24 hours), a solvent treatment (e.g., xylene, toluene, ethanol, isopropylalcohol), a surfactant (e.g., Tween 20, Triton X-100), and a treatment with a bacteriolytic enzyme (e.g., lysozyme treatment). Alternatively, the culture broth is subjected to a reaction after retaining it with adjusting temperature, pH and the like to enhance an enzymatic activity detected in the broth. In this case, the temperature may be set at 4° C. to 60° C., preferably 20° C. to 37° C. The pH may be set at 3 to 12, preferably 7 to 9. The time may be set for about 5 minutes to 20 days, preferably about 1 hour to 7 days. During retaining the broth, aeration and agitation may be or may not be carried out.

When both the L-amino acid aminotransferase and the decarboxylase are used in the production of the 2S,4R-Monatin from 4R-IHOG, the L-amino acid aminotransferase and the decarboxylase may be provided in the reaction solution in the following manner:

L-amino acid aminotransferase (extracted enzyme) and decarboxylase (extracted enzyme);

L-amino acid aminotransferase-producing microorganism and decarboxylase (extracted enzyme);

L-amino acid aminotransferase (extracted enzyme) and decarboxylase-producing microorganism;

L-amino acid aminotransferase-producing microorganism and decarboxylase-producing microorganism; and L-amino acid aminotransferase- and decarboxylase-producing microorganism.

Preferably, the L-amino acid aminotransferase- and decarboxylase-producing microorganism may be a transformant. Such a transformant can be made by i) introducing an expression vector of the L-amino acid aminotransferase into the decarboxylase-producing microorganism, ii) introducing an expression vector of the decarboxylase into the L-amino acid aminotransferase-producing microorganism, (iii) introducing a first expression vector of the L-amino acid aminotransferase and a second expression vector of the decarboxylase into a host microorganism, and (iv) introducing an expression vector of the L-amino acid aminotransferase and the decarboxylase into the host microorganism. Examples of the expression vector of the L-amino acid aminotransferase and the decarboxylase include i') an expression vector containing a first expression unit composed of a first polynucleotide encoding the L-amino acid aminotransferase and a first promoter operatively linked to the first polynucleotide, and a second expression unit composed of a second polynucleotide encoding the decarboxylase and a second promoter operatively linked to the second polynucleotide; and ii') an expression vector containing a first polynucleotide encoding the L-amino acid aminotransferase, a second polynucleotide encoding the decarboxylase and a promoter operatively linked to the first polynucleotide and the second polynucleotide (vector capable of expressing polycistronic mRNA). The first polynucleotide encoding the L-amino acid aminotransferase may be located upstream or downstream the second polynucleotide encoding the decarboxylase.

(1-2) Method for Producing 2S,4R-Monatin from IPA and pyruvate

The production method of the present invention may further comprise condensing IPA and the pyruvate to form 4R-IHOG in order to prepare 4R-IHOG. The condensation of IPA and the pyruvate can be carried out by the organic chemistry process, or an enzymatic method using an aldolase. The method for forming 4R-IHOG by condensing IPA and the pyruvate by the organic chemistry process is disclosed in, for example, International Publication WO2003/059865 and US Patent Application Publication No. 2008/0207920. The method for forming 4R-IHOG by condensing IPA and the pyruvate by the enzymatic method using the aldolase is disclosed in, for example, International Publication WO2003/056026, JP 2006-204285-A, US Patent Application Publication No. 2005/0244939 and International Publication WO2007/103989. Therefore, in the present invention, these methods can be used in order to prepare 4R-IHOG from IPA and the pyruvate.

IPA used for the preparation of 4R-IHOG is an unstable compound. Therefore, the condensation of IPA and the pyruvate may be carried out in the presence of a stabilizing factor for IPA. Examples of the stabilizing factor for IPA include superoxide dismutase (e.g., see International Publication WO2009/028338) and mercaptoethanol (e.g., see International Publication WO2009/028338). For example, the transformant expressing the superoxide dismutase is disclosed in International Publication WO2009/028338. Thus, such a transformant may be used in the method of the present invention.

The reaction to form 4R-IHOG from IPA and the pyruvate and the reaction to form the 2S,4R-Monatin from 4R-IHOG may be progressed separately or in parallel. These reactions may be carried out in one reactor. When these reactions are carried out in one reactor, these reactions can be carried out by adding the substrates and the enzymes sequentially or simultaneously. Specifically, when the reaction to form 4R-IHOG from IPA and the pyruvate by the enzymatic method using the aldolase and the reaction to form the 2S,4R-Monatin from 4R-IHOG by the L-amino acid aminotransferase are carried out, (1) IPA, the pyruvate and the aldolase, and (2) the L-amino acid and the L-amino acid aminotransferase may be added in one reactor sequentially or simultaneously. A salt form of pyruvate (e.g., sodium salt) may be added to the reaction solution. Pyruvate may be added to the reaction solution in any manner (e.g., batch method, or feed method). The concentration of pyruvate in the reaction solution may be, for example, 0.1 mM to 10 M, preferably 1 mM to 1 M.

In a preferred embodiment, the production method of the present invention is combined with the above reaction 1" as follows. In this case, the pyruvate irreversibly formed from the oxaloacetate is utilized for the preparation of 4R-IHOG. In other words, at least a part of the pyruvate used for the formation of 4R-IHOG can be from the pyruvate formed from the oxaloacetate by action of the oxaloacetate decarboxylase. In this case, it should be noted that an initial amount of the pyruvate in the reaction system is not necessarily important if an amount of the L-amino acid present in the reaction system is sufficient because the pyruvate is formed from the oxaloacetate in conjunction with the formation of the 2S,4R-Monatin. Therefore, the larger amount of the L-amino acid may be added to the reaction system compared with the pyruvate.

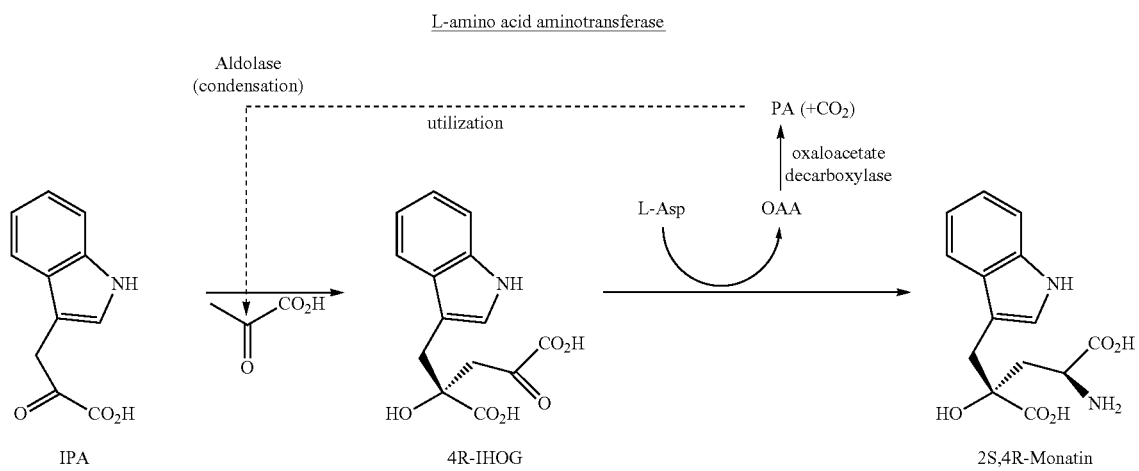

When the aldolase is used in the production of 4R-IHOG from IPA and the pyruvate, the contact of IPA and the pyruvate with the aldolase can be accomplished by allowing IPA, the pyruvate and the aldolase extracted from an aldolase-producing microorganism (extracted enzyme) or the aldolase-producing microorganism to coexist in the reaction solution (e.g., culture medium). Examples of the aldolase-producing microorganism include microorganisms that naturally produce the aldolase and transformants that express the aldolase. Examples of the extracted enzyme include a purified enzyme, a crude enzyme, an immobilized enzyme, a culture broth, and a treated product of the culture broth (e.g., an aldolase-containing fraction prepared from the above aldolase-producing microorganism, a disrupted product of and a lysate of the above aldolase-producing microorganism). Examples of the treatment for obtaining the treated product of the culture broth from the culture broth include a heat treatment (42° C. to 80° C., pH 3 to 12, 1 minute to 24 hours), a solvent treatment (e.g., xylene, toluene), a surfactant treatment. The culture broth may be used under a condition of 4° C. to 60° C., pH 3 to 12, and 5 minutes to 20 days (with or without aeration and agitation). The aldolase-producing microorganism may further express other enzyme(s) (e.g., superoxide dismutase, L-amino acid aminotransferase, decarboxylase). Alternatively, a microorganism that produces the other enzyme in addition to the aldolase-producing microorganism may be allowed to coexist in the reaction solution. Those described in the production method (1-1) of the present invention can be used as the reaction solution.

Preferably, the aldolase-, L-amino acid aminotransferase- and decarboxylase-producing microorganism may be a transformant. The expression of the aldolase, the L-amino acid aminotransferase and the decarboxylase may be carried out using the same transformant, or it may be carried out with a combination of two transformants, or the three enzymes may be expressed in separate transformants. the aldolase, L-amino acid aminotransferase and decarboxylase genes are expressed in the same transformant, these genes may be integrated into its chromosome, or the aldolase, L-amino acid aminotransferase and decarboxylase genes are inserted to one vector. Alternatively, an expression vector of the L-amino acid aminotransferase may be introduced to a microorganism which produces the decarboxylase and aldolase, or a first expression vector of the L-amino acid aminotransferase and a second expression vector of the decarboxylase and the aldolase may be introduced to a host microorganism. Examples of the expression vector of the aldolase, the L-amino acid aminotransferase and the decarboxylase include i') an expression vector containing a first expression unit composed of a first polynucleotide encoding the L-amino acid aminotransferase and a first promoter operatively linked to the first polynucleotide, a second expression unit composed of a second polynucleotide encoding the decarboxylase and a second promoter operatively linked to the second polynucleotide, and a third expression unit composed of a third polynucleotide encoding the decarboxylase and a third promoter operatively linked to the third polynucleotide; and ii') an expression vector containing a first expression unit composed of a first polynucleotide encoding the L-amino acid aminotransferase, a second polynucleotide encoding the decarboxylase and a promoter operatively linked to the first polynucleotide and the second polynucleotide, and a second expression unit composed of a third polynucleotide encoding the aldolase and a promoter operatively linked to the third polynucleotide (a vector capable of expressing a polycistronic mRNA). The positions of genes encoding the L-amino acid aminotransferase, the decarboxylase and the aldolase on a plasmid are not particularly limited.

Various conditions such as the temperature, the pH value and the time period in the reaction can be appropriately established as long as the objective reaction can progress. For example, the conditions of the enzymatic method using the aldolase may be the same as those described in the production method (1-1) of the present invention.

(1-3) Method for Producing 2S,4R-Monatin or a Salt Thereof From Tryptophan or a Salt Thereof.

The production method of the present invention may further comprise deaminating a tryptophan (Trp) in order to prepare IPA. Trp includes L-Trp, D-Trp and a mixture of L-Trp and D-Trp. The deamination of Trp can be performed by the organic chemistry technique and the enzymatic method using a deamination enzyme.

Various methods are known as the method for deaminating Trp to form IPA by the organic chemistry technique. Examples of such a method include the method in which the tryptophan is used as a starting material and reacted with pyridine aldehyde in the presence of a base for dehydration of a proton acceptor (e.g., see JP Sho-62-501912 and International Publication WO1987/000169), and the method of subjecting to acid hydrolysis after a condensation reaction using indole and ethyl-3-bromopyruvate ester oxime as raw materials (e.g., European Patent Application Publication No. 421946).

As used herein, the term "deamination enzyme" refers to the enzyme capable of forming IPA from Trp. The formation of IPA from Trp is essentially conversion of the amino group ($-NH_2$) in Trp to an oxy group ($=O$). Therefore, the enzymes that catalyze this reaction are sometimes termed as other names such as an amino acid deaminase, an aminotransferase and an amino acid oxidase. Therefore, the term "deamination enzyme" means any enzyme that can form IPA from Trp, and the enzymes having the other name (e.g., amino acid deaminase, aminotransferase, amino acid oxidase) which catalyze the reaction to form IPA from Trp are also included in the "deamination enzyme."

Examples of the method for forming IPA from Trp using the amino acid deaminase or an amino acid deaminase-producing microorganism include the method disclosed in International Publication WO2009/028338. A general formula of the reaction catalyzed by the amino acid deaminase includes the following formula: Amino acid+$H_2O$→2-oxo acid+$NH_3$.

Examples of the method for forming IPA from Trp using the aminotransferase or an aminotransferase-producing microorganism include the methods disclosed in East Germany Patent DD 297190, JP Sho-59-95894-A, International Publication WO2003/091396 and US Patent Application Publication No. 2005/028226.

Examples of the method for forming IPA from Trp using the L-amino acid oxidase or an L-amino acid oxidase-producing microorganism include the methods disclosed in U.S. Pat. No. 5,002,963, John A. Duerre et al. (Journal of Bacteriology 1975, vol. 121, No. 2, p656-663), JP Sho-57-146573, International Publication WO2003/056026 and International Publication WO2009/028338. The general formula of the reaction catalyzed by the amino acid oxidase includes the following formula: Amino acid+$O_2$+$H_2O$→2-Oxo acid+$H_2O_2$+$NH_3$. For the purpose of suppressing the degradation of the compound by hydrogen peroxide as the by-product produced at that time, a hydrogen peroxide-degrading enzyme such as a catalase may be added in the reaction solution.

The reaction to form IPA from Trp, the reaction to form 4R-IHOG from IPA and the pyruvate and the reaction to form 2S,4R-Monatin from 4R-IHOG may be progressed separately or in parallel. These reactions may be carried out in one reactor. When these reactions are carried out in one reactor, these reactions can be carried out by adding the substrates and the enzymes sequentially or simultaneously. Specifically, when the reaction to deaminate Trp by the enzymatic method using the deamination enzyme to form IPA, the reaction to form 4R-IHOG from IPA and the pyruvate by the enzymatic method using the aldolase, and the reaction to form 2S,4R-Monatin from 4R-IHOG by the L-amino acid aminotransferase are carried out, (1) Trp and the deamination enzyme, (2) the pyruvate and the aldolase, and (3) the L-amino acid and the L-amino acid aminotransferase may be added in one reactor sequentially or simultaneously.

When the deamination enzyme is used in the production of IPA from Trp, the contact of Trp with the deamination enzyme can be accomplished by allowing Trp and the deamination enzyme extracted from a deamination enzyme-producing microorganism (extracted enzyme) or the deamination enzyme-producing microorganism to coexist in the reaction solution. Examples of the deamination enzyme-producing microorganism include microorganisms that naturally produce the deamination enzyme and transformants that express the deamination enzyme. For example, the pTB2 strain described in Example 2 of WO 2009/028338 (the modified strain of E. coli introduced with the amino acid deaminase gene derived from the strain of Providencia rettgeri) may be used. An operative promoter (e.g., phoA, phoC, trp, lac, or tac promoter) may be linked to the deaminase gene in the plasmid. When E. coli is used as a host, a plasmid capable of expressing a deaminase may be introduced to a host having a deletion of a certain gene such as aspC gene. Examples of the extracted enzyme include a purified enzyme, a crude enzyme, an immobilized enzyme, a cuture broth, and a treated product of the culture broth (e.g., a deamination enzyme-containing fraction prepared from the above deamination enzyme-producing microorganism, a disrupted product of and a lysate of the above deamination enzyme-producing microorganism). Examples of the treatment for obtaining the treated product of the culture broth from the culture broth include a heat treatment (42° C. to 80° C., pH 3 to 12, 1 minute to 24 hours), a solvent treatment (e.g., xylene, toluene, ethanol, isopropylalcohol), a surfactant (e.g., Tween 20, Triton X-100), and a treatment with a bacteriolytic enzyme (e.g., lysozyme treatment). Alternatively, the culture broth is subjected to a reaction after retaining it with adjusting temperature, pH and the like to enhance an enzymatic activity detected in the broth. In this case, the temperature may be set at 4° C. to 60° C., preferably 20° C. to 37° C. In addition, the pH may be set at 3 to 12, preferably 7 to 9. The time may be set for about 5 minutes to 20 days, preferably about 1 hour to 7 days. During retaining the broth, aeration and agitation may be or may not be carried out. The deamination enzyme-producing microorganism may further express the other enzyme(s) (e.g., aldolase, superoxide dismutase, L-amino acid aminotransferase, decarboxylase). Alternatively, the other enzyme-producing microorganism in addition to the deamination enzyme-producing microorganism may be allowed to coexist in the reaction solution. Those described in the production method (1-1) of the present invention can be used as the reaction solution. Trp is preferably L-trp. A salt form of Trp may be added to the reaction solution. The concentration of Trp in the reaction solution is, for example, 1 mM to 3 M, preferably 20 mM to 1 M, more preferably 20 mM to 300 mM.

Various conditions such as the temperature, the pH value and the time period in the reaction can be appropriately established as long as the objective reaction can progress. For example, the conditions of the enzymatic method using the deamination enzyme may be the same as those described in the production method (1-1) of the present invention.

In a preferred embodiment, when the production method (1-3) of the present invention is carried out in one reactor, the deaminase, the aldolase, the L-amino acid aminotransferase, and the oxaloacetate decarboxylase, and/or one or more transformants expressing them are used. The superoxide dimustase, and/or a transformant expressint it may be further used. These enzymes may be mutants. For an expression system of the enzymes, the aforementioned transformants can be used. Specifically, a transformant carrying the expression vector of a gene of interest in its cytoplasm, a transformant introduced with a gene of interest on its genome, and a transformant which carries the expression vector of a gene of interest in its cytoplasm, and which is introduced with a gene of interest on its genome. For an expression vector used in the preparation of the transformant, the aforementioned expression vector can be used.

In a preferred embodiment, when the production method (1-3) of the present invention is carried out in one reactor, a reaction solution containing a certain concentrations of L-Trp, L-Asp, PA, a buffer (e.g., phosphate buffer, Tris buffer) and PLP can be used. The concentration of L-Trp is, for example, 1 mM to 3 M, preferably 10 mM to 1 M, more preferably 50 mM to 300 mM. The concentration of L-Asp is, for example, 1 mM to 3 M, preferably 100 mM to 1 M, more preferably 200 mM to 400 mM. L-Asp may be a salt form (e.g., sodium salt, potassium salt) or a free form. When L-Asp is used in a free form, pH may be appropriately adjusted after supplying it in the reaction solution. In this case, an alkaline solution (e.g., NaOH aqueous solution, KOH aqueous solution) may be used for the adjustment of pH. The concentration of PA is, for example, 1 mM to 3 M, preferably 10 mM to 100 mM. PA may be a salt form (e.g., sodium salt, potassium salt) or a free form. When PA is used in a free form, pH may be adjusted after supplying it in the reaction solution. The concentration of PLP is, for example, 1 µM to 100 mM, preferably 10 µM to 1 mM. The reaction solution may further contain magnesium, phosphate, and antifoaming agent.

When magnesium is used as a salt, the salt form of magnesium is not particularly limited, and examples of the salt form include magnesium chloride and magnesium sulfate. The concentration of magnesium is, for example, 0.1 mM to 100 mM, preferably 0.5 mM to 5 mM. In addition, the phosphate is used as a salt, the salt form of the phosphate is not particularly limited, and examples of the salt form include a potassium salt (e.g., monopotassium salt, dipotassium salt, tripotassium salt) and a sodium salt (e.g., monosodium salt, disodium salt, trisodium salt). The concentration of the phosphate is, for example, 1 mM to 100 mM, preferably 10 mM to 50 mM. The antifoaming agent is not particularly limited, and examples of the antifoaming agent include GD113K. The concentration of the antifoaming agent is not particularly limited, and is 0.0001% to 1% (v/v), preferably 0.001% to 0.1% (v/v). The reaction condition such as pH, temperature, aeration, agitation and time can be appropriately set. The pH of the reaction solution is, for example, 5 to 10, preferably 6 to 9, more preferably 7 to 8. The control of pH during the reaction may be achieved by adding an acid or alkaline appropriately. The acid or alkaline used in this case is not particularly limited, and examples of the acid or alkaline include hydrochloric acid, phosphoric acid, sulfuric acid, ammonium gas, ammonium aqueous solution, NaOH aqueous solution, and KOH aqueous solution. The concentration of the acid or alkaline used in the adjustment of pH is not particularly limited. It is, for example, 0.1 N to 20 N, preferably 3 N to 12 N, when a solution of the acid or alkaline is used. The reaction temperature is, for example, 10° C. to 50° C., preferably 20° C. to 40° C., more preferably 25° C. to 35° C. When a container capable of controlling aeration and agitation (e.g., jar fermenter) is used for the reaction, the concentration of dissolved oxygen in the reaction solution can be set by controlling the conditions on aeration and agitation. A person skilled in the art can set the conditions on aeration and agitation according to the used container. For example, when a jar fermenter with a volume of 1 litter is used, the condition on aeration is, for example, 1/200 to 1 vvm, preferably 1/100 to 1/10 vvm. The condition on agitation is, for example, 100 rpm to 1000 rpm, preferably 400 rpm to 700 rpm. Examples of the enzyme to be added to the reaction include a purified enzyme, a microorganism expressing an enzyme, a treated product of a microorganism expressing an enzyme, a cuture broth containing a microorganism expressing an enzyme, and a treated product of a culture broth containing a microorganism expressing an enzyme. Examples of the treatment for obtaining the treated product of the culture broth from the culture broth include a heat treatment (42° C. to 80° C., pH 3 to 12, 1 minute to 24 hours), a solvent treatment (e.g., xylene, toluene, ethanol, isopropylalcohol), a surfactant (e.g., Tween 20, Triton X-100), and a treatment with a bacteriolytic enzyme (e.g., lysozyme treatment). Alternatively, the culture broth is subjected to a reaction after retaining it with adjusting temperature, pH and the like to enhance an enzymatic activity detected in the broth. In this case, the temperature of the culture broth may be 4° C. to 60° C., preferably 20° C. to 37° C. The pH of the culture broth may be 3 to 12, preferably 7 to 9. The retaining time may be about 5 minutes to 20 days, preferably about 1 hour to 7 days. During retaining the broth, aeration and agitation may be or may not be carried out.

Each enzyme to be added to the reaction solutions can be appropriately determined by measuring an activity of each enzyme previously. The deaminease activity, the aldolase activity, the L-amino acid aminotransferase activity, and the oxaloacetate decarboxylase activity can be measured by the following methods.

Deaminase activity: 10 mM L-Phe, 100 mM $NH_4C$, 100 mM Tris-HCl (pH 8.0), 0.25 mM NADH and phenylalanine dehydrogenase (manufactured by UNITIKA, derived from *Thermoactinomyces intermedius*) at 25° C. The activity is calculated from the reduction of the absorbance measured at 340 nm.

L-amino acid aminotransferase activity (L-Asp/α-KG activity): 100 mM L-Asp-Na-1aq, 10 mM α-KG-2Na, 50 µM PLP, 100 mM Tris-HCl (pH 8.0), 0.25 mM NADH and 2 U/mL of MDH at 25° C. The activity is calculated from the reduction of the absorbance at 340 nm. Malic dehydrogenase from porcine heart (Sigma) was used as MDH.

Aldolase activity: 2 mM 4-phenyl-4-hydroxy-2-oxo glutarate (PHOG), 100 mM Tris-HCl (pH 7.0), 1 mM $MgCl_2$, 0.25 mM NADH, 10 U/ml lactate dehydrogenase (manufactured by ORIENTAL YEAST Co., Ltd., derived from *Leuconostoc mesenteroides*) at 25° C. The activity is calculated from the reduction of the absorbance at 340 nm.

Oxaloacetate decarboxylase activity: 1 mM oxaloacetate, 100 mM Tris-HCl (pH 8.0), 0.25 mM NADH, 10 U/ml lactate dehydrogenase (manufactured by ORIENTAL YEAST Co., Ltd., derived from *Leuconostoc mesenteroides*) at 25° C. The activity is calculated from the reduction of the absorbance at 340 nm.

Based on the enzymatic activities determined as mentioned above, the amounts of enzymes to be added to the reaction solution may be as follows. The amount of the deaminease to be added to the reaction solution is, for example, 0.1 to 20 U/ml, preferably 0.5 to 2 U/ml. The amount of the aldolase to be added to the reaction solution is, for example, 1 to 1000 U/ml, preferably 10 to 100 U/ml. The amount of the L-amino acid aminotransferase to be added to the reaction solution is, for example, 1 to 1000 U/ml, preferably 10 to 100 U/ml. The amount of the oxaloacetate decarboxylase to be added to the reaction solution is, for example, 0.01 U/ml or more, preferably 0.1 U/ml or more. Each substrate may be added to a reaction system by a batch method or a feed method. The enzyme, the microorganism expressing the enzyme, the treated product of the microorganism expressing the enzyme, the cuture broth containing the microorganism expressing the enzyme, and the treated product of the culture broth containing the microorganism expressing the enzyme may also be added to the reaction system by a batch method or a feed method. The reaction time is, for example, 2 to 100 hours, preferably 4 to 50 hours, more preferably 8 to 25 hours. The reaction solution may be sterilized under an appropriate condition (e.g., temperature, pH, time).

When the production method (1-2) of the present invention is carried out in one reactor, such a production method can be carried out similar to the production method (1-3) of the present invention.

The purified 2S,4R-Monatin can be obtained by taking advantage of known purification methods such as column treatment, crystallization treatment and extraction treatment for a 2S,4R-Monatin-containing reaction solution obtained by any of the production methods (1-1), (1-2) and (1-3) of the present invention. The purified 2S,4R-Monatin can be provided to a method (2) for producing 2R,4R-Monatin or a salt thereof. The 2S,4R-Monatin-containing reaction solution obtained by any of the production methods (1-1), (1-2) and (1-3) of the present invention can also be directly provided to the method (2) for producing the 2R,4R-Monatin or the salt thereof.

(2) Method for Producing 2R,4R-Monatin or a Salt Thereof

The present invention provides a method (2) for producing 2R,4R-Monatin or the salt thereof. The production method of the present invention comprises performing the production method (1) of the present invention to form the 2S,4R-Monatin or a salt thereof, and isomerizing the 2S,4R-Monatin or the salt thereof to form 2R,4R-Monatin or a salt thereof.

The isomerization of the 2S,4R-monatin to the 2R,4R-Monatin can be performed by any method that enables the isomerization (e.g., see International Publication WO2005/082850 and International Publication WO03/059865). However, in terms of enhancing a yield of the 2R,4R-Monatin, the isomerization of the 2S,4R-Monatin is preferably performed by epimerization-crystallization (e.g., see International Publication WO2005/082580). The epimerization-crystallization is a method in which the isomerization reaction and the crystallization are performed simultaneously. In this case, the isomerization reaction at position 2 to convert the 2S,4R-Monatin into the 2R,4R-Monatin and the crystallization of the converted 2R,4R-Monatin are performed simultaneously by the epimerization-crystallization.

In the epimerization-crystallization, the isomerization reaction may be performed in the presence of an aldehyde. The aldehyde includes an aliphatic aldehyde and an aromatic aldehyde, and the aromatic aldehyde is preferred. A purified 2S,4R-Monatin or a 2S,4R-Monatin-containing reaction solution may be used as the 2S,4R-Monatin used for the isomerization reaction.

For the aliphatic aldehyde, for example, a saturated or unsaturated aldehyde having 1 to 7 carbon atoms, such as formaldehyde, acetaldehyde, propionaldehyde, n-butyl aldehyde, 1-butyl aldehyde, n-valeraldehyde, capronaldehyde, n-heptylaldehyde, acrolein or methacrolein can be used.

For the aromatic aldehyde, the aromatic aldehyde such as benzaldehyde, salicylaldehyde, m-hydroxybenzaldehyde, p-hydroxybenzaldehyde, o-nitrobenzaldehyde, p-nitrobenzaldehyde, 5-nitrosalicylaldehyde, 3,5-dichlorosalicylaldehyde, anisaldehyde, o-vanillin, vanillin, furfural, pyridoxal or 5-phosphate pyridoxal can be used. Particularly, pyridoxal, 5-nitrosalicylaldehyde, or 3,5-dichlorosalicylaldehyde is preferred as the aromatic aldehyde.

The aldehyde can be used in the range of 0.01 to 1 mol equivalent and more preferably 0.05 to 0.5 mol equivalent to the Monatin present in the system.

The epimerization-crystallization is performed in the presence of the aldehyde, and a mixed solvent of water and an organic solvent is used as a solvent. The organic solvent miscible with the water is used as the organic solvent, and particularly, alcohol such as methanol, ethanol, propanol or isopropanol is preferred. Two or more different kinds of organic solvents may be used in mixture. A volume ratio of the organic solvent to the water is set in the range of preferably 1:0.01 to 1:1 and more preferably 1:0.1 to 1:0.5 (organic solvent:water).

The temperature in the epimerization-crystallization is set in the range of preferably 0 to 100° C. and more preferably 40 to 80° C. The time period for performing the epimerization-crystallization is set in the range of preferably 10 hours to one week and more preferably 15 hours to 96 hours.

The pH value is set in the range of 4 to 13, preferably 4.5 to 10 and more preferably 5 to 9. The pH value can be adjusted using an acid or an alkali. The acid to be used is not particularly limited, and an organic acid such as acetic acid, or an inorganic acid such as hydrochloric acid or sulfuric acid can be used. The alkali is not also particularly limited, and an alkali metal hydroxide such as sodium hydroxide or potassium hydroxide, or an organic base such as ammonia or amine can be used.

Each compound obtained by the above method can be isolated and purified by optionally combining known separation and purification procedures such as concentration, reduced pressure concentration, solvent extraction, crystallization, recrystallization, solvent transfer, a treatment with activated charcoal, and treatments with chromatography and the like using ion exchange resin or synthetic adsorption resin. The salts of the compound used in the method of the present invention and the compound (objective compound) produced by the method of the present invention can be produced, for example, by adding the inorganic acid or the organic acid to the objective compound according to the method publicly known per se. The objective compound and the salt thereof may be hydrate, and both hydrate and non-hydrate are included in the scope of the present invention. The compounds (e.g., Trp, IPA, 4R-IHOG, 2S,4R-Monatin) used for the production methods of the present invention may be the forms of various salts such as sodium salts, potassium salts and ammonium salts. The compounds (e.g., IPA, 4R-IHOG, 2S,4R-Monatin, 2R,4R-Monatin) obtained by the production method of the present invention may also be the forms of various salts.

The present invention will be described in detail by the following Examples, but the present invention is not limited by these Examples.

EXAMPLES

Analytical Condition of HPLC

In Examples 1 to 7, if HPLC analysis was performed, the HPLC analysis was performed under the condition shown in the Example.

In Examples 8 to 15, the HPLC analysis was performed under the condition shown below.

Detector: Ultraviolet absorption spectrometer (measured wavelength: 210 nm)

Column temperature: 40° C.

Column: CAPCELLPAK C18 Type MGII, inner diameter: 3 mm, length: 25 cm, and particle diameter: 5 μm, Shiseido Co., Ltd.

Mobile phase: Solution A (aqueous solution of 20 mM potassium dihydrogen phosphate:acetonitrile=95:5) and solution B (aqueous solution of 20 mM potassium dihydrogen phosphate:acetonitrile=60:40)

Gradient program: See the following Table 1

TABLE 1

Gradient program

| Time (min) | Mobile phase A (%) | Mobile phase B (%) |
|---|---|---|
| 0.0 | 100 | 0 |
| 15.0 | 100 | 0 |
| 40.0 | 0 | 100 |
| 45.0 | 0 | 100 |
| 45.1 | 100 | 0 |

Flow: 0.45 mL/minute
Injection amount: 20 μL
Analysis time period: 60 minutes

Example 1

Formation of 2S,4R-Monatin from 4R-IHOG Using Extraction Solution from *Bacillus altitudinis* AJ1616 Microbial Cells

*Bacillus altitudinis* AJ1616 was streaked on CM2G agar medium (10 g/L of yeast extract, 10 g/L of polypeptone, 5 g/L of glucose, 5 g/L of sodium chloride, 15 g/L of agar, pH 7.0), and cultured at 30° C. for 2 days.

One loopful of the resulting microbial cells was inoculated to 3 mL of an enzyme production medium (10 g/L of yeast extract, 10 g/L of polypeptone, 1 g/L of glucose, 3 g/L of dipotassium hydrogen phosphate, 1 g/L of potassium dihydrogen phosphate, 0.1 g/L of magnesium sulfate heptahydrate, 5 g/L of ammonium sulfate) in a test tube, which was then cultured with shaking at 30° C. for 16 hours.

The microbial cells were collected from 2 mL of the cultured medium by centrifugation, washed with and suspended in 20 mM Tris-HCl (pH 7.6) to prepare 1 mL of a microbial cell suspension.

1 g of glass beads (0.1 mm) was added to 1 mL of this microbial cell suspension, and the microbial cells were disrupted using a multi beads shocker (Yasui Kikai Co., Ltd.). The resulting disrupted cell solution was centrifuged to use a supernatant as a microbial cell extract.

A 2S,4R-Monatin synthesis reaction solution (0.1 mL) (9.5 mM 4R-IHOG, 0.5 mM 4S-IHOG, 100 mM L-Asp, 50 μM PLP, 100 mM Tris-HCl, pH 8.0) was prepared so that 0.05 mL of the *Bacillus* altitudinis AJ1616 microbial cell extract was contained. The reaction solution was reacted at 30° C. for 20 hours. After termination of the reaction, the formed 2S,4R-Monatin was quantified, and its concentration was 0.21 mM.

The 2S,4R-Monatin was quantified using UPLC (Waters). The analytical condition is as follows.
Mobile phase: 20 mM $KH_2PO_4$/asetonitrile=100/5
Flow rate: 0.15 mL/minute
Column temperature: 40° C.
Detection: UV 210 nm
Column: ACQUITY UPLC BEH C18, 2.1×50 mm, 1.7 μm (Waters).

Example 2

Purification of Aminotransferase Derived from *Bacillus altitudinis* AJ1616

An aminotransferase for forming the 2S,4R-Monatin was purified from a soluble fraction of *Bacillus altitudinis* AJ1616 as follows. The reaction for synthesizing 2S,4R-Monatin and the quantification of 2S,4R-Monatin were performed in the same manner as in Example 1.

(1) Preparation of Soluble Fraction

*Bacillus altitudinis* AJ1616 was streaked on CM2G agar medium (10 g/L of yeast extract, 10 g/L of polypeptone, 5 g/L of glucose, 5 g/L of sodium chloride, 15 g/L of agar, pH 7.0), and cultured at 30° C. for 2 days.

One loopful of the resulting microbial cells was inoculated to 160 mL of TB (Terrific Broth) medium in a 500 mL Sakaguchi flask, which was then cultured with shaking at 30° C. for 16 hours. The microbial cells were collected from about 2000 mL of the cultured medium by centrifugation, washed with and suspended in 20 mM Tris-HCl (pH 7.6), 100 mM NaCl, and then disrupted by sonication at 4° C. for 30 minutes. Microbial cell debris was removed from the disrupted solution by centrifugation, and the resulting supernatant was used as a soluble fraction.

(2) Anion Exchange Chromatography

The above soluble fraction was applied onto an anion exchange chromatography column HiLoad 26/10 Q Sepharose HP (supplied from GE Health Care Bioscience, CV=53 mL) equilibrated with 20 mM Tris-HCl (pH 7.6), 100 mM NaCl, and adsorbed to the carrier. Proteins that had not been adsorbed to the carrier (unadsorbed proteins) were washed out with 20 mM Tris-HCl (pH 7.6), 100 mM NaCl, and subsequently the adsorbed proteins were eluted by linearly changing the concentration of NaCl from 100 mM to 500 mM at a flow rate of 8 mL/minute. A 2S,4R-Monatin forming activity was measured in each fraction, and detected in the fractions corresponding to about 200 mM NaCl.

(3) Hydrophobic Chromatography

The fractions in which the 2S,4R-Monatin forming activity had been detected were combined, and ammonium sulfate and Tris-HCl (pH 7.6) were added thereto at final concentrations of 1.4 M and 20 mM, respectively. This solution was applied to a hydrophobic chromatography column HiLoad 16/10 Phenyl Sepharose HP (supplied from GE Health Care Bioscience, CV=20 mL) equilibrated with 1.4 M ammonium sulfate, 20 mM Tris-HCl (pH 7.6), and adsorbed to the carrier. Unadsorbed proteins that had not been adsorbed to the carrier were washed out with 1.4 M ammonium sulfate, 20 mM Tris-HCl (pH 7.6), and subsequently, a 2S,4R-Monatin forming enzyme was eluted by linearly changing the concentration of ammonium sulfate from 1.4 M to 0 M at a flow rate of 3 mL/minute. The 2S,4R-Monatin forming activity was measured in each fraction, and detected in the fractions corresponding to about 1.0 M ammonium sulfate.

(4) Gel Filtration Chromatography

The fractions in which the 2S,4R-Monatin forming activity had been detected were combined and concentrated using Amicon Ultra-15 30K (Millipore). The resulting concentrated solution was diluted with 20 mM Tris-HCl (pH 7.6), 150 mM NaCl. This solution was applied to a gel filtration column HiLoad 16/60 Superdex 200 pg (supplied from GE Health Care Bioscience, CV=120 mL) equilibrated with 20 mM Tris-HCl (pH 7.6), 150 mM NaCl, and eluted at a flow rate of 1 mL/minute. This manipulation confirmed the 2S,4R-Monatin forming activity in a location estimated as a molecular weight of about 120 kDa.

(5) Anion Exchange Chromatography

The fractions in which the 2S,4R-Monatin forming activity had been detected were combined and applied to an anion exchange chromatography column Mono Q 5/5 (supplied from Pharmacia (GE Health Care Bioscience), CV=1 mL) equilibrated with 20 mM Tris-HCl, 100 mM NaCl (pH 7.6), and adsorbed to the carrier. Proteins that had not been adsorbed to the carrier (unadsorbed proteins) were washed out with 20 mM Tris-HCl (pH 7.6), 100 mM NaCl, and subsequently the adsorbed proteins were eluted by linearly changing the concentration of NaCl from 100 mM to 500 mM at a flow rate of 0.5 mL/minute. The 2S,4R-Monatin forming activity was measured in each fraction, and detected in the fractions corresponding to about 200 mM NaCl.

(6) SDS-PAGE

The obtained fractions were subjected to SDS-PAGE, and a band around 45 kDa was observed in the active fraction. This band was subjected to analysis of an N-terminal amino acid sequence as a candidate for the aminotransferase for forming the 2S,4R-Monatin. The band was also subjected to the analysis of an internal amino acid sequence.

Example 3

Determination of N-Terminal and Internal Amino Acid Sequences of Aminotransferase Derived from *Bacillus altitudinis* AJ1616

The purified enzyme solution obtained in Example 2 was subjected to the analysis of the N-terminal amino acid sequence, and the sequence SGFTALSEAELNDLY (SEQ ID NO:4) was obtained as the N-terminal amino acid sequence. The sample in SDS-PAGE gel was treated with trypsin (pH 8.0, 35° C., 20 hours), and subsequently subjected to reverse phase HPLC to separate peptide fragments. The amino acid sequences in the fractionated fractions were analyzed, and the sequence QLDLSMGMLDVV (SEQ ID NO:5) was obtained as the internal amino acid sequence. Both the N-terminal amino acid sequence and the internal amino acid sequence exhibited high homology to the aminotransferase derived from *Bacillus pumilus* SAFR-032 (YP_001487343).

Example 4

Cloning of Aminotransferase Gene Derived from *Bacillus altitudinis* AJ1616

*Bacillus altitudinis* AJ1616 was cultured in the same manner as in Example 1. The microbial cells were collected from the cultured medium by centrifugation, and genomic DNA was extracted.

A DNA fragment including an aminotransferase gene was amplified by PCR using the obtained genomic DNA as a template. For primers, the primer Bp-u300-f (5'-ctcaggaag-caggcgcaaaaagattaattt-3' (SEQ ID NO:6) and the primer Bp-d200-r (5'-ggatgctgtctttgtcatcccaaagtggat-3' (SEQ ID NO:7) were used, which were designed from DNA sequences of upstream 300 bp and downstream 200 bp in the aminotransferase gene with reference to the genomic DNA sequence of *Bacillus pumilus* SAFR-032 (CP000813). PCR was performed using KOD-plus-ver. 2 (Toyobo) under the following condition.

| 1 cycle | 94° C., 2 min |
|---|---|
| 25 cycles | 98° C., 10 sec |
| | 55° C., 10 sec |
| | 68° C., 60 sec |
| 1 cycle | 68° C., 60 sec |
| | 4° C. |

A nucleotide sequence of about 1800 bp of the amplified DNA fragment was determined, and the nucleotide sequence was shown to include 1308 bp of ORF that had the high homology to the aminotransferase gene derived from *Bacillus pumilus* SAFR-032 (NC_009848). The homology was 89% in the DNA sequences and 93% in the amino acid sequences.

The N-terminal amino acid sequence and the internal amino acid sequence obtained in Example 3 were found in this sequence. Thus, it was thought that the aminotransferase gene having the 2S,4R-Monatin forming activity could have been acquired.

Example 5

Expression of Aminotransferase Derived from *Bacillus altitudinis* AJ1616 in *E. coli*

(1) Construction of Plasmid Expressing Aminotransferase Derived from *Bacillus altitudinis* AJ1616

A DNA fragment including the aminotransferase gene derived from *Bacillus* altitudinis AJ1616 was amplified by PCR using the genomic DNA of *Bacillus* altitudinis AJ1616 as the template. The primer 1616AT-Nde-f (5'-ggaattccatAT-GAGCGGTTTTACAGCGTT-3': SEQ ID NO:8) and the primer 1616-xho-r (5'-gtcaaggagttttctcgagTACCGTTG-GTGCTGATTGAC-3': SEQ ID NO:9) were used as the primers. A NdeI sequence in the aminotransferase gene was converted using the primer 1616-delNde-f (5'-GGATTGAAGGAACAcATGAAAAAGCATGC-3': SEQ ID NO:10) and the primer 1616-delNde-r (5'-GCAT-GCTTTTTCATgTGTTCCTTCAATCC-3': SEQ ID NO:11). PCR was performed using KOD-plus-ver. 2 (Toyobo) under the following condition.

| 1 cycle | 94° C., 2 min |
|---|---|
| 25 cycles | 98° C., 10 sec |
| | 55° C., 10 sec |
| | 68° C., 60 sec |
| 1 cycle | 68° C., 60 sec |
| | 4° C. |

The resulting DNA fragment of about 1300 bp was treated with restriction enzymes NdeI and XhoI, and then ligated to pET-22b (Novagen) likewise treated with NdeI and XhoI. *E. coli* JM109 was transformed with this solution containing the ligated product, the objective plasmid was extracted from ampicillin resistant colonies, and this plasmid was designated as pET-22-1616AT-His. This plasmid expresses the aminotransferase derived from *Bacillus altitudinis* AJ1616 which has the His-tag to C-terminus end (1616AT-His).

(2) Purification of 1616AT-His from *E. coli* Expression Strain

The constructed expression plasmid pET-22-1616AT-His was introduced into *E. coli* BL21 (DE3). One loopful of the resulting transformant was inoculated to 160 mL of Overnight Express Instant TB Medium (Novagen) containing 100 mg/L of ampicillin in a 500 mL Sakaguchi flask, and cultured with shaking at 37° C. for 16 hours. After the termination of the cultivation, microbial cells were collected from about 1000 mL of the resulting cultured medium by centrifugation, washed with and suspended in 20 mM Tris-HCl (pH 7.6), 100 mM NaCl and 20 mM imidazole, and disrupted by sonication at 4° C. for 30 minutes. Microbial cell debris was removed from the disrupted solution by centrifugation, and the resulting supernatant was used as a soluble fraction.

The obtained soluble fraction was applied to a His-tag protein purification column HisPrep FF 16/10 (supplied from Pharmacia (GE Health Care Bioscience), CV-20 mL) equilibrated with 20 mM Tris-HCl (pH 7.6), 100 mM NaCl and 20 mM imidazole, and adsorbed to the carrier. Proteins that had not been adsorbed to the carrier (unadsorbed proteins) were washed out with 20 mM Tris-HCl (pH 7.6), 100 mM NaCl and 20 mM imidazole, and subsequently the adsorbed proteins were eluted by linearly changing the concentration of imidazole from 20 mM to 250 mM at a flow rate of 3 mL/minute.

The obtained fractions were combined and concentrated using Amicon Ultra-15 30K (Millipore). The concentrated solution was diluted with 20 mM Tris-HCl (pH 7.6), 100 mM NaCl, and applied to the anion exchange chromatography column HiLoad 16/10 Q Sepharose HP (supplied from GE health Care Bioscience, CV=20 mL) equilibrated with 20 mM Tris-HCl (pH 7.6), 100 mM NaCl, and adsorbed to the carrier. The proteins that had not been adsorbed to the carrier (unadsorbed proteins) were washed out with 20 mM Tris-HCl (pH 7.6), 100 mM NaCl, and subsequently the adsorbed proteins were eluted by linearly changing the concentration of NaCl from 100 mM to 500 mM at a flow rate of 3 mL/minute.

The 2S,4R-Monatin forming activity was measured in each eluted fraction, and the fractions in which the 2S,4R-Monatin forming activity had been confirmed were combined and concentrated using Amicon Ultra-15 30K (Millipore). The concentrated solution was diluted with 20 mM Tris-HCl (pH 7.6) to use as a 1616AT-His solution.

Example 6

Synthesis Reaction of 2S,4R-Monatin Using 1616AT-His

The 2S,4R-Monatin was quantified by HPLC analysis. The analytical condition was as follows.
Mobile phase: 20 mM $KH_2PO_4$/acetonitrile=100/5
Flow rate: 1.0 mL/minute
Column temperature: 40° C.
Detection: UV 280 nm
Column: CAPCELL PAK MGII, 4.6×150 mm, 3 μm, (Shiseido Co., Ltd.)

(1) Synthesis of 2S,4R-Monatin from 4R-IHOG

The 1616AT-His solution prepared so as to contain 0.5 mg of 1616AT-His (Example 5) was added to 0.1 mL of the reaction solution (9.5 mM 4R-IHOG, 0.5 mM 4S-IHOG, 80 mM L-Asp, 50 μM PLP, 100 mM Tris-HCl, pH 8.0), and then reacted at 25° C. for 12 hours. After the termination of the reaction, the formed 2S,4R-Monatin was quantified, and its concentration was 8.6 mM.

(2) Synthesis of 2S,4R-Monatin from Indole Pyruvate (IPA) and Pyruvate (PA)

A reaction mixture was prepared so as to contain 0.5 mg of 1616AT-His (the 1616AT-His solution in Example 5 was used), 0.01 mg of SpAld (a solution having an aldolase activity, the preparation method of the solution is explained in detail below, see also JP 2006-204285-A) and 1 U of oxaloacetate decarboxylase (Sigma, O4878) in 0.1 mL of a reaction solution (50 mM IPA, 100 mM PA, 100 mM L-Asp, 1 mM $MgCl_2$, 50 μM PLP, 100 mM Tris-HCl, 100 mM potassium phosphate buffer, pH 8.0), and reacted at 25° C. for 2 hours. After the termination of the reaction, the formed 2S,4R-Monatin was quantified, and its concentration was 5.0 mM.

(3) Synthesis of 2S,4R-Monatin from L-Trp

A reaction mixture was prepared so as to contain 5 mg of 1616AT-His (the 1616AT-His solution in Example 5 was used), 0.2 mg of SpAld, 0.4 mL of the cultured medium (TB medium) of pTB2 strain (a bacterial strain capable of expressing a deamination enzyme, the preparation method of the bacterial strain is explained in detail below, see also WO2009/028338) in the Sakaguchi flask, 200 U of superoxide dismutase (Sigma, S8160) and 10 U of oxaloacetate decarboxylase (Sigma, O4878) in 1.0 mL of a reaction solution (50 mM L-Trp, 100 mM PA, 400 mM L-Asp, 1 mM $MgCl_2$, 50 μM PLP, 100 mM Tris-HCl, 100 mM potassium phosphate buffer, pH 6.5), and reacted at 25° C. for 12 hours. The reaction was performed using a test tube with shaking at 140 rpm. After the termination of the reaction, the formed 2S,4R-Monatin was quantified, and its concentration was 22 mM (44% of yield).

SpAld was prepared by the following method.

A DNA fragment including a SpAld gene was amplified by PCR using plasmid DNA, ptrpSpALD described in Example 5 in JP 2006-204285-A as the template. The primer SpAld-f-NdeI (5'-GGAATTCCATATGACCCAGACGCGCCT-CAA-3': SEQ ID NO:12) and the primer SpAld-r-HindIII (5'-GCCCAAGCTTTCAGTACCCCGCCAGTTCGC-3':
SEQ ID NO:13) were used. E. coli rare codons (6L-ctc, 13L-ctc, 18P-ccc, 38P-ccc, 50P-ccc, 77P-ccc, 81P-ccc and 84R-cga) in an aldolase gene were converted to 6L-ctg, 13L-ctg, 18P-ccg, 38P-ccg, 50P-ccg, 77P-ccg, 81P-ccg and 84R-cgc, respectively. When 6L was converted, the primer 6L-f (5'-ACCCAGACGCGCCTGAACGGCATCATCCG-3':
SEQ ID NO:14) and the primer 6L-r (5'-CGGATGATGC-CGTTCAGGCGCGTCTGGGT-3': SEQ ID NO:15) were used. When 13L was converted, the primer 13L-f (5'-AT-CATCCGCGCTCTGGAAGCCGGCAAGCC-3': SEQ ID NO:16) and the primer 13L-r (5'-GGCTTGCCGGCTTCCA-GAGCGCGGATGAT-3': SEQ ID NO:17) were used. When 18P was converted, the primer 18P-f (5'-GAAGCCG-GCAAGCCGGCTTTCACCTGCTT-3': SEQ ID NO:18) and the primer 18P-r (5'-AAGCAGGTGAAAGCCGGCTTGC-CGGCTTC-3': SEQ ID NO:19) were used. When 38P was converted, the primer 38P-f (5'-CTGACCGATGCCCCG-TATGACGGCGTGGT-3': SEQ ID NO:20) and the primer 38P-r (5'-ACCACGCCGTCATACGGGGCATCGGTCAG-3': SEQ ID NO:21) were used. When 50P was converted, the primer 50P-f (5'-ATGGAGCACAACCCGTACGAT-GTCGCGGC-3': SEQ ID NO:22) and the primer 50P-r (5'-GCCGCGACATCGTACGGGTTGTGCTCCAT-3': SEQ ID NO:23) were used. When 77P, 81P and 84P were converted, the primer 77P-81P-84R-f (5'-CGGTCGCGCCGTCGGT-CACCCCGATCGCGCGCATCCCGGCCA-3': SEQ ID NO:24) and the primer 77P-81P-84R-r (5'-TGGCCGGGAT-GCGCGCGATCGGGGTGACCGACGGCGCGACCG-3': SEQ ID NO:25) were used. PCR was performed using KOD-plus (Toyobo) under the following condition.

| 1 cycle | 94° C., 2 min |
|---|---|
| 25 cycles | 94° C., 15 sec |
| | 55° C., 15 sec |
| | 68° C., 60 sec |
| 1 cycle | 68° C., 60 sec |
| | 4° C. |

The resulting DNA fragment of about 900 bp was treated with the restriction enzymes NdeI and HindIII, and ligated to pSFN Sm_Aet (Examples 1, 6 and 12 in International Publication WO2006/075486) likewise treated with NdeI and HindIII. E. coli JM109 was transformed with this solution containing the ligated product. The objective plasmid was extracted from ampicillin resistant strains, and this plasmid was designated as pSFN-SpAld.

One loopful of E. coli JM 109/pSFN-SpAld that was the bacterial strain carrying the constructed plasmid pSFN-SpAld was inoculated to 50 mL of LB liquid medium containing 100 mg/L of ampicillin in a 500 mL Sakaguchi flask, and cultured with shaking at 36° C. for 8 hours. After the termination of the culture, 0.0006 mL of the obtained cultured medium was added to 300 mL of a seed liquid medium (10 g of glucose, 5 g of ammonium sulfate, 1.4 g of potassium dihydrogen phosphate, 0.45 g of hydrolyzed soybeans as a nitrogen amount, 1 g of magnesium sulfate heptahydrate, 0.02 g of iron (II) sulfate heptahydrate, 0.02 g of manganese (II) sulfate pentahydrate, 1 mg of thiamin hydrochloride, 0.1 mL of Disfoam GD-113K (NOF Corporation), pH 6.3, made to one liter with water) containing 100 mg/L of ampicillin in a 1000 mL volume of jar fermenter, and seed cultivation was started. The seed cultivation was performed at 33° C. with ventilation at 1/1 vvm with stirring at 700 rpm and controlling pH at 6.3 with ammonia until glucose was consumed. Then, 15 mL of the cultured medium obtained as above was added to 285 mL of a main liquid medium (15 g of glucose, 5 g of ammonium sulfate, 3.5 g of phosphoric acid, 0.45 g of hydrolyzed soybeans as the nitrogen amount, 1 g of magnesium sulfate heptahydrate, 0.05 g of iron (II) sulfate heptahydrate, 0.05 g of manganese (II) sulfate pentahydrate, 1 mg of thiamin hydrochloride, 0.1 mL of Disfoam GD-113K (NOF Corporation), pH 6.3, made to 0.95 L with water) containing 100 mg/L of ampicillin in a 1000 mL volume of jar fermenter, and main cultivation was started. The main cultivation was performed at 36° C. with ventilation at 1/1 vvm, pH was controlled to 6.3 with ammonia, and stirring was controlled at 700 rpm or more so that the concentration of dissolved oxygen was 5% or more. After glucose contained in the main medium was consumed, the cultivation was continued with dropping a glucose solution at 500 g/L for total 50 hours.

Microbial cells were collected by centrifugation from 100 mL of the obtained cultured medium, washed with and suspended in 20 mM Tris-HCl (pH 7.6), and disrupted by sonication at 4° C. for 30 minutes. Microbial cell debris was removed from the disrupted solution by centrifugation, and the obtained supernatant was used as a soluble fraction.

The above soluble fraction was applied to the anion exchange chromatography column HiLoad 26/10 Q Sepharose HP (supplied from GE health Care Bioscience, CV=53 mL) equilibrated with 20 mM Tris-HCl (pH 7.6), and adsorbed to the carrier. The proteins that had not been adsorbed to the carrier (unadsorbed proteins) were washed out with 20 mM Tris-HCl (pH 7.6), and subsequently, the adsorbed proteins were eluted by linearly changing the concentration of NaCl from 0 mM to 500 mM at a flow rate of 8 mL/minute. Fractions having an aldolase activity were combined, and ammonium sulfate and Tris-HCl (pH 7.6) were added thereto at final concentrations of 1 M and 20 mM, respectively.

The resulting solution was applied to the hydrophobic chromatography column HiLoad 16/10 Phenyl Sepharose HP (supplied from GE health Care Bioscience, CV=20 mL) equilibrated with 1 M ammonium sulfate, 20 mM Tris-HCl (pH 7.6), and adsorbed to the carrier. The proteins that had not been adsorbed to the carrier were washed out with 1 M ammonium sulfate, 20 mM Tris-HCl (pH 7.6), and subsequently, the adsorbed proteins were eluted by linearly changing the concentration of ammonium sulfate from 1 M to 0 M at a flow rate of 3 mL/minute. The fractions having the aldolase activity were combined and concentrated using Amicon Ultra-15 10K (Millipore). The obtained concentrated solution was diluted with 20 mM Tris-HCl (pH 7.6), and used as a SpAld solution. The aldolase activity was measured as an aldol degradation activity using PHOG as the substrate under the following condition.

Reaction condition: 50 mM Phosphate buffer (pH 7.0), 2 mM PHOG, 0.25 mM NADH, 1 mM $MgCl_2$, 16 U/mL lactate dehydrogenase, an absorbance at 340 nm was measured at 25° C.

pTB2 strain was prepared by the following method.

One loopful of pTB2 strain described in Example 2 in International Publication WO2009/028338 was inoculated to 50 mL of the TB liquid medium containing 100 mg/L of ampicillin in a 500 mL Sakaguchi flask, and cultured with shaking at 37° C. for 16 hours. The obtained cultured medium was used as the cultured medium of pTB2 strain in the Sakaguchi flask (TB medium).

Example 7

Synthesis of 2S,4R-Monatin by Microorganisms Having 2S,4R-Monatin Forming Activity (1) Synthesis of 2S,4R-Monatin by Bacteria Rhizobium radiobacter LAT1, Rhizobium radiobacter AJ11568, Dietzia maris AJ2788, Stenotrophomonas sp. AJ3447, Stenotrophomonas sp. AJ13127, Pseudomonas chlororaphis subsp. chlororaphis NBRC3904, Micrococcus luteus NBRC3067, Stenotrophomonas sp. AJ11634, Pseudomonas putida NBRC12668, Ochrobactrum pseudogrignonense AJ3735, Stenotrophomonas sp. AJ1591, Stenotrophomonas sp. AJ3839, Brevundimonas diminuta AJ3958, Pseudomonas citronocllolis ATCC13674, Arthrobacter sp. AJ1436, Rhizobium sp. AJ12469, Rhizobium radiobacter AJ2777, Burkholderia sp. AJ3084, Microbacterium sp. AJ2787, Pseudomonas taetrolens ATCC4683, Rhizobium radiobacter ATCC4452, Rhizobium radiobacter AJ2557, Carnimonas sp. AJ3230, Rhizobium radiobacter NBRC12667, Pseudomonas fragi NBRC3458, Rhizobium radiobacter NBRC12664, Corynebacterium ammoniagenes NBRC12072, Pseudomonas sp. AJ1594, Rhizobium radiobacter ATCC6466, Pseudomonas synxantha NBRC3912, Rhizobium radiobacter ATCC4720, or Pseudomonas sp. AJ2438 was applied onto a nutrient broth (NB) agar medium or the CM2G agar medium (10 g/L of yeast extract, 10 g/L of polypeptone, 5 g/L of glucose, 5 g/L of NaCl, 15 g/L of agar, pH 7.0), and cultured at 30° C. for 2 days.

One loopful of the obtained microbial cells was inoculated to 3 mL of an enzyme production medium (10 g/L of yeast extract, 10 g/L of polypeptone, 1 g/L of glucose, 3 g/L of dipotassium hydrogen phosphate, 1 g/L of potassium dihydrogen phosphate, 0.1 g/L of magnesium sulfate heptahydrate, 5 g/L of ammonium sulfate) in a test tube, which was then cultured with shaking at 30° C. for 16 hours. The microbial cells were collected from 2 mL of the cultured medium by centrifugation, washed with and suspended in 20 mM Tris-HCl (pH 7.6) to prepare 1 mL of a microbial cell suspension.

Then, 1 g of glass beads (0.1 mm) was added to 1 mL of this microbial cell suspension, and the microbial cells were disrupted using the multi beads shocker (Yasui Kikai Co., Ltd.). The resulting disrupted cell solution was centrifuged to use a supernatant as a microbial cell extract.

The reaction of synthesizing 2S,4R-Monatin and the quantification of 2S,4R-Monatin were performed in the same manner as in Example 1, and amounts of the 2S,4R-Monatin which was formed were as follows (Table 2)

TABLE 2

Amount of 2S,4R-Monatin which was produced

| Microorganism | Amount of 2S,4R-Monatin which was formed |
|---|---|
| Rhizobium radiobacter LAT1 | 3.8 mM |
| Rhizobium radiobacter AJ11568 | 3.5 mM |
| Dietzia maris AJ2788 | 3.2 mM |
| Stenotrophomonas sp. AJ3447 | 2.7 mM |
| Stenotrophomonas sp. AJ13127 | 2.7 mM |
| Pseudomonas chlororaphis subsp. chlororaphis NBRC3904 | 2.6 mM |
| Micrococcus luteus NBRC3067 | 2.3 mM |
| Stenotrophomonas sp. AJ11634 | 2.2 mM |
| Pseudomonas putida NBRC12668 | 2.2 mM |
| Ochrobactrum pseudogrignonense AJ3735 | 2.2 mM |
| Stenotrophomonas sp. AJ1591 | 2.1 mM |
| Stenotrophomonas sp. AJ3839 | 2.1 mM |
| Brevundimonas diminuta AJ3958 | 2.0 mM |
| Pseudomonas citronocllolis ATCC13674 | 1.9 mM |
| Arthrobacter sp. AJ1436 | 1.7 mM |
| Rhizobium sp. AJ12469 | 1.6 mM |
| Rhizobium radiobacter AJ2777 | 1.5 mM |
| Burkholderia sp. AJ3084 | 1.5 mM |
| Microbacterium sp. AJ2787 | 1.5 mM |
| Pseudomonas taetrolens ATCC4683 | 1.4 mM |
| Rhizobium radiobacter ATCC4452 | 1.4 mM |
| Rhizobium radiobacter AJ2557 | 1.4 mM |
| Carnimonas sp. AJ3230 | 1.4 mM |
| Rhizobium radiobacter NBRC12667 | 1.3 mM |
| Pseudomonas fragi NBRC3458 | 1.3 mM |
| Rhizobium radiobacter NBRC12664 | 1.3 mM |
| Corynebacterium ammoniagenes NBRC12072 | 1.2 mM |
| Pseudomonas sp. AJ1594 | 1.2 mM |
| Rhizobium radiobacter ATCC6466 | 1.2 mM |
| Pseudomonas synxantha NBRC3912 | 1.1 mM |
| Rhizobium radiobacter ATCC4720 | 1.1 mM |
| Pseudomonas sp. AJ2438 | 1.0 mM |

(2) Synthesis of 2S,4R-Monatin by Actinomycete

*Nocardia globerula* ATCC21022 was applied onto a YMPG agar medium (3 g/L of yeast extract, 3 g/L of malt extract, 5 g/L of polypeptone, 10 g/L of glucose, 15 g/L of agar, pH 7.0), and cultured at 30° C. for 2 days.

One loopful of the obtained microbial cells was inoculated to 3 mL of a YMPG medium (3 g/L of yeast extract, 3 g/L of malt extract, 5 g/L of polypeptone, 10 g/L of glucose, pH 7.0) in a test tube, and cultured with shaking at 30° C. for 16 hours. The microbial cells were collected from 2 mL of the cultured medium by centrifugation, washed with and suspended in 20 mM Tris-HCl (pH 7.6) to prepare 1 mL of a microbial cell suspension.

Then, 1 g of glass beads (0.1 mm) was added to 1 mL of this microbial cell suspension, and the microbial cells were disrupted using the multi beads shocker (Yasui Kikai Co., Ltd.). The resulting disrupted cell solution was centrifuged to use a supernatant as a microbial cell extract.

The reaction of synthesizing 2S,4R-Monatin and the quantification of 2S,4R-Monatin were performed in the same manner as in Example 1, and amount of the 2S,4R-Monatin which was formed was as follows (Table 3)

TABLE 3

Amount of 2S,4R-Monatin which was formed

| Microorganism | Amount of 2S4R-Monatin which was formed |
|---|---|
| Nocardia globerula ATCC21022 | 0.57 mM |

(3) Synthesis of 2S,4R-Monatin by Yeast

*Lodderomyces elongisporus* CBS2605, *Candida norvegensis* NBRC0970, *Candida inconspicua* NBRC0621 or *Yarrowia lypolytica* NBRC0746 was applied onto a YPD agar medium (10 g/L of yeast extract, 20 g/L of polypeptone, 20 g/L of glucose, 15 g/L of agar), and cultured at 30° C. for 2 days.

One loopful of the obtained microbial cells was inoculated to 3 mL of a YPD medium (10 g/L of yeast extract, 20 g/L of polypeptone, 20 g/L of glucose) in a test tube, and cultured with shaking at 30° C. for 16 hours. The microbial cells were collected from 2 mL of the cultured medium by centrifugation, washed with and suspended in 20 mM Tris-HCl (pH 7.6) to prepare 1 mL of a microbial cell suspension.

Then, 1 g of glass beads (0.5 mm) was added to 1 mL of this microbial cell suspension, and the microbial cells were disrupted using the multi beads shocker (Yasui Kikai Co., Ltd.). The resulting disrupted cell solution was centrifuged to use a supernatant as a microbial cell extract.

The reaction of synthesizing 2S,4R-Monatin and the quantification of 2S,4R-Monatin were performed in the same manner as in Example 1, and amount of the 2S,4R-Monatin which was formed were as follows (Table 4)

TABLE 4

Amount of 2S,4R-Monatin which was formed

| Microorganism | Amount of 2S4R-Monatin which was formed |
|---|---|
| Lodderomyces elongisporus CBS2605 | 0.57 mM |
| Candida norvegensis NBRC0970 | 0.55 mM |
| Candida inconspicua NBRC0621 | 0.52 mM |
| Yarrowia lypolytica NBRC0746 | 0.52 mM |

Example 8

Production of 2S,4R-Monatin Potassium Salt Dihydrate

After 149.00 g of ethanol was added to a reduction reaction concentrated solution (containing 36.62 g (125.28 mmol) of Monatin, (2S,4R):(2R,4R)=32:68), 0.25 g of 2R,4R-Monatin potassium salt monohydrate was added as seed crystals, and the mixture was stirred at 56° C. for 4 hours to perform preferential crystallization of the 2R,4R-Monatin potassium salt monohydrate. The crystallized crystals were separated by filtration (wet crystals 31.27 g) to obtain 225.80 g of a mother solution (containing 22.41 g (76.68 mmol) of Monatin, (2S,4R):(2R,4R)=53:47). This mother solution was cooled to 10° C. and stirred for 5 hours to crystallize 2S,4R-Monatin potassium salt dihydrate. The crystals were separated by filtration (wet crystals 32.74 g), and dried under reduced pressure to yield 9.88 g (15.68 mmol) of the objective 2S,4R-Monatin potassium salt dihydrate (HPLC purity: 55.5%). Then, 9.35 g of the crude crystals were dissolved in 25.37 g of water, and 58.99 g of ethanol was added to this dissolved solution, which was stirred at 25° C. for 5 hours to refine the 2S,4R-Monatin potassium salt dehydrate by crystallization. The crystals were separated by filtration (wet crystals 4.49 g), and dried under reduced pressure to yield 3.75 g (9.62 mmol) of the objective 2S,4R-Monatin potassium salt dihydrate (HPLC purity: 96.0%).

A water content and a potassium content of the obtained crystals (2S,4R-Monatin potassium salt dihydrate) were analyzed by a water measurement method and a cation analysis method using ion chromatography. Details of the performed water measurement method and cation analysis method are shown below.
(Water Measurement Method)
Measurement apparatus: Hiranuma Automatic Water Measurement Apparatus AQV-2000 (supplied from Hiranuma Sangyo Corporation)
Measurement condition: Titration solution=Hydranal Composite 5K (supplied from Riedel de Haen)
(Cation Analysis Method)
 Apparatus: Tosoh IC2001
 Column: TSKgel SuperIC-Cation (4.6×150 mm)
 Guard column: TSKgel SuperIC-Cation (1 cm)
Suppress gel: TSKgel TSKsuppressIC-C
Column temperature: 40° C.
Eluant flow: 0.7 mL/minute
Sample injection amount: 30 μL
Detection: Electric conductivity
Eluant composition: 2.2 mM methanesulfonic acid+1.0 mM 18-crown-6-ether+0.5 mM histidine mixed aqueous solution
$^1$H NMR (400 MHz, D$_2$O) δ: 2.11 (dd, J=19.0, 27.0 Hz, 1H), 2.39 (dd, J=5.0, 27.0 Hz, 1H), 3.14 (s, 2H), 3.90 (dd, J=5.0, 19.0 Hz, 1H), 7.06 (m, 1H), 7.13 (m, 1H), 7.15 (s, 1H), 7.40 (d, 8.5 Hz, 1H), 7.6 (d, 8.5 Hz, 1H)
ESI-MS Calculated value: C$_{14}$H$_{16}$N$_2$O$_5$=292.11
ESI-MS Analyzed value: C$_{14}$H$_{16}$N$_2$O$_5$=290.9 [M-H]$^-$ Example 9

Isomerization Reaction Using 5-Nitrosalicylaldehyde 0.15 g (0.38 mmol) of the 2S,4R-Monatin potassium salt dihydrate was added to 10.0 g of an aqueous solution of 70% ethanol, and completely dissolved at 60° C. 7.6 mg (0.045 mmol) of 5-nitrosalicylaldehyde and 7.5 μL (0.13 mmol) of acetic acid were added to that dissolved solution, and stirred at 60° C. for 48 hours. The reaction solution was analyzed and quantified by HPLC, and a molar ratio of 2S,4R-Monatin and 2R,4R-Monatin in the reaction solution was 1:2.1.

Example 10

Isomerization Reaction Using Pyridoxal Hydrochloride Salt 0.15 g (0.38 mmol) of the 2S,4R-Monatin potassium salt dihydrate was added to 10.0 g of the aqueous solution of 70% ethanol, and completely dissolved at 60° C. 9.1 mg (0.045 mmol) of pyridoxal hydrochloride and 7.5 μL (0.13 mmol) of acetic acid were added to that dissolved solution, and stirred at 60° C. for 48 hours. The reaction solution was analyzed and quantified by HPLC, and the molar ratio of 2S,4R-Monatin and 2R,4R-Monatin in the reaction solution was 1:1.3.

Example 11

Isomerization Reaction Using Pyridoxal 5-Phosphate Monohydrate 0.15 g (0.38 mmol) of the 2S,4R-Monatin potassium salt dihydrate was added to 10.0 g of the aqueous solution of 70% ethanol, and completely dissolved at 60° C. 12.8 mg (0.048 mmol) of pyridoxal 5-phosphate monohydrate and 7.5 μL (0.13 mmol) of acetic acid were added to that dissolved solution, and stirred at 60° C. for 48 hours. The reaction solution was analyzed and quantified by HPLC, and the molar ratio of 2S,4R-Monatin and 2R,4R-Monatin in the reaction solution was 1:1.1.

Example 12

Isomerization Reaction Using Salicylaldehyde 0.15 g (0.38 mmol) of the 2S,4R-Monatin potassium salt dihydrate was added to 10.0 g of the aqueous solution of 70% ethanol, and completely dissolved at 60° C. 5.3 mg (4.6 μL, 0.043 mmol) of salicylaldehyde and 7.5 μL (0.13 mmol) of acetic acid were added to that dissolved solution, and stirred at 60° C. for 48 hours. The reaction solution was analyzed and quantified by HPLC, and the molar ratio of 2S,4R-Monatin and 2R,4R-Monatin in the reaction solution was 1:0.6.

Example 13

Isomerization Reaction Using 3,5-Dichlorosalicylaldehyde 0.15 g (0.38 mmol) of the 2S,4R-Monatin potassium salt dihydrate was added to 10.0 g of the aqueous solution of 70% ethanol, and completely dissolved at 60° C. 8.1 mg (0.042 mmol) of 3,5-dichlorosalicylaldehyde and 7.5 μL (0.13 mmol) of acetic acid were added to that dissolved solution, and stirred at 60° C. for 48 hours. The reaction solution was analyzed and quantified by HPLC, and the molar ratio of 2S,4R-Monatin and 2R,4R-Monatin in the reaction solution was 1:1.5.

Example 14

Production of 2R,4R-Monatin Potassium Salt Monohydrate by Isomerization-Crystallization Using 2S,4R-Monatin Potassium Salt Dihydrate as Starting Material The 2S,4R-Monatin potassium salt dihydrate is added to an aqueous solution of 20% ethanol and completely dissolved at 60° C. 5 molar percent 5-Nitrosalicylaldehyde relative to the 2S,4R-Monatin, and 30 molar percent acetic acid relative to the 2S,4R-Monatin are added to this dissolved solution, and stirred for 48 hours. Ethanol at a final concentration of 70% is added to this reaction solution (2S,4R-Monatin:2R,4R-Monatin=1:2.1), subsequently one percent 2R,4R-Monatin potassium salt monohydrate relative to the 2R,4R-Monatin in the reaction solution is added as the seed crystals thereto, and the mixture is stirred at 60° C. for 48 hours to perform the isomerization-crystallization. The crystallized crystals are separated by filtration, and dried under reduced pressure to yield the objective 2R,4R-Monatin potassium salt monohydrate.

Example 15

Isomerization Reaction Using Glyoxylic Acid 0.15 g (0.38 mmol) of the 2S,4R-Monatin potassium salt dihydrate was added to 10.0 g of the aqueous solution of 70% ethanol, and completely dissolved at 60° C. 5.1 mg (0.069 mmol) of glyoxylic acid and 7.5 μL (0.13 mmol) of acetic acid were added to that dissolved solution, and stirred at 60° C. for 48 hours. The reaction solution was analyzed and quantified by HPLC, and the molar ratio of 2S,4R-Monatin and 2R,4R-Monatin in the reaction solution was 1:0.07

Example 16

Production of L-Amino Acid Aminotransferase (LAT) Mutants Derived from AJ1616 Strain and Measurement of Specific Activity for Various Keto Acids (1) Production of Mutated LAT-Expressing Plasmid by Site-Directed Mutagenesis Plasmids expressing a mutated LAT derived from AJ1616 strain were produced by site-directed mutagenesis in accordance with protocols of QuickChange Site-Directed Mutagenesis Kit supplied from Stratagene. One set of primers designed so that a mutation (substitution) was introduced into a target nucleotide residue and became complementary in respective chains of double stranded DNA was synthesized. The produced mutants and the nucleotide sequences of the primers used for the production of the mutants are shown in Tables 5 and 6, respectively. The mutant plasmids were produced using pET22-AJ1616LAT-His(C) as the template under the following PCR condition:

| | |
|---|---|
| 1 cycle | 95° C., 1 min |
| 18 cycles | 95° C., 30 sec |
| | 55° C., 1 min |
| | 68° C., 8 min |
| after completion of the cycles | 4° C. |

The template pET22-AJ1616LAT-His(C) was cleaved by treating with the restriction enzyme Dpn I (37° C., one hour) cleaving by recognition of methylated DNA, and subsequently *E. coli* JM109 was transformed with the resulting reaction solution. The plasmid was collected from the transformant, and it was confirmed by sequencing the nucleotides that the mutation (substitution) of the target nucleotide residue had been introduced. ID136 that was a double mutant of S258G/I289A was constructed by making an S258G mutant plasmid followed by repeating the same manipulation using the primers for introducing an I289A mutation. ID189 that was a double mutant of K39R/T288G was constructed by making an ID166 (T288G) mutant plasmid followed by repeating the same manipulation using the primers for introducing a K39R mutation. ID296 that was a double mutant of Q287E/T288G was constructed by making a T288G mutant plasmid followed by repeating the same manipulation using the primers for introducing a Q287E/T288G mutation.

TABLE 5

Mutants which were prepared

| ID | Mutants |
|---|---|
| ID136 | S258G/I289A |
| ID166 | T288G |
| ID189 | K39R/T288G |
| ID296 | Q287E/T288G |

TABLE 6

Nucleotide sequences of primers used for introducing mutation

| Mutants | Primer names | Nucleotide sequences (SEQ ID NOs) |
|---|---|---|
| K39R | K39R_FW | gacatgtctagagggcgtccttcaccaaaacag (SEQ ID NO: 26) |
| | K39R_RV | ctgttttggtgaaggacgccctctagacatgtc (SEQ ID NO: 27) |
| S258G | S258G_FW | gttcgcctctactggtaaaattacgttccc (SEQ ID NO: 28) |
| | S258G_RV | gggaacgtaattttaccagtagaggcgaac (SEQ ID NO: 29) |
| T288G | T288G_FW | cagctatcagttcaaggcattgggccagataaaatc (SEQ ID NO: 30) |
| | T288G_RV | gattttatctggcccaatgccttgaactgatagctg (SEQ ID NO: 31) |
| I289A | I289A_FW | ctatcagttcaaaccgctgggccagataaaatc (SEQ ID NO: 32) |
| | I289A_RV | gattttatctggcccagcggtttgaactgatag (SEQ ID NO: 33) |
| Q287E/T288G | Q287E_T288G_FW | Cagctatcagttgaaggcattgggccag (SEQ ID NO: 34) |
| | Q287E_T288G_RV | ctggcccaatgccttcaactgatagctg (SEQ ID NO: 35) |

(2) Expression and Purification of Mutated LAT

E. coli JM109 (DE3) was transformed with the obtained mutant AJ1616 LAT-expressing plasmid to produce a mutant AJ1616 LAT-expressing strain. Microbial cells of the mutant AJ1616 LAT-expressing strain pET22-AJ1616LATmut-His (C)/E. coli JM109 (DE3) that was grown on an LB-amp (100 mg/L) plate were inoculated to 100 mL of Overnight Express Instant TB Medium (Novagen) containing 100 mg/L of ampicillin, and cultured with shaking at 37° C. for 16 hours using a Sakaguchi flask. After completion of the cultivation, the microbial cells were collected from the resulting medium by centrifugation, washed with and suspended in 20 mM Tris-HCl (pH 7.6), 300 mM NaCl and 10 mM imidazole, followed by being sonicated. Microbial cell debris was removed from the disrupted suspension by centrifugation, and the resulting supernatant was used as a soluble fraction. The resulting soluble fraction was applied onto a His-tagged protein purification column, His TALON superflow 5 ml Cartridge (Clontech) equilibrated with 20 mM Tris-HCl (pH 7.6), 300 mM NaCl and 10 mM imidazole, and absorbed to the carrier. Proteins that had not been absorbed to the carrier (unabsorbed proteins) were washed out with 20 mM Tris-HCl (pH 7.6), 300 mM NaCl and 10 mM imidazole, and subsequently, the absorbed proteins were eluted using 20 mM Tris-HCl (pH 7.6), 300 mM NaCl and 150 mM imidazole at a flow rate of 5 mL/minute. Resulting fractions were combined, and the combined fraction was concentrated using Amicon Ultra-15 30K (Millipore). The concentrated fraction was diluted with 20 mM Tris-HCl (pH 7.6) to use as a mutant AJ1616 LAT solution. If necessary, the purification was performed by increasing the amount of the medium and the number of the His TALON columns to be connected.

(3) Measurement of Protein Concentration

A protein concentration was measured using a protein assay CBB solution (diluted to 5 folds for the use) supplied from Nacalai Tesque. The protein concentration was calculated by preparing a standard curve using solutions containing 0.05, 0.1, 0.25 and 0.5 mL/mL BSA as the standards.

(4) Measurement of Activity for L-Asp/α-KG, L-Asp/PA and L-Asp/±MHOG by Colorimetric Assay The activity of AJ1616 LAT for various substrates was measured. 100 mM L-Asp was used as an amino donor substrate in a transamination reaction, and a specific activity for 10 mM various keto acids was measured by a colorimetric assay.

Activity for L-Asp/α-KG (α-ketoglutaric acid): measured in 100 mM L-Asp-Na, 10 mM α-KG-2Na, 50 µM PLP, 100 mM Tris-HCl (pH 8.0), 0.25 mM NADH, and 2 U/mL MDH at 25° C. The activity was calculated from the reduction of absorbance at 340 nm. Malic dehydrogenase from porcine heart (Sigma) was used as MDH. The activity for L-Asp/α-KG is shown in the column "α-KG" of the aminotransferase activity in Table 9.

Activity for L-Asp/PA: measured in 100 mM L-Asp-Na, 10 mM PA-2Na, 50 µM PLP, 100 mM Tris-HCl (pH 8.0), 0.25 mM NADH, and 2 U/mL MDH (same as above) at 25° C. The activity was calculated from the reduction of the absorbance at 340 nm. The activity for L-Asp/PA is shown in the column "PA" of the aminotransferase activity in Table 9.

Activity for L-Asp/(±)-MHOG (4-hydroxy-4-methyl-2-ketoglutarate): measured in 100 mM L-Asp-Na, 10 mM (±)-MHOG, 50 µl PLP, 100 mM Tris-HCl (pH 8.0), 0.25 mM NADH, 2 U/mL MDH and 10 U/mL LDH at 25° C. The activity was calculated from the reduction of the absorbance at 340 nm. D-Lactate dehydrogenase from Leuconostoc mesenteroides (Oriental Yeast) was used as LDH. LDH was added in order to remove PA in a trace amount contaminated in (±)-MHOG. The activity for L-Asp/(±)-MHOG is shown in the column "(±)-MHOG" of the aminotransferase activity in Table 9.

(5) Measurement of Activity for L-Asp/4R-IHOG and L-Asp/IPA

The activity of forming 2S,4R-Monatin from 4R-IHOG, which was an objective activity, and the activity of forming a byproduct L-Trp from IPA were measured. 100 mM L-Asp was used as the amino donor substrate in the transamination reaction, the transamination reaction to 10 mM keto acid was performed. The amount of formed amino acid was quantified by UPLC or HPLC, and the specific activity was calculated.

Activity for L-Asp/4R-IHOG (10 mM): measured in 100 mM L-Asp-Na, 10 mM 4R-IHOG (containing 4S-IHOG in a trace amount), 50 µM PLP, and 100 mM Tris-HCl (pH 8.0) at 25° C. Formed 2S,4R-Monatin and 2S,4S-Monatin were quantified by UPLC analysis. The reaction was stopped using a 200 mM citrate Na solution (pH 4.5). The activity for L-Asp/4R-IHOG is shown in the column "4R-IHOG" of the aminotransferase activity in Table 9.

Activity for L-Asp/IPA: measured in 100 mM L-Asp-Na, 10 mM IPA, 50 µM PLP, and 100 mM Tris-HCl (pH 8.0) (pH was adjusted to 8.0 with 1 N NaOH after preparing the reaction solution) at 25° C. Formed Trp was quantified by the UPLC analysis. The reaction was stopped using the 200 mM citrate Na solution (pH 4.5). The activity for L-Asp/IPA is shown in the column "IPA" of the aminotransferase activity in Table 9.

Formed Monatin and Trp were quantified using ACQUITY UPLC system supplied from Waters. A measurement condition is shown below. The reaction in 0.2 mL was performed for 15 minutes, and then stopped. The reaction solution after stopping the reaction was centrifuged, and then about 0.2 mL of the supernatant was subjected to the UPLC analysis. Results obtained by measurement using serial dilutions in which the concentrations of the samples and a blank fell into the range of 0.01 to 0.05 mM were employed as activity values.

TABLE 7

| UPLC | |
|---|---|
| Column: | ACQUITY UPLC HSS T3 2.1 × 50 mm |
| Column Temp.: | 40° C. |
| Sample Temp.: | 4° C. |
| Detection: | UV 210 nm |
| Injection vol.: | 5 µl |
| Mobile Phase A: | 20 mM KH2PO4 (Filt.) |
| Mobile Phase B: | ACN |
| Flow rate: | 0.5 ml/min |
| Method: | 20 mM KH2PO4__05__HSS |

| Time (min) | A (%) | B (%) |
|---|---|---|
| 0 | 96 | 4 |
| 1.9 | 96 | 4 |
| 2.0 | 60 | 40 |
| 2.2 | 60 | 40 |
| 2.3 | 96 | 4 |
| 3.0 | 96 | 4 |

2S,4R-Monatin, 2S,4S-Monatin and Trp can be quantified separately at 1.1 minutes, 1.5 minutes and 1.3 minutes, respectively.

The quantification using HPLC under the following analysis condition was also performed in conjunction with the above.

HPLC condition (quantification condition for Monatin, Trp, IPA, IAA (indole acetate), IAD (indole aldehyde))

Column: CAPCELL PAK C18 TYPE MGII 3 4.6 mm×150 mm (Shiseido)
Column temperature: 40° C.
Detection wavelength: 280 nm
Flow rate: 1.0 mL/minute
Mobile phase: A: 20 mM $KH_2PO_4/CH_3CN=100/5$, B: $CH_3CN$

TABLE 8

| Time (min) | A (%) | B (%) |
|---|---|---|
| 0 | 100 | 0 |
| 6 | 100 | 0 |
| 11 | 90 | 10 |
| 25 | 90 | 10 |
| 26 | 100 | 0 |
| 30 | 100 | 0 |

(6) Results of Measuring Specific Activity of AJ1616 Strain LAT Mutants Against Various Keto Acids The results of the specific activity against 10 mM keto acid are shown in Table 9, which were measured with the produced mutant and L-Asp as the amino donor. The objective activity of forming 2S,4R-Monatin using 4R-IHOG as the substrate was enhanced in any of the produced mutants. Concerning relative values of side reaction relative to the objective activity, the activity of producing the byproduct L-Trp, the activity of producing the byproduct MHG (4-hydroxy-4-methyl glutamate), and the activity of producing the byproduct L-Ala, relative to the objective activity (activity of forming 2S,4R-Monatin) were reduced in any of the mutants.

TABLE 9

Specific activities of mutants relative to various keto acids.

| ID | Mutants | Aminotransferase activity (U/mg) | | | | | Relative values of side reaction relative to activity of forming 2S,4R-Monatin (SR) | | |
|---|---|---|---|---|---|---|---|---|---|
| | | α-KG | PA | ±MHOG | 4R-IHOG | IPA | Trp/SR | MHG/SR | Ala/SR |
| WT | WT | 235 | 0.45 | 1.3 | 0.92 | 0.11 | 0.12 | 1.45 | 0.49 |
| 136 | S258G/I289A | 14 | 0.06 | 0.09 | 6.8 | 0.54 | 0.08 | 0.01 | 0.01 |
| 166 | T288G | 184 | 0.23 | 2.1 | 6.7 | 0.28 | 0.04 | 0.31 | 0.03 |
| 189 | K39R/T288G | 90 | 0.23 | 1.6 | 9.7 | 0.31 | 0.03 | 0.17 | 0.02 |
| 296 | Q287E/T288G | 50 | 0.18 | 1.5 | 11.1 | 0.24 | 0.02 | 0.14 | 0.02 |

Example 17

Construction of *E. coli* JM109 ΔaspC Strain and Production of Broth Containing Expressed Deaminase

*E. coli* JM109 ΔaspC was constructed by following methods. *E. coli* JM109/pKD46 was cultured at 30° C. overnight on the LB-amp (100 mg/L) plate. Obtained microbial cells were inoculated to 50 mL of LB (containing 100 mg/L of Amp and 10 mM L-arabinose). This was cultured with shaking at 30° C. using the Sakaguchi flask. When $OD_{610}$ became about 0.6, a cultivation temperature was changed to 37° C. and the cultivation was continued with shaking for additional one hour. The microbial cells were collected from the resulting medium by centrifugation, washed with 10% glycerol, and collected again by centrifugation. These were suspended in 10% glycerol to use as competent cells.

Amplification by PCR was performed with pMW118-attL-cat-attR as the template using the primer aspC-L1 (5'-TTTGAGAACATTACCGCCGCTCCTGC-CGACCCGATTCTGGGCtgaagcctgctttttta t-3': SEQ ID NO:36) and the primer aspC-R1 (5'-CAGCACTGCCA-CAATCGCTTCGCACAGCGGAGCCATGT-TATCcgctcaagttagtataa a-3: SEQ ID NO:37). The resulting PCR product was extracted from agarose to use as a DNA fragment for aspC gene disruption. PCR was performed using KOD-plus-ver.2 (Toyobo).

The competent cells were transformed with the purified DNA fragment, and an objective transformant was selected on an LB-Cm (20 mg/L) plate at 37° C. It was confirmed by colony PCR that attL-cat-attR was inserted into the aspC gene region of the transformant. The primers used are the primer aspC-up (5'-AACCTCTTGGCAACGGTAAAAAAGCT-GAAC-3': SEQ ID NO: 38), the primer attL-1 (5'-TAGT-GACCTGTTCGTTGC-3': SEQ ID NO:39), the primer aspC-down (5'-GCCTGCGCAAAGTCGTATGTTTGGTCTGGA-5': SEQ ID NO:40), and the primer attR-1 (5'-TTACGTTTCTCGT-TCAGC-3': SEQ ID NO:41). Z-taq (TAKARA) was used for PCR.

The obtained transformant was inoculated to 3 mL of LB (Cm 20 mg/L), and cultured with shaking at 37° C. for 6 hours. Microbial cells were collected from the resulting medium by centrifugation, washed with 10% glycerol, and the microbial cells were collected again by centrifugation. These were suspended in 10% glycerol to use as competent cells. The competent cells were transformed with pMW-intxis-ts in order to remove the Cm resistant gene sequence inserted in the genomic DNA. An objective transformant was selected on the LB-amp (100 mg/L) plate at 30° C. The obtained transformant was cultured on the LB plate at 42° C. overnight, and the microbial cells were streaked on the LB-amp (100 mg/L) plate and on the LB-Cm (20 mg/L) plate, respectively and cultured at 37° C. The transformant was confirmed not to grow on both the plate containing Amp and the plate containing Cm. Further the removal of the Cm resistant gene was confirmed by colony PCR using the primer aspC-up (5'-AACCTCTTGGCAACGGTAAAAAAGCT-GAAC-3': SEQ ID NO:38) and the primer aspC-down (5'-GCCTGCGCAAAGTCGTATGTTTGGTCTGGA-5': SEQ ID NO:40). Z-tag (TAKARA) was used for PCR.

The obtained strain was designated as an aspC-deficient strain, *E. coli* JM109ΔaspC. A deaminase-expressing strain pTB2/*E. coli* JM109ΔaspC was constructed by transforming *E. coli* JM109ΔaspC with a deaminase-expressing plasmid, pTB2. This bacterial strain was cultured on the LB-amp (100 mg/L) at 37° C. overnight. The obtained microbial cells were inoculated to 100 mL of TB-amp (100 mg/L) and cultured with shaking at 37° C. for 16 hours using the Sakaguchi flask. The resulting medium was used as Ps_aad broth.

Example 18

Construction of Oxaloacetate Decarboxylase-Expressing Strain

Synthesis of an OAA decarboxylase gene derived from *Pseudomonas putida* KT2440 strain was asked GenScript, and a plasmid DNA in which a DNA fragment including the OAA decarboxylase gene had been inserted in pUC57 was obtained. A frequency of codon usage was optimized for expression in *E. coli* (see SEQ ID NOS:42 and 43). This plasmid was cleaved with NdeI and XhoI, inserted into pET22b cleaved with NdeI and XhoI, and the resulting plasmid was designated as pET22-PpODC-His(C). *E. coli* BL21 (DE3) was transformed with the resulting plasmid to obtain a PpODC-His(C)-expressing strain, pET22-PpODC-His(C)/*E. coli* BL21 (DE3). Microbial cells of the PpODC-His(C)-expressing strain, pET22-PpODC-His(C)/*E. coli* BL21 (DE3) grown on the LB-amp (100 mg/L) plate were inoculated to 100 mL of Overnight Express Instant TB Medium (Novagen), and cultured with shaking at 30° C. for 16 hours using the Sakaguchi flask. After the termination of cultivation, microbial cells were collected from the resulting medium, and washed with and suspended in 20 mM Tris-HCl (pH 7.6), 300 mM NaCl and 10 mM imidazole, followed by being sonicated. Microbial cell debris was removed from the disrupted solution by centrifugation, and the resulting supernatant was used as a soluble fraction. The resulting soluble fraction was applied onto a His-tagged protein purification column, His TALON superflow 5 ml Cartridge (Clontech) equilibrated with 20 mM Tris-HCl (pH 7.6), 300 mM NaCl and 10 mM imidazole, and absorbed to the carrier. Proteins that had not been absorbed to the carrier (unabsorbed proteins) were washed out with 20 mM Tris-HCl (pH 7.6), 300 mM NaCl and 10 mM imidazole, and subsequently, the absorbed proteins were eluted using 20 mM Tris-HCl (pH 7.6), 300 mM NaCl and 150 mM imidazole at a flow rate of 5 mL/minute. Resulting fractions were combined, and the obtained solution was concentrated using Amicon Ultra-15 10K (Millipore). The obtained solution was diluted with 20 mM Tris-HCl (pH 7.6) to use as a PpODC solution.

An ODC activity was measured under the condition shown below.

The measurement of the ODC activity was performed under the following condition.

10 mM OAA, 100 mM Tris-HCl (pH 8.0), 0.25 mM NADH and 10 U/mL of LDH at 25° C. The activity was calculated from the reduction of the absorbance at 340 nm. D-Lactate dehydrogenase from *Leuconostoc mesenteroides* (Oriental Yeast) was used as LDH. The reaction and the analysis on a scale of 1 mL were performed, and activity values in serial dilutions in which a measured value [(sample Δ340 nm/min)-(blank Δ340 nm/min)] fell onto the range of 0.05 to 0.15 were employed. The enzyme was diluted with 20 mM Tris-HCl (pH 7.6) and 0.01% BSA.

Example 19

One-Pot Synthesis Reaction of 2S,4R-Monatin from 100 Mm L-Trp (Wt, ID136, ID166)

A reaction was performed for 22 hours using the purified mutant AJ1616 LAT under the following condition. The reaction was performed in a volume of 1 mL using a test tube. Sampling was performed after 14, 18 and 22 hours. The sample was diluted with TE buffer, which was then ultrafiltrated using an Amicon Ultra-0.5 mL centrifugation type filter 10 kDa, and a filtrate was analyzed. HPLC was used for the analysis.

Reaction condition: 100 mM L-Trp, 50 mM PA-Na, 300 mM L-Asp-Na, 1 mM MgCl$_2$, 50 µl PLP, 100 mM Tris-HCl, 20 mM KPB, pH 7.0, 40% Ps_aad broth, 0.2 mg/mL of purified SpAld enzyme, 10 U/mL of commercially available OAA DCase enzyme, 2 U/mL of purified mutant AJ1616 LAT enzyme (vs 10 mM 4R-IHOG), and 200 U/mL of commercially available SOD enzyme at 25° C. at 140 rpm.

Methods for preparing the enzyme subjected to the reaction are described below.

Ps_aad broth: Prepared according to the method described in Example 17.

Purified SpAld enzyme: A jar cultivation of the SpAld-expressing strain was performed according to the method described in Example 6, and the thermal treatment at 60° C. was further performed for one hour. Microbial cells were collected from 100 mL of the resulting medium after the thermal treatment by centrifugation, and washed with and suspended in 20 mM Tris-HCl (pH 7.6), followed by being sonicated. Microbial cell debris was removed from the disrupted solution by centrifugation. The resulting supernatant was used as a soluble fraction. Ammonium sulfate and Tris-HCl (pH 7.6) were added so that this soluble fraction contained 1 M ammonium sulfate and 20 mM Tris-HCl (pH 7.6). This solution was applied onto a hydrophobic chromatography column HiLoad 26/10 Phenyl Sepharose HP (supplied from GE Healthcare Bioscience, CV=53 mL) equilibrated with 1 M ammonium sulfate and 20 mM Tris-HCl (pH 7.6), and absorbed to the carrier. Unabsorbed proteins which had not been absorbed to the carrier were washed out with 1 M ammonium sulfate and 20 mM Tris-HCl (pH 7.6). Subsequently, the absorbed proteins were eluted by linearly changing the concentration of ammonium sulfate from 1 M to 0 M at a flow rate of 8 mL/minute. Fractions in which the activity had been detected were combined, and the obtained solution was concentrated using Amicon Ultra-15 10k (Millipore). The resulting concentrated solution was diluted with 20 mM Tris-HCl (pH 7.6) to use as an SpAld solution. A PHOG degrading activity measurement method was used for measuring the aldolase activity (measured in 2 mM PHOG, 50 mM KPB, 1 mM MgCl$_2$, 0.25 mM NADH, and 16 U/mL of LDH at 25° C. (pH 7.0). The activity was calculated from the reduction of the absorbance at 340 nm). D-Lactate dehydrogenase from *Leuconostoc mesenteroides* (Oriental Yeast) was used as LDH.

Mutant AJ1616 LAT: Microbial cells of the mutant AJ1616 LAT-expressing strain, pET22-AJ1616LATmut-His(C)/*E. coli* JM109 (DE3) grown on the LB-amp (100 mg/L) plate were inoculated to 100 mL of Overnight Express Instant TB Medium (Novagen) containing 100 mg/L of ampicillin, and cultured with shaking at 37° C. for 16 hours using the Sakaguchi flask. After the termination of cultivation, the microbial cells were collected from the resulting medium, and washed with and suspended in 20 mM Tris-HCl (pH 7.6), 300 mM NaCl and 10 mL imidazole, followed by being sonicated. Microbial cell debris was removed from the disrupted solution by centrifugation, and the resulting supernatant was used as a soluble fraction. The resulting soluble fraction was applied onto a His-tagged protein purification column, His TALON superflow 5 ml Cartridge (Clontech) equilibrated with 20 mM Tris-HCl (pH 7.6), 300 mM NaCl and 10 mM imidazole, and absorbed to the carrier. Proteins that had not been absorbed to the carrier (unabsorbed proteins) were washed out with 20 mM Tris-HCl (pH 7.6), 300 mM NaCl and 10 mM imidazole, and subsequently, the absorbed proteins were eluted using 20 mM Tris-HCl (pH 7.6), 300 mM NaCl and 150 mM imidazole at a flow rate of 5 mL/minute. Resulting fractions were combined, and the obtained solution was concentrated using Amicon Ultra-15 30K (Millipore). The concentrated solution was diluted with 20 mM Tris-HCl (pH 7.6) to use as a mutant AJ1616 LAT solution. If necessary, the purification was performed by increasing the amount of the culture medium and the number of the His TALON columns to be connected.

OAA DCase: Oxaloacetate decarboxylase from *Pseudomonas* sp. (Sigma) was used. The value described by the manufacturer was used as the amount of the enzyme (U).

SOD: Superoxide dismutase from bovine liver (Sigma) was used. The value described by the manufacturer was used as the amount of the enzyme (U).

As a result of the one-pot reaction, the yield of 2S,4R-Monatin was enhanced in cases of using the produced ID136 and ID166 mutant enzymes compared with the wild enzyme (Table 10).

TABLE 10

Yield of 2S,4R-Monatin in one-pot reaction using 100 mM Trp as substrate

| ID | Mutants | Yield of 2S,4R-Monatin in one-pot reaction (vs. yield of Trp (%)) | | |
|----|---------|-------|-------|-------|
|    |         | 14 hr | 18 hr | 22 hr |
| WT | WT | 23 | 30 | 30 |
| 136 | S258G/I289A | 68 | 77 | 72 |
| 166 | T288G | 84 | 83 | 85 |

Example 20

One-Pot Synthesis Reaction of 2S,4R-Monatin from 100 Mm Trp (ID166 on Scale of 400 mL)

A reaction was performed for 6 hours using purified AJ1616 LAT-ID166 under the following condition. The reaction was performed in a volume of 400 mL using a 1 liter volume jar. Sampling was appropriately performed, the sample was diluted with TE buffer, which was then ultrafiltrated using an Amicon Ultra-0.5 mL centrifugation type filter 10 kDa, and a filtrate was analyzed. HPLC and capillary electrophoresis were used for the analysis.

Reaction condition: 100 mM L-Trp, 50 mM PA-Na, 300 mM L-Asp-Na, 1 mM $MgCl_2$, 50 μM PLP, 20 mM KPB (pH 7.6), pH<7.6 (1 M $H_2SO_4$), 40% Ps_aad broth, 10% SpAld broth, 5 U/mL of PpODC, 4 U/mL of AJ1616 LAT-ID166 (vs 10 mM 4R-IHOG) and 100 U/mL of SOD at 25° C. at 500 rpm, and with air at 20 mL/min (1/20 vvm).

pTB2/*E. coli* JM109ΔaspC broth was used as Ps_aad broth. The thermally treated broth described in Example 19 was used as SpAld broth. The purified enzyme described in Example 18 was used as PpODC. Superoxide dismutase from bovine liver (Sigma) was used as SOD.

Figure 4:
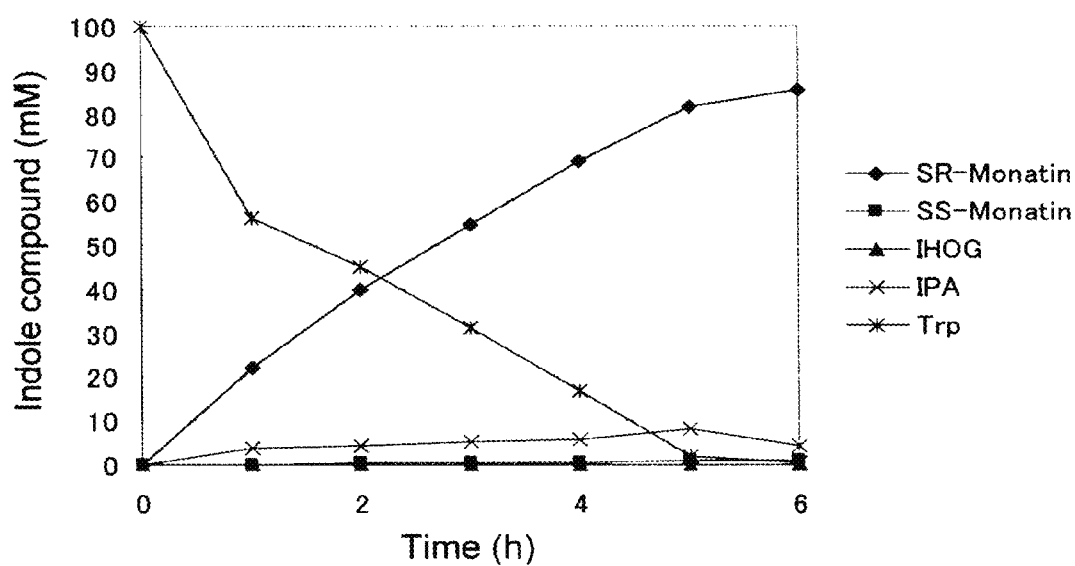
FIG. 4 is a graph showing a reaction of forming 2S,4R-Monatin from L-Trp in 400 ml scale using the L-amino acid aminotransferase mutant (ID166). SR-Monatin: 2S,4R-Monatin; SS-Monatin: 2S,4S-Monatin; IHOG: 4R-IHOG; Trp: L-Trp.

As a result, the accumulation of 86 mM 2S,4R-Monatin was confirmed after 6 hours (FIG. 4). The yield relative to L-Trp calculated after calibrating the solution amount was 89%.

Example 21

One-Pot Synthesis Reaction of 2S,4R-Monatin from 150 mM L-Trp (ID189 on Scale of 80 mL)

A reaction was performed for 27 hours using purified AJ1616 LAT-ID189 under the following condition. The reaction was performed in a volume of 80 mL using a 250 mL volume jar. Sampling was appropriately performed, the sample was diluted with TE buffer, which was then ultrafiltrated using the Amicon Ultra-0.5 mL centrifugation type filter 10 kDa, and a filtrate was analyzed. HPLC and capillary electrophoresis were used for the analysis.

Reaction condition: 150 mM L-Trp, 50 mM PA-Na, 400 mM L-Asp-Na, 1 mM $MgCl_2$, 50 μM PLP, 20 mM KPB (pH 7.6), pH<7.6 (1 M $H_2SO_4$), 40% Ps_aad broth, 10% SpAld broth, 5 U/mL of PpODC, 4 U/mL of AJ1616 LAT-ID189 (vs 10 mM 4R-IHOG) and 100 U/mL of SOD at 25° C. (380 rpm), and with air at 4 mL/min (1/20 vvm).

pTB2/*E. coli* JM109ΔaspC broth was used as the Ps_aad broth. The thermally treated broth described in Example 19 was used as the SpAld broth. The purified enzyme described in Example 18 was used as PpODC. Superoxide dismutase from bovine liver (Sigma) was used as SOD.

Figure 5:
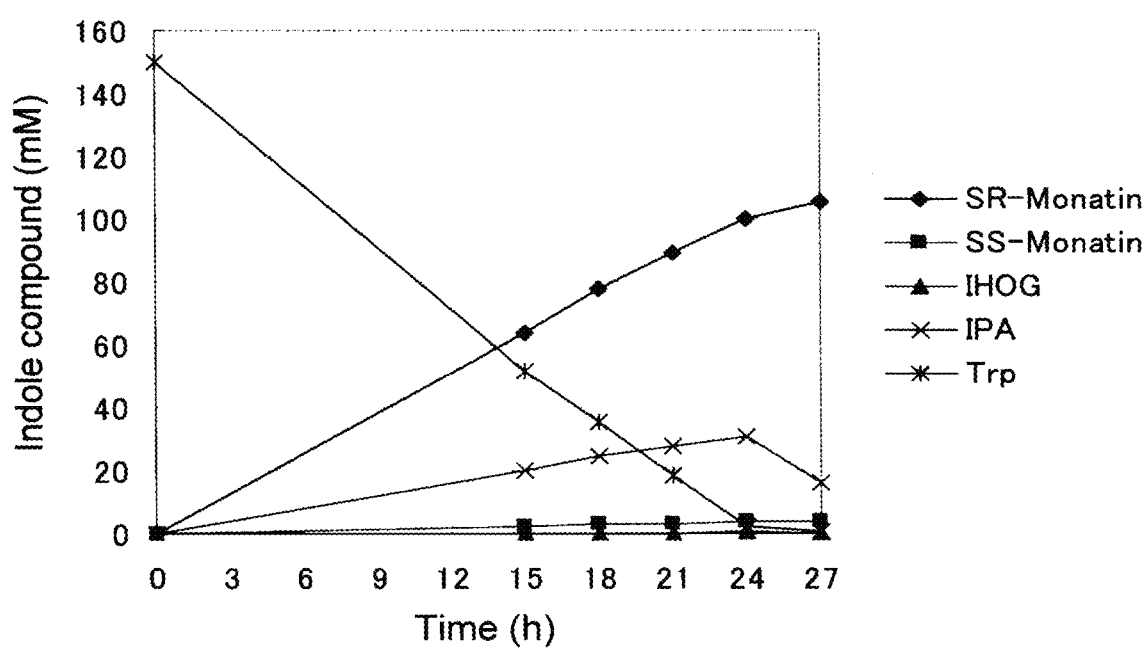
FIG. 5 is a graph showing a reaction of forming 2S,4R-Monatin from L-Trp in 80 ml scale using the L-amino acid aminotransferase mutant (ID189). The abbreviations are similar to those of FIG. 4.

As a result, the accumulation of 105 mM 2S,4R-Monatin was confirmed after 27 hours (FIG. 5). The yield relative to L-Trp calculated after calibrating the solution amount was 78% (FIG. 5).

Example 22

Isolation of 2S,4R-Monatin 2.59 g Of ZN charcoal was added to 435.66 g of a permeated solution obtained by treating 435.45 g of the enzyme reaction solution in Example 20 (lot 101213 J4) with UF (MWCO: 3000), and the mixture was stirred at room temperature (about 26° C.) for one hour. The activated charcoal was filtrated with a Kiriyama filter (5C), and the resulting filtrate was transferred to a 1 liter four-necked flask. The flask was immersed in an incubator at 5° C., the solution was neutralized with 35% hydrochloric acid to adjust pH to 3.5, and stirred using a mechanical stirrer (120 rpm). Then, 48 mg of seed crystals were added, and 1 N hydrochloric acid was sequentially added using a pH controller and a peristaltic pump to keep a target pH because the pH value elevated when the crystals began to precipitate. A slurry solution obtained by stirring for 24 hours was filtrated, the crystals were washed with 10 mL of water, and the wet crystals were dried under reduced pressure at 40° C. to yield 6.81 g of 2S,4R-Monatin. The quality of the obtained crystals was confirmed by HPLC and $^1$H-NMR analysis.

HPLC area purity (210 nm): 98.4%
$^1$H-NMR (in $D_2O+K_2CO_3$)
2.08-2.14 (1H, dd), 2.35-2.39 (1H, dd), 3.09-3.17 (2H, dd), 3.85-3.88 (1H, dd), 7.04-7.15 (3H, m), 7.39-7.41 (1H, m), 7.64-7.66 (1H, d).

Example 23

Synthesis of 2R,4R-Monatin 3.10 g (10.4 mmol) Of 2S,4R-Monatin obtained in Example 22 and 1.165 g (10.4 mmol) of 50% KOH were dissolved in 3.27 g of water, and further 1.3 g of EtOH, 0.0869 g (0.052 mmol) of 5-nitrosalicylaldehyde, and 0.187 g (3.12 mmol) of acetic acid were added thereto. After 25 hours, 20.5 g of EtOH and 10 mg of seed crystals (2R,4R-Monatin) were added, and the mixture was stirred for additional 46.5 hours. The resulting slurry solution was cooled to room temperature, and then filtrated. The crystals were washed with 4 g of 85% EtOH-water, and the wet crystals were dried under reduced pressure at 40° C. to yield 2.3 g of crude 2R,4R-Monatin. 2.1 g of the resulting crude 2R,4R-Monatin was dissolved in 6 mL of water, 0.2 g of BA charcoal was added, and the mixture was stirred at room temperature (around 25° C.) for one hour and then filtrated with a 0.45 μm membrane filter. The filtrate was concentrated to 6.38 g under reduced pressure. 12 g Of EtOH was dripped to the concentrated filtrate at 45° C., which was then stirred for one hour. Further, 13.5 g of EtOH was quantitatively dripped over one hour, which was then stirred at 45° C. for 16 hours and subsequently cooled to 25° C. The resulting slurry solution was filtrated, the crystals were washed with 3 g of 85% EtOH-water, and the wet crystals were dried under reduced pressure at 40° C. to yield 1.9 g (5.46 mmol) of 2R,4R-Monatin. The obtained crystals, the mother solution, and the washing solution were analyzed by HPLC to analyze yield and quality.

HPLC area purity (210 nm): 99.9%

$^1$H-NMR (in $D_2O$)

1.93-2.00 (1H, dd), 2.57-2.61 (1H, dd), 2.99-3.02 (1H, d), 3.19-3.22 (1H, d), 3.55-3.56 (1H, dd), 7.04-7.15 (3H, m), 7.39-7.41 (1H, m), 7.64-7.66 (1H, d).

TABLE 11

| HPLC analysis condition | |
| --- | --- |
| DEGASSER | DGU-20A$_3$ [SHIMAZU] |
| PUMP | LC-20AD [SHIMAZU, Two units] |
| Column oven | CTO-20AC [SHIMAZU] |
| DIODE ARRAY DETECTOR | SPD-M20A [SHIMAZU] |
| Auto sampler | SIL-20AC$_{HT}$ [SHIMAZU] |
| COMMUNICATION BUS MODULE | CBM-20A |
| System | LC solution [SHIMAZU] |
| Column | CAPCELL PAC C18 Type MG II 5 μm 3.0 mm φ × 250 mm [supplied from Shiseido] |
| Column temperature | 40° C. |
| Detection wavelength | 210 nm |
| Flow rate | 0.35 ml/min |
| Composition of mobile solution | Solution A: 20 mM KH$_2$PO$_4$/CH$_3$CN = 100/5 Solution B: 20 mM KH$_2$PO$_4$/CH$_3$CN = 30/70 |
| Injection amount | 5 μl |
| Autosampler solution | CH$_3$CN/H$_2$O = 30/70 |

| | Time (min) | Solution A (%) | Solution B (%) |
| --- | --- | --- | --- |
| Gradient pattern | 0 | 100 | 0 |
| | 15 | 100 | 0 |
| | 40 | 46 | 54 |
| | 45 | 46 | 54 |
| | 45.1 | 100 | 0 |
| | 60 | 100 | 0 |

Example 24

One-Pot Synthesis Reaction of 2S,4R-Monatin from 150 mM L-Trp (ID296 on Scale of 80 mL)

A reaction was performed for 51 hours using purified AJ1616 LAT-ID296 under the following condition. The reaction was performed in a volume of 80 mL using a 250 mL volume jar. Sampling was appropriately performed, the sample was diluted with TE buffer, which was then ultrafiltrated using the Amicon Ultra-0.5 mL centrifugation type filter 10 kDa, and a filtrate was analyzed. HPLC was used for the analysis.

Reaction condition: 150 mM L-Trp, 50 mM PA-Na, 400 mM L-Asp-Na, 1 mM MgCl$_2$, 50 μM PLP, 20 mM KPB (pH 7.6), pH<7.6 (1 M H$_2$SO$_4$), 40% Ps_aad broth, 10% SpAld broth, 5 U/mL of PpODC, 4 U/mL of AJ1616 LAT-ID296 (vs 10 mM 4R-IHOG) and 100 U/mL of SOD at 25° C. (380 rpm), and with air at 4 mL/min (1/20 vvm).

pTB2/*E. coli* JM109ΔaspC broth was used as the Ps_aad broth. The thermally treated broth described in Example 19 was used as the SpAld broth. The purified enzyme described in Example 18 was used as PpODC. Superoxide dismutase from bovine liver (Sigma) was used as SOD.

Figure 6:
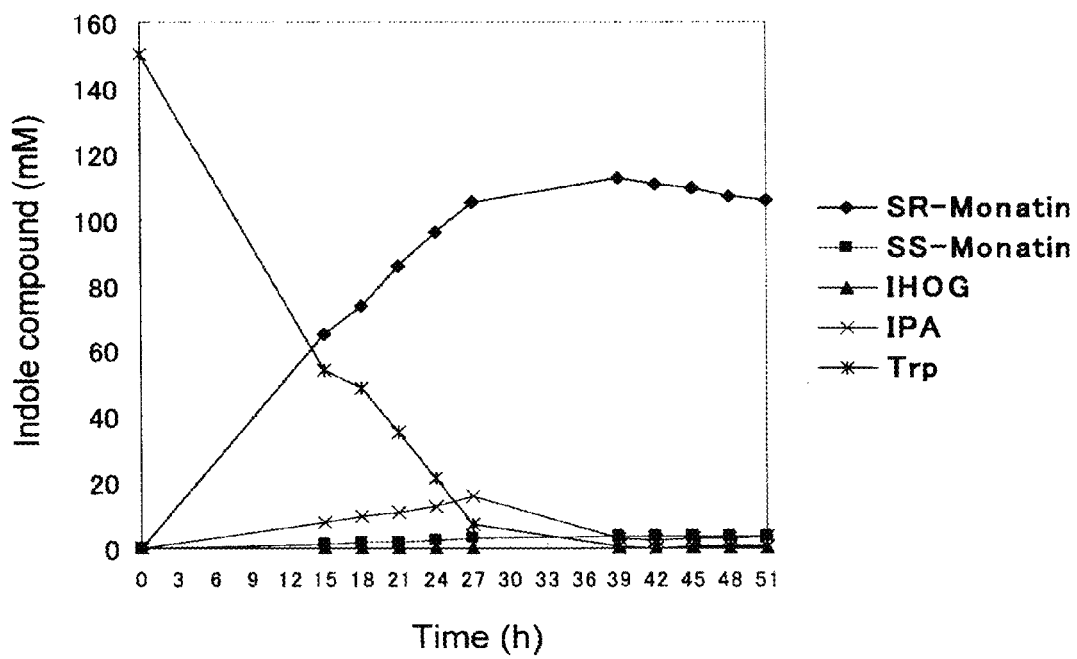
FIG. 6 is a graph showing a reaction of forming 2S,4R-Monatin from L-Trp in 80 ml scale using the L-amino acid aminotransferase mutant (ID296). The abbreviations are similar to those of FIG. 4.

As a result, the accumulation of 113 mM 2S,4R-Monatin was confirmed after 39 hours (FIG. 6). The yield relative to L-Trp calculated after calibrating the solution amount was 86% (FIG. 6).

Example 25

Purification of Aminotransferase Derived from *Rhizobium* Radiobacter AJ3976

An aminotransferase that forms 2S,4R-Monatin was purified from a soluble fraction of *Rhizobium* radiobacter AJ3976 as follows. The reaction was performed in 100 mM L-Asp-Na-1aq, 10 mM 4R-IHOG (containing 4S-IHOG in a trace amount), 50 μM PLP, and 100 mM Tris-HCl (pH 8.0) at 25° C. The formed 2S,4R-Monatin was quantified by UPLC analysis.

TABLE 12-1

| UPLC | |
| --- | --- |
| Column: | ACQUITY UPLC HSS T3 2.1 × 50 mm |
| ColumnTemp.: | 40° C. |
| Sample Temp.: | 4° C. |
| Detection: | UV 210 nm |
| Injection vol.: | 5 μl |
| Mobile Phase A: | 20 mM KH2PO4 (Filt.) |
| Mobile Phase B: | ACN |
| Flow rate: | 0.5 ml/min |
| Method: | 20 mM KH2PO4_05_HSS |

| Time (min) | A (%) | B (%) |
| --- | --- | --- |
| 0 | 96 | 4 |
| 1.9 | 96 | 4 |
| 2.0 | 60 | 40 |
| 2.2 | 60 | 40 |
| 2.3 | 96 | 4 |
| 3.0 | 96 | 4 |

(1) Preparation of Soluble Fraction

Microbial cells of *Rhizobium* radiobacter AJ3976 were spread on an LB agar medium and cultured at 30° C. for two days.

One loopful of the obtained microbial cells was inoculated to 160 mL of an enzyme production medium (10 g/L of yeast extract, 10 g/L of trypton, 1 g/L of glucose, 3 g/L of dipotassium hydrogen phosphate, 1 g/L of potassium dihydrogen phosphate, 0.1 g/L of magnesium sulfate heptahydrate, and 5 g/L of ammonium sulfate) in a 500 mL Sakaguchi flask, and cultured at 30° C. for 20 hours with shaking. The microbial cells were collected from about 1920 mL of the resulting cultured medium by centrifugation, washed with and suspended in 20 mM Tris-HCl (pH 7.6), and sonicated at 4° C. for 30 minutes. Microbial cell debris was removed from the sonicated cell suspension by the centrifugation, and the resulting supernatant was used as a soluble fraction.

(2) Anion Exchange Chromatography

The above soluble fraction was applied onto an anion exchange chromatographic column HiLoad 26/10 Q Sepharose HP (supplied from GE Healthcare Bioscience, CV=53 mL) equilibrated with 20 mM Tris-HCl (pH 7.6) and absorbed to the carrier. Proteins that had not been absorbed to the carrier (unabsorbed protein) were washed out with 20 mM Tris-HCl (pH 7.6). Subsequently, proteins that had been absorbed to the carrier were eluted by linearly changing a concentration of NaCl from 0 mM to 500 mM at a flow rate of 2 mL/minute. A 2S,4R Monatin-forming activity was measured in each eluted fraction, and the 2S,4R-Monatin-forming activity was detected in fractions corresponding to about 250 mM NaCl.

(3) Hydrophobic Chromatography

The fractions in which the 2S,4R-Monatin-forming activity had been detected were combined, and ammonium sulfate and Tris-HCl (pH 7.6) were added thereto so that the concentrations of ammonium sulfate and Tris-HCl (pH 7.6) were 1.0 M and 20 mM, respectively. The resulting solution was applied onto a hydrophobic chromatographic column HiLoad 16/10 Phenyl Sepharose HP (supplied from GE Healthcare Bioscience, CV=20 mL) equilibrated with 1.0 M ammonium sulfate and 20 mM Tris-HCl (pH 7.6), and absorbed to the carrier. Unabsorbed proteins that had not been absorbed to the carrier were washed out using 1.0 M ammonium sulfate and 20 mM Tris-HCl (pH 7.6). Subsequently, a 2S,4R-Monatin-forming enzyme was eluted by linearly changing the concentration of ammonium sulfate from 1.0 M to 0 M at a flow rate of 3 mL/minute. The 2S,4R-Monatin-forming activity was measured in each obtained fraction, and the 2S,4R-Monatin-forming activity was detected in fractions corresponding to about 0.9 M of ammonium sulfate.

(4) Gel Filtration Chromatography

The fractions in which the 2S,4R-Monatin-forming activity had been detected were combined, and concentrated using Amicon Ultra-15 10k (Millipore). The resulting concentrated solution was diluted with 20 mM Tris-HCl (pH 7.6) and 150 mM NaCl. The resulting solution was applied onto a gel filtration column HiLoad 16/60 Superdex 200 pg (supplied from GE Healthcare Bioscience, CV-120 mL) equilibrated with 20 mM Tris-HCl (pH 7.6) and 150 mM NaCl, and proteins were eluted at a flow rate of 1 mL/minute. This manipulation confirmed the 2S,4R-Monatin-forming activity at a position in which a molecular weight was estimated to be about 100 kDa.

(5) SDS-PAGE

The resulting fraction was subjected to SDS-PAGE, and a single band derived from the active fraction was detected near 47 kDa. This band was subjected to analysis of an N-terminal amino acid sequence as a candidate of the aminotransferase that forms 2S,4R-Monatin.

Example 26

Determination of N-Terminal Amino Acid Sequence of Aminotransferase Derived from Rhizobium Radiobacter AJ3976

The purified enzyme solution obtained in Example 25 was subjected to the analysis of the N-terminal amino acid sequence, and the N-terminal amino acid sequence of AFLADILSRVKPSATIAVTQ (SEQ ID NO:44) was obtained. The N-terminal amino acid sequence showed a high homology to that of aspartate aminotransferase (AAK87940) derived from *Agrobacterium tumefaciens* str. C58.

Example 27

Cloning of Aminotransferase Gene Derived from Rhizobium Radiobacter AJ3976

The microbial cells of *Rhizobium* radiobacter AJ3976 were cultured in the same manner as in Example 25. The microbial cells were collected from the cultured medium by centrifugation, and genomic DNA was extracted therefrom.

A DNA fragment including the aminotransferase gene was amplified by PCR using the obtained genomic DNA as a template. Primers were designed from DNA sequences of upstream 100 bp and downstream 100 bp of the aminotransferase gene with reference to the genomic DNA sequence of *Agrobacterium tumefaciens* str. C58. The primer Ag-u100-f (5'-ctggtgcagataagccggcttttgacc-3': SEQ ID NO:45) and the primer Ag-d100-r (5'-ccaccttcatcatgctgctgtttctcg-3': SEQ ID NO:46) were used. PCR was performed using KOD-plus-ver. 2 (Toyobo) under the following condition.

1 cycle at 94° C. for 2 minutes
25 cycles at 98° C. for 10 seconds
55° C. for 10 seconds and
68° C. for 60 seconds
1 cycle at 68° C. for 60 seconds, and
4° C.

The nucleotide sequence of the amplified DNA fragment of about 1400 bp was determined, and was shown to be the nucleotide sequence including 1203 bp of ORF (SEQ ID NOs: 47 and 48), which had the high homology to the aspartate aminotransferase gene (Atu2196) derived from *Agrobacterium tumefaciens* str. C58. The homology was 92% in their DNA sequences and 97% in their amino acid sequences.

This amino acid sequence was consistent with the N-terminal amino acid sequence obtained in Example 26. Thus, it has been thought that the aminotransferase gene having the 2S,4R-Monatin-forming activity could be acquired.

Example 28

Expression of Aminotransferase Derived from Rhizobium Radiobacter AJ3976 in *E. Coli*

(1) Construction of Expression Plasmid for Aminotransferase Derived from *Rhizobium* Radiobacter AJ3976

A DNA fragment including the aminotransferase gene derived from *Rhizobium* radiobacter AJ3976 was amplified by PCR with the genomic DNA of *Rhizobium* radiobacter AJ3976 as the template. The primer 3976AT-Nde-f (5'-ggaattccatATGGCCTTCCTTGCCGACATTCTCT-3': SEQ ID NO:49) and the primer 3976-xho-r (5'-actccgctcgagACGGCAATCGGCGCAGAAACGCTGA-3': SEQ ID NO:50) were used. PCR was performed using KOD-plus-ver. 2 (Toyobo) under the following condition.

1 cycle at 94° C. for 2 minutes
25 cycles at 98° C. for 10 seconds
55° C. for 10 seconds and
68° C. for 60 seconds
1 cycle at 68° C. for 60 seconds, and
4° C.

The resulting DNA fragment was treated with restriction enzymes NdeI and XhoI, and ligated to pET-22b (Novagen) likewise treated with NdeI and XhoI. *E. coli* JM109 was transformed with this ligation solution, an objective plasmid was selected from ampicillin resistant colonies, and this plasmid was designated as pET-22-3976AT-His. In this plasmid, the aminotransferase derived from *Rhizobium* radiobacter AJ3976 which having a His-tag added to a C-terminus end (3976AT-His) is expressed.

(2) Purification of 3976AT-HIS from *E. Coli* Strain Expressing 3976AT-HIS

The constructed expression plasmid pET-22-3976AT-His was introduced into *E. coli* BL21 (DE3), and one loopful of the transformant was inoculated to 160 mL of Overnight Express Instant TB Medium (Novagen) containing 100 mg/L of ampicillin in a 500 mL Sakaguchi flask, and the Sakaguchi flask was shaken at 37° C. for 16 hours. After completion of the cultivation, microbial cells were collected from about 1000 mL of the cultured medium by centrifugation, washed with and suspended in 20 mM Tris-HCl (pH 7.6), 100 mM NaCl and 20 mM imidazole, and sonicated at 4° C. for 30 minutes. Microbial cell debris was removed from the sonicated cell suspension by centrifugation, and the resulting supernatant was used as a soluble fraction.

The obtained soluble fraction was applied onto a His-tag protein purification column HisPrep FF 16/10 (supplied from Pharmacia (GE Healthcare Bioscience), CV=20 mL) equilibrated with 20 mM Tris-HCl (pH 7.6), 100 mM NaCl and 20 mM imidazole to absorb proteins to the carrier. Proteins that had not been absorbed to the carrier (unabsorbed protein) were washed out with 20 mM Tris-HCl (pH 7.6), 100 mM NaCl and 20 mM imidazole. Subsequently, the absorbed proteins were eluted by linearly changing the concentration of imidazole from 20 mM to 250 mM at a flow rate of 3 mL/minute.

The obtained fractions were combined and concentrated using Amicon Ultra-15 30k (Millipore). The concentrated solution was diluted with 20 mM Tris-HCl (pH 7.6), and then applied onto an anion exchange chromatographic column HiLoad 16/10 Q Sepharose HP (supplied from GE Healthcare Bioscience, CV=20 mL) equilibrated with 20 mM Tris-HCl (pH 7.6) to absorb proteins to the carrier. Proteins that had not been absorbed to the carrier (unabsorbed protein) were washed out with 20 mM Tris-HCl (pH 7.6). Subsequently, the proteins that had been absorbed to the carrier were eluted by linearly changing the concentration of NaCl from 0 mM to 500 mM at a flow rate of 3 mL/minute.

The 2S,4R Monatin-forming activity was measured in each eluted fraction, and the fractions in which the 2S,4R Monatin-forming activity had been detected were combined, and concentrated using Amicon Ultra-15 30k (Millipore). The concentrated solution was diluted with 20 mM Tris-HCl (pH 7.6), and used as a 3976AT-His solution.

Example 29

Results of Measuring Specific Activity of AJ3976LAT for Various Keto Acids (1) Measurement of Activity for L-Asp/α-KG, L-Asp/PA and L-Asp/(±)-MHOG by Colorimetric Method The activity of AJ3976LAT for various substrates was measured. The specific activities for 10 mM various keto acids were measured by a colorimetric method, using 100 mM L-Asp as an amino donor substrate for a transamination reaction.

Activity for L-Asp/α-KG: 100 mM L-Asp-Na-1aq, 10 mM α-KG-2Na, 50 µM PLP, 100 mM Tris-HCl (pH 8.0), 0.25 mM NADH and 2 U/mL of MDH at 25° C. The activity was calculated from the reduction of the absorbance measured at 340 nm. Malic dehydrogenase from porcine heart (Sigma) was used as MDH. The activity for L-Asp/α-KG is shown in the column "α-KG" of the aminotransferase activity in Table 13.

Activity for L-Asp/PA: 100 mM L-Asp-Na-1aq, 10 mM PA-Na, 50 µM PLP, 100 mM Tris-HCl (pH 8.0), 0.25 mM NADH, and 2 U/mL of MDH (same as above) at 25° C. The activity was calculated from the reduction of the absorbance measured at 340 nm. The activity for L-Asp/PA is shown in the column "PA" of the aminotransferase activity in Table 13.

Activity for L-ASP/(±)-MHOG: 100 mM L-Asp-Na-1aq, 10 mM (±)-MHOG, 50 µM PLP, 100 mM Tris-HCl (pH 8.0), 0.25 mM NADH, 2 U/mL of MDH (same as above), and 10 U/mL of LDH at 25° C. The activity was calculated from the reduction of the absorbance measured at 340 nm. D-Lactate dehydrogenase from *Leuconostoc mesenteroides* (Oriental Yeast) was used as LDH. LDH was added in order to remove PA in a trace amount existed in (±)-MHOG. The activity for L-Asp/(±)-MHOG is shown in the column "(±)-MHOG" of the aminotransferase activity in Table 13.

(2) Measurement of Activity for L-Asp/4R-IHOG, L-Asp/(±)-IHOG and L-Asp/IPA

The activity to form the 2S,4R-Monatin from 4R-IHOG, the activity to form the 2S,4R-Monatin and 2S,4S-Monatin from (±)-IHOG, which are objective activities, and the activity to form L-Trp as a by-product from IPA were measured individually. The transamination reaction to 10 mM keto acid was performed using 100 mM L-Asp as the amino donor substrate, and the amount of the formed amino acid was quantified by UPLC to calculate the specific activity.

Activity for L-Asp/4R-IHOG: 100 mM L-Asp-Na-1aq, 10 mM 4R-IHOG (containing 4S-IHOG in a trace amount), 50 µM PLP, and 100 mM Tris-HCl (pH 8.0) at 25° C. The formed 2S,4R-Monatin and 2S,4S-Monatin were quantified by UPLC analysis.

A solution of 200 mM sodium citrate (pH 4.5) was used as a solution for stopping the reaction. The activity for L-Asp/4R-IHOG is shown in the column "4R-IHOG" of the aminotransferase activity in Table 13.

Activity for L-Asp/(±)-IHOG: 100 mM L-Asp-Na-1aq, 10 mM (±)-IHOG, 50 µM PLP, and 100 mM Tris-HCl (pH 8.0) at 25° C. The formed 2S,4R-Monatin and 2S,4S-Monatin were quantified by the UPLC analysis. A solution of 200 mM sodium citrate (pH 4.5) was used as a solution for stopping the reaction. The activity for L-Asp/4R-IHOG is shown in the column "(±)-IHOG" of the aminotransferase activity in Table 13.

Activity for L-Asp/IPA: 100 mM L-Asp-Na-1aq, 10 mM IPA, 50 µM PLP, and 100 mM Tris-HCl (pH 8.0) (pH was adjusted to 8.0 with 1 N NaOH after preparing the reaction solution) at 25° C. Formed Trp was quantified by the UPCL analysis. A solution of 200 mM sodium citrate (pH 4.5) was used as a solution for stopping the reaction. The activity for L-Asp/IPA is shown in the column "IPA" of the aminotransferase activity in Table 13.

The formed Monatin and Trp were quantified using ACQUITY UPLC system supplied from Waters. The condition for the measurement is shown below. 0.2 mL of the reaction solution was reacted for 15 minutes, then the reaction was stopped. The reaction solution after stopping the reaction was centrifuged, and about 0.2 mL of the supernatant was subjected to the UPLC analysis.

TABLE 12-2

| UPLC | |
|---|---|
| Column: | ACQUITY UPLC HSS T3 2.1 × 50 mm |
| Column Temp.: | 40° C. |
| Sample Temp.: | 4° C. |
| Detection: | UV 210 nm |
| Injection vol.: | 5 µl |
| Mobile Phase A: | 20 mM KH2PO4 (Filt.) |
| Mobile Phase B: | ACN |
| Flow rate: | 0.5 ml/min |
| Method: | 20 mM KH2PO4__05__HSS |

| Time (min) | A (%) | B (%) |
|---|---|---|
| 0 | 96 | 4 |
| 1.9 | 96 | 4 |

TABLE 12-2-continued

| UPLC | | |
|------|------|------|
| 2.0 | 60 | 40 |
| 2.2 | 60 | 40 |
| 2.3 | 96 | 4 |
| 3.0 | 96 | 4 |

The 2S,4R-Monatin, the 2S,4S-Monatin and Trp can be quantified distinctively at 1.1 minutes, 1.5 minutes and 1.3 minutes, respectively.

(3) Results of Measuring Specific Activity of AJ3976LAT for Various Keto Acids

The results of measuring the specific activity for 10 mM keto acid when 3976-AT-His was used and L-Asp was used as the amino donor are shown in Table 13.

TABLE 13

Specific activity of AJ3976LAT for various keto acids
Aminotransferase activity (U/mg)

| α-KG | PA | ±MHOG | 4R-IHOG | | ±IHOG | | IPA |
|------|-----|-------|---------|------|--------|------|-----|
|      |     |       | SR      | SS   | SR     | SS   |     |
| 106  | 4.0 | 48    | 0.58    | 1.5  | 0.052  | 3.7  | 0.012 |

Example 30

Reaction for Synthesis of 2S,4R-Monatin Using pET-22-3976AT-His/*E. coli* BL21 (DE3)

One loopful of microbial cells of pET-22-3976AT-His/*E. coli* BL21 (DE3) prepared in Example 28 was inoculated to 3 mL of Overnight Express Instant TB medium (Novagen) containing 100 mg/L of ampicillin in a test tube, and the test tube was then shaken at 37° C. for 16 hours. After the completion of the cultivation, the microbial cells were collected from 1 mL of the cultured medium by centrifugation, and suspended in 1 mL of BugBuster Master Mix (Novagen). The resulting suspension was incubated at room temperature for 15 minutes to lyse the microbial cells. Microbial cell debris was removed by centrifugation, and the resulting supernatant was used as a soluble fraction.

The reaction for the synthesis of the 2S,4R-Monatin from 4R-IHOG was carried out using the obtained soluble fraction. To 0.1 mL of a reaction solution [100 mM L-Asp-Na-1aq, 10 mM 4R-IHOG (containing 4S-IHOG in a trace amount), 50 μM PLP, and 100 mM Tris-HCl (pH 8.0)], 0.05 mL of the above soluble fraction was added, and the mixture was reacted at 25° C. for one hour. After the completion of the reaction, the formed 2S,4R-Monatin was quantified to be 0.84 mM. The 2S,4R-Monatin was quantified by the UPLC analysis. The condition for the analysis is the same in Example 29.

Example 31

Purification of Aminotransferase Derived from *Rhizobium* sp. AJ12469

Aminotransferase that forms 2S,4R-Monatin was purified from the soluble fraction of *Rhizobium* sp. AJ12469 as follows. The synthetic reaction and quantification of 2S,4R-Monatin was carried out in the same manner as in Example 25.

(1) Preparation of Soluble Fraction

Microbial cells of *Rhizobium* sp. AJ12469 were spread on the LB agar medium, and cultured at 30° C. for two days. One loopful of the resulting microbial cells was inoculated to 160 mL of an enzyme production medium (10 g/L of yeast extract, 10 g/L of trypton, 1 g/L of glucose, 3 g/L of dipotassium hydrogen phosphate, 1 g/L of potassium dihydrogen phosphate, 0.1 g/L of magnesium sulfate heptahydrate, and 5 g/L of ammonium sulfate) in a 500 mL Sakaguchi flask, and cultured at 30° C. for 16 hours with shaking. The microbial cells were collected from about 1920 mL of the resulting cultured medium by centrifugation, washed with and suspended in 20 mM Tris-HCl (pH 7.6), and sonicated at 4° C. for 30 minutes. The microbial cell debris was removed from the sonicated cell suspension by centrifugation, and the resulting supernatant was used as a soluble fraction.

(2) Anion Exchange Chromatography

The above soluble fraction was applied onto an anion exchange chromatographic column HiLoad 26/10 Q Sepharose HP (supplied from GE Healthcare Bioscience, CV=53 mL) equilibrated with 20 mM Tris-HCl (pH 7.6) to be absorbed to the carrier. Proteins that had not been absorbed to the carrier (unabsorbed protein) were washed out with 20 mM Tris-HCl (pH 7.6). Subsequently, proteins that had been absorbed to the carrier were eluted by linearly changing the concentration of NaCl from 0 mM to 500 mM at a flow rate of 8 mL/minute. The 2S,4R Monatin-forming activity was measured in each eluted fraction, and the 2S,4R-Monatin-forming activity was detected in fractions corresponding to about 200 mM NaCl.

(3) Hydrophobic Chromatography

The fractions in which the 2S,4R-Monatin-forming activity had been detected were combined, and ammonium sulfate and Tris-HCl (pH 7.6) were added thereto so that the concentrations of ammonium sulfate and Tris-HCl (pH 7.6) were 1.5 M and 20 mM, respectively. The resulting solution was applied onto the hydrophobic chromatographic column HiLoad 16/10 Phenyl Sepharose HP (supplied from GE Healthcare Bioscience, CV=20 mL) equilibrated with 1.5 M ammonium sulfate and 20 mM Tris-HCl (pH 7.6) to be absorbed to the carrier. Unabsorbed proteins that had not been absorbed to the carrier were washed out using 1.5 M ammonium sulfate and 20 mM Tris-HCl (pH 7.6). Subsequently, the 2S,4R-Monatin-forming enzyme was eluted by linearly changing the concentration of ammonium sulfate from 1.5 M to 0 M at a flow rate of 3 mL/minute. The 2S,4R-Monatin-forming activity was measured in obtained each fraction, and the 2S,4R-Monatin-forming activity was detected in fractions corresponding to about 0.8 M ammonium sulfate.

(4) Gel Filtration Chromatography

The fractions in which the 2S,4R-Monatin-forming activity had been detected were combined, and concentrated using Amicon Ultra-15 10k (Millipore). The resulting concentrated solution was diluted with 20 mM Tris-HCl (pH 7.6) and 150 mM NaCl. The resulting solution was applied onto a gel filtration column HiLoad 16/60 Superdex 200 pg (supplied from GE Healthcare Bioscience, CV=120 mL) equilibrated with 20 mM Tris-HCl (pH 7.6) and 150 mM NaCl, and proteins were eluted at a flow rate of 1 mL/minute. This manipulation confirmed the 2S,4R-Monatin-forming activity at a position at which the molecular weight was estimated to be about 100 kDa.

(5) Anion Exchange Chromatography

The fractions in which the 2S,4R-Monatin-forming activity had been detected were combined, and the resulting solution was applied onto an anion exchange chromatographic column Mono Q 5/5 (supplied from Pharmacia (GE Healthcare Bioscience, CV=1 mL) to absorb proteins to the carrier. Proteins that had not been absorbed to the carrier (unabsorbed proteins) were washed out with 20 mM Tris-HCl (pH 7.6). Subsequently, the absorbed proteins were eluted by linearly changing the concentration of NaCl from 0 mM to 500 mM at a flow rate of 0.5 mL/minute. The 2S,4R-Monatin-forming activity was measured in each fraction, and the 2S,4R-Monatin-forming activity was detected in the fractions corresponding to about 300 mM NaCl.

(6) SDS-PAGE

The obtained fractions were subjected to SDS-PAGE, and a band derived from the active fraction was detected near 47 kDa. This band was subjected to the analysis of the N-terminal amino acid sequence as the candidate for the aminotransferase that forms 2S,4R-Monatin.

Example 32

Determination of N-Terminal Amino Acid Sequence of Aminotransferase Derived from Rhizobium sp. AJ12469

The purified enzyme solution obtained in Example 31 was subjected to the analysis of the N-terminal amino acid sequence, and an N-terminal amino acid sequence of AFLADILSRVKPSATIAVTQ (SEQ ID NO:51) was obtained. The N-terminal amino acid sequence showed the high homology to aspartate aminotransferase (AAK87940) derived from *Agrobacterium tumefaciens* str. C58.

Example 33

Cloning of Aminotransferase Gene Derived from Rhizobium sp. AJ12469

The microbial cells of *Rhizobium radiobacter* AJ3976 were cultured in the same manner as in Example 31. The microbial cells were collected from the cultured medium by centrifugation, and genomic DNA was extracted therefrom.

A DNA fragment containing the aminotransferase gene was amplified by PCR with the obtained genomic DNA as the template. Primers were designed from DNA sequences of upstream 100 bp and downstream 100 bp of the aminotransferase gene with reference to the genomic DNA sequence of *Agrobacterium tumefaciens* str. C58. The primer Ag-u100-f (5'-ctggtgcagataagccggcttttgacc-3': SEQ ID NO:45) and the primer Ag-d100-r (5'-ccaccttcatcatgctgctgtttctcg-3': SEQ ID NO:46) were used. PCR was performed using KOD-plus-ver. 2 (Toyobo) under the following condition.

1 cycle at 94° C. for 2 minutes
25 cycles at 98° C. for 10 seconds
55° C. for 10 seconds and
68° C. for 60 seconds
1 cycle at 68° C. for 60 seconds, and
4° C.

A nucleotide sequence of the amplified DNA fragment of about 1400 bp was determined, and was shown to be the nucleotide sequence including 1203 bp of ORF (SEQ ID NOs:52 and 53), which had the high homology to the aspartate aminotransferase gene (Atu2196) derived from *Agrobacterium tumefaciens* str. C58. The homology was 97% in their DNA sequences and 99% in their amino acid sequences.

This amino acid sequence was consistent with the N-terminal amino acid sequence obtained in Example 32. Thus, it has been thought that the aminotransferase gene having the 2S,4R-Monatin-forming activity could be acquired.

Example 34

Expression of Aminotransferase Derived from Rhizobium sp. AJ12469 in *E. coli*

(1) Construction of Expression Plasmid for Aminotransferase Derived from Rhizobium sp. AJ12469

A DNA fragment containing an aminotransferase gene derived from *Rhizobium* sp. AJ12469 was amplified by PCR with the genomic DNA of *Rhizobium* sp. AJ12469 as the template. The primer 12469AT-Nde-f (5'-ggaattccatATGGC-CTTCCTTGCCGACATTCTCT-3': SEQ ID NO:54) and the primer 12469-xho-r (5'-actccgctcgagGCGGCAATCGGCG-CAGAAACGCTGA-3': SEQ ID NO:55) were used. PCR was performed using KOD-plus-ver. 2 (Toyobo) under the following condition.

1 cycle at 94° C. for 2 minutes
25 cycles at 98° C. for 10 seconds
55° C. for 10 seconds and
68° C. for 60 seconds
1 cycle at 68° C. for 60 seconds, and
4° C.

The resulting DNA fragment was treated with restriction enzymes NdeI and XhoI, and ligated to pET-22b (Novagen) likewise treated with NdeI and XhoI. *E. coli* JM109 was transformed with this ligation solution, an objective plasmid was selected from ampicillin resistant colonies, and this plasmid was designated as pET-22-12469AT-His. In this plasmid, the aminotransferase derived from *Rhizobium* sp. AJ12469 which has a His-tag added to the C-terminus end (12469AT-His) is expressed.

(2) Purification of 12469AT-His from *E. coli* Strain Expressing 12469AT-His

The constructed expression plasmid pET-22-12469AT-His was introduced into *E. coli* BL21 (DE3), and one loopful of the transformant was inoculated to 160 mL of Overnight Express Instant TB Medium (Novagen) containing 100 mg/L of ampicillin in a 500 mL Sakaguchi flask, and the Sakaguchi flask was shaken at 37° C. for 16 hours. After the completion of the cultivation, microbial cells were collected from about 1000 mL of the cultured medium by centrifugation, washed with and suspended in 20 mM Tris-HCl (pH 7.6), 100 mM NaCl and 20 mM imidazole, and sonicated at 4° C. for 30 minutes. The microbial cell debris was removed from the sonicated cell suspension by centrifugation, and the resulting supernatant was used as a soluble fraction.

The obtained soluble fraction was applied onto the His-tag protein purification column HisPrep FF 16/10 (supplied from Pharmacia (GE Healthcare Bioscience), CV=20 mL) equilibrated with 20 mM Tris-HCl (pH 7.6), 100 mM NaCl and 20 mM imidazole to absorb proteins to the carrier. Proteins that had not been absorbed to the carrier (unabsorbed protein) were washed out with 20 mM Tris-HCl (pH 7.6), 100 mM NaCl and 20 mM imidazole. Subsequently, absorbed proteins were eluted by linearly changing the concentration of imidazole from 20 mM to 250 mM at a flow rate of 3 mL/minute.

The obtained fractions were combined and concentrated using Amicon Ultra-15 30k (Millipore). The concentrated solution was diluted with 20 mM Tris-HCl (pH 7.6), and then applied onto the anion exchange chromatographic column HiLoad 16/10 Q Sepharose HP (supplied from GE Healthcare Bioscience, CV=20 mL) equilibrated with 20 mM Tris-HCl (pH 7.6) to absorb proteins to the carrier. Proteins that had not been absorbed to the carrier (unabsorbed protein) were washed out with 20 mM Tris-HCl (pH 7.6). Subsequently, absorbed proteins were eluted by linearly changing the concentration of NaCl from 0 mM to 500 mM at a flow rate of 3 mL/minute.

The 2S,4R-Monatin-forming activity was measured in each eluted fraction. The fractions in which the 2S,4R-Monatin-forming activity had been detected were combined, and concentrated using Amicon Ultra-15 30k (Millipore). The concentrated solution was diluted with 20 mM Tris-HCl (pH 7.6) to use as a 12469AT-His solution.

Example 35

Results of Measuring Specific Activity of AJ12469LAT for Various Keto Acids (1) Measurement of Activity for L-Asp/α-KG, L-Asp/PA and L-Asp/(±)-MHOG by Colorimetric Method The activity of AJ12469LAT for various substrates was measured. The specific activity for 10 mM keto acid was measured by the colorimetric method, using 100 mM L-Asp as the amino donor substrate for the transamination reaction.

Activity for L-Asp/α-KG: 100 mM L-Asp-Na-1aq, 10 mM α-KG-2Na, 50 µM PLP, 100 mM Tris-HCl (pH 8.0), 0.25 mM NADH and 2 U/mL of MDH at 25° C. The activity was calculated from the reduction of the absorbance measured at 340 nm. Malic dehydrogenase from porcine heart (Sigma) was used as MDH. The activity for L-Asp/α-KG is shown in the column "α-KG" of the aminotransferase activity in Table 15.

Activity for L-Asp/PA: 100 mM L-Asp-Na-1aq, 10 mM PA-Na, 50 µM PLP, 100 mM Tris-HCl (pH 8.0), 0.25 mM NADH, and 2 U/mL of MDH (same as above) at 25° C. The activity was calculated from the reduction of the absorbance measured at 340 nm. The activity for L-Asp/PA is shown in the column "PA" of the aminotransferase activity in Table 15.

Activity for L-ASP/(±)-MHOG: 100 mM L-Asp-Na-1aq, 10 mM (±)-MHOG, 50 µM PLP, 100 mM Tris-HCl (pH 8.0), 0.25 mM NADH, 2 U/mL of MDH (same as above), and 10 U/mL of LDH at 25° C. The activity was calculated from the reduction of the absorbance measured at 340 nm. D-Lactate dehydrogenase from *Leuconostoc mesenteroides* (Oriental Yeast) was used as LDH. LDH was added in order to remove PA in a trace amount contaminated in (±)-MHOG. The activity for L-Asp/(±)-MHOG is shown in the column "(±)-MHOG" of the aminotransferase activity in Table 15.

(2) Measurement of Activity for L-Asp/4R-IHOG, L-Asp/(±)-IHOG and L-Asp/IPA

The activity to form 2S,4R-Monatin from 4R-IHOG, the activity to form 2S,4R-Monatin and 2S,4S-Monatin from (±)-IHOG, which are the objective activities, and the activity to form L-Trp as a by-product from IPA were measured individually. The transamination reaction to 10 mM keto acid was performed using 100 mM L-Asp as the amino donor substrate for the transamination reaction, and the amount of the formed amino acid was quantified by UPLC to calculate the specific activity.

Activity for L-Asp/4R-IHOG: 100 mM L-Asp-Na-1aq, 10 mM 4R-IHOG (containing 4S-IHOG in a trace amount), 50 µM PLP, and 100 mM Tris-HCl (pH 8.0) at 25° C. Formed 2S,4R-Monatin and 2S,4S-Monatin were quantified by the UPLC analysis. A solution of 200 mM sodium citrate (pH 4.5) was used as a solution for stopping the reaction. The activity for L-Asp/4R-IHOG is shown in the column "4R-IHOG" of the aminotransferase activity in Table 15.

Activity for L-Asp/(±)-IHOG: 100 mM L-Asp-Na-1aq, 10 mM (±)-IHOG, 50 µM PLP, and 100 mM Tris-HCl (pH 8.0) at 25° C. The formed 2S,4R-Monatin and 2S,4S-Monatin were quantified by the UPLC analysis. A solution of 200 mM sodium citrate (pH 4.5) was used as a solution for stopping the reaction. The activity for L-Asp/(±)-IHOG is shown in the column "(±)-IHOG" of the aminotransferase activity in Table 13.

Activity for L-Asp/IPA: 100 mM L-Asp-Na-1aq, 10 mM IPA, 50 µM PLP, and 100 mM Tris-HCl (pH 8.0) (pH was adjusted to 8.0 with 1 N NaOH after preparing the reaction solution) at 25° C. Formed Trp was quantified by the UPCL analysis. A solution of 200 mM sodium citrate (pH 4.5) was used as a solution for stopping the reaction. The activity for L-Asp/IPA is shown in the column "IPA" of the aminotransferase activity in Table 15.

The formed Monatin and Trp were quantified using ACQUITY UPLC system supplied from Waters. The condition for the measurement is shown below. 0.2 mL of the reaction solution was reacted for 15 minutes, then the reaction was stopped. The reaction solution after stopping the reaction was centrifuged, and about 0.2 mL of the supernatant was subjected to the UPLC analysis.

TABLE 14

| UPLC | |
|---|---|
| Column: | ACQUITY UPLC HSS T3 2.1 × 50 mm |
| Column Temp.: | 40° C. |
| Sample Temp.: | 4° C. |
| Detection: | UV 210 nm |
| Injection vol.: | 5 µl |
| Mobile Phase A: | 20 mM KH2PO4 (Filt.) |
| Mobile Phase B: | ACN |
| Flow rate: | 0.5 ml/min |
| Method: | 20 mM KH2PO4_05_HSS |

| Time (min) | A (%) | B (%) |
|---|---|---|
| 0 | 96 | 4 |
| 1.9 | 96 | 4 |
| 2.0 | 60 | 40 |
| 2.2 | 60 | 40 |
| 2.3 | 96 | 4 |
| 3.0 | 96 | 4 |

The 2S,4R-Monatin, the 2S,4S-Monatin and Trp can be quantified distinctively at 1.1 minutes, 1.5 minutes and 1.3 minutes, respectively.

(3) Results of Measuring Specific Activity of AJ12469LAT for Various Keto Acids

The results of measuring the specific activity for 10 mM keto acid when 12469-AT-His was used and 100 mM L-Asp was used as the amino donor are shown in Table 15.

TABLE 15

Specific activity of AJ12469LAT for various keto acids
Aminotransferase acitivity (U/mg)

| | | | 4R-IHOG | | ±IHOG | | |
|---|---|---|---|---|---|---|---|
| α-KG | PA | ±MHOG | SR | SS | SR | SS | IPA |
| 96 | 4.8 | 44 | 0.56 | 1.6 | 0.066 | 3.3 | 0.016 |

Example 36

Reaction for Synthesis of 2S,4R-Monatin Using pET-22-12469AT-His/*E. coli* BL21 (DE3)

One loopful of microbial cells of pET-22-12469AT-His/*E. coli* BL21 (DE3) prepared in Example 34 was inoculated to 3 mL of Overnight Express Instant TB medium (Novagen) containing 100 mg/L of ampicillin in a test tube, and the test tube was then shaken at 37° C. for 16 hours. After the completion of the cultivation, the microbial cells were collected from 1 mL of the cultured medium by centrifugation, and suspended in 1 mL of BugBuster Master Mix (Novagen). The resulting suspension was incubated at room temperature for 15 minutes to lyse the microbial cells. The microbial cell debris was removed by centrifugation, and the resulting supernatant was used as a soluble fraction.

The reaction for the synthesis of the 2S,4R-Monatin from 4R-IHOG was carried out using the obtained soluble fraction. To 0.1 mL of a reaction solution [100 mM L-Asp-Na-1aq, 10 mM 4R-IHOG (containing 4S-IHOG in a trace amount), 50 µM PLP, and 100 mM Tris-HCl (pH 8.0)], 0.05 mL of the above soluble fraction was added, and the mixture was reacted at 25° C. for one hour. After the completion of the reaction, the amount of the formed 2S,4R-Monatin was quantified to be 0.87 mM. The 2S,4R-Monatin was quantified by the UPLC analysis. The condition for the analysis is the same as that in Example 29.

Example 37

Purification of Aminotransferase Derived from *Corynebacterium ammoniagenes* AJ1444

Aminotransferase that formed the 2S,4R-Monatin was purified from a soluble fraction from *Corynebacterium ammoniagenes* AJ1444 as follows. The synthetic reaction and quantification of the 2S,4R-Monatin were carried out in the same manner as in Example 25.

(1) Preparation of Soluble Fraction

Microbial cells of *Corynebacterium ammoniagenes* AJ1444 were spread on the LB agar medium and cultured at 30° C. for two days.

One loopful of the obtained microbial cells was inoculated to 160 mL of the enzyme production medium (10 g/L of yeast extract, 10 g/L of trypton, 1 g/L of glucose, 3 g/L of dipotassium hydrogen phosphate, 1 g/L of potassium dihydrogen phosphate, 0.1 g/L of magnesium sulfate heptahydrate, and 5 g/L of ammonium sulfate) in a 500 mL Sakaguchi flask, and cultured at 30° C. for 16 hours with shaking. The microbial cells were collected from about 1760 mL of the cultured medium by centrifugation, washed with and suspended in 20 mM Tris-HCl (pH 7.6), and disrupted by adding glass beads and using a multibead shocker (Yasui Kikai Corporation). The microbial cell debris was removed from the disrupted cell suspension by centrifugation, and the resulting supernatant was used as a soluble fraction.

(2) Ammonium Sulfate Precipitation

Ammonium sulfate was added to the above soluble fraction so that a final concentration of ammonium sulfate was 90% (w/w), and an ammonium sulfate precipitate was obtained by centrifugation.

(3) Hydrophobic Chromatography

The above ammonium sulfate precipitate was dissolved in 1.0 M ammonium sulfate and 20 mM Tris-HCl (pH 7.6). This solution was applied onto the hydrophobic chromatographic column HiLoad 26/10 Phenyl Sepharose HP (supplied from GE Healthcare Bioscience, CV=53 mL) equilibrated with 1.0 M ammonium sulfate and 20 mM Tris-HCl (pH 7.6) to absorb proteins to the carrier. Unabsorbed proteins that had not been absorbed to the carrier were washed out with 1.0 M ammonium sulfate and 20 mM Tris-HCl (pH 7.6). Subsequently, the 2S,4R-Monatin-forming enzyme was eluted by linearly changing the concentration of ammonium sulfate from 1.0 M to 0 M at a flow rate of 3 mL/minute. The 2S,4R-Monatin-forming activity was measured in each eluted fraction, and detected in fractions corresponding to about 0.2 M ammonium sulfate.

(4) Anion Exchange Chromatography

The fractions in which the 2S,4R-Monatin-forming activity had been detected were combined, and dialyzed against 20 mM Tris-HCl (pH 7.6) overnight. The resulting solution was applied onto the anion exchange chromatographic column HiLoad 16/10 Q Sepharose HP (supplied from GE Healthcare Bioscience, CV=20 mL) equilibrated with 20 mM Tris-HCl (pH 7.6) to absorb proteins to the carrier. Proteins that had not been absorbed to the carrier (unabsorbed proteins) were washed out with 20 mM Tris-HCl (pH 7.6). Subsequently, absorbed proteins were eluted by linearly changing the concentration of NaCl from 0 mM to 500 mM at a flow rate of 2.25 mL/minute. The 2S,4R-Monatin-forming activity was measured in each eluted fraction, and detected in the fractions corresponding to about 400 mM NaCl.

(5) Gel Filtration Chromatography

The fractions in which the 2S,4R-Monatin-forming activity had been detected were combined, and concentrated using Amicon Ultra-15 10k (Millipore). The resulting concentrated solution was diluted with 20 mM Tris-HCl (pH 7.6) and 150 mM NaCl. The resulting solution was applied onto the gel filtration column HiLoad 16/60 Superdex 200 pg (supplied from GE Healthcare Bioscience, CV=120 mL) equilibrated with 20 mM Tris-HCl (pH 7.6) and 150 mM NaCl, and proteins were eluted at a flow rate of 1.2 mL/minute. This manipulation confirmed the 2S,4R-Monatin-forming activity at a position at which the molecular weight was estimated to be about 85 kDa.

(6) Anion Exchange Chromatography

The fractions in which the 2S,4R-Monatin-forming activity had been detected were combined, and the resulting solution was applied onto the anion exchange chromatographic column Mono Q 5/5 (supplied from Pharmacia (GE Healthcare Bioscience), CV-1 mL) to absorb proteins to the carrier. Proteins that had not been absorbed to the carrier (unabsorbed proteins) were washed out with 20 mM Tris-HCl (pH 7.6). Subsequently, absorbed proteins were eluted by linearly changing the concentration of NaCl from 0 mM to 500 mM at a flow rate of 1 mL/minute. The 2S,4R-Monatin-forming activity was measured in each fraction, and the 2S,4R-Monatin-forming activity was detected in the fractions corresponding to about 400 mM NaCl.

(7) SDS-PAGE

The obtained fractions were subjected to SDS-PAGE, and a band derived from the active fraction was detected near 43 kDa. This band was subjected to the analysis of the N-terminal amino acid sequence as the candidate for the aminotransferase that forms the 2S,4R-Monatin.

Example 38

Determination of N-Terminal Amino Acid Sequence of Aminotransferase Derived from *Corynebacterium ammoniagenes* AJ1444

The purified enzyme solution obtained in Example 37 was subjected to the analysis of the N-terminal amino acid sequence, and the N-terminal amino acid sequence of MSXIAQXILDQ (SEQ ID NO:112) was obtained. This N-terminal amino acid sequence showed the high homology to aspartate aminotransferase (ZP_03935516) derived from *Corynebacterium striatum* ATCC6940 and aspartate aminotransferase (ZP_06838515) derived from *Corynebacterium ammoniagenes* DSM20306.

Example 39

Cloning of Aminotransferase Gene Derived from *Corynebacterium ammoniagenes* AJ1444

Microbial cells of *Corynebacterium ammoniagenes* AJ1444 were cultured in the same manner as in Example 37. The microbial cells were collected from the resulting cultured medium by centrifugation, and genomic DNA was extracted therefrom.

A DNA fragment including the aminotransferase gene was amplified by PCR with the obtained genomic DNA as the template. The primer Co-d50-r (5'-cttccttggaacaagtcgaggaagac-3': SEQ ID NO:56) designed from the DNA sequence of downstream 50 bp of the aminotransferase gene with reference to the genomic DNA sequence of *Corynebacterium ammoniagenes* DSM20306, and the primer Co-800-f (5'-gctatcgcacaattccaccgcaccctt-3': SEQ ID NO:57) designed with reference to partial sequences that had the high homology between the aspartate aminotransferase (ZP_03935516) derived from *Corynebacterium striatum* ATCC6940 and the aspartate aminotransferase (ZP_06838515) derived from *Corynebacterium ammoniagenes* DSM20306 were used. PCR was performed using KOD-plus-ver. 2 (Toyobo) under the following condition.

1 cycle at 94° C. for 2 minutes
25 cycles at 98° C. for 10 seconds
55° C. for 10 seconds and
68° C. for 60 seconds
1 cycle at 68° C. for 60 seconds, and
4° C.

A nucleotide sequence of about 400 bp of the amplified DNA fragment was determined, and the primer Co-890-r (5'-acatcgttaagcaagcgaaccaccag-3': SEQ ID NO:58) and the primer Co-1060-r (5'-gaaagacaagcgaatgtggtgctcg-3': SEQ ID NO:59 were designed based on that nucleotide sequence. PCR was performed using LA PCR in vitro Cloning Kit (Takara). PCR was performed using KOD-plus-ver. 2 (Toyobo) under the following condition.

1 cycle at 94° C. for 2 minutes
25 cycles at 98° C. for 10 seconds
55° C. for 10 seconds and
68° C. for 60 seconds
1 cycle at 68° C. for 60 seconds, and
4° C.

As a result, the nucleotide sequence including 1134 bp of ORF (SEQ ID NOs: 60 and 61), which has the high homology to the aspartate aminotransferase gene (HMPREF0281_02480) derived from *Corynebacterium ammoniagenes* DSM20306 was determined. The homology was 76% in their DNA sequences and 82% in their amino acid sequences.

This amino acid sequence was consistent with the N-terminal amino acid sequence obtained in Example 38. Thus, it has been thought that the aminotransferase gene having the 2S,4R-Monatin-forming activity could be acquired.

Example 40

Expression of Aminotransferase Derived from *Corynebacterium ammoniagenes* AJ1444 in *E. coli*

(1) Construction of Expression Vector for Aminotransferase Derived from *Corynebacterium ammoniagenes* AJ1444

A DNA fragment including the aminotransferase gene derived from *Corynebacterium ammoniagenes* AJ1444 was amplified by PCR with the genomic DNA of *Corynebacterium ammoniagenes* AJ1444 as the template. The primer 1444AT-Nde-f (5'-ggaattccatATGAGCCACATCGCTCAACGCATCC-3': SEQ ID NO:62) and a primer 1444-xho-r (5'-actccgctcgagGGACTTTTCGAAGTATTGGCGAATG-3': SEQ ID NO:63) were used. PCR was performed using KOD-plus-ver. 2 (Toyobo) under the following condition.

1 cycle at 94° C. for 2 minutes
25 cycles at 98° C. for 10 seconds
55° C. for 10 seconds and
68° C. for 60 seconds
1 cycle at 68° C. for 60 seconds, and
4° C.

The resulting DNA fragment was treated with the restriction enzymes NdeI and XhoI, and ligated to pET-22b (Novagen) likewise treated with NdeI and XhoI. *E. coli* JM109 was transformed with this ligation solution, an objective plasmid was selected from ampicillin resistant *E. coli* colonies, and this plasmid was designated as pET-22-1444AT-His. In this plasmid, the aminotransferase derived from *Corynebacterium ammoniagenes* AJ1444 which has the His-tag added to the C-terminus end (1444AT-His) is expressed.

(2) Purification of 1444AT-His from *E. coli* Strain Expressing 1444AT-His

The constructed expression plasmid pET-22-1444AT-His was introduced into *E. coli* BL21 (DE3), and one loopful of the transformant was inoculated to 160 mL of Overnight Express Instant TB Medium (Novagen) containing 100 mg/L of ampicillin in a 500 mL Sakaguchi flask, and the Sakaguchi flask was shaken at 37° C. for 16 hours. After completion of the cultivation, microbial cells were collected from about 1000 mL of the cultured medium by centrifugation, washed with and suspended in 20 mM Tris-HCl (pH 7.6), 300 mM NaCl and 10 mM imidazole, and sonicated at 4° C. for 30 minutes. The microbial cell debris was removed from the sonicated cell suspension by centrifugation, and the resulting supernatant was used as a soluble fraction.

The obtained soluble fraction was applied onto a His-tag protein purification column His TALON superflow 5 mL Centrifuge (Clontech) equilibrated with 20 mM Tris-HCl (pH 7.6), 300 mM NaCl and 10 mM imidazole to absorb proteins to the carrier. Proteins that had not been absorbed to the carrier (unabsorbed protein) were washed out with 20 mM Tris-HCl (pH 7.6), 300 mM NaCl and 10 mM imidazole. Subsequently, absorbed proteins were eluted using 20 mM Tris-HCl (pH 7.6), 300 mM NaCl and 150 mM imidazole at a flow rate of 5 mL/minute.

The obtained fractions were combined and concentrated using Amicon Ultra-15 30k (Millipore). The concentrated solution was diluted with 20 mM Tris-HCl (pH 7.6), and then applied onto the anion exchange chromatographic column HiLoad 16/10 Q Sepharose HP (supplied from GE Healthcare Bioscience, CV=20 mL) equilibrated with 20 mM Tris-HCl (pH 7.6) to absorb proteins to the carrier. Proteins that had not been absorbed to the carrier (unabsorbed protein) were washed out with 20 mM Tris-HCl (pH 7.6). Subsequently, unabsorbed proteins were eluted by linearly changing the concentration of NaCl from 0 mM to 500 mM at a flow rate of 3 mL/minute.

The 2S,4R-Monatin-forming activity was measured in each eluted fraction. The fractions in which the 2S,4R-Monatin-forming activity had been detected were combined, and concentrated using Amicon Ultra-15 30k (Millipore). The concentrated solution was diluted with 20 mM Tris-HCl (pH 7.6) to use as a 1444AT-His solution.

Example 41

Results of Measuring Specific Activity of AJ1444LAT for Various Keto Acids (1) Measurement of Activity for L-Asp/α-KG, L-Asp/PA, L-Asp/(±)-MHOG, L-Glu/PA and L-Glu/(±)-MHOG by Colorimetric Method The activity of AJ1444LAT for various substrates was measured. The specific activity for 10 mM keto acid was measured by colorimetric method, using 100 mM L-Asp or L-Glu as the amino donor substrate for the transamination reaction.

Activity for L-Asp/α-KG: 100 mM L-Asp-Na-1aq, 10 mM α-KG-2Na, 50 μM PLP, 100 mM Tris-HCl (pH 8.0), 0.25 mM NADH and 2 U/mL of MDH at 25° C. The activity was calculated from the reduction of the absorbance measured at 340 nm. Malic dehydrogenase from porcine heart (Sigma) was used as MDH. The activity for L-Asp/α-KG is shown in the column "α-KG" of the aminotransferase activity in Table 17.

Activity for L-Asp/PA: 100 mM L-Asp-Na-1aq, 10 mM PA-Na, 50 μl PLP, 100 mM Tris-HCl (pH 8.0), 0.25 mM NADH, and 2 U/mL of MDH (same as above) at 25° C. The activity was calculated from the reduction of the absorbance measured at 340 nm. The activity for L-Asp/PA is shown in the column "PA" of the aminotransferase activity in Table 17.

Activity for L-Asp/(±)-MHOG: 100 mM L-Asp-Na-1aq, 10 mM (±)-MHOG, 50 μM PLP, 100 mM Tris-HCl (pH 8.0), 0.25 mM NADH, 2 U/mL of MDH (same as above), and 10 U/mL of LDH at 25° C. The activity was calculated from the reduction of the absorbance measured at 340 nm. D-Lactate dehydrogenase from *Leuconostoc mesenteroides* (Oriental Yeast) was used as LDH. LDH was added in order to remove PA in a trace amount contaminated in (±)-MHOG. The activity for L-Asp/(±)-MHOG is shown in the column "(±)-MHOG" of the aminotransferase activity in Table 17.

Activity for L-Glu/PA: 100 mM L-Glu-Na, 10 mM PA, 50 μM PLP, 100 mM Tris-HCl (pH 8.0), 100 mM NH$_4$Cl, 0.25 mM NADH and 10 U/mL of GDH at 25° C. The activity was calculated from the reduction of the absorbance measured at 340 nm. L-Glutamic dehydrogenase from bovine liver (Sigma) was used as GDH. The activity for L-Glu/PA is shown in the column "PA" of the aminotransferase activity in Table 17.

Activity for L-Glu/(±)-MHOG: 100 mM L-Glu-Na, 10 mM (±)-MHOG, 50 μl PLP, 100 mM Tris-HCl (pH 8.0), 100 mM NH$_4$Cl, 0.25 mM NADH, and 10 U/mL of GDH at 25° C. The activity was calculated from the reduction of the absorbance measured at 340 nm. The activity for L-Glu/(±)-MHOG is shown in the column "(±)-MHOG" of the aminotransferase activity in Table 17.

(2) Measurement of Activity for L-Asp/4R-IHOG, L-Asp/(±)-IHOG, L-Asp/IPA, L-Glu/4R-IHOG and L-Glu/IPA The activity to form 2S,4R-Monatin from 4R-IHOG, the activity to form 2S,4R-Monatin and 2S,4S-Monatin from (±)-IHOG, which are the objective activities, and the activity to form L-Trp as the by-product from IPA were measured individually. The transamination reaction to 10 mM keto acid was performed using 100 mM L-Asp or L-Glu as the amino donor substrate of the transamination reaction, and the amount of the formed amino acid was quantified by UPLC to calculate the specific activity.

Activity for L-Asp/4R-IHOG: 100 mM L-Asp-Na-1aq, 10 mM 4R-IHOG (containing 4S-IHOG in a trace amount), 50 μM PLP, and 100 mM Tris-HCl (pH 8.0) at 25° C. The formed 2S,4R-Monatin and 2S,4S-Monatin were quantified by UPLC analysis.

A solution of 200 mM sodium citrate (pH 4.5) was used as a solution for stopping the reaction. The activity for L-Asp/4R-IHOG is shown in the column "4R-IHOG" of the aminotransferase activity in Table 17.

Activity for L-Asp/(±)-IHOG: 100 mM L-Asp-Na-1aq, 10 mM (±)-IHOG, 50 μM PLP, and 100 mM Tris-HCl (pH 8.0) at 25° C. The formed 2S,4R-Monatin and 2S,4S-Monatin were quantified by UPLC analysis. A solution of 200 mM sodium citrate (pH 4.5) was used as a solution for stopping the reaction. The activity for L-Asp/(±)-IHOG is shown in the column "(±)-IHOG" of the aminotransferase activity in Table 17.

Activity for L-Asp/IPA: 100 mM L-Asp-Na-1aq, 10 mM IPA, 50 μM PLP, and 100 mM Tris-HCl (pH 8.0) (pH was adjusted to 8.0 with 1 N NaOH after preparing the reaction solution) at 25° C. The formed Trp was quantified by UPCL analysis. A solution of 200 mM sodium citrate (pH 4.5) was used as a solution for stopping the reaction. The activity for L-Asp/IPA is shown in the column "IPA" of the aminotransferase activity in Table 17.

Activity for L-Glu/4R-IHOG: 100 mM L-Glu-Na, 10 mM 4R-IHOG (containing 4S-IHOG in a trace amount), 50 μM PLP, and 100 mM Tris-HCl (pH 8.0) at 25° C. The formed 2S,4R-Monatin and 2S,4S-Monatin were quantified by UPLC analysis. A solution of 200 mM sodium citrate (pH 4.5) was used as a solution for stopping the reaction. The activity for L-Glu/4R-IHOG is shown in the column "4R-IHOG" of the aminotransferase activity in Table 17.

Activity for L-Glu/IPA: 100 mM L-Glu-Na, 10 mM IPA, 50 μM PLP, and 100 mM Tris-HCl (pH 8.0) (pH was adjusted to 8.0 with 1 N NaOH after preparing the reaction solution) at 25° C. The formed Trp was quantified by UPCL analysis. A solution of 200 mM sodium citrate (pH 4.5) was used as a solution for stopping the reaction. The activity for L-Glu/IPA is shown in the column "IPA" of the aminotransferase activity in Table 17.

The formed Monatin and Trp were quantified using ACQUITY UPLC system supplied from Waters. The condition for the measurement is shown below. 0.2 mL of the reaction solution was reacted for 15 minutes, then the reaction was stopped. The reaction solution after stopping the reaction was centrifuged, and about 0.2 mL of the supernatant was subjected to UPLC analysis.

TABLE 16

| UPLC | |
|---|---|
| Column: | ACQUITY UPLC HSS T3 2.1 × 50 mm |
| Column Temp.: | 40° C. |
| Sample Temp.: | 4° C. |
| Detection: | UV 210 nm |
| Injection vol.: | 5 μl |
| Mobile Phase A: | 20 mM KH2PO4 (Filt.) |
| Mobile Phase B: | ACN |
| Flow rate: | 0.5 ml/min |
| Method: | 20 mM KH2PO4_05_HSS |

| Time (min) | A (%) | B (%) |
|---|---|---|
| 0 | 96 | 4 |
| 1.9 | 96 | 4 |
| 2.0 | 60 | 40 |
| 2.2 | 60 | 40 |
| 2.3 | 96 | 4 |
| 3.0 | 96 | 4 |

The 2S,4R-Monatin, 2S,4S-Monatin and Trp can be quantified distinctively at 1.1 minutes, 1.5 minutes and 1.3 minutes, respectively.

(3) Results of Measuring Specific Activity of AJ1444LAT for Various Keto Acids

The results of measuring the specific activity for 10 mM keto acid when 1444-AT-His was used and L-Asp was used as the amino donor are shown in Table 17.

TABLE 17

Specific activity of AJ1444LAT for various keto acids
Aminotransferase activity (U/mg)

| | α-KG | PA | ±MHOG | 4R-IHOG SR | 4R-IHOG SS | ±IHOG SR | ±IHOG SS | IPA |
|---|---|---|---|---|---|---|---|---|
| L-Asp | 4.0 | 1.7 | 2.7 | 2.4 | 0.26 | 0.91 | 1.7 | 0.085 |
| L-Glu | — | 8.7 | 145 | 200 | 15 | — | — | 0.21 |

Example 42

Reaction for Synthesis of 2S,4R-Monatin Using pET-22-1444AT-His/*E. coli* BL21 (DE3)

One loopful of microbial cells of pET-22-1444AT-His/*E. coli* BL21 (DE3) prepared in Example 40 was inoculated to 3 mL of Overnight Express Instant TB medium (Novagen) containing 100 mg/L of ampicillin in a test tube, and the test tube was then shaken at 37° C. for 16 hours. After the completion of the cultivation, the microbial cells were collected from 1 mL of the cultured medium by centrifugation, and suspended in 1 mL of BugBuster Master Mix (Novagen). The resulting suspension was left stand at room temperature for 15 minutes to lyse the microbial cells. The microbial cell debris was removed by centrifugation, and the resulting supernatant was used as a soluble fraction.

The reaction for the synthesis of 2S,4R-Monatin from 4R-IHOG was carried out using the obtained soluble fraction. To 0.1 mL of the reaction solution [100 mM L-Asp-Na-1aq, 10 mM 4R-IHOG (containing 4S-IHOG in a trace amount), 50 µM PLP, and 100 mM Tris-HCl (pH 8.0)], 0.05 mL of the above soluble fraction was added, and the mixture was reacted at 25° C. for one hour. After the completion of the reaction, the amount of the formed 2S,4R-Monatin was quantified to be 0.13 mM. The 2S,4R-Monatin was quantified by the UPLC analysis. The condition for the analysis is the same as that in Example 29.

Example 43

One-Pot Reaction for Synthesis of 2S,4R-Monatin from 20 mM L-Trp (AJ3976LAT, AJ12469LAT, AJ1444LAT)

A reaction was performed under the following condition for 12 hours using purified 3976AT-His, 12469AT-His and 1444AT-His. The reaction was performed in 1 mL using a test tube. The reaction solution was appropriately sampled, the sample was diluted with TE buffer, ultrafiltrated using an Amicon Ultra-0.5 mL centrifugal filter 10 kDa (Millipore), and the resulting filtrate was analyzed. HPLC and capillary electrophoresis were used for the analysis.

Reaction condition: 20 mM L-Trp, 40 mM PA-Na, 160 mM L-Asp-Na-1aq, 1 mM MgCl$_2$, 50 µM PLP, 100 mM Tris-HCl, 20 mM KPB (pH 7.0), 20% Ps_aad broth, 30 U/mL of purified SpAld enzyme, 10 U/mL of commercially available OAA DCase enzyme, 2 U/mL of purified LAT enzyme (vs 10 mM 4R-IHOG), and 200 U/mL of commercially available SOD enzyme at 25° C. at 120 rpm.

The methods for preparing the enzymes subjected to the reaction are shown below.

Ps_aad broth: it was prepared according to the method described in Example 17.

Purified SpAld enzyme: it was prepared according to the method described in Example 19.

AJ3976LAT, AJ12469LAT and AJ1444LAT: they are prepared according to the methods described in Examples 28, 34 and 40.

OAA DCase: oxaloacetate decarboxylase from *Pseudomonas* sp. (Sigma) was used. A value described by the manufacturer was used as an enzyme amount (U).

SOD: superoxide dismutase from bovine liver (Sigma) was used. A value described by the manufacturer was used as an enzyme amount (U).

As a result of the one-pot reactions, 12 mM, 11 mM and 13 mM 2S,4R-Monatin were formed after 4 hours using AJ3976LAT, AJ12469LAT and AJ1444LAT, respectively, and their yields from L-Trp were 58%, 53% and 64%, respectively.

Example 44

One-Pot Reaction for Synthesis of 2S,4R-Monatin from 50 mM Trp (AJ3976 on Scale of 80 mL)

A reaction was performed for 12 hours using purified 3976AT-HIs under the following condition. The reaction was performed in a volume of 80 mL using a 250 mL volume mini-jar. The reaction solution was appropriately sampled, the sample was diluted with TE buffer, which was then ultrafiltrated using the Amicon Ultra-0.5 mL centrifugal filter 10 kDa (Millipore), and the resulting filtrate was analyzed. HPLC and capillary electrophoresis were used for the analysis.

Reaction condition: 50 mM L-Trp, 50 mM PA-Na, 200 mM L-Asp-Na-1aq, 1 mM MgCl$_2$, 50 µl PLP, 100 mM Tris-HCl (pH 7.6), 20 mM KPB (pH 7.6), 0.0025% GD113K, pH<7.6 (1 M H$_2$SO$_4$), 20% Ps_aad broth, 30 U/mL of purified SpAld enzyme, 10 U/mL of commercially available OAA DCase enzyme, 2 U/mL of purified LAT enzyme (vs 10 mM 4R-IHOG), and 200 U/mL of commercially available SOD enzyme at 25° C. at 350-400 rpm with air at 8 mL/minute (1/10 vvm).

The methods for preparing the enzymes subjected to the reaction are shown below.

Ps_aad broth: it was prepared according to the method described in Example 17.

Purified SpAld enzyme: it was prepared according to the method described in Example 19.

AJ3976LAT: it was prepared according to the methods described in Examples 28.

OAA DCase: oxaloacetate decarboxylase from *Pseudomonas* sp. (Sigma) was used. The value described by the manufacturer was used as the enzyme amount (U).

SOD: superoxide dismutase from bovine liver (Sigma) was used. The value described by the manufacturer was used as the enzyme amount (U).

As a result of the one-pot reaction, 27 mM 2S,4R-Monatin was confirmed to be accumulated after 8 hours, and the yield from L-Trp which was calculated after calibrating the solution amounts was 56%.

Example 45

Expression of in Silico Selected Aminotransferase in *E. coli*

(1) Construction of Expression Plasmid for in Silico Selected Aminotransferase

A DNA sequence obtained by conferring a NdeI recognition sequence and a XhoI recognition sequence to the 5'-end and 3'-end of the genetic sequence of the aminotransferase selected in silico was subjected to Optimum Gene Codon Optimization Analysis supplied by GenScript to obtain synthesized DNA, an expression efficiency of which had been optimized in *E. coli*. Types of the aminotransferase are as follows.

Putative aminotransferase derived from *Deinococcus Geothermalis* DSM 11300 (Dge, ABF45244) (SEQ ID NOs: 64 and 65), hypothetical protein derived from *Corynebacterium glutamicum* R (Cg1, BAF53276) (SEQ ID NOs: 66 and 67), Lysn, alpha-aminoadipate aminotransferase derived from *Thermus thermophilus* HB27 (TtHB, AAS80391) (SEQ ID NOs: 68 and 69), aminotransferase (Putative) derived from *Thermotoga Maritima* (Tma1, AAD36207) (SEQ ID NOs: 70 and 71), human kynurenine aminotransferase II Homologue derived from *Pyrococcus Horikoshii* Ot3 (PhoH, 1X0M) (SEQ ID NOs: 72 and 73), aspartate aminotransferase derived from *Phormidium Lapideum* (Pla, BAB86290) (SEQ ID NOs: 74 and 75), aspartate aminotransferase derived from *Thermus Thermophilus* (Tth, BAD69869) (SEQ ID NOs: 76 and 77), aromatic aminotransferase derived from *Pyrococcus Horikoshii* Ot3 (PhoA, 1DJU) (SEQ ID NOs: 78 and 79), Mj0684 derived from *Methanococcus jannaschii* (Mja, AAB98679) (SEQ ID NOs: 80 and 81), aspartate aminotransferase derived from *Thermotoga Maritima* (Tma2, AAD36764) (SEQ ID NOs: 82 and 83), aspartate aminotransferase derived from *Saccharomyces cerevisiae* (Sce, CAY81265) (SEQ ID NOs: 84 and 85), aspartate aminotransferase derived from *Eubacterium rectale* (Ere, ACR74350) (SEQ ID NOs: 86 and 87), aspartate aminotransferase derived from *Bacillus pumilus* SAFR-032 (Bpu, ABV62783) (SEQ ID NOs: 88 and 89), putative transcriptional regulator (GntR family) derived from *Bacillus cellulosilyticus* DSM 2522 (Bce, ADU30616) (SEQ ID NOs: 90 and 91), aspartate aminotransferase aspC derived from *Bacillus* species (strain YM-2) (Bsp, AAA22250) (SEQ ID NOs: 92 and 93), aspartate aminotransferase aatB derived from *Sinorhizobium meliloti* 1021 (SmeB, CAC47870) (SEQ ID NOs: 94 and 95), branched-chain amino-acid aminotransferase derived from *Methanothermobacter thermautotrophicus* str. Delta H (Mth, AAB85907) (SEQ ID NOs: 96 and 97), aspartate aminotransferase derived from *Lactobacillus acidophilus* (Lba, AAV43507) (SEQ ID NOs: 98 and 99), aspartate aminotransferase aatA derived from *Sinorhizobium meliloti* 1021 (SmeA, CAC46904) (SEQ ID NOs: 100 and 101), hypothetical serine aminotransferase derived from *Pyrococcus horikoshi* OT3 (PhoS, BAA30413) (SEQ ID NOs: 102 and 103), PLP-dependent aminotransferases derived from *Thermoanaerobacter tengcongensis* MB4 (Tte, AAM24436) (SEQ ID NOs: 104 and 105), putative transcriptional regulator (GntR family) derived from *Clostridium cellulolyticum* H10 (Cce, ACL75101) (SEQ ID NOs: 106 and 107), aspartate aminotransferase AspT derived from *Rhodococcus erythropolis* PR4 (Rer, BAH31070) (SEQ ID NOs: 108 and 109), and transcriptional regulator derived from *Saccharophagus degradans* 2-40 (Sde, ABD82545) (SEQ ID NOs: 110 and 111).

TABLE 18

Comparison of percent identities of amino acid sequences

| ID | Abbreviation | Amino acid sequence identity (%) to AJ1616LAT | Amino acid sequence identity (%) to AJ3976LAT |
|---|---|---|---|
| 1 | Dge | 46 | 23 |
| 2 | Cgl | 46 | 30 |
| 3 | TtHB | 20 | 22 |
| 4 | Tma1 | 21 | 20 |
| 5 | PhoH | 20 | 22 |
| 6 | Pla | 18 | 45 |
| 7 | Tth | 17 | 47 |
| 8 | PhoA | 16 | 39 |
| 9 | Mja | 17 | 33 |
| 10 | Tma2 | 15 | 27 |
| 11 | Sce | 20 | 19 |
| 12 | Ere | 30 | 26 |
| 13 | Bpu | 93 | 23 |
| 14 | Bce | 67 | 22 |
| 15 | Bsp | 17 | 45 |
| 16 | SmeB | 20 | 58 |
| 17 | Mth | 17 | 16 |
| 18 | Lba | 20 | 24 |
| 19 | SmeA | 21 | 89 |
| 20 | PhoS | 19 | 15 |
| 21 | Tte | 17 | 48 |
| 22 | Cce | 61 | 24 |
| 23 | Rer | 49 | 16 |
| 24 | Sde | 49 | 26 |

The synthesized DNA was treated with the restriction enzymes NdeI and XhoI, and ligated to pET-22b (Novagen) likewise treated with NdeI and XhoI. *E. coli* JM109 was transformed with this ligation solution, the objective plasmids were selected from ampicillin resistant colonies, and these plasmid were designated as pET-22-AT-His. In these plasmids, the aminotransferases having the His-tag added to the C terminus end (AT-His) are expressed.

(2) Purification of AT-His from *E. coli* Strains Expressing AT-His

Each of the constructed plasmids pET-22-AT-His was introduced into *E. coli* BL21 (DE3), and one loopful of the transformant was inoculated to 100 mL of Overnight Express Instant TB Medium (Novagen) containing 100 mg/L of ampicillin in a 500 mL Sakaguchi flask, and the Sakaguchi flask was shaken for 16 hours. The shaking was performed for Lba at 25° C., for Dge, Pla, Tth, Tma2, Sce, Ere, Bpu, Bce, Bsp, SmeA, PhoS, Rer and Sde at 30° C., for Cg1, TtHB, PhoH, PhoA, SmeB, Tte and Cce at 37° C., and for Tma1, Mja and Mth at 42° C. After the completion of the cultivation, microbial cells were collected from the cultured medium by the centrifugation, washed with and suspended in 20 mM Tris-HCl (pH 7.6), 300 mM NaCl and 10 mM imidazole, and sonicated. The microbial cell debris was removed from the sonicated cell suspension by the centrifugation, and the resulting supernatant was used as a soluble fraction.

The obtained soluble fraction was applied onto the His-tag protein purification column His TALON superflow 5 mL Centrifuge (Clontech) equilibrated with 20 mM Tris-HCl (pH 7.6), 300 mM NaCl and 10 mM imidazole to absorb proteins to the carrier. Proteins that had not been absorbed to the carrier (unabsorbed protein) were washed out with 20 mM Tris-HCl (pH 7.6), 300 mM NaCl and 10 mM imidazole. Subsequently, absorbed proteins were eluted using 20 mM Tris-HCl (pH 7.6), 300 mM NaCl and 150 mM imidazole at a flow rate of 5 mL/minute. The obtained fractions were combined and concentrated using Amicon Ultra-15 10k (Millipore). The concentrated solution was diluted with 20 mM Tris-HCl (pH 7.6) to use as a LAT solution. If necessary,

Example 46

One-Pot Reaction for Synthesis of 2S,4R-Monatin from 20 mM L-Trp

Each reaction was performed under the following condition for 15 hours using purified various AT-His. The reaction was performed in a volume of 1 mL using a test tube. After the completion of the reaction, each sample was diluted with TE buffer, ultrafiltrated using the Amicon Ultra-0.5 mL centrifugal filter 10 kDa (Millipore), and the resulting filtrate was analyzed. HPLC and capillary electrophoresis were used for the analysis.

Reaction condition: 20 mM L-Trp, 40 mM PA-Na, 160 mM L-Asp-Na-1aq, 1 mM $MgCl_2$, 50 μM PLP, 100 mM Tris-HCl, 20 mM KPB (pH 7.0), 20% Ps_aad broth, 30 U/mL of purified SpAld enzyme, 10 U/mL of commercially available OAA DCase enzyme, 1 mg/mL of purified LAT enzyme, and 200 U/mL of commercially available SOD enzyme at 25° C. at 120 rpm.

The methods for preparing the enzymes subjected to the reaction were shown below.

Ps_aad broth: it was prepared according to the method described in Example 17.

Purified SpAld enzyme: it was prepared according to the method described in Example 19.

Various LAT: they were prepared according to the method described in Example 45.

OAA DCase: oxaloacetate decarboxylase from *Pseudomonas* sp. (Sigma) was used. The value described by the manufacturer was used as the enzyme amount (U).

SOD: superoxide dismutase from bovine liver (Sigma) was used. The value described by the manufacturer was used as the enzyme amount (U).

Results of the one-pot reactions are shown in Table 19. The 2S,4R-Monatin at 11 mM, 16 mM, 6 mM and 8 mM were formed using Tth, Bpu, SmeA and Sde, respectively, and their yields from L-Trp were 55%, 78%, 28% and 42%, respectively.

TABLE 19

Yields of 2S,4R-Monatin in one-pot reaction using 20 mM Trp as substrate

| ID | Abbreviation | Yield from Trp (%) |
|---|---|---|
| 1 | Dge | 4.4 |
| 2 | Cgl | 5.1 |
| 3 | TtHB | 1.5 |
| 4 | Tma1 | N.D. |
| 5 | PhoH | 0.2 |
| 6 | Pla | 14.0 |
| 7 | Tth | 55.0 |
| 8 | PhoA | N.D. |
| 9 | Mja | N.D. |
| 10 | Tma2 | 2.6 |
| 11 | Sce | 0.4 |
| 12 | Ere | 0.3 |
| 13 | Bpu | 78.0 |
| 14 | Bce | 0.3 |
| 15 | Bsp | 3.6 |
| 16 | SmeB | 2.6 |
| 17 | Mth | 0.4 |
| 18 | Lba | 1.0 |
| 19 | SmeA | 28.0 |
| 20 | PhoS | 0.1 |
| 21 | Tte | 6.2 |
| 22 | Cce | 6.5 |
| 23 | Rer | 0.5 |
| 24 | Sde | 42.0 |

Example 47

One-Pot Reaction for Synthesis of 2S,4R-Monatin from 20 mM L-Trp (Tth, Bpu, SmeA and Sde)

Reactions were performed under the following condition for 15 hours using purified various AT-His. The reaction was performed in a volume of 1 mL using a test tube. After the completion of the reaction, the sample was diluted with TE buffer, ultrafiltrated using the Amicon Ultra-0.5 mL centrifugal filter 10 kDa (Millipore), and the resulting filtrate was analyzed. HPLC and capillary electrophoresis were used for the analysis.

Reaction condition: 20 mM L-Trp, 40 mM PA-Na, 160 mM L-Asp-Na-1aq, 1 mM $MgCl_2$, 50 μM PLP, 100 mM Tris-HCl, 20 mM KPB (pH 7.0), 20% Ps_aad broth, 30 U/mL of purified SpAld enzyme, 10 U/mL of commercially available OAA DCase enzyme, 3 mg/mL of purified LAT enzyme (12 mg/mL of Tth, 1 mg/mL of Bpu), and 200 U/mL of commercially available SOD enzyme at 25° C. at 120 rpm.

The methods for preparing the enzymes subjected to the reaction are shown below.

Ps_aad broth: it was prepared according to the method described in Example 17.

Purified SpAld enzyme: it was prepared according to the method described in Example 19.

Various LAT: they were prepared according to the method described in Example 45.

OAA DCase: oxaloacetate decarboxylase from *Pseudomonas* sp. (Sigma) was used. The value described by the manufacturer was used as the enzyme amount (U).

SOD: superoxide dismutase from bovine liver (Sigma) was used. The value described by the manufacturer was used as the enzyme amount (U).

The results of the one-pot reactions are shown in Table 20. The 2S,4R-Monatin at 18 mM, 17 mM, 11 mM and 12 mM were formed using Tth, Bpu, SmeA and Sde, respectively, and their yields from L-Trp were 92%, 87%, 54% and 61%, respectively.

TABLE 20

Yields of 2S,4R-Monatin in one-pot reaction using 20 mM Trp as substrate

| Abbreviation | Yield from Trp (%) |
|---|---|
| Tth | 92 |
| Bpu | 87 |
| SmeA | 54 |
| Sde | 61 |

Example 48

One-Pot Reaction for Synthesis of 2S,4R-Monatin from 100 mM L-Trp (Tth, Bpu, SmeA and Sde)

Reactions were performed under the following condition for 18 hours using purified various AT-His, Tth, Bpu, SmeA and Sde. The reaction was performed in a volume of 1 mL using a test tube. After the completion of the reaction, the sample was diluted with TE buffer, ultrafiltrated using the Amicon Ultra-0.5 mL centrifugal filter 10 kDa (Millipore), and the resulting filtrate was analyzed. HPLC and capillary electrophoresis were used for the analysis.

Reaction condition: 100 mM L-Trp, 50 mM PA-Na, 300 mM L-Asp-Na-1aq, 1 mM $MgCl_2$, 50 µM PLP, 100 mM Tris-HCl, 20 mM KPB (pH 7.0), 40% Ps_aad broth, 60 U/mL of purified SpAld enzyme, 10 U/mL of commercially available OAA DCase enzyme, 3 mg/mL of purified LAT enzyme (12 mg/mL for Tth), and 200 U/mL of commercially available SOD enzyme at 25° C. at 150 rpm.

The methods for preparing the enzymes subjected to the reaction are shown below.

Ps_aad broth: it was prepared according to the method described in Example 17.

Purified SpAld enzyme: it was prepared according to the method described in Example 19.

Various LAT: they were prepared according to the method described in Example 45.

OAA DCase: oxaloacetate decarboxylase from *Pseudomonas* sp. (Sigma) was used. The value described by the manufacturer was used as the enzyme amount (U).

SOD: superoxide dismutase from bovine liver (Sigma) was used. The value described by the manufacturer was used as the enzyme amount (U).

The results of the one-pot reactions are shown in Table 21. The 2S,4R-Monatin at 72 mM, 46 mM, 6.4 mM and 20 mM were formed using Tth, Bpu, SmeA and Sde, respectively, and their yields from L-Trp were 72%, 46%, 6.4% and 20%, respectively.

TABLE 21

Yields of 2S,4R-MOnatin in one pot reaction using 100 mM Trp as substrate

| Abbreviation | Yield from Trp (%) |
|---|---|
| Tth | 72 |
| Bpu | 46 |
| SmeA | 6.4 |
| Sde | 20 |

(Information on Microorganisms)

The microorganisms specified by deposit numbers which are described herein can be available from certain deposit authority. The microorganisms described in Table 22 have been depsited to National Institute of Advanced Industrial Science and Technology, International Patent Organism Depositary (1-1-1 Central No. 6 Higashi, Tsukuba-shi, Ibaraki Prefecture, Japan) on the following dates, and the following deposit numbers have been conferred to them. As described in Table 22, these microorganisms are currently classified in the following ways as a result of reidentification, although different names were previously conferred to them.

TABLE 22

| Current names for microorganims (Previous names for microorganims) | Deposit number | Deposited date |
|---|---|---|
| *Bacillus altitudinis* AJ1616 (*Bacillus* sp. AJ1616) | FERM-BP 11429 | Oct. 4, 2011 |
| *Stenotrophomonas* sp. AJ3447 (*Xanthomonas oryzae* AJ3447) | FERM-BP 11422 | Sep. 30, 2011 |
| *Stenotrophomonas* sp. AJ11634 (*Xanthomonas albilineans* AJ11634) | FERM-BP 11423 | Sep. 30, 2011 |
| *Ochrobactrum pseudogrignonense* AJ3735 (*Pseudomonas betainovorans* AJ3735) | FERM-BP 11432 | Oct. 4, 2011 |
| *Stenotrophomonas* sp. AJ1591 (*Pseudomonas putrefaciens* AJ1591) | FERM-BP 11419 | Sep. 27, 2011 |
| *Stenotrophomonas* sp. AJ3839 (*Pseudomonas peptidolytica* AJ3839) | FERM-BP 11416 | Sep. 15, 2011 |
| *Brevundimonas diminuta* AJ3958 (*Pseudomonas hydrogenovora* AJ3958) | FERM-BP 11425 | Sep. 30, 2011 |
| *Rhizobium* sp. AJ12469 (*Alcaligenes faecalis* AJ12469) | FERM-BP 11430 | Oct. 4, 2011 |
| *Carnimonas* sp. AJ3230 (*Achromobacter brunificans* AJ3230) | FERM-BP 11431 | Oct. 4, 2011 |
| *Pseudomonas* sp. AJ1594 (*Pseudomonas ovalis* AJ1594) | FERM-BP 11424 | Sep. 30, 2011 |

In addition, the microorganisms described in Table 23 are currently classified in the following ways as a result of reidentification, although different names were previously conferred to them. The bacterial strain, *Stenotrophomonas* sp. AJ13127 is identical to the known bacterial strain specified by the deposit number FERM-BP 5568.

TABLE 23

Current names for microorganims
(Previous names for microorganims)

*Rhizobium radiobacter* LAT1
(*Rhizobium* sp. LAT1)
*Rhizobium radiobacter* AJ11568
(*Pseudomonas umorosa* AJ11568)
*Dietzia maris* AJ2788
(*Pseudomonas tabaci* AJ2788)
*Stenotrophomonas* sp. AJ13127
(*Stenotrophomonas* sp. AJ13127)
*Arthrobacter* sp. IAM1390
(*Arthrobacter ureafaciens* IAM1390)
*Burkholderia* sp. AJ3084
(*Pseudomonas multivorans* AJ3084)
*Rhizobium radiobacter* AJ2557
(*Alcaligenes metalcaligenes* AJ2557)
*Pseudomonas* sp. LMG2833
(*Achromobacter butyri* LMG2833)

INDUSTRIAL APPLICABILITY

As described above, the methods of the present invention are useful for producing the Monatin which can be used as the sweetener.

SEQUENCE LISTING FREE TEXT

SEQ ID NO:1: Nucleotide sequence of aminotransferase gene derived from *Bacillus* altitudinis SEQ ID NO:2: Amino acid sequence of aminotransferase derived from *Bacillus* altitudinis SEQ ID NO:3: Nucleotide sequence of aminotransferase gene (nucleotide numbers 231-1538) and the upstream and downstream regions thereof which are derived from *Bacillus altitudinis*

SEQ ID NO:4: Amino acid sequence of a fragment of aminotransferase derived from *Bacillus altitudinis*

SEQ ID NO:5: Amino acid sequence of a fragment of aminotransferase derived from *Bacillus altitudinis*

SEQ ID NO:6: Forward primer for amplifying DNA fragment containing aminotransferase gene derived from *Bacillus altitudinis* (Bp-u200-f)

SEQ ID NO:7: Reverse primer for amplifying DNA fragment containing aminotransferase gene derived from *Bacillus altitudinis* (Bp-d200-r)

SEQ ID NO:8: Forward primer for amplifying DNA fragment containing aminotransferase gene derived from *Bacillus altitudinis* (1616AT-Nde-f)

SEQ ID NO:9: Reverse primer for amplifying DNA fragment containing aminotransferase gene derived from *Bacillus altitudinis* (1616-xho-r)

SEQ ID NO:10: Forward primer for converting DNA sequence recognized by NdeI, which is found on aminotransferase gene derived from *Bacillus altitudinis* (1616-delNde-f)

SEQ ID NO:11: Reverse primer for converting DNA sequence recognized by NdeI, which is found on aminotransferase gene derived from *Bacillus altitudinis* (1616-delNde-r)

SEQ ID NO:12: Forward primer for amplifying DNA fragment containing SpAld gene (SpAld-f-NdeI)

SEQ ID NO:13: Reverse primer for amplifying DNA fragment containing SpAld gene (SpAld-r-HindIII)

SEQ ID NO:14: Forward primer for converting rare codon 6L in SpAld gene (6L-f)

SEQ ID NO:15: Reverse primer for converting rare codon 6L in SpAld gene (6L-r)

SEQ ID NO:16: Forward primer for converting rare codon 13L in SpAld gene (13L-f)

SEQ ID NO:17: Reverse primer for converting rare codon 13L in SpAld gene (13L-r)

SEQ ID NO:18: Forward primer for converting rare codon 18P in SpAld gene (18P-f)

SEQ ID NO:19: Reverse primer for converting rare codon 18P in SpAld gene (18P-r)

SEQ ID NO:20: Forward primer for converting rare codon 38P in SpAld gene (38P-f)

SEQ ID NO:21: Reverse primer for converting rare codon 38P in SpAld gene (38P-r)

SEQ ID NO:22: Forward primer for converting rare codon 50P in SpAld gene (50P-f)

SEQ ID NO:23: Reverse primer for converting rare codon 50P in SpAld gene (50P-r)

SEQ ID NO:24: Forward primer for converting rare codons 77P, 81P and 84R in SpAld gene (77P-81P-84R-f)

SEQ ID NO:25: Reverse primer for converting rare codons 77P, 81P and 84R in SpAld gene (77P-81P-84R-r)

SEQ ID NO:26: Forward primer for preparing the aminotransferase mutant K39R derived from *Bacillus altitudinis* AJ1616 (K39R_FW)

SEQ ID NO:27: Reverse primer for preparing the aminotransferase mutant K39R derived from *Bacillus altitudinis* AJ1616 (K39R_RV)

SEQ ID NO:28: Forward primer for preparing the aminotransferase mutant S258G derived from *Bacillus altitudinis* AJ1616 (S258G_FW)

SEQ ID NO:29: Reverse primer for preparing the aminotransferase mutant S258G derived from *Bacillus altitudinis* AJ1616 (S258G_RV)

SEQ ID NO:30: Forward primer for preparing the aminotransferase mutant T288G derived from *Bacillus altitudinis* AJ1616 (T288G_FW)

SEQ ID NO:31: Reverse primer for preparing the aminotransferase mutant T288G derived from *Bacillus altitudinis* AJ1616 (T288G_RV)

SEQ ID NO:32: Forward primer for preparing the aminotransferase mutant I289A derived from *Bacillus altitudinis* AJ1616 (I289A_FW)

SEQ ID NO:33: Reverse primer for preparing the aminotransferase mutant I289A derived from *Bacillus altitudinis* AJ1616 (I289A_RV)

SEQ ID NO:34: Forward primer for preparing the aminotransferase mutant Q287E/T288G derived from *Bacillus altitudinis* AJ1616 (Q287E/T288G_FW)

SEQ ID NO:35: Reverse primer for preparing the aminotransferase mutant Q287E/T288G derived from *Bacillus altitudinis* AJ1616 (Q287E/T288G_RV)

SEQ ID NO:36: Primer for preparing a DNA fragment for destroying aspC gene (aspC-L1)

SEQ ID NO:37: Primer for preparing a DNA fragment for destroying aspC gene (aspC-R1)

SEQ ID NO:38: Primer for confirming the insertion of attL-cat-attR in the region of aspC gene (aspC-up)

SEQ ID NO:39: Primer for confirming the insertion of attL-cat-attR in the region of aspC gene (attL-1)

SEQ ID NO:40: Primer for confirming the insertion of attL-cat-attR in the region of aspC gene (aspC-down)

SEQ ID NO:41: Primer for confirming the insertion of attL-cat-attR in the region of aspC gene (attR-1)

SEQ ID NO:42: Nucleotide sequence of oxaloacetate decarboxylase gene derived from *Pseudomonas putida*

SEQ ID NO:43: Amino acid sequence of oxaloacetate decarboxylase derived from *Pseudomonas putida*

SEQ ID NO:44: Amino acid sequence of a fragment of aminotransferase derived from *Rhizobium* radiobacter SEQ ID NO:45: Forward primer which is designed based on the genomic DNA sequence from *Agrobacterium tumefaciens* str. C58 (Ag-u100-f)

SEQ ID NO:46: Reverse primer which is designed based on the genomic DNA sequence from *Agrobacterium tumefaciens* str. C58 (Ag-d100-r)

SEQ ID NO:47: Nucleotide sequence of aminotransferase gene derived from *Rhizobium* radiobacter SEQ ID NO:48: Amino acid sequence of aminotransferase derived from *Rhizobium* radiobacter SEQ ID NO:49: Forward primer for amplifying DNA fragment containing aminotransferase gene derived from *Rhizobium* radiobacter (3976AT-Nde-f)

SEQ ID NO:50: Reverse primer for amplifying DNA fragment containing aminotransferase gene derived from *Rhizobium* radiobacter (3976-xho-r)

SEQ ID NO:51: Amino acid sequence of a fragment of aminotransferase derived from *Rhizobium* sp.

SEQ ID NO:52: Nucleotide sequence of aminotransferase gene derived from *Rhizobium* sp.

SEQ ID NO:53: Amino acid sequence of aminotransferase derived from *Rhizobium* sp.

SEQ ID NO:54: Forward primer for amplifying DNA fragment containing aminotransferase gene derived from *Rhizobium* sp. (12469AT-Nde-f)

SEQ ID NO:55: Reverse primer for amplifying DNA fragment containing aminotransferase gene derived from *Rhizobium* sp. (12469-xho-r)

SEQ ID NO:56: Forward primer which is designed based on the genomic DNA sequence from *Corynebacterium ammoniagenes* DSM20306 (Co-d50-r)
SEQ ID NO:57: Reverse primer which is designed based on a homologus region between the genomic DNA sequences corresponding to the aspartate aminotransferases from *Corynebacterium striatum* ATCC6940 (ZP_03935516) and from *Corynebacterium ammoniagenes* DSM20306
SEQ ID NO:58: Forward primer for amplifying DNA fragment containing aminotransferase gene derived from *Corynebacterium ammoniagenes* (Co-890-r)
SEQ ID NO:59: Reverse primer for amplifying DNA fragment containing aminotransferase gene derived from *Corynebacterium ammoniagenes* (Co-1060-r)
SEQ ID NO:60: Nucleotide sequence of aminotransferase gene derived from *Corynebacterium ammoniagenes*
SEQ ID NO:61: Amino acid sequence of aminotransferase derived from *Corynebacterium ammoniagenes*
SEQ ID NO:62: Forward primer for amplifying DNA fragment containing aminotransferase gene derived from *Corynebacterium ammoniagenes* (1444AT-Nde-f)
SEQ ID NO:63: Reverse primer for amplifying DNA fragment containing aminotransferase gene derived from *Corynebacterium ammoniagenes* (1444-xho-r)
SEQ ID NO:64: Nucleotide sequence of aminotransferase gene derived from *Deinococcus geothermalis*
SEQ ID NO:65: Amino acid sequence of aminotransferase derived from *Deinococcus geothermalis*
SEQ ID NO:66: Nucleotide sequence of aminotransferase gene derived from *Corynebacterium glutamicum*
SEQ ID NO:67: Amino acid sequence of aminotransferase derived from *Corynebacterium glutamicum*
SEQ ID NO:68: Nucleotide sequence of aminotransferase gene derived from *Thermus thermophilus*
SEQ ID NO:69: Amino acid sequence of aminotransferase derived from *Thermus thermophilus*
SEQ ID NO:70: Nucleotide sequence of aminotransferase gene derived from *Thermotoga maritima*
SEQ ID NO:71: Amino acid sequence of aminotransferase derived from *Thermotoga maritima*
SEQ ID NO:72: Nucleotide sequence of aminotransferase gene derived from *Pyrococcus horikoshii*
SEQ ID NO:73: Amino acid sequence of aminotransferase derived from *Pyrococcus horikoshii*
SEQ ID NO:74: Nucleotide sequence of aminotransferase gene derived from *Phormidium lapideum*
SEQ ID NO:75: Amino acid sequence of aminotransferase derived from *Phormidium lapideum*
SEQ ID NO:76: Nucleotide sequence of aminotransferase gene derived from *Thermus thermophilus*
SEQ ID NO:77: Amino acid sequence of aminotransferase derived from *Thermus thermophilus*
SEQ ID NO:78: Nucleotide sequence of aminotransferase gene derived from *Pyrococcus horikoshii*
SEQ ID NO:79: Amino acid sequence of aminotransferase derived from *Pyrococcus horikoshii*
SEQ ID NO:80: Nucleotide sequence of aminotransferase gene derived from *Methanococcus jannaschii*
SEQ ID NO:81: Amino acid sequence of aminotransferase derived from *Methanococcus jannaschii*
SEQ ID NO:82: Nucleotide sequence of aminotransferase gene derived from *Thermotoga maritima*
SEQ ID NO:83: Amino acid sequence of aminotransferase derived from *Thermotoga maritima*
SEQ ID NO:84: Nucleotide sequence of aminotransferase gene derived from *Saccharomyces cerevisiae*
SEQ ID NO:85: Amino acid sequence of aminotransferase derived from *Saccharomyces cerevisiae*
SEQ ID NO:86: Nucleotide sequence of aminotransferase gene derived from *Eubacterium* rectale
SEQ ID NO:87: Amino acid sequence of aminotransferase derived from *Eubacterium* rectale
SEQ ID NO:88: Nucleotide sequence of aminotransferase gene derived from *Bacillus pumilus*
SEQ ID NO:89: Amino acid sequence of aminotransferase derived from *Bacillus pumilus*
SEQ ID NO:90: Nucleotide sequence of aminotransferase gene derived from *Bacillus cellulosilyticus*
SEQ ID NO:91: Amino acid sequence of aminotransferase derived from *Bacillus cellulosilyticus*
SEQ ID NO:92: Nucleotide sequence of aminotransferase gene derived from *Bacillus* sp.
SEQ ID NO:93: Amino acid sequence of aminotransferase derived from *Bacillus* sp.
SEQ ID NO:94: Nucleotide sequence of aminotransferase gene derived from *Sinorhizobium meliloti*
SEQ ID NO:95: Amino acid sequence of aminotransferase derived from *Sinorhizobium meliloti*
SEQ ID NO:96: Nucleotide sequence of aminotransferase gene derived from *Methanothermobacter thermautotrophicus*
SEQ ID NO:97: Amino acid sequence of aminotransferase derived from *Methanothermobacter thermautotrophicus*
SEQ ID NO:98: Nucleotide sequence of aminotransferase gene derived from *Lactobacillus acidophilus*
SEQ ID NO:99: Amino acid sequence of aminotransferase derived from *Lactobacillus acidophilus*
SEQ ID NO:100: Nucleotide sequence of aminotransferase gene derived from *Sinorhizobium meliloti*
SEQ ID NO:101: Amino acid sequence of aminotransferase derived from *Sinorhizobium meliloti*
SEQ ID NO:102: Nucleotide sequence of aminotransferase gene derived from *Pyrococcus horikoshii*
SEQ ID NO:103: Amino acid sequence of aminotransferase derived from *Pyrococcus horikoshii*
SEQ ID NO:104: Nucleotide sequence of aminotransferase gene derived from *Thermoanaerobacter tengcongensis*
SEQ ID NO:105: Amino acid sequence of aminotransferase derived from *Thermoanaerobacter tengcongensis*
SEQ ID NO:106: Nucleotide sequence of aminotransferase gene derived from *Clostridium cellulolyticum*
SEQ ID NO:107: Amino acid sequence of aminotransferase derived from *Clostridium cellulolyticum*
SEQ ID NO:108: Nucleotide sequence of aminotransferase gene derived from *Rhodococcus erythropolis*
SEQ ID NO:109: Amino acid sequence of aminotransferase derived from *Rhodococcus erythropolis*
SEQ ID NO:110: Nucleotide sequence of aminotransferase gene derived from *Saccharophagus degradans*
SEQ ID NO:111: Amino acid sequence of aminotransferase derived from *Saccharophagus degradans*
SEQ ID NO:112: Amino acid sequence of a fragment of aminotransferase derived from *Corynebacterium ammoniagenes*

The invention claimed is:

1. A method for producing 2S,4R-Monatin or a salt thereof, comprising contacting 4R form of 4-(indole-3-yl-methyl)-4-hydroxy-2-oxoglutaric acid (4R-IHOG) with an L-amino acid aminotransferase in the presence of an L-amino acid to form the 2S,4R-Monatin,
wherein the L-amino acid aminotransferase consists of an amino acid sequence having 95% or more identity to the amino acid sequence of SEQ ID NO: 2.

2. The production method of claim 1, wherein a keto acid formed from the L-amino acid due to the action of the L-amino acid aminotransferase is contacted with a decarboxylase to degrade said keto acid.

3. The production method of claim 1, wherein the L-amino acid is L-aspartate.

4. The production method of claim 3, wherein oxaloacetate formed from the L-aspartate due to the action of the L-amino acid aminotransferase is contacted with an oxaloacetate decarboxylase to degrade said oxaloacetate to irreversibly form pyruvate.

5. The production method of claim 1, wherein the L-amino acid aminotransferase is derived from a microorganism belonging to the genus *Arthrobacter, Bacillus, Candida, Corynebacterium, Lodderomyces, Micrococcus, Microbacterium, Nocardia, Pseudomonas, Rhizobium, Stenotrophomonas, Dietzia, Ochrobactrum, Brevundimonas, Burkholderia, Carnimonas, Yarrowia, Clostridium, Deinococcus, Eubacterium, Lactobacillus, Methanothermobacter, Phormidium, Pyrococcus, Rhodococcus, Saccharomyces, Saccharophagus, Sinorhizobium, Thermoanaerobacter, Thermotoga* or *Thermus*.

6. The production method of claim 5, wherein the L-amino acid aminotransferase is derived from *Arthrobacter* sp., *Bacillus altitudinis, Bacillus cellulosilyticus, Bacillus pumilus, Bacillus* sp., *Candida norvegensis, Candida inconspicua, Corynebacterium ammoniagenes, Corynebacterium glutamicum, Lodderomyces elongisporus, Micrococcus luteus, Microbacterium* sp., *Nocardia globerula, Pseudomonas chlororaphis, Pseudomonas citronocllolis, Pseudomonas fragi, Pseudomonas putida, Pseudomonas synxantha, Pseudomonas taetrolens, Pseudomonas* sp., *Rhizobium radiobacter, Rhizobium* sp., *Stenotrophomonas* sp., *Dietzia marls, Ochrobactrum pseudogrignonense, Brevundimonas diminuta, Burkholderia* sp., *Carnimonas* sp., *Yarrowia lypolytica, Clostridium cellulolyticum, Deinococcus geothermalis, Eubacterium rectale, Lactobacillus acidophilus, Methanothermobacter thermautotrophicus, Phormidium lapideum, Pyrococcus horikoshii, Rhodococcus erythropolis, Saccharomyces cerevisiae, Saccharophagus degradans, Sinorhizobium meliloti, Thermoanaerobacter tengcongensis, Thermotoga maritima,* or *Thermus thermophilus*.

7. The production method of claim 1, wherein the L-amino acid aminotransferase comprises one or more mutations of amino acid residues selected from the group consisting of the amino acid residues at position 39, position 109, position 128, position 150, position 258, position 287, position 288, position 289, position 303, position 358 and position 431 in the amino acid sequence of SEQ ID NO: 2.

8. The production method of claim 7, wherein the one or more mutations of amino acid residues are selected from the group consisting of:
i) substitution of the lysine at position 39 with an arginine;
ii) substitution of the serine at position 258 with a glycine;
iii) substitution of the glutamine at position 287 with a glutamic acid;
iv) substitution of the threonine at position 288 with a glycine;
v) substitution of the isoleucine at position 289 with an alanine;
vi) substitution of the aspartic acid at position 109 with a glycine;
vii) substitution of the histidine at position 150 with a tyrosine;
viii) substitution of the phenylalanine at position 303 with a leucine;
ix) substitution of the aspartic acid at position 358 with a tyrosine;
x) substitution of the serine at position 431 with a threonine; and
xi) substitution of the glutamic acid at position 128 with a glycine.

9. The production method of claim 1, wherein the 4R-IHOG is contacted with the L-amino acid aminotransferase using a transformant that expresses the L-amino acid aminotransferase.

10. The production method of claim 1, further comprising condensing indole-3-pyruvate and pyruvate to form the 4R-IHOG.

11. The production method of claim 10, wherein the indole-3-pyruvate and the pyruvate are condensed by contacting the indole-3-pyruvate and the pyruvate with an aldolase.

12. The production method of claim 10, wherein at least part of the pyruvate used in the formation of the 4R-IHOG is from pyruvate formed from the oxaloacetate due to the action of an oxaloacetate decarboxylase.

13. The production method of claim 10, further comprising deaminating a tryptophan to form the indole-3-pyruvate.

14. The production method of claim 13, wherein the tryptophan is deaminated by contacting the tryptophan with a deamination enzyme.

15. The production method of claim 10, wherein the production of the 2S,4R-Monatin or the salt thereof is carried out in one reactor.

16. The production method of claim 13, wherein the production of the 2S,4R-Monatin or the salt thereof is carried out in one reactor.

\* \* \* \* \*